(12) United States Patent
Clogston et al.

(10) Patent No.: US 9,617,333 B2
(45) Date of Patent: *Apr. 11, 2017

(54) SCLEROSTIN ANTIBODY CRYSTALS AND FORMULATIONS THEREOF

(71) Applicant: AMGEN INC., Thousand Oaks, CA (US)

(72) Inventors: Christi L. Clogston, Camarillo, CA (US); Twinkle R. Christian, Newbury Park, CA (US); Timothy D. Osslund, Camarillo, CA (US); Elisabeth Freeman, Murrieta, CA (US)

(73) Assignee: AMGEN INC., Thousand Oaks, CA (US)

( * ) Notice: Subject to any disclaimer, the term of this patent is extended or adjusted under 35 U.S.C. 154(b) by 35 days.

This patent is subject to a terminal disclaimer.

(21) Appl. No.: 14/832,268

(22) Filed: Aug. 21, 2015

(65) Prior Publication Data

US 2016/0083460 A1 Mar. 24, 2016

Related U.S. Application Data

(63) Continuation of application No. 14/006,010, filed as application No. PCT/US2012/030364 on Mar. 23, 2012, now Pat. No. 9,145,457.

(60) Provisional application No. 61/467,868, filed on Mar. 25, 2011.

(51) Int. Cl.
| | | |
|---|---|---|
| *C07K 16/18* | (2006.01) | |
| *A61K 39/35* | (2006.01) | |
| *C07K 16/22* | (2006.01) | |
| *A61K 39/395* | (2006.01) | |
| *A61K 39/00* | (2006.01) | |

(52) U.S. Cl.
CPC ........ *C07K 16/18* (2013.01); *A61K 39/39591* (2013.01); *C07K 16/22* (2013.01); *A61K 2039/505* (2013.01); *C07K 2317/76* (2013.01)

(58) Field of Classification Search
None
See application file for complete search history.

(56) References Cited

U.S. PATENT DOCUMENTS

| | | | |
|---|---|---|---|
| 4,331,647 A | 5/1982 | Goldenberg | |
| 4,376,110 A | 3/1983 | David et al. | |
| 4,411,993 A | 10/1983 | Gillis | |
| 4,427,115 A | 1/1984 | Laipply | |
| 4,543,439 A | 9/1985 | Frackelton, Jr. et al. | |
| RE32,011 E | 10/1985 | Zimmerman et al. | |
| 4,837,440 A | 6/1989 | Burtscher et al. | |
| 4,902,614 A | 2/1990 | Wakabayashi et al. | |
| 5,070,108 A | 12/1991 | Margolis | |
| 5,145,684 A | 9/1992 | Liversidge et al. | |
| 5,223,409 A | 6/1993 | Ladner et al. | |
| 5,399,363 A | 3/1995 | Liversidge et al. | |
| 5,453,492 A | 9/1995 | Butzow et al. | |
| 5,466,468 A | 11/1995 | Schneider et al. | |
| 5,543,158 A | 8/1996 | Gref et al. | |
| 5,552,157 A | 9/1996 | Yagi et al. | |
| 5,565,213 A | 10/1996 | Nakamori et al. | |
| 5,567,434 A | 10/1996 | Szoka, Jr. | |
| 5,571,714 A | 11/1996 | Dasch et al. | |
| 5,627,052 A | 5/1997 | Schrader | |
| 5,641,515 A | 6/1997 | Ramtoola | |
| 5,698,426 A | 12/1997 | Huse | |
| 5,738,868 A | 4/1998 | Shinkarenko et al. | |
| 5,780,263 A | 7/1998 | Hastings et al. | |
| 5,795,587 A | 8/1998 | Gao et al. | |
| 5,795,965 A | 8/1998 | Tsuchiya et al. | |
| 5,811,238 A | 9/1998 | Stemmer et al. | |
| 5,830,721 A | 11/1998 | Stemmer et al. | |
| 5,837,458 A | 11/1998 | Minshull et al. | |
| 5,877,397 A | 3/1999 | Lonberg et al. | |
| 6,054,561 A | 4/2000 | Ring | |
| 6,057,421 A | 5/2000 | Muller et al. | |
| 6,117,911 A | 9/2000 | Grainger et al. | |
| 6,133,426 A | 10/2000 | Gonzalez et al. | |
| 6,180,370 B1 | 1/2001 | Queen et al. | |
| 6,207,153 B1 | 3/2001 | Dan et al. | |
| 6,395,511 B1 | 5/2002 | Brunkow et al. | |
| 6,489,445 B1 | 12/2002 | Brunkow et al. | |
| 6,495,736 B1 | 12/2002 | Brunkow et al. | |
| 6,703,199 B1 | 3/2004 | Koide | |
| 6,803,453 B1 | 10/2004 | Brunkow et al. | |
| 6,806,055 B2 | 10/2004 | Berman et al. | |
| 6,815,201 B2 | 11/2004 | Pinter | |
| 6,818,748 B2 | 11/2004 | Fulton et al. | |
| 7,192,583 B2 | 3/2007 | Brunkow et al. | |

(Continued)

FOREIGN PATENT DOCUMENTS

| | | |
|---|---|---|
| CN | 101980722 | 2/2011 |
| JP | 4-141095 | 5/1992 |

(Continued)

OTHER PUBLICATIONS

Ahamed et al. "Phase Behaviour of Intact Monoclonal Antibody", Biochemical Journal, Jul. 2007, vol. 93, pp. 610-619.*
A diagram of a relevant part of the human genome (D64), citation in Appeal, European Patent No. 1133558, dated Apr. 15, 2010.
Abbas et. al. (Eds.), Cellular and Molecular Immunology, Third Edition, Section II, p. 54 (1997).
Alberts et. al. (Eds.), Molecular Biology of the Cell, Third Edition, Chapter 23, p. 1212 (1994).

(Continued)

*Primary Examiner* — Suzanne M Noakes
(74) *Attorney, Agent, or Firm* — Marshall, Gerstein & Borun LLP

(57) ABSTRACT

Described herein are anti-sclerostin antibody crystals, methods of making such antibody crystals and formulations comprising the antibody crystals.

13 Claims, 21 Drawing Sheets

(56) References Cited

U.S. PATENT DOCUMENTS

| | | |
|---|---|---|
| 7,226,902 B2 | 6/2007 | Winkler et al. |
| 7,381,409 B2 | 6/2008 | Winkler et al. |
| 7,572,899 B2 | 8/2009 | Brunkow et al. |
| 7,578,999 B2 | 8/2009 | Winkler et al. |
| 7,592,429 B2 | 9/2009 | Paszty et al. |
| 7,642,238 B2 | 1/2010 | Shaughnessy |
| 7,758,858 B2 | 7/2010 | Brunkow et al. |
| 7,833,525 B2 | 11/2010 | Shenoy et al. |
| 7,868,134 B2 | 1/2011 | Winkler et al. |
| 7,872,106 B2 | 1/2011 | Paszty et al. |
| 8,178,099 B2 | 5/2012 | Ellies |
| 2002/0136719 A1 | 9/2002 | Shenoy et al. |
| 2003/0165410 A1 | 9/2003 | Taylor |
| 2003/0166247 A1 | 9/2003 | Brunkow et al. |
| 2003/0186915 A1 | 10/2003 | Pan et al. |
| 2003/0229041 A1 | 12/2003 | Sutherland et al. |
| 2004/0009535 A1 | 1/2004 | Brunkow et al. |
| 2004/0023356 A1 | 2/2004 | Krumlauf et al. |
| 2004/0058321 A1 | 3/2004 | Brunkow et al. |
| 2004/0141875 A1 | 7/2004 | Doshi |
| 2004/0146888 A1 | 7/2004 | Paszty et al. |
| 2004/0158045 A1 | 8/2004 | Brunkow et al. |
| 2005/0014650 A1 | 1/2005 | Seitz et al. |
| 2005/0085418 A1 | 4/2005 | Winkler et al. |
| 2005/0106683 A1 | 5/2005 | Winkler et al. |
| 2005/0238646 A1 | 10/2005 | Ledbetter et al. |
| 2006/0233801 A1 | 10/2006 | Brunkow et al. |
| 2007/0072797 A1 | 3/2007 | Robinson et al. |
| 2007/0110747 A1 | 5/2007 | Paszty et al. |
| 2007/0292444 A1 | 12/2007 | Krumlauf et al. |
| 2008/0182788 A1 | 7/2008 | Brunkow et al. |
| 2008/0234219 A1 | 9/2008 | Brunkow et al. |
| 2009/0074763 A1 | 3/2009 | Padhi et al. |
| 2009/0117118 A1 | 5/2009 | Winkler et al. |
| 2009/0304713 A1 | 12/2009 | Paszty et al. |
| 2010/0015665 A1 | 1/2010 | Latham et al. |
| 2010/0036091 A1 | 2/2010 | Robinson et al. |
| 2010/0151524 A1 | 6/2010 | Winkler et al. |
| 2011/0044978 A1 | 2/2011 | Ke et al. |
| 2011/0097342 A1 | 4/2011 | Paszty et al. |
| 2011/0150866 A1 | 6/2011 | Brunkow et al. |
| 2013/0203965 A1 | 8/2013 | Latham et al. |
| 2015/0166648 A1 | 6/2015 | Fraunhofer et al. |

FOREIGN PATENT DOCUMENTS

| | | |
|---|---|---|
| WO | WO-91/13152 | 9/1991 |
| WO | WO-92/01047 | 1/1992 |
| WO | WO-92/02551 | 2/1992 |
| WO | WO-92/06693 | 4/1992 |
| WO | WO-95/30003 | 11/1995 |
| WO | WO-96/04375 | 2/1996 |
| WO | WO-98/21335 | 5/1998 |
| WO | WO-99/03996 | 1/1999 |
| WO | WO-99/06554 | 2/1999 |
| WO | WO-99/15556 | 4/1999 |
| WO | WO-00/32773 | 6/2000 |
| WO | WO-00/44777 | 8/2000 |
| WO | WO-00/75317 | 12/2000 |
| WO | WO-01/64885 | 9/2001 |
| WO | WO-01/92308 | 12/2001 |
| WO | WO-01/98491 | 12/2001 |
| WO | WO-02/24888 | 3/2002 |
| WO | WO-02/30463 | 4/2002 |
| WO | WO-02/072636 | 9/2002 |
| WO | WO-03/050513 | 6/2003 |
| WO | WO-03/087763 | 10/2003 |
| WO | WO-03/106657 | 12/2003 |
| WO | WO-2004/082608 | 9/2004 |
| WO | WO-2004/094477 | 11/2004 |
| WO | WO-2004/098491 | 11/2004 |
| WO | WO-2005/003158 | 1/2005 |
| WO | WO-2005/014650 | 2/2005 |
| WO | WO-2005/115356 | 12/2005 |
| WO | WO-2006/015373 | 2/2006 |
| WO | WO-2006/065746 | 6/2006 |
| WO | WO-2006/102070 | 9/2006 |
| WO | WO-2006/119062 | 11/2006 |
| WO | WO-2006/119107 | 11/2006 |
| WO | WO-2007/080129 | 7/2007 |
| WO | WO-2008/061013 | 5/2008 |
| WO | WO-2008/092894 | 8/2008 |
| WO | WO-2008/115732 | 9/2008 |
| WO | WO-2008/121301 | 10/2008 |
| WO | WO-2008/133722 | 11/2008 |
| WO | WO-2009/020654 | 2/2009 |
| WO | WO-2009/039175 | 3/2009 |
| WO | WO-2009/047356 | 4/2009 |
| WO | WO-2009/056634 | 5/2009 |
| WO | WO-2009/079471 | 6/2009 |
| WO | WO-2009/131553 | 10/2009 |
| WO | WO-2009/149189 | 12/2009 |
| WO | WO-2010/100179 | 9/2010 |
| WO | WO-2010/100200 | 9/2010 |
| WO | WO-2010/115932 | 10/2010 |
| WO | WO-2010/130830 | 11/2010 |
| WO | WO-2012/028683 | 3/2012 |
| WO | WO-2012/058393 | 5/2012 |
| WO | WO-2013101451 | 7/2013 |

OTHER PUBLICATIONS

Albertsen et. al., A physical map and candidate genes in the BRCA1 region on chromosome 17q12-21. Nat. Genet., 7:472-9 (1994).

Alting-Mees et. al., Monoclonal antibody expression libraries: A rapid alternative to hybridomas. Strat. Molec. Biol., 3:1-9 (1990).

Alves et. al., Sclerosteosis: A marker of Dutch ancestry? Rev. Bras. Genet., 4:825-34 (1982).

Andersson et. al., Molecular genetics and pathophysiology of 17β-hydroxysteriod dehydrogenase 3 deficiency. J. Clin. Endrocrinol. Metab., 81(1): 130-6 (1996).

Angal et. al., A single amino acid substitution abolishes the heterogeneity of chimeric mouse/human (IgG4) antibody. Mol. Immunol., 30(1):105-8 (1993).

Annex EW6 to Declaration filed in connection with the European Patent EP 1133558 Opposition, Expert opinion of Prof. Dr. Edgar Wingender, dated Sep. 24, 2009.

Annex regarding the purported relevance of gene/peptides mentioned by Professor Arnett, dated Mar. 18, 2011.

Anonymous, Amgen presents denosumab and sclerostin antibody data at American Society for Bone and Mineral Research Annual Meeting. Amgen Media Press Release. <www.amgen.com/media/media_pr_detail.jsp?releaseID-907028> (2006).

Anonymous, UCB on track. UCB News <http://hugin.info/133973/R/1176122/233395.pdf> (2007).

Arnett et. al., Effect of pH on bone resorption by rat osteoclasts in vitro. Endocrinol., 119(1): 119-124 (1986).

Attana Application Example, cited in Opposition against European Patent No. 1721979 by Opponent: Novartis AG, dated Jun. 15, 2011.

Avsian-Kretchmer et. al., Comparative genomic analysis of the eight-membered ring cystine knot-containing bone morphogenetic protein antagonists. Molec. Endocrinol., 18(1):1-12 (2004).

Babcook et. al., A novel strategy for generating monoclonal antibodies from single, isolated lymphocytes producing antibodies of defined specificities. Proc. Natl. Acad. Sci. USA, 93:7843-8 (1996).

Baines et. al., Purification of immunoglobulin G (IgG). Meth. Molec. Biol., 10:79-104 (1992).

Balemans et. al., Extracellular regulation of BMP signaling in vertebrates: A cocktail of modulators. Dev. Biol., 250:231-50 (2002).

Balemans et. al., Increased bone density in sclerosteosis is due to the deficiency of a novel secreted protein (SOST). Hum. Mol. Genet., 10:537-43 (2001).

Balemans et. al., Localization of the gene for sclerosteosis to the van Buchem disease-gene region on chromosome 17q12-q21. Am. J. Hum. Genet., 64:1661-9 (1999).

Balint et. al., Antibody engineering by parsimonious mutagenesis. Gene, 137(1):109-18 (1993).

(56) References Cited

OTHER PUBLICATIONS

Basu et al., Protein crystals for the delivery of bipharmceuticals. *Exp. Opin. Biol. Ther.*, 4(3):301-17 (2004).
Bateman et. al., Granulins: The structure and function of an emerging family of growth factors. *J. Endocrino.*, 158: 145-51 (1998).
Baxevanis (Ed.) et. al., Bioinformatics: A practical guide to the analysis of genes and proteins, John Wiley & Sons, Inc. p. 234 (1998).
Beighton et. al., Heterozygous manifestations in the heritable disorders of the skeleton. *Pediatr. Radiol.*, 27: 397-401 (1997).
Beighton et. al., The clinical features of sclerosteosis. *Clin. Genet.*, 25:175-81 (1984).
Beighton et. al., The syndromic status of sclerosteosis and van Buchem disease. *Ann. Intern. Med.*, 84:393-7 (1976).
Bellows et. al., Parathyroid hormone reversibly suppresses the differentiation of osteoprogenitor cells in functional osteoblasts. *Endocrinol.*, 127(6): 3111-6 (1990).
Bendayan, Possibilities of false immunocytochemical results generated by the use of monoclonal antibodies: The example of the anti-proinsulin antibody. *J. Histochem. Cytochem.*, 43(9):881-6 (1995).
Bendig, Humanization of rodent monoclonal antibodies by CDR grafting. *Methods*, 8:83-93 (1995).
Bergfeld et. al., Release of ATP from human erythrocytes in response to a brief period of hypoxia and hypercapnia. *Cardiovascular Res.*, 26: 40-7 (1992).
Berman et. al., The protein data bank. *Acta. Cryst.*, 58(1):899-907 (2002).
Bigger versions of Figures from Declaration of Professor Teresa Attwood, citation in Appeal, European Patent No. 1133558, dated Apr. 13, 2010.
Bird et. al., Single-chain antigen-binding proteins. *Science*, 242:423-6 (1988).
Birren et. al., EMBL sequence database accession No. AC003098.2, Nov. 14, 1997.
Bishop (Ed.), Guide to Human Genome Computing, Second Edition, Academic Press, Chapter 1: Introduction to human genome computer via the world wide web, pp. 1-14 (2003).
Black et. al., A somatic cell hybrid map of the long arm of human chromosome 17, containing the familial breast cancer ILocus (BRCAI). *Am. J. Hum. Genet.*, 52:702-10 (1993).
Blum et. al., Study plan for German students in the summer of 1998, University Bioinformatik lecture announcement (1998).
Boden et. al., Glucocorticoid-induced differentiation of fetal rat calvarial osteoblasts is mediated by bone morphogenetic protein-6. *Endocrinology*, 138(7):2820-8 (1997).
Boerner et. al., Production of antigen-specific human monoclonal antibodies from in vitro-primed human splenocytes. *J. Immunol.*, 147:86-95 (1991).
Bonaldo et. al., EMBL Sequence Database Accession No. AI113131, Sep. 4, 1998.
Bonaldo et. al., Normalization and subtraction: Two approaches to facilitate gene discovery. *Genome Res.*, 6(9):791-806 (1996).
Bondestam, Ligands & Signaling Components of the Transforming Growth Factor, Helsinki University Biomedical Dissertations (2002).
Bork et. al., Go hunting in sequence databases by watch out for the traps. *Trends Genet.*, 12: 425-7 (1996).
Bos et. al., Ras ongoenes in human cancer: A review. *Cancer Res.*, 49: 4682-9 (1989).
Bost et. al., Antibodies against a peptide sequence within the HIV envelope protein crossreacts with human interleukin-2. *Immunol. Invest.*, 17(6&7):577-86 (1988).
Bostrom et. al., Ligand and signaling components of the transforming growth factor β family. *J. Orth. Res.*, 13:357-67 (1995).
Bottcher et. al., NCBI Sequence database accession No. NM_004329, Aug. 2, 2009.
Bouffard et. al., A physical map of human chromosome 7: An integrated YAC contig map with average STS spacing of 79 kb. *Genome Res.*, 7: 673-92 (1997).

Bowie et. al., A method to identify protein sequences that fold into a known three-dimensional structure. *Science*, 253:164-70 (1991).
Bowie et. al., Deciphering the message in protein sequences: Tolerance to amino acid substitutions. *Science*, 247(4948):1306-10 (1990).
Bradley et. al., Modifying the mouse: Design and desire. *Bio/Technology*, 10:534-9 (1992).
Brandao-Burch et. al., Acidosis inhibits bone formation by osteoblasts in vitro by preventing mineralization. *Calcif. Tissue Int.*, 77: 167-74 (2005).
Brenner et. al., Population statistics of protein structures: Lessons from structural classifications. *Curr. Op. Struct Biol.*, 7(3):369-76 (1997).
Brown, Hybridization analysis of DNA blots, *Current Protocols in Protein Science*, 13:A.4H.1-A.4H.9 (1990).
Brown, Hybridization analysis of DNA blots, *Current Protocols in Protein Science*, 2.10.1-2.10.16 (2000).
Bruggemann et. al., Production of human antibody repertoires in transgenic mice. *Curr. Opin. Biotechnol.*, 8:455-8 (1997).
Brunkow et. al., Bone dysplasia sclerosteosis results from loss of the SOST gene product, a novel cysteine knot-containing protein. *Am. J. Hum. Genet.*, 68:577-89 (2001).
Burton et. al., Human antibodies from combinatorial libraries. *Adv. Immunol.*, 57:191-280 (1994).
Butcher et. al., Increased salt concentration reversibly destabilizes p53 quaternary structure and sequence-specific DNA binding. *Biochem. J.*, 298: 513-6 (1994).
Byrne et. al., CD4+CD45RBHi T cell transfer induced colitis in mice is accompanied by osteopenia which is treatable with recombinant human osteoprotegerin. *Gut.*, 54:78-86 (2005).
Campbell et. al., Totipotency or multipotentiality of cultured cells: Applications and progress. *Theriogenology*, 47:63-72 (1997).
Caverzasio et. al., Characteristics and regulation of Pi transport in osteogenic cells for bone metabolism. *Kindey Int.*, 49: 975-80 (1996).
Chan et. al., A new paradigm in the treatment of osteoporosis: Wnt pathway proteins and their antagonists. *Curr. Opin. Invest. Drugs*, 8:293-8 (2007).
Chandran et. al., Recent trends in drug delivery systems: Liposomal drug delivery system—Preparation and characterization. *Indian J. Exp. Biol.*, 35(8):801-9 (1997).
Charlier et. al., A pore mutation in a novel KQT-like potassium channel gene in an idiopathic epilepsy family. *Nat. Genet.*, 18:53-5 (1998).
Chenu et. al., Glutamate receptors are expressed by bone cells and are involved in bone resorption. *Bone*, 22(4): 295-9 (1998).
Chou et. al., Empirical predication of protein conformation. *Ann. Rev. Biochem.*, 47:251-76 (1979).
Chou et. al., Prediction of the secondary structure of proteins from their amino acid sequence. *Adv. Enzymol. Relat. Areas Mol. Biol.*, 47:145-8 (1978).
Clark, Antibody humanization: A case of the 'Emperor's New Clothes'?. *Immunology Today*, 21(8):397-402 (2000).
Cogan et. al., NCBI Sequence Database Accession No. NM_033346, Jul. 19, 2005.
Collins, Identifying human disease genes by positional cloning. The Harvey Lectures, Series 86:149-64 (1992).
Collins, Positional cloning moves from perditional to traditional. *Nat. Genet.*, 9:347-50 (1995).
Colman, Effects of amino acid sequence changes on antibody-antigen interactions. *Biomolec. Res. Inst.*, 55:33-6 (1994).
Communication from the European Patent Office providing an "Observation by a Third Party according to Article 115 EPC" submitted in connection with the Opposition to European Patent No. 1 133 558, dated Dec. 3, 2008.
Cook et. al., Structural basis for a functional antagonist in the transforming growth factor β superfamily. *J. Biol. Chem.*, 280(48):40177-86 (2005).
Cormier, Markers of bone metabolism. *Curr. Opin. in Rheu.*, 7:243-8 (1995).
Couvreur et. al., Polyalkylcyanoacrylates as colloidal drug carriers. *Crit. Rev. Ther. Drug Carrier Syst.*, 5(1):1-20 (1988).

(56) References Cited

OTHER PUBLICATIONS

Craig et. al., Sclerostin binds and regulates the activity of cysteine rich protein 61. *Biochem. Biophys. Res. Commun.*, 293(1): 36-40 (2010).

Craig et. al., Sclerostin-erbB-3 interactions: Modulation of erbB-3 activity by sclerostin. *Biochem. Biophys. Res. Commun.*, 402: 421-4 (2010).

Crameri et. al., DNA shuffling of a family of genes from diverse species accelerates directed evolution. *Nature*, 391:288-91 (1998).

Dall'Acqua et. al., Antibody humanization by framework shuffling. *Methods*, 36(1):43-60 (2005).

Davies, et. al., Affinity improvement of single antibody VH domains: Residues in all three hypervariable regions affect antigen binding. *Immunotechnology*, 2(3): 169-79 (1996).

de Jong et. al., Evolution of the α-crystallin/small heat-shock protein family. *Mol. Biol. Evol.*, 10(1): 103-26 (1993).

Dean et. al., Matrix vesicles produced by osteoblast-like cells in culture become significantly enriched in proteoglycan-degrading metalloproteinases after addition of β-glycerophosphate and ascorbic acid. *Calcif. Tissue*, 54: 399-408 (1994).

Declaration filed in connection with the European Patent EP 1133558 Opposition, Expert opinion of Dr. Auristela Freire de Paes Alves, Ph.D., dated Sep. 9, 2009.

Declaration filed in connection with the European Patent EP 1133558 Opposition, Expert opinion of Dr. Walter Sebald, dated Sep. 24, 2009.

Declaration filed in connection with the European Patent EP 1133558 Opposition, Expert opinion of Prof. Dr. Edgar Wingender, dated Sep. 24, 2009.

Declaration filed in connection with the European Patent EP 1133558 Opposition, Expert opinion of Prof. Dr. Thomas Muller, dated Sep. 23, 2009.

Declaration of Alistair J. Henry, citation in Appeal, European Patent No. 1133558, dated Apr. 2, 2010.

Declaration of Dr. Martyn Robinson, submitted in Opposition to European Patent No. 1133558, dated Jan. 13, 2008.

Declaration of Dr. Mary E. Brunkow, submitted in Opposition to European Patent No. 1133558, dated Jan. 9, 2008.

Declaration of Dr. Raymond Dalgleish dated Dec. 8, 2011, citation in Appeal, European Patent No. 1133558.

Declaration of Prof. Edgar Wingender filed in connection with that Opposition regarding European Patent EP 1133558 B1, dated Mar. 10, 2011.

Declaration of Professor Teresa Attwood, citation in Appeal, European Patent No. 1133558, dated Apr. 13, 2010.

Declaration of Tim Arnett, citation in Appeal, European Patent No. 1133558, dated Apr. 2, 2010.

Delmas et. al., The use of biochemical markers of bone turnover in osteoporosis. *Osteoporosis International*, Suppl. 6:S2-17 (2000).

Diagram of the candidate interval, citation by Propriator in Opposition against European Patent No. 1721979 on Feb. 20, 2012.

Dreuth et al., Protein crystals and their stability. *J. Crystal Growth*, 122:107-9 (1992).

Ducy et. al., 5-HT and bone biology. *Curr. Opin. Pharmacol.*, 11: 34-8 (2011).

Ducy et. al., Genetic control of cell differentiation in the skeleton. *Curr. Opin. Cell Biol.*, 10: 614-9 (1998).

Durham et. al., Alterations in insulin-like growth factor (IGF)-dependent IGF-binding protein-4 proteolysis in transformed osteoblastic cells. *Endocrinology*, 136(4):1374-80 (1995).

Ebara et. al., Mechanism for the action of bone morphogenetic proteins and regulation of their activity. *Spine*, 27(165):S10-5 (2002).

Eli Lilly Statement of Grounds of Appeal, Opposition to European Patent Application No. 1133558 B1, dated Sep. 28, 2009.

Eli Lilly, Biacore experiment comparison results, Setup assay to measure BMP binding to captured SOST, referenced on p. 41 of reference C193, dated Sep. 28, 2009.

Epstein et. al., Endocrine function in sclerosteosis. *S. Afr. Med. J.*, 55:1105-10 (1979).

European Patent Office Communication, Opposition to European Patent No. 1133558, dated Nov. 4, 2008.

European Patent Office, "Opinion of the Enlarged Board of Appeal dated Dec. 1992 G 1/92", available from [http://documents.epo.org/projects/babylon/eponet.nsf/0/907016FA57B46FD0C12572C8006CD2E2/$File/g920001.pdf], cited Jun. 15, 2011.

Expert Opinion from Dr. Catalina Lopez-Correa, submitted in Opposition to European Patent No. 1133558, dated Mar. 6, 2009.

Expert opinion of Professor Dr.-Ing Ulrich Vollrath, citation in Appeal of European Patent No. 1133558, dated Apr. 12, 2005.

Extract from Sigma Aldrich catalogue, cited in Opposition against European Patent No. 1721979 by Opponent: Laudens, dated Jun. 15, 2011.

Eyre et. al., Characterization of aromatase and 17β-hydroxysteroid dehydrogenase expression in rat osteoblastic cells. *J. Bone Miner. Res.*, 13(6): 996-1004 (1998).

Foster et. al., Establishment of interference in osteoblasts by an osteopetrosis-inducing Avian Leukosis virus. *Virology*, 205: 376-8 (1994).

Fouser et. al., Feedback regulation of collagen gene expression: A Trojan horse approach. *Proc. Natl. Acad. Sci. USA*, 88: 10158-62 (1991).

Frost et. al., On the rat model of human osteopenias and osteoporoses. *Bone and Mineral*, 18:227-36 (1992).

Fujiwara et. al., GenBank Sequence Database Accession No. D79813, Feb. 9, 1996.

Gardner et. al., Bone mineral density in sclerosteosis; Affected individuals and gene carriers. *J. Clin. Endocrinol. Metab.*, 90(12): 6392-5 (2005).

Gavarini et. al., Opposite effects of PSD-95 and MPP3 PDZ proteins on serotonin 5-hydroxytryptamine2C receptor desensitization and membrane stability. *Molec. Biol.*, 17: 4619-31 (2006).

Gazzerro et. al., Bone morphogenetic proteins induce the expression of noggin which limits their activity in cultured rat osteoblasts. *J. Clin. Invest.*, 102(12):2106-14 (1998).

Gazzerro et. al., Potential drug targets within bone morphogenetic protein signaling pathways. *Curr. Opin. Pharmacol.*, 7: 325-3 (2007).

Geissler et la., Male pseudohermaphroditism caused by mutations of testicular 17β-hydroxysteroid hehydrogenase 3. *Nat. Genetics*, 7: 34-9 (1994).

Gencic et. al., Conservative amino acid substitution in the myelin proteolipid protein of Jimpymsd mice. *J. Neurosci.*, 10(1):117-24 (1990).

Geysen et. al., Cognitive features of continuous antigenic determinants. *J. Molec. Recog.*, 1(1):32-41 (1988).

Gitelman et. al., Vgr-1/BMP-6 induces osteoblastic differentiation of pluripotential mesenchymal cells. *Cell Growth & Differentiation*, 6:827-36 (1995).

Glasky et. al., Stability of specific immunoglobulin secretion by EBV-transformed lymphoblastoid cells and human-murine heterohybridomas. *Hybridoma*, 8:377-89 (1989).

Gowen et. al., Actions of recombinant human γ-interferon and tumor necrosis factor α on the proliferation and osteoblastic characteristics of human trabecular bone cells in vitro. *Arthritis Rheumatism*, 31(12): 1500-7 (1988).

Graner et. al., Splice variants of the *Drosophila* PS2 integrins differentially interact with RGD—containing fragments of the extracellular proteins tiggrin, Ten-m and D-Iaminin α2. *J. Biol. Chem.*, 273(29): 18235-41 (1998).

Green et al., Cytosolic pH regulation in osteoblasts. *J. Gen. Physiol.*, 95: 121-45 (1990).

Green et. al., Antigen-specific human monoclonal antibodies from mice engineered with human Ig heavy and light chain YACs. *Nat. Genet.*, 7:13 (1994).

Greene et. al., Screening Recombinant DNA Libraries. *Current Protocols in Molecular Biology*, Ch. 6(1) (1990).

Gribskov et. al., Profile analysis. *Meth. Enzym.*, 183:146-59 (1990).

Gribskov et. al., Profile analysis: Detection of distantly related proteins. *Proc. Nat. Acad. Sci. USA*, 84(13):4355-8 (1987).

Groeneveld et. al., Bone morphogenetic proteins in human bone regeneration. *Eur. J. Endocrinol.*, 142:9-21 (2000).

(56) References Cited

OTHER PUBLICATIONS

Gronthos et. al., Integrin expression and function on human osteoblast-like cells. *J. Bone Miner. Res.*, 12(8): 1189-97 (1997).
Groppe et. al., Structural basis of BMP signalling inhibition by the cystine knot protein noggin. *Nature*, 420:636-42 (2002).
Guinness-Hey, Increased trabecular bone mass in rats treated with human synthetic parathyroid hormone. *Metab. Bone Dis. Relat. Res.*, 5:177-81 (1984).
Hagedorn et al., I. Protamine insulinate, *J. Am. Med. Assn.*, 106:177-80 (1936).
Harlow et. al., Antibodies: A Laboratory Manual, Cold Spring Harbor Laboratory, 141-157 (1988).
Harris, Processing of C-terminal lysine and arginine residues of proteins isolated from mammalian cell culture. *J. Chromatogr.*, 705:129-34 (1995).
Hart et. al., Crystal structure of the human TβR2 ectodomain-TGF-β3 complex. *Nat. Struc. Biol.*, 9(3):203-8 (2002).
Hay et. al., ATCC Cell Line and Hybridomas, American Type Culture Collection, 8th Ed., pp. 149, 258, 428 (1994).
He et. al., High-throughput dynamic light scattering method for measuring viscosity of concentrated protein solutions. *Anal. Biochem.*, 399(1): 141-3 (2010).
Heinecke et. al., Receptor oligomerization and beyond: A case study in bone morphogenetic proteins, *BMC Biol.*, 7: 59 (2009).
Hill et. al., Multiple extracellular signals promote osteoblast survival and apoptosis. *Endocrinology*, 138(9):3849-58 (1997).
Hillier et. al., EMBL Sequence Database Accession No. AA393939, May 19, 1997.
Hillier et. al., GenBank Sequence Database Accession No. AA393768, Apr. 24, 1997.
Hillier et. al., Generation and analysis of 280,000 human expressed sequence tags. *Genome Res.*, 6: 807-28 (1996).
Hilliker et. al., Truncation of the amino terminus of PTH alters its anabolic activity on bone in vivo. *Bone*, 19(5): 469-77 (1996).
Hirschhorn, Letter to the editor: Dominance and homozygosity in man. *Am. J. Med. Genetics*, 18: 541 (1984).
Hock et. al., Perspective: Osteoblast apoptosis and bone turnover. *J. Bone Miner. Res.*, 16(6):975-84 (2001).
Hoffman et. al., BMP Signaling Pathways in Cartilage and Bone Formation, *Crit. Rev. Eukaryotic Gene Exp.*, 11(1-3):23-45 (2001).
Hoggard et. al., Localization of leptin receptor mRNA splice variants in murine peripheral tissues by RT-PCR and in situ hybridization. *Biochem. Biophys. Res. Commun.*, 232: 383-7 (1997).
Hollinger et. al., Engineered antibody fragments and the rise of single domains. *Nat. Biotech.*, 23(9):1126-36 (2005).
Holm et. al., Protein folds and families: Sequence and structure alignments. *Nucl. Acid Res.*, 27(1):244-7 (1999).
Holt, et. al., Domain antibodies: Proteins for therapy. *Trends Biotechnol.*, 21(11):484-90 (2003).
Hoogenboom et. al., By-passing immunisation: Human antibodies from synthetic repertoires of germline VH gene segmens rearranged in vitro. *J. Molec. Biol.*, 227:381-8 (1992).
Hoogewerf et. al., Glycosaminoglycans mediate cell surface oligomerization of chemokines. *Biochemistry*, 36: 13570-8 (1997).
Horton et. al., Arg-Gly-Asp (RGD) peptides and the anti-vitronectin receptor antibody 23C6 inhibit dentine resorption and cell spreading by osteoclasts. *Exp. Cell Res.*, 195: 368-75 (1991).
Hsu et. al., The Xenopus dorsalizing factor gremlin indentified a novel family of secreted proteins that antagonize BMP activities. *Molec. Cell*, 1:673-83 (1998).
Hufner et. al., Evidence for an osteoblast-activating factor in a patient with peripheral T-cell lymphoma and osteosclerosis. *Klin. Wochenscher.*, 67: 402-7 (1989).
Hulley et. al., Inhibition of mitogen-activated protein kinase activity and proliferation of an early osteoblast cell line (MBA 15.4) by dexamethasone: Role of protein phosphatases. *Endocrinol.*, 139(5): 2423-31 (1998).
Huse et. al., Generation of a large combinatorial library of the immunoglobulin repertoire in phage lambda. *Science*, 246:1275-81 (1989).

Hwang et. al., Use of human germline genes in a CDR homoloy-based approach to antibody humanization. *Methods*, 36(1):35-42 (2005).
Ide et. al., GenBank Sequence Database Accession No. BAA19765, Feb. 7, 1999.
Ide et. al., GenBank Sequence Datacase Accession No. D89675, Feb. 7, 1999.
Iemura et. al., Direct binding of follistatin to a complex of bone-morphogenetic protein and its receptor inhibits ventral and epidermal cell fates in early Xenopus embryo. *Proc. Natl. Acad. Sci. USA*, 95:9337-42 (1998).
Innis et. al., Evolutionary trace analysis of TGF-B and related growth factors: Implications for stie-directed mutagenesis. *Protein Engineering*, 13(12):839-47 (2000).
Jakobovits et. al., Production of antigen-specific human antibodies from mice engineered with human heavy and light chain YACsa. *Ann. N. Y. Acad. Sci.*, 764:525-35 (1995).
Jee et. al., Overview: Animal models of osteopenia and osteoporosis. *J. Musculoskel. Neuron. Interact.*, 1:193-207 (2001).
Jen et al., Diamons in the rough: Protein crystals from a formulation perspective, *Pharm. Res.* 18:1483-8 (2001).
Jenkins, Three solutions of the protein solubility problem. *Protein Science*, 7:376-82 (2008).
Jilka et. al., Increased bone formation by prevention of osteoblast apoptosis with parathyroid hormone. *J. Clin. Invest.*, 104:439-46 (1999).
Jilka et. al., Osteoblast programmed cell death (apoptosis): Modulation by growth factors and cytokines. *J. Bone Miner. Res.*, 13(5): 793-802 (1998).
Jones, Progress in protein structure predication. *Curr. Opin. Struct Biol.*, 7(3):377-387 (1997).
Johnson, The trials and tribulations of producing the first genetically engineered drug. *Nat. Rev. Drug Discovery*, 2:747-51 (2003).
Kabat et. al., Sequences of proteins of immunological interest, U.S. Department of Health and Human Services, *NIH, USA* (1987) (Table of Contents).
Kalu, The ovariectomized rat model of postmenopausal bone loss. *Bone and Mineral*, 15:175-92 (1991).
Kang et. al., Linkage of recognition and replication functions by assembling combinatorial antibody Fab libraries along phage surfaces. *Proc. Natl. Acad. Sci. USA*, 88:4363-6 (1991).
Katagiri et. al., The non-osteogenic mouse pluripotent cell line, C3H10T1/2, is induced to differentiate into osteoblastic cells by recombinant human bone morphogenetic protein-2. *Biochem. Biophys. Res. Comm.*, 172(1):295-9 (1990).
Kawabata et. al., Signal transduction by bone morphogenetic proteins. *Cytokine and Growth Factor Reviews*, 9(1):49-61 (1998).
Keller et. al., Molecular recognition of BMP-2 and BMP receptor IA. *Nat. Struct Mol. Biol.*, 11(5):481-488 (2004).
Khalil, TGF-β: From latent to active. *Microbes and Infection*, 1(15):1255-63 (1999).
Khosla et. al., Concise review for primary-care physicians. Treatment pptions for osteoporosis. *Mayo Clin. Proc.*, 70:978-82 (1995).
Kirsch et. al., BMP-2 antagonists emerge from alterations in the low-affinity binding epitope for receptor BMPR-II, *EMBO J.*, 19(13): 3314-24 (2000).
Kohler et. al., Continuous cultures of fused cells secreting antibody of predefined specificity. *Nature*, 256:495 (1975).
Koli et. al., Latency, activation, and binding proteins of TGF-. *Microscopy Res. Tech.*, 52:354-62 (2001).
Koreth et. al., Microsatellites and PCR genomic analysis. *J. Pathology*, 178:239-48 (1996).
Kramer et. al., The gapped duplex DNA approach to oligonucle-otide-directed mutation construction. *Nuc. Acids Res.*, 12:9441 (1984).
Krause et. al., Distinct modes of inhibition by sclerostin on bone morphogenetic protein and Wnt signaling pathways. *J. Biol. Chem.*, 285(53): 41614-26 (2010).
Kunkel et. al., Rapid and efficient site-specific mutagenesis without phenoypic selection. *Meth. Enzymol.*, 154:367-82 (1987).
Kunkel, Rapid and efficient site-specific mutagenesis without phenotypic selection. *Proc. Natl. Acad. Sci. USA*, 82:488-92 (1985).

(56) References Cited

OTHER PUBLICATIONS

Kurahashi et. al., Regions of genomic instability on 22q11 and 11q23 as the etiology for the recurrent constitutional t (11;22). *Hum. Molec. Genet.*, 9: 1665-70 (2000).
Kusu et. al., Sclerostin is a novel secreted osteoclast-dervied bone morphogenetic protein antagonist with unique ligand specificity. *J. Biol. Chem.*, 278:24113-7 (2003).
Labat et. al., Retroviral expression in mononuclear blood cells isolated from a patient with osteopetrosis (Albers-Schonberg disease). *J. Bone Miner. Res.*, 5(5): 425-35 (1989).
Labat, A new approach to the study of the origin of genetic disease: Retroviral etiology of osteopetrosis. *Biomed. Pharmacother.*, 45: 23-7 (1991).
Lasic, Novel applications of liposomes. *Trends Biotechnol.*, 16(7):307-21 (1998).
Latham, The biochemical and cellular characterization of sclerostin, The causative gene for sclerostenosis. *Calcified Tissue International*, 70(4):244 (2002).
Leppert et. al., Benign familial neonatal epilepsy with mutations in two potassium channel genes. *Curr. Opin. Neurol.*, 12: 143-7 (1999).
Lewiecki et. al., Sclerostin monoclonal antibody therapy with AMG 785: A potential treatment for osteoporosis. *Exp. Opin. Biol. Ther.*, 11(1): 117-27 (2011).
Li et. al., Sclerostin binds to LRP5/6 and antagonizes canonical Wnt signaling. *J. Biol. Chem.*, 280: 19883-7 (2005).
Li et. al., Treatment with an anti-sclerostin antibody directly stimulates bone formation in a dose-dependent manner in ovariectomized rats with established osteopenia. J. Bone Min. Res., 22(Suppl. S1): S65 (2007).
Lian et. al., Bone Formation: Osteoblast Lineage Cells, Growth Factors, Matrix Proteins, and the Mineralization Process, Primer on the Metabolic Bone Diseases and Disorders of Mineral Metabolism, 4th Edition, 14-29 (1999).
Lierop et. al., Van Buchem disease: Clinical, biochemical and densitometric features of patients and disease carriers. *J. Bone Miner. Res. Accepted Article* (2012).
Liu et. al., Gen Bank Sequence Database Accession No. U25110, Feb. 2, 1996.
Liu et. al., Human type II receptor for bone morphogenic proteins (BMPs): Extension of the two-kinase receptor model to the BMPs. *Molec. Cell. Biol.*, 15(7):3479-86 (1995).
Lonberg et. al., Antigen-specific human antibodies from mice comprising four distinct genetic modifications. *Nature*, 368:856 (1994).
Loots et. al., Genomic deletion of a long-range bone enhancer misregulates sclerostin in Van Buchem disease. *Genome Res.*, 15: 928-35 (2005).
Low et. al., Mimicking somatic hypermutation: Affinity maturation of antibodies displayed on bacteriophage using a bacterial mutator strain. *J. MoL Biol.*, 250:350-68 (1996).
Lowik et. al., Wnt signaling is involved in the inhibitory action of sclerostin on BMP-stimulated bone formation. *J. Musculoskeleton Neuronal Interact.* 6: 357 (2006).
Luckman et. al., Heterocycle-containing bisphosphonates cause apoptosis and inhibit bone resorption by preventing protein prenylation: Evidence from structure-activity relationships in J774 macrophages. *J. Bone Miner. Res.*, 13(11): 1668-78 (1998).
Luckman et. al., Nitrogen-containing bisphosphonates inhibit the mevalonate pathway and prevent post-translational prenylation of GTP-binding proteins, including Ras. *J. Bone Miner. Res.*, 13(4): 581-9 (1998).
Malone et. al., Bone anabolism achieved by reducing sclerostin bioavailability with an anti-sclerostin antibody. 37th International Sun Valley Workshop on Skeletal Tissue Biology. Aug. 5-8, 2007.
Mango et. al., Carboxy-terminal truncation activates glp-1 protein to specify vulval fates in Caenorhabditis elegans. *Lett. Nature*, 352: 811-15 (1991).

Margalit et. al., Comparative analysis of structurally defined herparin binding sequences reveals a distinct spatial distribution of basic residues. *J. Biol. Chem.*, 268 (26): 19228-31 (1993).
Margalit, Liposome-mediated drug targeting in topical and regional therapies. *Crit. Rev. Ther. Drug Carrier Syst.*, 12(2-3):233-61 (1995).
Marks et. al., By-passing immunization: Building high affinity human antibodies by chain shuffling. *Bio/Technology*, 10:779-83 (1992).
Matthews et. al., Adenovirus protein-protein interactions: Hexon and protein VI. *J. Gen. Virol.*, 75: 3365-74 (1994).
Mayer et. al., Differentiation of osteogenetic cells: Systems and regulators, Z. Orthop., 130: 276-84 (1992)—Abstract Only.
McClung et. al., Inhibition of sclerostin with AMG 785 in postmenopausal women with low bone mineral density: Phase 2 trial results—Abstract presented at the 2012 meeting of the American Society for Bone and Mineral Reasearch (2012).
Memorandum C, Munich Diplomatic Conference, Sep. 1 to Oct. 6, 1973.
Minabe-Saegusa et. al., Genbank Sequence Database Accession No. AB011030, Jun. 23, 1998.
Minutes of the oral proceedings before the opposition division for Opposition against European Patent No. 1721979, dated May 10, 2013.
Miyazono et. al., Divergence and convergence of TGF-β/BMP signaling. *J. Cell. Physiol.*, 187:265-76 (2001).
Miyazono et. al., TGF-β signaling by Smad proteins. *Adv. Immunology*, 75:115-57 (2000).
Morais et. al., In vitro biomineralization by osteoblast-like cells I. Retardation of tissue mineralization by metal salts. *Biomaterials*, 19: 13-21 (1998).
Mori et. al., A novel amino acid substitution a the receptor-binding site on the hemaglutinin of H3N2 influenza A viruses isolated from 6 cases with acute encephalopathy during 1997-1998 season in Tokyo. *Arch. Virol.*, 144: 147-55 (1999).
Morrison et. al., ATP is a potent stimulator of the activation and formation of rodent osteoclasts. *J. Physiol.*, 511.2: 495-500 (1998).
Mosekilde et. al., Assessing bone quality—Animcal models in preclininical osteoporosis research. *Bone*, 17 (4): 343S-52S (1995).
Moult, The current state of the art in protein structure predicion. *Curr. Opin. Biotech.*, 7(4):422-7 (1996).
Mullins et. al., Perspectives series: Molecular medicine in genetically engineered animals; Transgenesis in the rat and larger mammals. *J. Clin. Invest.*, 97(7):1557-60 (1996).
Muntoni et. al., A mutation in the dystrophin gene selectively affecting dystrophin expression in the heart. *J. Clin. Invest.*, 96: 693-9 (1995).
Nagaraja et. al., X chromosome map at 75-kb STS resolution, revealing extremes of recombination and GC content. *Genome Res.*, 7: 210-22 (1997).
Nakase et. al., Transient and localized expression of bone morphogenetic protein 4 messenger RNA during fracture healing. *J. Bone Miner. Res.*, 9(5):651-9 (1994).
Nelson, Positional cloning reaches maturity. *Curr. Opin. Genet. Devel.*, 5:298-303 (1995).
Nickel et. al., The crystal structure of the BMP-2: BMPR-1A complex and the generation of BMP-2 antagonists. *J. Bone Joint Surg.*, 83-A:S1-7-S1-14 (2001).
Nicolas et. al., An age-related decrease in the concentration of insulin-like growth factor binding protein-5 in human cortical bone. *Calcif. Tissue Int.*, 57:206-12 (1995).
Nifuji et. al., Coordinated expression of noggin and bone morphogenetic proteins (BMPs) during early skeletogenesi and induction of noggin expression by BMP-7. *J. Bone Miner. Res.*, 14(12):2057-66 (1999).
Nisonoff et. al., Separation of univalent fragments from the bivalent rabbit antidody molecule by reduction of disulfide bonds. *Arch. Biochem. Biophys.*, 89:230-44 (1960).
Niu et. al., Sclerostin inhibition leads to increased periosteal and endocortical bone formation as well as decreased cortical porosity in aged ovariectomized rats. *J. Bone Min. Res.*, 22(Suppl. S1) S65 (2007).

(56) References Cited

OTHER PUBLICATIONS

Nordsletten et. al., The neuronal regulation of fracture healing. *Acta Orthop Scand.*, 65(3): 299-304 (1994).
Notice of Opposition against European Patent No. 1133558, Opponent: Eli Lilly and Company, dated May 31, 2007.
Notice of Opposition against European Patent No. 1721979, Opponent: Eli Lilly & Company, dated Jun. 15, 2011.
Notice of Opposition against European Patent No. 1721979, Opponent: Laudens, dated Jun. 15, 2011.
Notice of Opposition against European Patent No. 1721979, Opponent: Novartis AG, dated Jun. 15, 2011.
Notice of Opposition to European Patent No. 1 133 558, dated May 29, 2007.
Nygren et. al., Scaffolds for engineering novel binding sites in proteins. *Curr. Opin. Struct. Biol.*, 7:463-9 (1997).
Observations of Opponent: Laudens in response to summons to oral proceedings in Opposition against European Patent No. 1721979, dated Feb. 25, 2013.
Oelgeschlager et. al., The evolutionarily conserved BMP-binding protein twisted gastrulation promotes BMP signalling. *Nature*, 405:757-63 (2000).
OMIM #607625, Niemann-pick disease, type C2 (2007).
Ominsky, et. al., Sclerostin monoclonal antibody treatment increases bone strength in aged osteopenic ovariectomozed rats. *J. Bone Min. Res.*, 21(1): S44 PRES1161 (2006). Abstract.
Opposition Decision for Opposition against European Patent No. 1721979, dated Aug. 2, 2013.
Opposition Statement of May 20, 2007 filed by Opponent 2 (Eli Lilly) against European Patent No. 1133558.
Oreffo et. al., Human bone marrow osteoprogenitors express estrogen receptor-alpha and bone morphogenetic proteins 2 and 4 mRNA during osteoblastic differentiation. *J. Cell. Biochem.*, 75:382-92 (1999).
Orriss et al., Purinergic signaling and bone remodeling. *Curr. Opin. Pharmacol.*, 10:322-30 (2010).
Utting et al., Hypoxia stimulates osteoclast formation from human peripheral blood. *Cell Biochem. Funct.*, 28:374-80 (2010).
Oshima et. al., TGF-β receeptor type II deficiency results in defects of yolk Sac hematopoiesis and vasculogenesis. *Dev. Biol.*, 179:297-302 (1996).
Padhi et. al., Anti-sclerostin antibody increases markers of bone formation in healthy postmenopausal women. *J. Bone Min. Res.*, 22: S37 (2007).
Padhi et. al., OC35—Effects of anti-sclerostin monoclonal antibody in healthy postmenopausal women. *Osteoporosis Int.*, 19: Suppl. 1: S19 (2008).
Padlan et. al., Structure of an antibody-antigen complex; Crystal structure of the HyHEL-10 Feb-lysozyme complex. *Proc. Natl. Acad. Sci. USA*, 86:5938-42 (1989).
Palokangas et. al., Endocytic pathway from the basal plasma membrane to the ruffled border membrane in bone-resorbing osteoclasts. *J. Cell Sci.*, 110: 1767-80 (1997).
Pandey et. al., Nucleotide sequence database: A gold mine for biologists. *TIBS.*, 24: 276-80 (1999).
Papapoulos et. al., Targeting sclerostin as potential treatment of osteoporosis. *Ann. Rheum. Dis.*, 70(Suppl. 1): I119-22 (2011).
Patel et. al., Current and potential future drug treatments for osteoporosis. *Ann. Rheumatic Dis.*, 55: 700-14 (1996).
Patten et. al., Applications of DNA shuffling to pharmaceuticals and vaccines. *Curr. Opin. Biotechnol.*, 8:724-33 (1997).
Pearson et. al., Effective protein sequence comparison. Chapter 15, pp. 227-258 (1996).
Pechenov et al., Injectable controlled release formulations incorporating protein crystals, *J. Control. Rel.*, 96:149-58 (2004).
Piao et. al., The proximal promotor region of the gene encoding human 17β-hydroxysteroid dehydrogenase type 1 contains GATA, AP-2, and Sp1 response elements: Analysis of promotor function in choriocarcinoma cells. *Endrocrinol.*, 138(8): 3417-25 (1997).
Piccolo et. al., The head inducer Cerberus is a multifunctional antagonist of nodal, BMP and Wnt signals. *Nature*, 397: 707-10 (1999).
Piek et. al., Specificity, diversity, and regulation of TGF-β superfamily signaling. *FASEB J.*, 13:2105-24 (1999).
Pietromonaco et. al., Protein kinase C-⊖ phosphorylation of moesin in the actin-binding sequence. *J. Biol. Chem.*, 273:7594-603 (1998).
Pignatti et. al., Tracking disease genes by reverse genetics. *J. Psychiar. Res.*, 26(4):287-98 (1992).
Pittenger et. al., Multilineage potential of adult human mesenchymal stem cells. *Science*, 284:143-7 (1999).
Pluckthun et. al., Expression of functional anitbody Fv and Fab fragments in *Escherichia coli. Meth. Enzymol.*, 178:497-515 (1989).
Pockwinse et. al., Expression of cell growth and bone specific genes at single cell resolution during development of bone tissue-like organization in primary osteoblast cultures. *J. Cell. Biol.*, 49:310-23 (1992).
Poole et. al., Sclerostin is a delayed secreted product of osteocytes that inhibit bone formation. *FESEB J.*, 19: 1842-4 (2005).
Porter, The hydrolysis of rabbit γ-globulin and antibodies with crystalline papain. *Biochem. J.*, 73:119-26 (1959).
Proprietor's Response to Opponent's Statement of Grounds of Appeal, European Patent No. 1133558, dated Apr. 15, 2010.
Proprietor's Response to Oppositions against European Patent No. 1721979, UCB Pharma S.A., dated Feb. 20, 2012.
Proprietor's Written submission in preparation for oral proceedings in Opposition against European Patent No. 1721979, Proprietor: UCB Pharma S.A., dated Feb. 25, 2013.
Quintanar-Guerrero et. al., Preparation techniques and mechanisms of formation of biodegradable nanoparticles from preformed polymers. *Drug Dev. Ind. Pharm.*, 24(12):1113-28 (1998).
Rachner et. al., Osteoporosis: Now and the future. *Lancet*, 377(9773): 1276-87 (2011).
Rawadi et. al., BMP-2 controls alkaline phosphatase expression and osteoblast mineralization by a Wnt autocrine loop. *J. Bone Min. Res.*, 18: 1842-53 (2003).
Reb, Antikorpergegen sclerostin, *Medical Tribune*, 39:12 (2007).
Reddi et. al., The *Escherichia coli* chaperonin 60 (groEL) is a potent stimulator of osteoclast formation. *J. Bone Miner. Res.*, 13(8): 1260-6 (1998).
Reddi, Interplay between bone morphogenetic proteins and cognate binding proteins in bone and cartilage development: Noggin, chordin and DAN. *Arthritis Res.*, 3(1):1-5 (2000).
Response to Proprietor's brief of Apr. 15, 2010, European Patent Opposition, EP-1133558 B1, dated Mar. 18, 2011.
Riggs, Overview of osteoporosis. *West J. Med.*, 154:63-77 (1991).
RnD Systems catalogue excerpt, cited in Opposition against European Patent No. 1721979 by Opponent: Novartis AG dated Jun. 15, 2011.
Roberts et. al., Essential functional interactions of SAFA, a *Saccharomyces cerevisiae* complex of Spt, Ada, and Gcn5 proteins, with the Snf/Swi and Srb/Mediator complexes. *Genetics*, 147: 451-65 (1997).
Robinson et. al., The sclerostin antibody project. *Hum. Antibodies*, 16: 36 (2007).
Roitt et la., Roitt's Essential Immunology, 9th Edition, pp. 90-91 (1997).
Rosenzweig et. al., Cloning and characterization of a human type II receptor for bone morphogenetic proteins. *Proc. Natl. Acad. Sci. USA*, 92:7632-7636 (1995).
Rosenzweig et. al., GenBank Sequence Database Accession No. CAA88759, Oct. 7, 2008.
Rosenzweig et. al., GenBank Sequence Database Accession No. Z48923, Oct. 7, 2008.
Rudikoff, et. al., Single amino acid substitution altering antigen-binding specificity. *Proc. Natl. Acad. Sci. USA*, 79:1979-83 (1982).
Ruppert et. al., Human bone morphogenetic protein 2 contains a heparin-binding site which modifies its biological activity. *Eur. J. Biochem.*, 237: 295-302 (1996).
Sada et. al., Adsorption equilibirum in immuno-affinity chromatography with polyclonal and monoclonal antibodies. *Biotechnol. Bioengin.*, 28 (1986). Abstract.

(56) References Cited

OTHER PUBLICATIONS

Sali et. al., Comparative protein modeling by satisfaction of spatial restraints. *J. Mol. Biol.*, 234(3):779-815 (1993).
Sambrook et. al., Synthetic oligonucleotide probes, molecular cloning—A Laboratory Manual, Ch.11:11.1-11.19 and 11.58-11.61 (1989).
Sanger et. al., DNA sequencing with chain-terminating inhibitors. *Proc. Natl. Acad. Sci. USA*, 74:5463-7 (1997).
Sastry et. al., Cloning of the immunological repertoire in *Escherichia coli* for generation of monoclonal catalytic antibodies: Construction of a heavy chain variable region-specific cDNA library. *Proc. Natl. Acad. Sci. USA*, 86:5728-32 (1989).
Scatchard et. al., The attractions of proteins for small molecules and ions. *Ann. N.Y. Acad. Sci.*, 51:660-72 (1949).
Scheufler et. al., Crystal structure of human bone morphogenetic protein-2 at 2.7 A resolution. *J. Mol. Biol.*, 287(1):101-15 (1999).
Schlebusch et. al., Production of a single-chain fragment of the murine anti-idiotypic antibody ACA125 as phage-displayed and soluble antibody by recombinant phage antibody technique. *Hybridoma*, 16:47-52 (1997).
Schlunegger et. al., Refined crystal structure of human transforming growth factor β2 at 1.95 A Resolution. *J. Mol. Biol.*, 231(2):445-458 (1993).
Schmidt et. al., Retrovirus-induced osteopetrosis in mice: Effects of viral infection on osteogenic differentiation in skeletoblast cell cultures. *Am. J. Pathol.*, 129(3): 503-10 (1987).
Schmitt et. al., Bone morphogenetic proteins: An update on basic biology and clinical relevance. *J. Orth. Res.*, 17:269-78 (1999).
Schwappacher et. al., NCBI Sequence Database Accession No. NM_001204, Aug. 16, 2009.
Scully et. al., BRCA1 is a component of the RNA polymerase II holoenzyme. *Proc. Natl. Acad. Sci. USA*, 94: 5605-10 (1997).
Second declaration of Martyn Robinson, citation in Appeal, European Patent No. 1133558, dated Apr. 15, 2010.
Serra et. al., Expression of a truncated, kinase-defective TGF-β type II receoptor in mouse skeletal tissue promotes terminal chondrocyte differentiation and osteoarthritis. *J. Cell. Biol.*, 139(2):541-52 (1997).
Shire, et al., Challegnes in the development of high concentration formulations. *J. Pharm. Sci.*, 93:1390-1402 (2004).
Sigmund, Viewpoint: Are studies in genetically altered mice out of control? *Arterioscier. Thromb. Vasc. Biol.*, 20:1425-9 (2000).
Silverman et. al., Sclerostin, *J. Osteoporosis*, 2010: 1-3 (2010).
Sippl et. al., Threading thrills and threats. *Structure*, 4(1):15-19 (1996).
Siris, Clinical Review: Paget's disease of bone. *J. Bone Miner. Res.*, 13(7): 1061-5 (1998).
Sivakumar et. al., New insights into extracellular matrix assembly and reorganization from dynamic imaging of extracellular matrix proteins in living osteoblasts. *J. Cell. Sci.*, 119(7):1350-60 (2006).
Skiple Skjerpen et. al., Binding of FGF-1 variants to protein kinase CK2 correlates with mitogenicity. *EMBO J.*, 21(15): 4058-69 (2002).
Slater et. al., Involvement of platelets in stimulating osteogenic activity. *J. Orthopaedic Res.*, 13: 655-63 (1995).
Smith et. al., Glucocorticoids inhibit development stage-specific osteoblast cell cycle. *J. Biol. Chem.*, 275:19992-20001 (2000).
Smith, TGF β inhibitors, new and unexpected requirements in vertebrate development. *TIG*, 15(1):3-5 (1999).
Sohocki et. al., A range of clinical phenotypes associated with mutations in CRX, a photoreceptor transcription-factor gene. *Am. J. Hum. Genet.*, 63: 1307-15 (1998).
Spranger, International classification of osteochondrodysplasias, *Eur. J. Pediatr.*, 151: 407-15 (1992).
Staehling-Hampton et. al., A 52-kb delection in the SOST-MEOX1 intergenic region on 17q12-q21 is associated with van Buchem disease in the Dutch population. *Am. J. Med. Gen.*, 110: 144-52 (2002).
Stanley et. al., DAN is a secreted glycopeotein related to Xenopus cerberus. *Mech. Dev.*, 77: 173-84 (1998).

Statement of Grounds of Appeal to Decision of Opposition against European Patent No. 1133558, dated Sep. 28, 2009.
Stenmark et. al., Distinct structural elements of rab5 define its functional specificity. *EMBO J.*, 13(3): 575-83 (1994).
Strachan et. al. (Eds.), Diagram from text book entitled Human Molecular Genetics, 2nd Edition (1999).
Strachan et. al. (Eds.), Human Molecular Genetics, 1st Edition, p. 420 (1996).
Strachan et. al., (Eds.), Human Molecular Genetics, 2nd Edition, Figure 15.4 (1999).
Submission in response to oral proceedings in Opposition against European Patent No. 1721979, Opponent: Eli Lilly, dated Apr. 24, 2013.
Sudo et. al., In vitro differentiation and calcification in a new clonal osteogenic cell line derived from newborn mouse calvaria. *J. Cell Biol.*, 96:191-8 (1983).
Summons to attend oral proceedings for Opposition against European Patent No. 1133558, dated Nov. 4, 2008.
Summons to attend oral proceedings in Opposition against European Patent No. 1721979, dated Nov. 12, 2012.
Sutherland et. al., Sclerostin romotes the apoptosis of human osteoblastic cells: A novel regulation of bone formation. *Bone*, 35:828-35 (2004).
Suzawa et. al., Extracellular matrix-associated bone morphogenetic proteins are essential for differentiation of murine osteoblastic cells in vitro. *Endocrinology*, 140:2125-33 (1999).
Sverdlov et. al., Perpetually mobile footprints of ancient infections in human genome. *FEBS Lett.*, 428: 1-6 (1998).
Sylatron label, cited in Opposition against European Patent No. 1721979 by Opponent: Novartis AG, dated Jun. 15, 2011.
Takakura, Drug delivery systems in gene therapy. *Nippon Rinsho*, 56(3):691-5 (1998) (Abstract Only).
Takeda et. al., GenBank Sequence Database Accession No. AAB33865, May 27, 1995.
Takeda et. al., GenBank Sequence Database Accession No. D38082, dated Dec. 27, 2006.
Takeda et. al., GenBank Sequence Database Accession No. S75359, May 27, 1995.
Takeda et. al., NCBI Sequence Database Accession No. NM_030849, Feb. 11, 2009.
Takeda, Expression of serine/threonine kinase receptors during ectopic bone formation induced by bone morphogenetic protein (BMP). *Kokubyo Gakkai Zasshi*, 61(4):512-26 (1994).
Tam et. al., TGF-β receptor expression on human keratinocytes: A 150 kDa GPI-anchored TGF-β1 binding protein forms a heteromeric complex with type I and type II receptors. *J. Cellular Biochem.*, 70:573-56 (1998).
Taylor et. al., Human immunoglobulin transgenes undergo rearrangement, somatic mutation and class switching in mice that lack endogenous IgM. *Int. Immun.*, 6:579 (1994).
The Merck Manual-Second Home Edition, Ch. 61:1-3 (2005).
Thompson et. al., Affinity maturation of a high-affinity human monoclonal antibody against the third hypervariable loop of human immunodeficiency virus: Use of phage display to improve affinity and broaden strain reactivity. *J. Mol. Biol.*, 256:7-88 (1996).
Thornton et. al., Prediction of progress at last. *Nature*, 354:105-6 (1991).
Tjaderhane et. al., A high sucrose diet decreases the mechanical strength of bones in growing rats. *J. Nutr.*, 128: 1807-10 (1998).
Tuncay et. al., Oxygen tension regulates osteoblast function. *Am. J. Orthod. Dentofac. Orthop.*, 105: 457-63 (1994).
UCB and Amgen announce positive phase 2 results of CDP7851/AMG785 in patients with post menopausal osteoporosis (PMO), dated Apr. 21, 2011—Citation in Opposition against European Patent No. 1721979.
Uitterlinden et. al., Relation of alleles of the collagen type Iα1 gene to bone density and the risk of osteoporotic fractures in postmenopausal women. *New Engl. J. Med.*, 338: 1016-21 (1998).
Valero et. al., Quaternary structure of casein kinase 2. *J. BioL Chem.*, 27(14): 8345-52 (1995).
van Bezooijen et. al., Sclerostin is an osteocyte-expressed negative regulator of bone formation, but not a classical BMP antagonist. *J. Exp. Med.*, 199: 805-14 (2004).

(56) References Cited

OTHER PUBLICATIONS van Bezooijen et. al., SOST/sclerostin, an osteocyte-derived negative regulator of bone formation, *Cytokine Growth Factor Rev.*, 16: 319-27 (2005).

van Bezooijen et. al., Wnt but not BMP signaling is involved in the inhibitory action of sclerostin on BMP-stimulated bone formation. *J. Bone. Miner. Res.*, 22:19-28 (2007).

Van Hul et. al., Van Buchem Disease (hyperostosis corticalis generalisata) maps to chromosome 17q12-a21. *Am. J. Hum. Genet.*, 2:391-9 (1998).

Vanier et. al., Recent advances in elucidating Niemann-Pick C disease. *Brain Pathol.*, 8: 163-74 (1998).

Veverka et. al., Characterization of the structural features and interactions of sclerostin. *J. Biol. Chem.*, 284(16): 10890-900 (2009).

Viter et. al., Analysis of antigenic structure of potato virus M Ukrainian strains. *Biopolimery I Kletka, Naukova Dumka, Kiev K, UK*, 16: 312-9 (2000).

Von Bubnoff et. al., Intracellular BMP signaling regulation in vertebrates: Pathway or network? *Dev. Biol.*, 239:1-14 (2001).

Wall, Transgenic livestock: Progress and prospects for the future. *Theriogenology*, 45:57-68 (1996).

Wang et. al., IFP 35 forms complexes with B-ATF, a member of the AP1 family of transcription factors. Biochem. Biophys. *Res. Commun.*, 229: 316-22 (1996).

Wang, Bone morphogenetic proteins (BMPs): Therapeutic potential in healing bony defects. *TIBTECH*, 11:379-83 (1993).

Warmington et. al., Sclerostin antagonism in adult rodents, via monoclonal antibody mediated blockade, increases bone mineral density and implicates sclerostia as a key regulator of bone mass during adulthood. *J. Bone Min. Res.*, 19:S56-7 (2004).

Warmington et. al., Sclerostin monoclonal antibody treatment of osteoporotic rats completely reverses one year of overiectomy-induced systemic bone loss, *J. Bone Min. Res.*, 20:S22 (2005).

Winkler et. al., Noggin and sclerostin bone morphogenetic protein antagonists form a mutually inhibitory complex. *J. Biol. Chem.*, 279(35): 36296-8 (2004).

Winkler et. al., Osteocyte control of bone formation via sclerostin, a novel BMP antagonist. *EMBO J.* 22: 6267-76 (2003).

Winkler et. al., Sclerostin inhibition of Wnt-3a-induced C3H10T1/2 cell differentiation is indirect and mediated by bone morphogenetic proteins. *J. Biol. Chem.* 280: 2498-502 (2005).

Winter et. al., Making antibodies by phase display technology. *Annu. Rev. Immunol.*, 12:433-55 (1994).

Wolff et. al., Monoclonal antibody homodimers: Enhanced antitumor activity in nude mice. Cancer Res., 53:2560-5 (1993).

Wollenberger et. al. (Eds.), Analytische Biochemie, Chapter 3, pp. 47-49 (2003).

Written submission—Observation by a Third Party According to Art.115 EPC, Opposition to European Patent No. 1133558, dated Nov. 25, 2008.

Written submission in response to summons to oral proceedings in Opposition against European Patent No. 1721979, Opponent: Norvartis AG, dated Feb. 25, 2013.

Written submission in response to summons to oral proceedings in Opposition against European Patent No. 1721979, Opponent: Eli Lilly Company, dated Feb. 25, 2013.

Written submission of Eli Lilly & Company to European Patent Office, Opposition to European Patent No. 1133558, dated May 29, 2007.

Written Submission of Eli Lilly & Company, Opposition to European Patent No. 1133558, dated Mar. 9, 2009.

Written submission of UCB S.A., Proprietor's Preliminary Response to the Opponent's submission of Mar. 9, 2009, Opposition to European Patent No. 1133558, dated Mar. 20, 2009.

Written submission of UCB S.A., Proprietor's Response to Opposition against European Patent No. 1133558, dated Mar. 14, 2008.

Yanagita et. al., USAG-1: A bone morphogenetic protein antagonist abundantly expressed in the kidney. *Biochem. Biophys. Res. Comm.* ,316: 490-550 (2004).

Yang et. al., CDR walking mutagenesis for the affinity maturation of a potent human Anti-HIV-1 antibody into the picomolar range. *J. Mol. Biol.*, 254:392-403 (1995).

Yang et al., Crystalline monoclonal antibodies for subcutaneous delivery. *Natl. Acad. U.S.A.*, 100(12): 6934-9 (2003).

Yates et. al., Inhibition of bone resorption by inorganic phosphate in mediated by both reduced osteoclast formation and decreased activity of mature osteoclasts. *J. Bone Miner. Res.*, 6(5): 476-8 (1990).

Yerges et. al., NCBI Sequence Database Accession No. NM_001203, Jul. 12, 2009.

Yerges et. al., NCBI Sequence Database Accession No. NP_001194, Jul. 12, 2009.

Yoshida et. al., Osteoinduction capability of recombinant human bone morphogenetic protein-2 in intramuscular and subcutaneous sites: An experimental study. *J. Cranio-Maxillofac. Surg.*, 26: 112-5 (1998).

Zambaux et. al., Influence of experimental parameters on the characteristics of poly(lactic acid) nanoparticles prepared by a double emulsion method. *J. Controlled Rel.*, 50(1-3):31-40 (1998).

Zhang et. al., Humanization of an anti-human TNF-β antibody by variable region resurfacing with the aid of molecular modeling. *Molec. Immunol.*, 42(12):1445-51 (2005).

Zimmerman et. al., The spemann organizer signal noggin binds and inactives bone morphogenetic protein 4. *Cell*, 86(4):599-606 (1996).

Zlotogora et. al., Dominance and homozygosity, *Am. J. Med. Genet.*, 68: 412-6 (1997).

zur Muhlen et. al., Solid lipid nanoparticles (SLN) for controlled drug delivery—Drug release and release mechanism. *Eur. J. Pharm. Biopharm.*, 45(2):149-55 (1998).

International Search Report and Written Opinion of the International Searching Authority, European Patent Office, PCT/US2012/030364, dated Aug. 6, 2012.

International Preliminary Report on Patentability No. PCT/US2012/030364, dated Oct. 1, 2013.

Funakoshi General Catalogue 2005-2006 for Instrumentation, 2005, pp. 478-479.

Terumo Syringe™ with needle, Feb. 28, 2007.

\* cited by examiner

FIGURE 1A

| # | Ab-30Rm + LISS Buffers + x%PEG3350 Osmolality data Ab-30Rm in A52SuPs20 Osmolality=337mOsm/Kg | | | | | | Hampton's LISS Buffers Osmolality |
|---|---|---|---|---|---|---|---|
| | LISS buffers | PEG 3350 concentration | | | | | |
| | | 4%PEG | 8%PEG | 12%PEG | 16%PEG | 20%PEG | 24%PEG | |
| 1 | 0.05 M Potassium Chloride pH2.0 | 144 | 172 | 192 | 243 | 280 | 349 | 105 |
| 2 | 0.05M Citric acid pH 3.0 | 138 | 173 | 186 | 226 | 288 | 321 | 68 |
| 3 | 0.05M Citric acid pH 3.5 | 152 | 177 | 193 | 235 | 292 | 342 | 82 |
| 4 | 0.05M Citric acid pH 4.0 | 131 | 192 | 197 | 237 | 295 | 347 | 97 |
| 5 | 0.05M Citric acid pH 4.5 | 151 | 210 | 203 | 245 | 303 | 342 | 108 |
| 6 | 0.05M Citric acid pH 5.0 | 161 | 190 | 212 | 252 | 322 | 350 | 121 |
| 7 | 0.05M Citric acid pH 5.5 | 179 | 184 | 210 | 249 | 308 | 359 | 133 |
| 8 | 0.05M MES pH 6.0 | 149 | 165 | 185 | 227 | 284 | 332 | 68 |
| 9 | 0.05 M Bis Tris pH 6.5 | 142 | 170 | 192 | 231 | 280 | 354 | 71 |
| 10 | 0.05 M Imidazole pH 7.0 | 142 | 149 | 186 | 230 | 280 | 315 | 71 |
| 11 | 0.05 M HEPES pH 7.5 | 141 | 167 | 192 | 238 | 284 | 349 | 74 |
| 12 | 0.05 M Tris pH 8.0 | 145 | 165 | 188 | 235 | 309 | 371 | 76 |
| 13 | 0.05 M Tris pH 8.5 | 138 | 170 | 190 | 223 | 286 | 354 | 65 |
| 14 | 0.05 M Glycine pH 9.0 | 139 | 197 | 185 | 225 | 285 | 348 | 55 |
| 15 | 0.05 M Glycine pH 9.5 | 146 | 193 | 207 | 233 | 322 | 323 | 67 |
| 16 | 0.05 M Glycine pH 10.0 | 124 | 187 | 194 | 240 | 280 | 351 | 78 |
| 17 | 0.05 M Sodium phosphate dibasic pH 11.0 | 156 | 196 | 209 | 253 | 303 | 363 | 132 |
| 18 | 0.05 M Sodium phosphate dibasic pH 12.0 | 148 | 143 | 211 | 264 | 311 | 408 | 154 |
| Falls within the osmolality range 250 – 350 mOsm/Kg | | | | | | | | |

Figure 2: Ab-30Rm crystal morphology in #12 0.05M Tris pH8.0 and different percentages of PEG3350
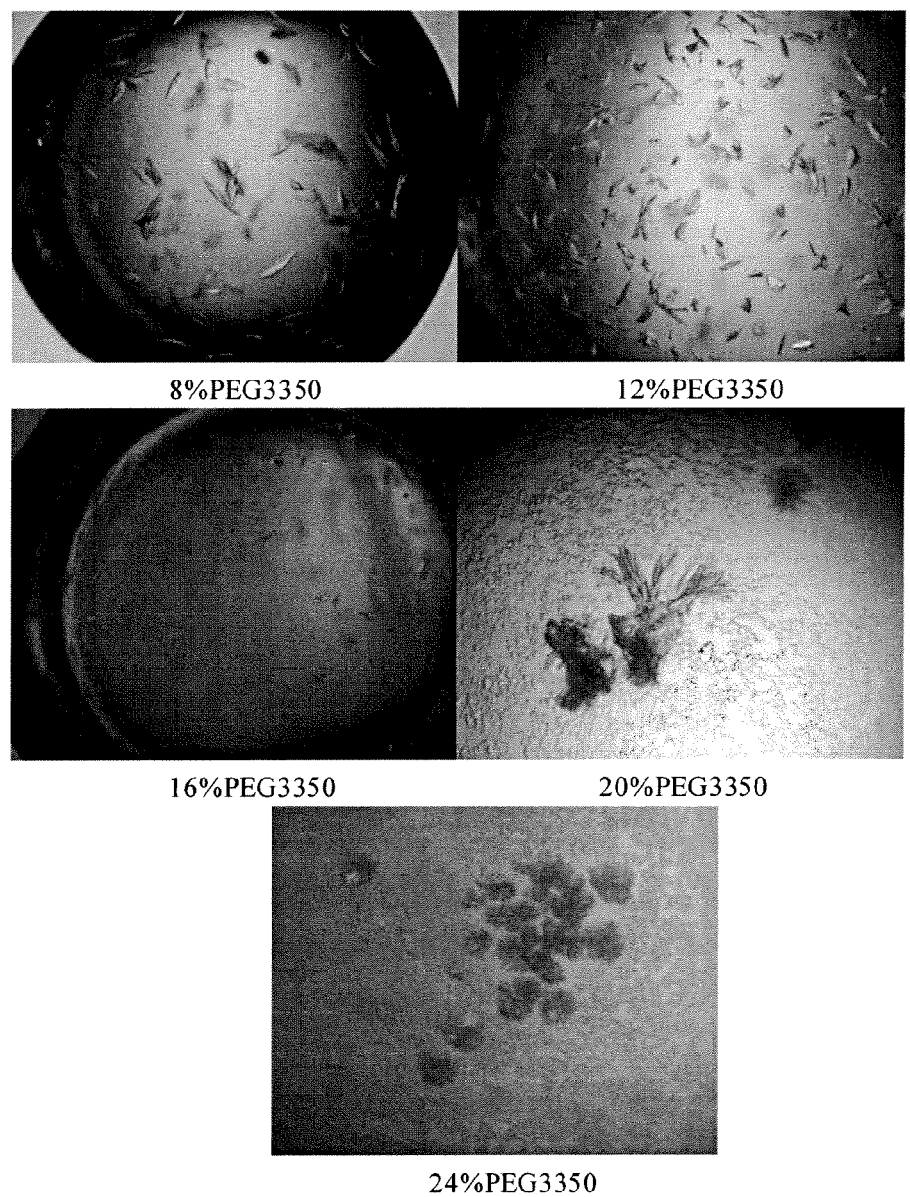

SEQUENCE LISTING

```
<160> NUMBER OF SEQ ID NOS: 35

<210> SEQ ID NO 1
<211> LENGTH: 213
<212> TYPE: PRT
<213> ORGANISM: Homo sapiens
<220> FEATURE:
<221> NAME/KEY: mat_peptide
<222> LOCATION: (25)..(213)

<400> SEQUENCE: 1

Met Gln Leu Pro Leu Ala Leu Cys Leu Val Cys Leu Leu Val His Thr
                 -20                 -15                 -10

Ala Phe Arg Val Val Glu Gly Gln Gly Trp Gln Ala Phe Lys Asn Asp
             -5                  -1   1               5

Ala Thr Glu Ile Ile Pro Glu Leu Gly Glu Tyr Pro Glu Pro Pro Pro
         10                  15                  20

Glu Leu Glu Asn Asn Lys Thr Met Asn Arg Ala Glu Asn Gly Gly Arg
 25                  30                  35                  40

Pro Pro His His Pro Phe Glu Thr Lys Asp Val Ser Glu Tyr Ser Cys
                 45                  50                  55

Arg Glu Leu His Phe Thr Arg Tyr Val Thr Asp Gly Pro Cys Arg Ser
                 60                  65                  70

Ala Lys Pro Val Thr Glu Leu Val Cys Ser Gly Gln Cys Gly Pro Ala
             75                  80                  85

Arg Leu Leu Pro Asn Ala Ile Gly Arg Gly Lys Trp Trp Arg Pro Ser
 90                  95                 100

Gly Pro Asp Phe Arg Cys Ile Pro Asp Arg Tyr Arg Ala Gln Arg Val
105                 110                 115                 120

Gln Leu Leu Cys Pro Gly Gly Glu Ala Pro Arg Ala Arg Lys Val Arg
                125                 130                 135

Leu Val Ala Ser Cys Lys Cys Lys Arg Leu Thr Arg Phe His Asn Gln
                140                 145                 150

Ser Glu Leu Lys Asp Phe Gly Thr Glu Ala Ala Arg Pro Gln Lys Gly
            155                 160                 165

Arg Lys Pro Arg Pro Arg Ala Arg Ser Ala Lys Ala Asn Gln Ala Glu
        170                 175                 180
```

Leu Glu Asn Ala Tyr
         185

<210> SEQ ID NO 2
<211> LENGTH: 321
<212> TYPE: DNA
<213> ORGANISM: Artificial Sequence
<220> FEATURE:
<223> OTHER INFORMATION: Humanized Antibody
<220> FEATURE:
<221> NAME/KEY: misc_feature
<223> OTHER INFORMATION: Ab-30 light variable

<400> SEQUENCE: 2

```
gacatccaga tgacccagtc tccatcctcc ctctccgcat ccgtaggcga ccgcgtaacc    60
ataacatgta gagcatctca agatatttcc aactatttga attggtacca acaaaaaccc   120
ggcaaagcac ctaaactcct catttactat acatcaagac tcctctccgg cgttccatca   180
cgattctcag gctccggctc cggcacagat ttcacactca ctatttcctc cctccaacca   240
gaagattttg caacctatta ctgtcaacaa ggcgatacac tcccatacac attcggcggc   300
ggcacaaaag ttgaaattaa a                                              321
```

<210> SEQ ID NO 3
<211> LENGTH: 107
<212> TYPE: PRT
<213> ORGANISM: Artificial Sequence
<220> FEATURE:
<223> OTHER INFORMATION: Humanized Antibody
<220> FEATURE:
<221> NAME/KEY: MISC_FEATURE
<223> OTHER INFORMATION: Ab-30 light variable

<400> SEQUENCE: 3

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Leu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Asp Thr Leu Pro Tyr
                85                  90                  95

Thr Phe Gly Gly Gly Thr Lys Val Glu Ile Lys
            100                 105

<210> SEQ ID NO 4
<211> LENGTH: 369
<212> TYPE: DNA
<213> ORGANISM: Artificial Sequence
<220> FEATURE:
<223> OTHER INFORMATION: Humanized Antibody
<220> FEATURE:
<221> NAME/KEY: misc_feature
<223> OTHER INFORMATION: Ab-30 heavy variable

<400> SEQUENCE: 4

```
gaggtgcagc tggtgcagag cggcgccgag gtaaaaaaac caggagcaag cgttaaagtt    60
tcttgtaaag caagcggata tacatttaca gattacaaca tgcattgggt aagacaagcg   120
```

```
ccaggacaag gattggaatg gatgggcgaa attaaccta atagtggagg agcaggctac    180
aatcaaaaat tcaaagggag agttacaatg acaacagaca caagcacttc aacagcatat    240
atggaactgc gatcacttag aagcgacgat acagctgtat actattgcgc acgacttggg    300
tatgatgata tatatgatga ctggtatttc gatgtttggg gccagggaac aacagttacc    360
gtctctagt                                                             369
```

```
<210> SEQ ID NO 5
<211> LENGTH: 123
<212> TYPE: PRT
<213> ORGANISM: Artificial Sequence
<220> FEATURE:
<223> OTHER INFORMATION: Humanized Antibody
<220> FEATURE:
<221> NAME/KEY: MISC_FEATURE
<223> OTHER INFORMATION: Ab-30 heavy variable

<400> SEQUENCE: 5

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Asn Met His Trp Val Arg Gln Ala Pro Gly Gln Gly Leu Glu Trp Met
        35                  40                  45

Gly Glu Ile Asn Pro Asn Ser Gly Gly Ala Gly Tyr Asn Gln Lys Phe
    50                  55                  60

Lys Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Leu Gly Tyr Asp Asp Ile Tyr Asp Asp Trp Tyr Phe Asp Val
            100                 105                 110

Trp Gly Gln Gly Thr Thr Val Thr Val Ser Ser
        115                 120
```

```
<210> SEQ ID NO 6
<211> LENGTH: 11
<212> TYPE: PRT
<213> ORGANISM: Artificial Sequence
<220> FEATURE:
<223> OTHER INFORMATION: Ratized Antibody
<220> FEATURE:
<221> NAME/KEY: MISC_FEATURE
<223> OTHER INFORMATION: Ab-30R and Ab-30Rm LCDR1

<400> SEQUENCE: 6

Arg Ala Ser Gln Asp Ile Ser Asn Tyr Leu Asn
1               5                   10
```

```
<210> SEQ ID NO 7
<211> LENGTH: 7
<212> TYPE: PRT
<213> ORGANISM: Artificial Sequence
<220> FEATURE:
<223> OTHER INFORMATION: Ratized Antibody
<220> FEATURE:
<221> NAME/KEY: MISC_FEATURE
<223> OTHER INFORMATION: Ab-30R and Ab-30Rm LCDR2

<400> SEQUENCE: 7

Tyr Thr Ser Arg Leu Leu Ser
1               5
```

<210> SEQ ID NO 8
<211> LENGTH: 9
<212> TYPE: PRT
<213> ORGANISM: Artificial Sequence
<220> FEATURE:
<223> OTHER INFORMATION: Ratized Antibody
<220> FEATURE:
<221> NAME/KEY: MISC_FEATURE
<223> OTHER INFORMATION: Ab-30R and Ab-30Rm LCDR3

<400> SEQUENCE: 8

Gln Gln Gly Asp Thr Leu Pro Tyr Thr
1               5

<210> SEQ ID NO 9
<211> LENGTH: 5
<212> TYPE: PRT
<213> ORGANISM: Artificial Sequence
<220> FEATURE:
<223> OTHER INFORMATION: Ratized Antibody
<220> FEATURE:
<221> NAME/KEY: MISC_FEATURE
<223> OTHER INFORMATION: Ab-30R and Ab-30Rm HCDR1

<400> SEQUENCE: 9

Asp Tyr Asn Met His
1               5

<210> SEQ ID NO 10
<211> LENGTH: 17
<212> TYPE: PRT
<213> ORGANISM: Artificial Sequence
<220> FEATURE:
<223> OTHER INFORMATION: Ratized Antibody
<220> FEATURE:
<221> NAME/KEY: MISC_FEATURE
<223> OTHER INFORMATION: Ab-30R and Ab-30Rm HCDR2

<400> SEQUENCE: 10

Glu Ile Asn Pro Asn Ser Gly Gly Ala Gly Tyr Asn Gln Lys Phe Lys
1               5                   10                  15

Gly

<210> SEQ ID NO 11
<211> LENGTH: 14
<212> TYPE: PRT
<213> ORGANISM: Artificial Sequence
<220> FEATURE:
<223> OTHER INFORMATION: Ratized Antibody
<220> FEATURE:
<221> NAME/KEY: MISC_FEATURE
<223> OTHER INFORMATION: Ab-30R and Ab-30Rm HCDR3

<400> SEQUENCE: 11

Leu Gly Tyr Asp Asp Ile Tyr Asp Asp Trp Tyr Phe Asp Val
1               5                   10

<210> SEQ ID NO 12
<211> LENGTH: 642
<212> TYPE: DNA
<213> ORGANISM: Artificial Sequence
<220> FEATURE:
<223> OTHER INFORMATION: Humanized Antibody
<220> FEATURE:
<221> NAME/KEY: misc_feature
<223> OTHER INFORMATION: Ab-30 light chain

<400> SEQUENCE: 12

```
gacatccaga tgacccagtc tccatcctcc ctctccgcat ccgtaggcga ccgcgtaacc    60
ataacatgta gagcatctca agatatttcc aactatttga attggtacca acaaaaaccc   120
ggcaaagcac ctaaactcct catttactat acatcaagac tcctctccgg cgttccatca   180
cgattctcag gctccggctc cggcacagat ttcacactca ctatttcctc cctccaacca   240
gaagattttg caacctatta ctgtcaacaa ggcgatacac tcccatacac attcggcggc   300
ggcacaaaag ttgaaattaa acgtacggtg gctgcaccat ctgtcttcat cttcccgcca   360
tctgatgagc agttgaaatc tggaactgcc tctgttgtgt gcctgctgaa taacttctat   420
cccagagagg ccaaagtaca gtggaaggtg gataacgccc tccaatcggg taactcccag   480
gagagtgtca cagagcagga cagcaaggac agcacctaca gcctcagcag caccctgacg   540
ctgagcaaag cagactacga gaaacacaaa gtctacgcct gcgaagtcac ccatcagggc   600
ctgagctcgc ccgtcacaaa gagcttcaac aggggagagt gt                     642
```

```
<210> SEQ ID NO 13
<211> LENGTH: 214
<212> TYPE: PRT
<213> ORGANISM: Artificial Sequence
<220> FEATURE:
<223> OTHER INFORMATION: Humanized Antibody
<220> FEATURE:
<221> NAME/KEY: MISC_FEATURE
<223> OTHER INFORMATION: Ab-30 light chain

<400> SEQUENCE: 13
```

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Leu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Asp Thr Leu Pro Tyr
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

-continued

<210> SEQ ID NO 14
<211> LENGTH: 1347
<212> TYPE: DNA
<213> ORGANISM: Artificial Sequence
<220> FEATURE:
<223> OTHER INFORMATION: Humanized Antibody
<220> FEATURE:
<221> NAME/KEY: misc_feature
<223> OTHER INFORMATION: Ab-30 heavy chain

<400> SEQUENCE: 14

```
gaggtgcagc tggtgcagag cggcgccgag gtaaaaaaac caggagcaag cgttaaagtt      60
tcttgtaaag caagcggata tacatttaca gattacaaca tgcattgggt aagacaagcg     120
ccaggacaag gattggaatg gatgggcgaa attaaccctA atagtggagg agcaggctac     180
aatcaaaaat tcaaagggag agttacaatg acaacagaca caagcacttc aacagcatat     240
atggaactgc gatcacttag aagcgacgat acagctgtat actattgcgc acgacttggg     300
tatgatgata tatatgatga ctggtatttc gatgtttggg gccagggaac aacagttacc     360
gtctctagtg cctccaccaa gggcccatcg gtcttccccc tggcgccctg ctccaggagc     420
acctccgaga gcacagcggc cctgggctgc ctggtcaagg actacttccc cgaaccggtg     480
acggtgtcgt ggaactcagg cgctctgacc agcggcgtgc acaccttccc agctgtccta     540
cagtcctcag gactctactc cctcagcagc gtggtgaccg tgccctccag caacttcggc     600
acccagacct acacctgcaa cgtagatcac aagcccagca caccaaggt ggacaagaca     660
gttgagcgca aatgttgtgt cgagtgccca ccgtgcccag caccacctgt ggcaggaccg     720
tcagtcttcc tcttcccccc aaaacccaag gacaccctca tgatctcccg gacccctgag     780
gtcacgtgcg tggtggtgga cgtgagccac gaagaccccg aggtccagtt caactggtac     840
gtggacggcg tggaggtgca taatgccaag acaaagccac gggaggagca gttcaacagc     900
acgttccgtg tggtcagcgt cctcaccgtt gtgcaccagg actggctgaa cggcaaggag     960
tacaagtgca aggtctccaa caaaggcctc ccagccccca tcgagaaaac catctccaaa    1020
accaaagggc agccccgaga accacaggtg tacaccctgc ccccatcccg ggaggagatg    1080
accaagaacc aggtcagcct gacctgcctg gtcaaaggct tctacccag cgacatcgcc    1140
gtggagtggg agagcaatgg gcagccggag aacaactaca agaccacacc tcccatgctg    1200
gactccgacg gctccttctt cctctacagc aagctcaccg tggacaagag caggtggcag    1260
caggggaacg tcttctcatg ctccgtgatg catgaggctc tgcacaacca ctacacgcag    1320
aagagcctct ccctgtctcc gggtaaa                                        1347
```

<210> SEQ ID NO 15
<211> LENGTH: 449
<212> TYPE: PRT
<213> ORGANISM: Artificial Sequence
<220> FEATURE:
<223> OTHER INFORMATION: Humanized Antibody
<220> FEATURE:
<221> NAME/KEY: MISC_FEATURE
<223> OTHER INFORMATION: Ab-30 heavy chain

<400> SEQUENCE: 15

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Asn Met His Trp Val Arg Gln Ala Pro Gly Gln Gly Leu Glu Trp Met
        35                  40                  45

```
Gly Glu Ile Asn Pro Asn Ser Gly Gly Ala Gly Tyr Asn Gln Lys Phe
    50                  55                  60

Lys Gly Arg Val Thr Met Thr Thr Asp Thr Ser Thr Ser Thr Ala Tyr
 65              70                  75                  80

Met Glu Leu Arg Ser Leu Arg Ser Asp Asp Thr Ala Val Tyr Tyr Cys
                 85                  90                  95

Ala Arg Leu Gly Tyr Asp Asp Ile Tyr Asp Asp Trp Tyr Phe Asp Val
            100                 105                 110

Trp Gly Gln Gly Thr Thr Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Asn Phe Gly Thr Gln Thr Tyr Thr Cys Asn Val
        195                 200                 205

Asp His Lys Pro Ser Asn Thr Lys Val Asp Lys Thr Val Glu Arg Lys
    210                 215                 220

Cys Cys Val Glu Cys Pro Pro Cys Pro Ala Pro Pro Val Ala Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Phe Arg Val
    290                 295                 300

Val Ser Val Leu Thr Val Val His Gln Asp Trp Leu Asn Gly Lys Glu
305                 310                 315                 320

Tyr Lys Cys Lys Val Ser Asn Lys Gly Leu Pro Ala Pro Ile Glu Lys
                325                 330                 335

Thr Ile Ser Lys Thr Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Met Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys
```

<210> SEQ ID NO 16
<211> LENGTH: 107
<212> TYPE: PRT
<213> ORGANISM: Rattus norvegicus
<220> FEATURE:
<221> NAME/KEY: MISC_FEATURE
<223> OTHER INFORMATION: Ab-30R light variable

<400> SEQUENCE: 16

```
Asp Ile Gln Met Thr Gln Ser Pro Ser Ser Leu Ser Ala Ser Leu Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Asp Gly Thr Val Lys Arg Leu Ile
        35                  40                  45

Tyr Tyr Thr Ser Arg Leu Leu Ser Gly Val Pro Ser Arg Phe Ser Gly
50                  55                  60

Ser Gly Ser Gly Thr Asp Tyr Ser Leu Ser Ile Ser Ser Leu Glu Ser
65                  70                  75                  80

Glu Asp Phe Ala Met Tyr Tyr Cys Gln Gln Gly Asp Thr Leu Pro Tyr
                85                  90                  95

Thr Phe Gly Gly Gly Thr Lys Leu Glu Leu Lys
            100                 105
```

<210> SEQ ID NO 17
<211> LENGTH: 123
<212> TYPE: PRT
<213> ORGANISM: Artificial Sequence
<220> FEATURE:
<223> OTHER INFORMATION: Ratized Antibody
<220> FEATURE:
<221> NAME/KEY: MISC_FEATURE
<223> OTHER INFORMATION: Ab-30R and Ab-30Rm heavy variable

<400> SEQUENCE: 17

```
Glu Val Gln Leu Gln Gln Ser Gly Pro Glu Leu Gln Arg Pro Gly Ala
1               5                   10                  15

Ser Val Lys Leu Ser Cys Lys Ala Ser Gly Tyr Thr Phe Thr Asp Tyr
            20                  25                  30

Asn Met His Trp Val Lys Gln Ser His Gly Lys Ser Leu Glu Trp Ile
        35                  40                  45

Gly Glu Ile Asn Pro Asn Ser Gly Ala Gly Tyr Asn Gln Lys Phe
50                  55                  60

Lys Gly Lys Ala Thr Leu Thr Ala Asp Lys Ser Ser Asn Thr Ala Tyr
65                  70                  75                  80

Met Glu Leu Ser Arg Leu Thr Ser Glu Asp Ser Ala Val Tyr Tyr Cys
                85                  90                  95

Ala Arg Leu Gly Tyr Asp Asp Ile Tyr Asp Asp Trp Tyr Phe Asp Val
            100                 105                 110

Trp Gly Gln Gly Thr Thr Val Thr Val Ser Ser
        115                 120
```

<210> SEQ ID NO 18
<211> LENGTH: 123
<212> TYPE: PRT
<213> ORGANISM: Rattus norvegicus
<220> FEATURE:
<221> NAME/KEY: MISC_FEATURE
<223> OTHER INFORMATION: Ab-30R light chain

<400> SEQUENCE: 18

```
Glu Val Gln Leu Gln Gln Ser Gly Pro Glu Leu Gln Arg Pro Gly Ala
1               5                   10                  15

Ser Val Lys Leu Ser Cys Lys Ala Ser Gly Tyr Thr Phe Thr Asp Tyr
            20                  25                  30

Asn Met His Trp Val Lys Gln Ser His Gly Lys Ser Leu Glu Trp Ile
        35                  40                  45

Gly Glu Ile Asn Pro Asn Ser Gly Gly Ala Gly Tyr Asn Gln Lys Phe
    50                  55                  60

Lys Gly Lys Ala Thr Leu Thr Ala Asp Lys Ser Ser Asn Thr Ala Tyr
65                  70                  75                  80

Met Glu Leu Ser Arg Leu Thr Ser Glu Asp Ser Ala Val Tyr Tyr Cys
                85                  90                  95

Ala Arg Leu Gly Tyr Asp Asp Ile Tyr Asp Asp Trp Tyr Phe Asp Val
            100                 105                 110

Trp Gly Gln Gly Thr Thr Val Thr Val Ser Ser
            115                 120
```

<210> SEQ ID NO 19
<211> LENGTH: 445
<212> TYPE: PRT
<213> ORGANISM: Artificial Sequence
<220> FEATURE:
<223> OTHER INFORMATION: Ratized Antibody
<220> FEATURE:
<221> NAME/KEY: MISC_FEATURE
<223> OTHER INFORMATION: Ab-30R and Ab-30Rm heavy chain

<400> SEQUENCE: 19

```
Glu Val Gln Leu Gln Gln Ser Gly Pro Glu Leu Gln Arg Pro Gly Ala
1               5                   10                  15

Ser Val Lys Leu Ser Cys Lys Ala Ser Gly Tyr Thr Phe Thr Asp Tyr
            20                  25                  30

Asn Met His Trp Val Lys Gln Ser His Gly Lys Ser Leu Glu Trp Ile
        35                  40                  45

Gly Glu Ile Asn Pro Asn Ser Gly Gly Ala Gly Tyr Asn Gln Lys Phe
    50                  55                  60

Lys Gly Lys Ala Thr Leu Thr Ala Asp Lys Ser Ser Asn Thr Ala Tyr
65                  70                  75                  80

Met Glu Leu Ser Arg Leu Thr Ser Glu Asp Ser Ala Val Tyr Tyr Cys
                85                  90                  95

Ala Arg Leu Gly Tyr Asp Asp Ile Tyr Asp Asp Trp Tyr Phe Asp Val
            100                 105                 110

Trp Gly Gln Gly Thr Thr Val Thr Val Ser Ser Ala Glu Thr Thr Ala
            115                 120                 125

Pro Ser Val Tyr Pro Leu Ala Pro Gly Thr Ala Leu Lys Ser Asn Ser
    130                 135                 140

Met Val Thr Leu Gly Cys Leu Val Lys Gly Tyr Phe Pro Glu Pro Val
145                 150                 155                 160

Thr Val Thr Trp Asn Ser Gly Ala Leu Ser Ser Gly Val His Thr Phe
                165                 170                 175

Pro Ala Val Leu Gln Ser Gly Leu Tyr Thr Leu Thr Ser Ser Val Thr
            180                 185                 190

Val Pro Ser Ser Thr Trp Ser Ser Gln Ala Val Thr Cys Asn Val Ala
        195                 200                 205

His Pro Ala Ser Ser Thr Lys Val Asp Lys Lys Ile Val Pro Arg Glu
    210                 215                 220
```

```
Cys Asn Pro Cys Gly Cys Thr Gly Ser Glu Val Ser Val Phe Ile
225                 230                 235                 240

Phe Pro Pro Lys Thr Lys Asp Val Leu Thr Ile Thr Leu Thr Pro Lys
            245                 250                 255

Val Thr Cys Val Val Val Asp Ile Ser Gln Asn Asp Pro Glu Val Arg
            260                 265                 270

Phe Ser Trp Phe Ile Asp Asp Val Glu Val His Thr Ala Gln Thr His
            275                 280                 285

Ala Pro Glu Lys Gln Ser Asn Ser Thr Leu Arg Ser Val Ser Glu Leu
            290                 295                 300

Pro Ile Val His Arg Asp Trp Leu Asn Gly Lys Thr Phe Lys Cys Lys
305                 310                 315                 320

Val Asn Ser Gly Ala Phe Pro Ala Pro Ile Glu Lys Ser Ile Ser Lys
                325                 330                 335

Pro Glu Gly Thr Pro Arg Gly Pro Gln Val Tyr Thr Met Ala Pro Pro
                340                 345                 350

Lys Glu Glu Met Thr Gln Ser Gln Val Ser Ile Thr Cys Met Val Lys
                355                 360                 365

Gly Phe Tyr Pro Pro Asp Ile Tyr Thr Glu Trp Lys Met Asn Gly Gln
370                 375                 380

Pro Gln Glu Asn Tyr Lys Asn Thr Pro Pro Thr Met Asp Thr Asp Gly
385                 390                 395                 400

Ser Tyr Phe Leu Tyr Ser Lys Leu Asn Val Lys Lys Glu Thr Trp Gln
                405                 410                 415

Gln Gly Asn Thr Phe Thr Cys Ser Val Leu His Glu Gly Leu His Asn
                420                 425                 430

His His Thr Glu Lys Ser Leu Ser His Ser Pro Gly Lys
                435                 440                 445

<210> SEQ ID NO 20
<211> LENGTH: 106
<212> TYPE: PRT
<213> ORGANISM: Artificial Sequence
<220> FEATURE:
<223> OTHER INFORMATION: Ratized Antibody
<220> FEATURE:
<221> NAME/KEY: MISC_FEATURE
<223> OTHER INFORMATION: Ab-30Rm light variable

<400> SEQUENCE: 20

Asp Ile Gln Met Thr Gln Ser Pro Ser Ser Leu Ser Ala Ser Leu Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Asp Gly Thr Val Lys Arg Leu Ile
        35                  40                  45

Tyr Thr Ser Arg Leu Leu Ser Gly Val Pro Ser Arg Phe Ser Gly Ser
    50                  55                  60

Gly Ser Gly Thr Asp Tyr Ser Leu Ser Ile Ser Ser Leu Glu Ser Glu
65                  70                  75                  80

Asp Phe Ala Met Tyr Tyr Cys Gln Gln Gly Asp Thr Leu Pro Tyr Thr
                85                  90                  95

Phe Gly Gly Gly Thr Lys Leu Glu Leu Lys
                100                 105

<210> SEQ ID NO 21
<211> LENGTH: 213
```

```
<212> TYPE: PRT
<213> ORGANISM: Artificial Sequence
<220> FEATURE:
<223> OTHER INFORMATION: Ratized Antibody
<220> FEATURE:
<221> NAME/KEY: MISC_FEATURE
<223> OTHER INFORMATION: Ab-30Rm light chain

<400> SEQUENCE: 21

Asp Ile Gln Met Thr Gln Ser Pro Ser Ser Leu Ser Ala Ser Leu Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Asp Gly Thr Val Lys Arg Leu Ile
        35                  40                  45

Tyr Thr Ser Arg Leu Leu Ser Gly Val Pro Ser Arg Phe Ser Gly Ser
    50                  55                  60

Gly Ser Gly Thr Asp Tyr Ser Leu Ser Ile Ser Ser Leu Glu Ser Glu
65                  70                  75                  80

Asp Phe Ala Met Tyr Tyr Cys Gln Gln Gly Asp Thr Leu Pro Tyr Thr
                85                  90                  95

Phe Gly Gly Gly Thr Lys Leu Glu Leu Lys Arg Ala Asp Ala Ala Pro
            100                 105                 110

Thr Val Ser Ile Phe Pro Pro Ser Thr Glu Gln Leu Ala Thr Gly Gly
        115                 120                 125

Ala Ser Val Val Cys Leu Met Asn Asn Phe Tyr Pro Arg Asp Ile Ser
    130                 135                 140

Val Lys Trp Lys Ile Asp Gly Thr Glu Arg Arg Asp Gly Val Leu Asp
145                 150                 155                 160

Ser Val Thr Asp Gln Asp Ser Lys Asp Ser Thr Tyr Ser Met Ser Ser
                165                 170                 175

Thr Leu Ser Leu Thr Lys Ala Asp Tyr Glu Ser His Asn Leu Tyr Thr
            180                 185                 190

Cys Glu Val Val His Lys Thr Ser Ser Ser Pro Val Val Lys Ser Phe
        195                 200                 205

Asn Arg Asn Glu Cys
    210

<210> SEQ ID NO 22
<211> LENGTH: 318
<212> TYPE: DNA
<213> ORGANISM: Artificial Sequence
<220> FEATURE:
<223> OTHER INFORMATION: Humanized Antibody
<220> FEATURE:
<221> NAME/KEY: misc_feature
<223> OTHER INFORMATION: Ab-31 light variable

<400> SEQUENCE: 22
gacatccaga tgacccagtc tccatcctcc ctgtctgcat ctgtaggtga ccgtgtcacc     60
atcacttgcc gcgcaagtca ggatattagc agctatttaa attggtatca gcagaaacca    120
gggaaagccc ctaagctcct gatctattct acttcccgtt tgaatagtgg ggtcccatca    180
cgcttcagtg gcagtggctc tgggacagat tcactctca ccatcagcag tctgcaacct     240
gaagattttg caacttacta ctgtcaacag gatattaaac ccctacgtt cggtcaaggc     300 accaaggtgg agatcaaa                                                  318

<210> SEQ ID NO 23
```

```
<211> LENGTH: 106
<212> TYPE: PRT
<213> ORGANISM: Artificial Sequence
<220> FEATURE:
<223> OTHER INFORMATION: Humanized Antibody
<220> FEATURE:
<221> NAME/KEY: MISC_FEATURE
<223> OTHER INFORMATION: Ab-31 light variable

<400> SEQUENCE: 23

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Ser Tyr
            20                  25                  30

Leu Asn Trp Tyr Gln Gln Lys Pro Gly Lys Ala Pro Lys Leu Leu Ile
        35                  40                  45

Tyr Ser Thr Ser Arg Leu Asn Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Asp Ile Lys His Pro Thr
                85                  90                  95

Phe Gly Gln Gly Thr Lys Val Glu Ile Lys
            100                 105

<210> SEQ ID NO 24
<211> LENGTH: 360
<212> TYPE: DNA
<213> ORGANISM: Artificial Sequence
<220> FEATURE:
<223> OTHER INFORMATION: Humanized Antibody
<220> FEATURE:
<221> NAME/KEY: misc_feature
<223> OTHER INFORMATION: Ab-31 heavy variable

<400> SEQUENCE: 24
gaggtgcagc tggtgcagtc tggggctgag gtgaagaagc ctgggtcctc ggtgaaggtc      60
tcctgcaagg cttctggttt taccttcacc gactatatta tgcactgggt gcgtcaggcc     120
cctggtcaag ggcttgagtg gatgggctat atcaacccct ataatgatga caccgaatac     180
aacgagaagt tcaagggccg tgtcacgatt accgcggaca atccacgag cacagcctac      240 atggagctga gcagcctgcg ctctgaggac acggccgtgt attactgtgc gcgttcgatt     300
tattactacg atgccccgtt tgcttactgg ggccaaggga ctctggtcac cgtctctagt     360

<210> SEQ ID NO 25
<211> LENGTH: 120
<212> TYPE: PRT
<213> ORGANISM: Artificial Sequence
<220> FEATURE:
<223> OTHER INFORMATION: Humanized Antibody
<220> FEATURE:
<221> NAME/KEY: MISC_FEATURE
<223> OTHER INFORMATION: Ab-31 heavy variable

<400> SEQUENCE: 25

Glu Val Gln Leu Val Gln Ser Gly Ala Glu Val Lys Lys Pro Gly Ser
1               5                   10                  15

Ser Val Lys Val Ser Cys Lys Ala Ser Gly Phe Thr Phe Thr Asp Tyr
            20                  25                  30

Ile Met His Trp Val Arg Gln Ala Pro Gly Gln Gly Leu Glu Trp Met
        35                  40                  45
```

```
Gly Tyr Ile Asn Pro Tyr Asn Asp Asp Thr Glu Tyr Asn Glu Lys Phe
    50                  55                  60

Lys Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Ser Ile Tyr Tyr Tyr Asp Ala Pro Phe Ala Tyr Trp Gly Gln
                100                 105                 110

Gly Thr Leu Val Thr Val Ser Ser
        115                 120

<210> SEQ ID NO 26
<211> LENGTH: 11
<212> TYPE: PRT
<213> ORGANISM: Artificial Sequence
<220> FEATURE:
<223> OTHER INFORMATION: Humanized Antibody
<220> FEATURE:
<221> NAME/KEY: MISC_FEATURE
<223> OTHER INFORMATION: Ab-31 LCDR1

<400> SEQUENCE: 26

Arg Ala Ser Gln Asp Ile Ser Ser Tyr Leu Asn
 1               5                  10

<210> SEQ ID NO 27
<211> LENGTH: 7
<212> TYPE: PRT
<213> ORGANISM: Artificial Sequence
<220> FEATURE:
<223> OTHER INFORMATION: Humanized Antibody
<220> FEATURE:
<221> NAME/KEY: MISC_FEATURE
<223> OTHER INFORMATION: Ab-31 LCDR2

<400> SEQUENCE: 27

Ser Thr Ser Arg Leu Asn Ser
 1               5

<210> SEQ ID NO 28
<211> LENGTH: 8
<212> TYPE: PRT
<213> ORGANISM: Artificial Sequence
<220> FEATURE:
<223> OTHER INFORMATION: Humanized Antibody
<220> FEATURE:
<221> NAME/KEY: MISC_FEATURE
<223> OTHER INFORMATION: Ab-31 LCDR3

<400> SEQUENCE: 28

Gln Gln Asp Ile Lys His Pro Thr
 1               5

<210> SEQ ID NO 29
<211> LENGTH: 5
<212> TYPE: PRT
<213> ORGANISM: Artificial Sequence
<220> FEATURE:
<223> OTHER INFORMATION: Humanized Antibody
<220> FEATURE:
<221> NAME/KEY: MISC_FEATURE
<223> OTHER INFORMATION: Ab-31 HCDR1

<400> SEQUENCE: 29

Asp Tyr Ile Met His
 1               5
```

<210> SEQ ID NO 30
<211> LENGTH: 17
<212> TYPE: PRT
<213> ORGANISM: Artificial Sequence
<220> FEATURE:
<223> OTHER INFORMATION: Humanized Antibody
<220> FEATURE:
<221> NAME/KEY: MISC_FEATURE
<223> OTHER INFORMATION: Ab-31 HCDR2

<400> SEQUENCE: 30

Tyr Ile Asn Pro Tyr Asn Asp Asp Thr Glu Tyr Asn Glu Lys Phe Lys
1               5                   10                  15
Gly

<210> SEQ ID NO 31
<211> LENGTH: 11
<212> TYPE: PRT
<213> ORGANISM: Artificial Sequence
<220> FEATURE:
<223> OTHER INFORMATION: Humanized Antibody
<220> FEATURE:
<221> NAME/KEY: MISC_FEATURE
<223> OTHER INFORMATION: Ab-31 HCDR3

<400> SEQUENCE: 31

Ser Ile Tyr Tyr Tyr Asp Ala Pro Phe Ala Tyr
1               5                   10

<210> SEQ ID NO 32
<211> LENGTH: 639
<212> TYPE: DNA
<213> ORGANISM: Artificial Sequence
<220> FEATURE:
<223> OTHER INFORMATION: Humanized Antibody
<220> FEATURE:
<221> NAME/KEY: misc_feature
<223> OTHER INFORMATION: Ab-31 light chain

<400> SEQUENCE: 32

```
gacatccaga tgacccagtc tccatcctcc ctgtctgcat ctgtaggtga ccgtgtcacc      60
atcacttgcc gcgcaagtca ggatattagc agctatttaa attggtatca gcagaaacca     120
gggaaagccc ctaagctcct gatctattct acttcccgtt tgaatagtgg ggtcccatca     180
cgcttcagtg gcagtggctc tgggacagat ttcactctca ccatcagcag tctgcaacct     240
gaagattttg caacttacta ctgtcaacag gatattaaac ccctacgttc ggtcaaggc      300 accaaggtgg agatcaaacg tacggtggct gcaccatctg tcttcatctt cccgccatct     360
gatgagcagt tgaaatctgg aactgcctct gttgtgtgcc tgctgaataa cttctatccc     420
agagaggcca aagtacagtg gaaggtggat aacgccctcc aatcgggtaa ctcccaggag     480
agtgtcacag agcaggacag caaggacagc acctacagcc tcagcagcac cctgacgctg     540
agcaaagcag actacgagaa acacaaagtc tacgcctgcg aagtcaccca tcagggcctg     600
agctcgcccg tcacaaagag cttcaacagg ggagagtgt                            639
```

<210> SEQ ID NO 33
<211> LENGTH: 213
<212> TYPE: PRT
<213> ORGANISM: Artificial Sequence
<220> FEATURE:
<223> OTHER INFORMATION: Humanized Antibody
<220> FEATURE:
<221> NAME/KEY: MISC_FEATURE
<223> OTHER INFORMATION: Ab-31 light chain

<400> SEQUENCE: 33

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Ser Tyr
            20                  25                  30

Leu Asn Trp Tyr Gln Gln Lys Pro Gly Lys Ala Pro Lys Leu Leu Ile
        35                  40                  45

Tyr Ser Thr Ser Arg Leu Asn Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Asp Ile Lys His Pro Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 34
<211> LENGTH: 1338
<212> TYPE: DNA
<213> ORGANISM: Artificial Sequence
<220> FEATURE:
<223> OTHER INFORMATION: Humanized Antibody
<220> FEATURE:
<221> NAME/KEY: misc_feature
<223> OTHER INFORMATION: Ab-31 heavy chain

<400> SEQUENCE: 34
gaggtgcagc tggtgcagtc tggggctgag gtgaagaagc ctgggtcctc ggtgaaggtc      60
tcctgcaagg cttctggttt taccttcacc gactatatta tgcactgggt gcgtcaggcc     120
cctggtcaag gcttgagtg gatgggctat atcaacccctt ataatgatga caccgaatac     180
aacgagaagt tcaagggccg tgtcacgatt accgcggaca atccacgag cacagcctac     240 atggagctga gcagcctgcg ctctgaggac acggccgtgt attactgtgc gcgttcgatt     300
tattactacg atgccccgtt tgcttactgg ggccaaggga ctctggtcac cgtctctagt     360
gcctccacca agggcccatc ggtcttcccc ctggcgccct gctccaggag cacctccgag     420
agcacagcgg ccctgggctg cctggtcaag gactacttcc ccgaaccggt gacggtgtcg     480
tggaactcag gcgctctgac cagcggcgtg cacaccttcc cagctgtcct acagtcctca     540
ggactctact ccctcagcag cgtggtgacc gtgccctcca gcaacttcgg cacccagacc     600
tacacctgca acgtagatca caagcccagc aacaccaagg tggacaagac agttgagcgc     660

-continued

```
aaatgttgtg tcgagtgccc accgtgccca gcaccacctg tggcaggacc gtcagtcttc    720
ctcttccccc caaaacccaa ggacaccctc atgatctccc ggacccctga ggtcacgtgc    780
gtggtggtgg acgtgagcca cgaagacccc gaggtccagt tcaactggta cgtggacggc    840
gtggaggtgc ataatgccaa gacaaagcca cgggaggagc agttcaacag cacgttccgt    900
gtggtcagcg tcctcaccgt tgtgcaccag gactggctga acggcaagga gtacaagtgc    960
aaggtctcca acaaaggcct cccagccccc atcgagaaaa ccatctccaa aaccaaaggg   1020
cagccccgag aaccacaggt gtacaccctg cccccatccc gggaggagat gaccaagaac   1080
caggtcagcc tgacctgcct ggtcaaaggc ttctacccca gcgacatcgc cgtggagtgg   1140
gagagcaatg ggcagccgga gaacaactac aagaccacac ctcccatgct ggactccgac   1200
ggctccttct cctctacag caagctcacc gtggacaaga gcaggtggca gcaggggaac   1260
gtcttctcat gctccgtgat gcatgaggct ctgcacaacc actacacgca gaagagcctc   1320
tccctgtctc cgggtaaa                                                 1338
```

<210> SEQ ID NO 35
<211> LENGTH: 446
<212> TYPE: PRT
<213> ORGANISM: Artificial Sequence
<220> FEATURE:
<223> OTHER INFORMATION: Humanized Antibody
<220> FEATURE:
<221> NAME/KEY: MISC_FEATURE
<223> OTHER INFORMATION: Ab-31 heavy chain

<400> SEQUENCE: 35

```
Glu Val Gln Leu Val Gln Ser Gly Ala Glu Val Lys Lys Pro Gly Ser
1               5                   10                  15

Ser Val Lys Val Ser Cys Lys Ala Ser Gly Phe Thr Phe Thr Asp Tyr
            20                  25                  30

Ile Met His Trp Val Arg Gln Ala Pro Gly Gln Gly Leu Glu Trp Met
        35                  40                  45

Gly Tyr Ile Asn Pro Tyr Asn Asp Asp Thr Glu Tyr Asn Glu Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Ile Tyr Tyr Tyr Asp Ala Pro Phe Ala Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Asn Phe Gly Thr Gln Thr Tyr Thr Cys Asn Val Asp His Lys
        195                 200                 205

Pro Ser Asn Thr Lys Val Asp Lys Thr Val Glu Arg Lys Cys Cys Val
    210                 215                 220
```

```
Glu Cys Pro Pro Cys Pro Ala Pro Pro Val Ala Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Gln Phe Asn Trp Tyr Val Asp Gly Val Glu Val His Asn Ala Lys Thr
            275                 280                 285

Lys Pro Arg Glu Glu Gln Phe Asn Ser Thr Phe Arg Val Val Ser Val
    290                 295                 300

Leu Thr Val Val His Gln Asp Trp Leu Asn Gly Lys Glu Tyr Lys Cys
305                 310                 315                 320

Lys Val Ser Asn Lys Gly Leu Pro Ala Pro Ile Glu Lys Thr Ile Ser
                325                 330                 335

Lys Thr Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Met Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
            435                 440                 445
```

SCLEROSTIN ANTIBODY CRYSTALS AND FORMULATIONS THEREOF

CROSS-REFERENCE TO RELATED APPLICATIONS

This is a continuation application of U.S. Non-Provisional application Ser. No. 14/006,010, filed Dec. 30, 2013, which is a National Stage of PCT/US2012/030364, filed Mar. 23, 2013, which is an application claiming the benefit of U.S. Provisional Application No. 61/467,868, filed Mar. 25, 2011, the disclosures of which are incorporated herein by reference in their entireties.

INCORPORATION BY REFERENCE OF MATERIAL SUBMITTED ELECTRONICALLY

This application contains, as a separate part of disclosure, a Sequence Listing in computer-readable form (46053B_SeqListing.txt; Size: 41,107 bytes; Created: Aug. 21, 2015), which is incorporated by reference in its entirety.

BACKGROUND

Monoclonal antibodies are extensively used as biotherapeutics with an increasing demand to meet high concentrations of over a 100 mg/ml for delivery. This presents a challenge for solubility limited proteins via a subcutaneous route, since the preferred subcutaneous administration limit is 1.2 ml (Yang, M. X., Shenoy, B., Disttler, M., Patel, R., McGrath, M., Pechenov, S., Margolin, A. L. (2003) Crystalline monoclonal antibodies for subcutaneous delivery, PNAS 100, 6934-6939). Development of a high concentration formulation poses a lot of challenges from a formulation, analytical, stability, manufacturing and drug delivery point of view (Shire, S. J., Zahra, S., Liu, J. (2004) Challenges in the development of high concentration formulations, *J. Pharm. Sci.* 93, 1390-1402). So far, high concentration formulation demands have been met by addition of excipients like amino acids, sugars and salts that increase stability, reduce aggregation and viscosity (Shire, supra and Jenkins, T. W. (1998) Three solutions of the protein solubility problem, *Protein Science* 7: 376-382).

Protein crystals are often viewed as only the intermediates to a protein structure but they also have an important role from a formulation perspective. Protein molecules in the crystalline form have the lowest entropy thus making them 3-6 kcal/mol more stable than in the liquid state (Dreuth, J., Haas, C. (1992) Protein crystals and their stability, *J. Crystal Growth* 122, 107-109). The main advantages of crystalline formulation include high protein concentration, lower viscosity, stability, elimination of frequent dosage due to high concentration and controlled release properties (Yang, supra, and Basu, S. K., Govardhan, C. P., Jung, C. W., Margolin, A. L. (2004) Protein crystals for the delivery of biopharmaceuticals, *Expert Opin. Biol. Thera.* 4, 301-317).

Crystallization conditions can be manipulated to achieve different morphologies for desired controlled release properties (Pechenov, S., Shenoy, B., Yang, M. X., Basu, S., Margolin, A. L. (2004) Injectable controlled release formulations incorporating protein crystals, *Journal of Controlled Release* 96, 149-158). Insulin crystalline formulations were first reported in 1920's and today, it is not only the first recombinant protein therapeutic approved by the FDA, it is also the first approved crystalline protein therapeutic (Hagedorn H. C.; Jensen, B. N.; Krarup, N. B.; Wodstrup, I. Protamine insulinate, (1936) J. Am. Med. Assn. 106, 177-180; Johnson, I. S. (2003) The trials and tribulations of producing the first genetically engineered drug. Nat. Rev. Drug. Discovery 2, 747-751; and Basu, S. K., Govardhan, C. P., Jung, C. W., Margolin, A. L. (2004) Protein crystals for the delivery of biopharmaceuticals, Expert Opin. Biol. Thera. 4, 301-317). Macromolecules are challenging to crystallize due to their inherent flexibility, but, once crystallized, often pose challenges from a formulation and regulatory perspective (Basu, supra, and Jen, A., Merkle, H. P. (2001) Diamonds in the rough: Protein crystals from a formulation perspective, Pharm. Res. 18, 1483-1488.).

SUMMARY OF THE INVENTION

The invention relates to crystals of anti-sclerostin immunoglobulin type G (IgG) antibodies (more specifically, Ab-30 and Ab-31) that are suitable for use in formulations for parenteral administration; solutions, salts and methods for producing such crystals; methods of using such crystals to prepare formulations for use as medicaments, and methods of using such formulations for treating mammals, specifically humans.

In the crystals or formulations described herein, anti-sclerostin IgG antibody in the crystals or formulation can comprise the heavy and light chain variable regions of any of Ab-30, Ab-30R, Ab-30Rm or Ab-31. Thus, in specific embodiments, the antibody is an IgG comprising the amino acid sequences of: (a) SEQ ID NO: 5 (Ab-30 heavy chain variable region), and SEQ ID NO: 3 (Ab-30 light chain variable region), preferably each fused to a suitable constant region, or (b) SEQ ID NO: 15 (Ab-30 mature heavy chain) and SEQ ID NO: 13 (Ab-30 mature light chain); (c) SEQ ID NO: 17 (Ab-30R heavy chain variable region), and SEQ ID NO: 16 (Ab-30R light chain variable region), preferably each fused to a suitable constant region; (d) SEQ ID NO: 17 (Ab-30Rm heavy chain variable region), and SEQ ID NO: 20 (Ab-30Rm light chain variable region); or (e) SEQ ID NO: 25 (Ab-31 heavy chain variable region), and SEQ ID NO: 23 (Ab-31 light chain variable region), preferably each fused to a suitable constant region. In some embodiments, the antibody comprises the mature heavy and light chains of Ab-30, Ab-30R, Ab-30Rm or Ab-31. In some embodiments, the antibody comprises amino acid sequences obtainable by expressing in mammalian host cells the cDNA encoding the heavy and/or light chain, or alternatively the heavy and/or light chain variable regions, preferably each fused to a suitable constant region, of any of antibodies Ab-30, Ab-30R, Ab-30Rm, or Ab-31, as described herein. Preferably, the antibody binds to sclerostin of SEQ ID NO: 1 with a Kd binding affinity of $10^{-7}$ M or less.

The antibody crystals described herein can be characterized, for example, by size, shape, morphology, salt content and other properties. In some embodiments, the crystal length ranges from about 100 μM to about 500 μM or from about 50 μM to about 100 μM, or from about 1 μM to about 50 μM, optionally with a morphology that is needle shaped, rod shaped, plate-shaped, block-shaped, UFO shaped, football shaped, leaf shaped, wheat shaped, singlet shaped, feather-shaped, ellipsoidal (or surfboard shaped), straw-shaped, chrysanthemum-shaped, or spherical or mixtures thereof. In some embodiments, the crystal length ranges from about 1 μm to about 10 μm, or from about 1 μm to about 15 μm, or from about 1 μm to about 20 μm or from about 1 μm to about 25 μm or from about 1 μm to about 30 μm, or from about 1 μm to about 35 μm, or from about 1 μm to about 40 μm, or from about 1 μm to about 45 μm, or from about 5 μm to about 10 μm, or from about 5 μm to about 15

μm, or from about 5 μm to about 20 μm, or from about 5 μm to about 25 μm, or from about 5 μm to about 30 μm, or from about 5 μm to about 35 μm, or from about 5 μm to about 40 μm, or from about 5 μm to about 45 μm, or from about 50 μm to about 75 μm or from about 50 μm to about 80 μm, or from about 50 μm to about 85 μm, or from about 50 μm to about 90 μm, or from about 50 μm to about 95 μm, or from about 100 μm to about 150 μm, or from about 100 μm to about 200 μm, or from about 100 μm to about 250 μm, or from about 100 μm to about 300 μm, or from about 100 μm to about 350 μm, or from about 100 μm to about 400 μm, or from about 100 μm to about 450 μm.

Optionally, the crystals are in clusters. The crystals are also characterized by x-ray diffraction. For example, Ab-30 crystals may exhibit a needle shape, rod shape, block shape, or plate shape, or a mixture thereof, or other shapes. Most of the Ab-30 crystals exhibited rod, needle or ellipsoid shapes. For example, Ab-31 crystals may exhibit a surfboard or ellipsoidal shape, or other shapes.

In some embodiments, the crystal length is about 5 μm, or about 10 μm, or about 15 μm, or about 20 μm, or about 25 μm, or about 30 μm, or about 35 μm, or about 40 μm, or about 45 μm, or about 50 μm, or about 55 μm, or about 60 μm, or about 65 μm, or about 70 μm, or about 75 μm, or about 80 μm, or about 85 μm, or about 90 μm, or about 95 μm, or about 100 μm, or about 125 μm, or about 150 μm, or about 175 μm, or about 200 μm, or about 250 μm, or about 300 μm, or about 350 μm, or about 400 μm, or about 450 μm, or about 500 μm. Regardless of the length of the crystals produced by the various crystallization conditions described herein, the length can be altered subsequently to a desired length by methods known in the art. For example, if the crystallization conditions produce an antibody crystal that is about 5 μm to about 100 μm or about 5 μm to about 500 μm or about 100 μm to about 500 μm in length, the crystal can be milled down to a shorter length such as a length in the range of about 5 μm to about 50 μm.

In some embodiments, the crystal growth conditions are modified to obtain a specific size, shape, length and/or morphology of the crystal in consideration. The crystal growth conditions are modified by any means known in the art including, but not limited to, change in pH, change in addition of precipitants, change in concentration of precipitant, change in temperature, and the inclusion of additives including, but not limited to salts (including, but not limited to, zinc acetate, zinc chloride, zinc sulfate, ammonium acetate, calcium acetate, lithium acetate dihydrate, magnesium acetate tetrahydrate, magnesium chloride, magnesium formate, magnesium nitrate, magnesium sulfate and combinations thereof), amino acids, sugars, carbohydrates, detergents (ionic non-ionic zwitter ion) and surfactants.

In some or any embodiments, the antibody crystals described herein are characterized by the type of salt in the crystallization reagent.

Suitable salts for the production of Ab-30 crystals include, but are not limited to, sodium dihydrogen phosphate, dipotassium hydrogen phosphate, sodium chloride, ammonium sulfate, potassium sodium tartrate tetrahydrate, tacsimate, sodium citrate dihydrate, sodium acetate trihydrate, di-ammonium tartrate, sodium malonate, acetate, calcium acetate, cacodylate, CHES, lithium sulfate, magnesium chloride, zinc acetate, cesium chloride, ammonium phosphate, sodium phosphase, potassium phosphate, sodium fluoride, potassium iodide, sodium iodide, ammonium iodide, sodium thiocyanate, potassium thiocyanate, sodium formate, potassium formate and ammonium formate. For example, other salts (including hydrates) for the production of Ab-30 crystals can include other dihydrogen phosphate salts, hydrogen phosphate salts, phosphate salts, fluoride salts, chloride salts, sulfate salts, tartrate salts, tacsimate salts, citrate salts, acetate salts, malonate salts, cacodylate salts, and iodide salts, thiocyanate salts, or formate salts; with, for example, monovalent (e.g. sodium, potassium, ammonium) or divalent cations (e.g. zinc, magnesium).

Suitable salts for the production of Ab-31 crystals include, but are not limited to, sodium chloride, potassium chloride, sodium acetate, potassium phosphate and histidine. For example, other salts for the production of Ab-31 crystals include chloride salts, acetate salts, or phosphate salts; with, for example, monovalent (e.g. sodium, potassium, ammonium) cations.

In some or any embodiments, the antibody crystals are characterized by crystallization additives, which can influence the crystal growth and/or shape. Suitable crystallization additives include, but are not limited to, precipitants such as PEG having a molecular weight of about 200 kDa to about 20,000 kDa, or about 400 kDa to about 20,000 kDa, or about 1000 kD to about 10,000 kD (e.g., PEG-3350 or PEG-8000) or 2-methyl-2,4-pentanediol (MPD), surfactants such as polysorbate 20, polysorbate 80, detergents (ionic, non-ionic and zwitter ion); amino acids, short peptides, small organic molecules, organic salts, nucleotides and carbohydrates. In some embodiments, the additives (e.g., PEG, MPD, glycerol) are at a concentration of about 0.1% to about 75% (w/v or v/v), or about 0.1-50% (w/v or v/v), or about 0.1-10% (w/v or v/v), or about 10% to about 50% (w/v or v/v), or about 20%-50% (w/v or v/v), or at least 10%, or at least 20% (w/v or v/v). In some or any embodiments, the crystals are also characterized by the process by which they are produced, including remaining impurities.

In some or any embodiments, the antibody crystals are produced under crystallization conditions comprising a crystallization reagent comprising succinic acid, HEPES and polyethylene glycol monomethyl ether 2000. For example, in some embodiments, the crystallization conditions comprise about 0.1 M to about 5 M, or about 0.1 M to about 2 M, or about 0.1 M to about 1 M, or about 1 M to about 5 M, or about 3 M to about 5 M, or about 2 M to about 4 M succinic acid (or about 0.1 M, or about 0.5 M, or about 1 M, or about 1.5 M, or about 2 M, or about 2.5 M, or about 3 M, or about 3.5 M, or about 4 M, or about 4.5 M, or about 5 M succinic acid); optionally further comprising about 0.1 M to about 5 M, or about 0.1 M to about 2 M, or about 0.1 M to about 1 M, or about 1 M to about 5 M, or about 3 M to about 5 M, or about 2 M to about 4 M HEPES (or about 0.1 M, or about 0.5 M, or about 1 M, or about 1.5 M, or about 2 M, or about 2.5 M, or about 3 M, or about 3.5 M, or about 4 M, or about 4.5 M, or about 5 M HEPES) at a pH of about 6 to about 9 or about 7 to about 8.5; and optionally about 0.1% to about 60% (w/v), or about 0.1% to about 1%, or about 1% to about 3%, or about 2% to about 4%, or about 3% to about 5% or about 20% to about 40%, or about 30% to about 60%, or about 10% to about 20%, or about 25% to about 30%, or about 15% to about 25% polyethylene glycol monomethyl ether 2000 (or about 0.1%, or about 0.5%, or about 1%, or about 1.5%, or about 2%, or about 2.5%, or about 3%, or about 3.5%, or about 4.5%, or about 5%, or about 10%, or about 15%, or about 20%, or about 25%, or about 30%, or about 35%, or about 40%, or about 45%, or about 50%, or about 55%, or about 60% polyethylene glycol monomethyl ether 2000). In some embodiments, the crystallization reagent comprises 1.0 M succinic acid; 0.1 M HEPES, pH 7; and 1% (w/v) polyethylene glycol monoethyl ether 2000.

In some or any embodiments, the antibody crystals are produced under crystallization conditions comprising a crystallization reagent comprising PEG-8000, imidazole, and calcium acetate. For example, in some embodiments, the crystallization reagent comprises about 1% to about 50%, or about 1% to about 5%, or about 5% to about 10%, or about 10% to about 15%, or about 20% to about 30%, or about 25% to about 50%, or about 30% to about 45% or about 40% to about 50% PEG-8000 (or about 1%, or about 2%, or about 3%, or about 4%, or about 5%, or about 6%, or about 7%, or about 8%, or about 9%, or about 10%, or about 11%, or about 12% or about 13%, or about 14%, or about 15%, or about 20%, or about 25%, or about 30%, or about 35%, or about 40%, or about 45% or about 50% PEG-8000); optionally further comprising about 0.05 M to about 5 M, or about 0.05 to about 0.1 M, or about 0.1 M to about 2 M, or about 0.1 M to about 1 M, or about 1 M to about 5 M, or about 3 M to about 5 M, or about 2 M to about 4 M imidazole (or about 0.05, or about 0.1 M, or about 0.5 M, or about 1 M, or about 1.5 M, or about 2 M, or about 2.5 M, or about 3 M, or about 3.5 M, or about 4 M, or about 4.5 M, or about 5 M imidazole); and optionally about 0.1 M to about 5 M or about 0.1 M to about 2 M, or about 0.1 M to about 1 M, or about 1 M to about 5 M, or about 3 M to about 5 M, or about 2 M to about 4 M (or about 0.1 M, or about 0.5 M, or about 1 M, or about 1.5 M, or about 2 M, or about 2.5 M, or about 3 M, or about 3.5 M, or about 4 M, or about 4.5 M, or about 5 M) calcium acetate. In some embodiments, the crystallization reagent comprises 10 % (w/v) PEG-8000, 0.1 M imidazole, and 0.2 M calcium acetate.

In some or any embodiments, the antibody crystals are produced under crystallization conditions comprising a crystallization reagent comprising PEG-8000, TRIS and magnesium chloride. For example, in some embodiments, the crystallization reagent comprises about 1% to about 50%, or about 1% to about 5%, or about 5% to about 10%, or about 10% to about 15%, or about 20% to about 30%, or about 25% to about 50%, or about 30% to about 45% or about 40% to about 50% PEG-8000 (or about 1%, or about 2%, or about 3%, or about 4%, or about 5%, or about 6%, or about 7%, or about 8%, or about 9%, or about 10%, or about 11%, or about 12% or about 13%, or about 14%, or about 15%, or about 20%, or about 25%, or about 30%, or about 35%, or about 40%, or about 45% or about 50% PEG-8000); optionally further comprising about 0.05 M to about 5 M, or about 0.05 M to about 1 M, or about 0.1 M to about 2 M, or about 0.1 M to about 1 M, or about 1 M to about 5 M, or about 3 M to about 5 M, or about 2 M to about 4 M TRIS (or about 0.05 M, or about 0.1 M, or about 0.5 M, or about 1 M, or about 1.5 M, or about 2 M, or about 2.5M, or about 3 M, or about 3.5 M, or about 4 M, or about 4.5 M, or about 5 M TRIS); and optionally about 0.05 M to about 5 M, or about 0.05 to about 1 M, or about 0.1 M to about 2 M, or about 0.1 M to about 1 M, or about 1 M to about 5 M, or about 3 M to about 5 M, or about 2 M to about 4 M magnesium chloride (or about 0.1 M, or about 0.5 M, or about 1 M, or about 1.5 M, or about 2 M, or about 2.5 M, or about 3 M, or about 3.5 M, or about 4 M, or about 4.5 M, or about 5 M magnesium chloride). In some embodiments, the crystallization reagent comprises 10% (w/v) PEG-8000, 0.1 M Tris, and 0.2 M magnesium chloride.

In some or any embodiments, the antibody crystals are produced under crystallization conditions comprising a crystallization reagent comprising PEG-1000, sodium/potassium phosphate and sodium chloride. For example, in some embodiments, the crystallization reagent comprises about 10% to about 80%, or about 10%-15%, or about 15% to about 20%, or about 20% to about 25%, or about 25% to about 30% or about 20% to about 30%, or about 40% to about 70%, or about 50% to about 80%, or about 30% to about 75% PEG-1000 (or about 10%, or about 15%, or about 20%, or about 25%, or about 30%, or about 35%, or about 40%, or about 45%, or about 50%, or about 55%, or about 60%, or about 65%, or about 70%, or about 75%, or about 80% PEG-1000); optionally further comprising about 0.05 M to about 5 M, or about 0.05 M to about 1 M, or about 0.1 M to about 2 M, or about 0.1 M to about 1 M, or about 1 M to about 5 M, or about 3 M to about 5 M, or about 2 M to about 4 M sodium/potassium phosphate (or about 0.05M, or about 0.1 M, or about 0.5 M, or about 1 M, or about 1.5 M, or about 2 M, or about 2.5 M, or about 3 M, or about 3.5 M, or about 4 M, or about 4.5 M, or about 5 M sodium/potassium phosphate); and optionally about 0.05 M to about 5 M, or about 0.05 M to about 1 M, or about 0.1 M to about 2 M, or about 0.1 M to about 1 M, or about 1 M to about 5 M, or about 3 M to about 5 M, or about 2 M to about 4 M sodium chloride (or about 0.1 M, or about 0.5 M, or about 1 M, or about 1.5 M, or about 2 M, or about 2.5 M, or about 3 M, or about 3.5 M, or about 4 M, or about 4.5 M, or about 5 M sodium chloride). In some embodiments, the crystallization reagent comprises 20% (w/v) PEG1000, 0.1 M sodium/potassium phosphate, and 0.2 M sodium chloride.

In some or any embodiments, the antibody crystals are produced under crystallization conditions comprising a crystallization reagent comprising PEG-8000, cacodylate, calcium acetate and glycerol. For example, in some embodiments, the crystallization reagent comprises about 1% to about 50% %, or about 1% to about 5%, or about 5% to about 10%, or about 10% to about 15%, or about 20% to about 30%, or about 25% to about 50%, or about 30% to about 45% or about 40% to about 50% PEG-8000 (or about 1%, or about 2%, or about 3%, or about 4%, or about 5%, or about 6%, or about 7%, or about 8%, or about 9%, or about 10%, or about 11%, or about 12% or about 13%, or about 14%, or about 15%, or about 20%, or about 25%, or about 30%, or about 35%, or about 40%, or about 45% or about 50% PEG-8000); optionally further comprising about 0.05 M to about 5 M or about 0.1 M to about 2 M, or about 0.1 M to about 1 M, or about 1 M to about 5 M, or about 3 M to about 5 M, or about 2 M to about 4 M cacodylate (or about 0.05 M, or about 0.06 M, or about 0.07 M, or about 0.8 M, or about 0.9 M, or about 1 M, or about 1.5 M or about 2 M, or about 2.5 M, or about 3 M, or about 3.5 M, or about 4 M, or about 4.5 M, or about 5 M cacodylate) at a pH of about 5 to about 7 , or about 6 to about 7 or about 6.5 ; optionally about 0.05 M to about 2 M, or about 0.5 M to about 1 M, or about 0.1 M to about 1 M, or about 5 M to about 1 M, or about 1 M to about 2 M calcium acetate (or about 0.05 M, or about 0.1 M, or about 0.12 M, or about 0.14 M, or about 0.16 M, or about 0.18 M, or about 0.2 M, or about 0.5 M, or about 1 M, or about 1.5 M, or about 2 M calcium acetate); and optionally about 1% to about 65% (w/v), or about 1% to about 10%, or about 1% to about 5%, or about 5% to about 10%, or about 10% to about 15%, or about 15% to about 20%, or about 20% to about 25%, or about 25% to about 30% or about 20% to about 30%, or about 35% to about 50%, or about 50% to about 65% glycerol (or about 10%, or about 15%, or about 20%, or about 25% or about 30% glycerol). In some embodiments, the crystallization reagent comprises about 14.4% (w/v) PEG-8000, 0.08 M cacodylate, 0.16 M calcium acetate and 20% (w/v) glycerol.

In some or any embodiments, the antibody crystals are produced under crystallization conditions comprising a crystallization reagent comprising isopropanol and sodium/potassium phosphate. For example, in some embodiments, the crystallization reagent comprises about 1% to about 100%, or about 1% to about 5%, or about 5% to about 10%, or about 10% to about 15%, or about 15% to about 20%, or about 20% to about 25%, or about 25% to about 30%, or about 20% to about 30%, or about 35% to about 50%, or about 40%, to about 60%, or about 75% to about 90% or about 80% to about 100% (v/v) isopropanol (or about 10%, or about 15%, or about 20%, or about 25% or about 30%, or about 35%, or about 40%, or about 45%, or about 50%, or about 55%, or about 60%, or about 65%, or about 70%, or about 75%, or about 80%, or about 85%, or about 90%, or about 95%, or about 100% (v/v) isopropanol); and optionally about 0.05 to about 4 M, or about 0.05 M to about 1 M, or about 0.1 M to about 1 M, or about 5 M to about 1 M, or about 1 M to about 2 M, or about 2 M to about 4 M, or about 3 M to about 4 M sodium/potassium phosphate (or about 0.1 M, or about 0.2 M, or about 0.3 M, or about 0.4 M, or about 0.5 M, or about 0.6 M, or about 0.7 M, or about 0.8 M, or about 0.9 M, or about 1 M, or about 1.5 M, or about 2 M, or about 2.5 M, or about 3 M, or about 3.5 M, or about 4 M sodium/potassium phosphate). In some embodiments, the crystallization reagent comprises about 19.9 % isopropanol and about 0.2 M sodium/potassium phosphate.

In some or any embodiments, the antibody crystals are produced under crystallization conditions comprising a crystallization reagent comprising a member selected from the group consisting of 2-propanol, ammonium phosphate dibasic, PEG-1000, ammonium sulfate, potassium/sodium tartrate, PEG-3000, PEG-8000, 1,4-butanediol, sodium chloride, ethanol, PEG-400, 2-methyl-2,4-pentanediol (MPD), Jeffamine M-600, PEG-10,000. For example, in some embodiments, the crystallization reagent comprises about 1% to about 50%, or about 10% to about 20%, or about 1% to about 10% or about 5% to about 10% or about 8% to about 12%, or about 15% to about 20%, or about 20% to about 35%, or about 40% to about 50% (v/v) 2-propanol (or about 1%, or about 5%, or about 10%, or about 15%, or about 20%, or about 25%, or about 30%, or about 35%, or about 40%, or about 45%, or about 50% (v/v) 2-propanol).

In some embodiments, the crystallization reagent comprises about 0.05 M to about 10 M, or about 0.5 M to about 1 M, or about 1 M to about 5 M, or about 5 M to about 10 M ammonium phosphate dibasic (or about 0.05 M, or about 0.1 M, or about 0.5 M, or about 1 M, or about 1.5 M, or about 2 M, or about 2.5 M, or about 3 M, or about 3.5 M, or about 4 M, or about 4.5 M, or about 5 M, or about 6 M, or about 6.5 M, or about 7 M, or about 7.5 M, or about 8 M, or about 8.5 M, or about 9 M, or about 9.5 M or about 10 M ammonium phosphate dibasic).

In some embodiments, the crystallization reagent comprises about 10% to about 80% or about 10% to about 15%, or about 15% to about 20%, or about 20% to about 25%, or about 25% to about 30% or about 20% to about 30%, or about 40% to about 70%, or about 50% to about 80%, or about 30% to about 75% (w/v) PEG-1000 (or about 10%, or about 15%, or about 20%, or about 25%, or about 30%, or about 35%, or about 40%, or about 45%, or about 50%, or about 55%, or about 60%, or about 65%, or about 70%, or about 75%, or about 80% (w/v) PEG-1000).

In some embodiments, the crystallization reagent comprises about 0.5 M to about 10 M, or about 0.5 M to about 1 M, or about 1 M to about 5 M, or about 5 M to about 10 M ammonium sulfate (or about 0.05 M, or about 0.1 M, or about 0.5 M, or about 1 M, or about 1.5 M, or about 2 M, or about 2.5 M, or about 3 M, or about 3.5 M, or about 4 M, or about 4.5 M, or about 5 M, or about 6 M, or about 6.5 M, or about 7 M, or about 7.5 M, or about 8 M, or about 8.5 M, or about 9 M, or about 9.5 M or about 10 M ammonium sulfate).

In some embodiments, the crystallization reagent comprises about 0.5 M to about 10 M, or about 0.5 M to about 1 M, or about 1 M to about 5 M, or about 5 M to about 10 M potassium/sodium tartrate (or about 0.05 M, or about 0.1 M, or about 0.5 M, or about 1 M, or about 1.5 M, or about 2 M, or about 2.5 M, or about 3 M, or about 3.5 M, or about 4 M, or about 4.5 M, or about 5 M, or about 6 M, or about 6.5 M, or about 7 M, or about 7.5 M, or about 8 M, or about 8.5 M, or about 9 M, or about 9.5 M or about 10 M potassium sodium tartrate).

In some embodiments, the crystallization reagent comprises about 1% to about 50%, or about 1% to about 5%, or about 1% to about 10%, or about 10% to about 20%, or about 15% to about 20%, or about 20% to about 25%, or about 25% to about 30%, or about 30% to about 50% (v/v) 1,4-butanediol (or about 1%, or about 5%, or about 10%, or about 15%, or about 20%, or about 25%, or about 30%, or about 35%, or about 40%, or about 45%, or about 50% (v/v) 1,4-butanediol).

In some embodiments, the crystallization reagent comprises about 0.5 M to about 10 M, or about 0.5 M to about 1 M, or about 1 M to about 5 M, or about 5 M to about 10 M sodium chloride (or about 0.05 M, or about 0.1 M, or about 0.5 M, or about 1 M, or about 1.5 M, or about 2 M, or about 2.5 M, or about 3 M, or about 3.5 M, or about 4 M, or about 4.5 M, or about 5 M, or about 6 M, or about 6.5 M, or about 7 M, or about 7.5 M, or about 8 M, or about 8.5 M, or about 9 M, or about 9.5 M or about 10 M sodium chloride).

In some embodiments, the crystallization reagent comprises about 10% to about 50%, or about 10% to about 20%, or about 14% to about 18%, or about 15% to about 20%, or about 20% to about 25%, or about 25% to about 30%, or about 30% to about 50% (v/v) ethanol (or about 1%, or about 5%, or about 10%, or about 15%, or about 20%, or about 25%, or about 30%, or about 35%, or about 40%, or about 45%, or about 50% (v/v) ethanol).

In some embodiments, the crystallization reagent comprises about 10% to about 80% or about 10% to about 15%, or about 15% to about 20%, or about 20% to about 25%, or about 25% to about 30% or about 20% to about 30%, or about 40% to about 70%, or about 50% to about 80%, or about 30% to about 75% (w/v) PEG-400, PEG-1000, PEG-3,000, PEG-8,000 or PEG-10,000 (or about 10%, or about 15%, or about 20%, or about 25%, or about 30%, or about 35%, or about 40%, or about 45%, or about 50%, or about 55%, or about 60%, or about 65%, or about 70%, or about 75%, or about 80% (w/v) PEG-400, PEG-1000, PEG-3,000, PEG-8,000 or PEG-10,000.

In some embodiments, the crystallization reagent comprises about 10% to about 50% (w/v) 2-methyl-2,4-pentanediol (MPD) (or about 10%, or about 15%, or about 20%, or about 25%, or about 30%, or about 35%, or about 40%, or about 45%, or about 50% (w/v) 2-methyl-2,4-pentanediol (MPD)).

In some embodiments, the crystallization reagent comprises about 1% to about 50%, or about 1% to about 10%, or about 5% to about 15%, or about 10% to about 20%, or about 20% to about 25%, or about 20% to about 30%, or about 15% to 25%, or about 30% to about 50% (v/v) Jeffamine M-600 (or about 1%, or about 5%, or about 10%, or about 15%, or about 20%, or about 25%, or about 30%, or about 35%, or about 40%, or about 45%, or about 50% (v/v) Jeffamine M-600).

Another aspect described herein provides methods of making the crystals described herein. In some embodiments, the method comprises combining a solution of antibody Ab-30, Ab-30R, Ab-30Rm or Ab-31 with a crystallization reagent comprising an appropriate salt, including any of the previously described salts, such that a crystal is formed. In any of the embodiments described herein, the salt in the crystallization reagent is present at a concentration of about 0.1 M to about 30 M, optionally about 0.1 M to about 10 M, or about 1 M to about 10 M or about 1 M to about 5 M or about 5 M to about 10 M. In some embodiments, the method comprises combining a solution of antibody Ab-30, Ab-30R, Ab-30Rm or Ab-31 with a crystallization reagent comprising succinic acid, PEG-1000, PEG-8000 or isopropanol such that a crystal is formed. For any of the crystal production methods described herein, in some embodiments, at least 80% (e.g., at least 85%, or at least 90%, or at least 95% or more) of the original amount of antibody in the solution is crystallized following the combining step. Determining the percent crystallized antibody can be performed by methods described, for example, in Example 5 or other methods known in the art.

Methods of making antibody crystals optionally further comprise removing at least a portion of the crystallization reagent (e.g., by centrifugation) after the crystals are formed. In some embodiments, the crystals are then placed into a solution comprising an organic additive (e.g., ethanol or isopropanol). In some embodiments, excipients (e.g., sucrose, trehalose or sorbitol) are added to the solution.

The methods of making the antibody crystals optionally further comprise the step of drying the crystals that have formed (e.g., by air drying the crystals or exposing the crystals to a vacuum or nitrogen gas).

Exemplary methods for producing the antibody crystals described herein include vapor diffusion and batch crystallization, which are known in the art.

Another aspect described herein are formulations (e.g., powder and liquid formulations comprising anti-sclerostin antibodies described herein) and methods of using antibody crystals described herein to prepare medicaments, such as formulations, for therapy of mammals including humans. Therapy of any of the conditions described herein is contemplated, optionally using any of the dosing and timing regimens described herein. The formulations comprise antibody crystals, e.g., Ab-30, Ab-30R, Ab-30Rm or Ab-31 crystals, having one or more of the properties described herein (e.g., size, length, shape, salt content, additive content, or other properties). In some embodiments, the Ab-30, Ab-30R, Ab-30Rm or Ab-31 crystals in the formulation have a length of about 20 µm to about 1 mm and are shaped as ellipsoids, rods and needles, or a mixture thereof. In some embodiments, the Ab-30, Ab-30R, Ab-30Rm or Ab-31 crystals in the formulation have a length of about 5 µm to about 500 µm and are shaped as ellipsoids, rods, and needles, or a mixture thereof.

In some or any embodiments, the formulation is sterile and comprises a crystal of an anti-sclerostin IgG antibody, wherein at least 70% (or at least 75%, or at least 80%, or at least 85% or at least 90%, or at least 95% or more) of the antibody is in crystalline form. In some embodiments, the anti-sclerostin IgG antibody in the formulation comprises light and heavy chain variable regions of SEQ ID NOS: 3 and 5, preferably having the amino acid sequences of SEQ ID NOS: 13 and 15.

The formulations are suitable for parenteral administration, e.g. are sterile; have endotoxin levels acceptable for parenteral administration, e.g. <0.25 EU/mL or 0.008 EU/mg; and comprise pharmaceutically acceptable excipients. The formulations are also preferably of high protein concentrations, e.g., at least 100 mg of antibody per ml of formulation, or at least 120 mg/ml, or at least 140 mg/ml, or at least 160 mg/ml, or at least 180 mg/ml, or at least 200 mg/ml, or at least 220 mg/ml, or at least 240 mg/ml or higher. In some embodiments, the formulation comprises a concentration of at least 140 mg of antibody dispersed in 1.5 ml or less of liquid. In exemplary embodiments, such formulations have a viscosity of about about 10 cP or less, optionally 8 cP or less or 6 cP or less. The term "viscosity" as used herein refers to "absolute viscosity." Absolute viscosity, sometimes called dynamic or simple viscosity, is the product of kinematic viscosity and fluid density: Absolute Viscosity=Kinematic Viscosity×Density. The dimension of kinematic viscosity is $L^2/T$ where L is a length and T is a time. Commonly, kinematic viscosity is expressed in centistokes (cSt). The SI unit of kinematic viscosity is $mm^2/s$, which is 1 cSt. Absolute viscosity is expressed in units of centipoise (cP). The SI unit of absolute viscosity is the millipascal-second ($mPa^{-s}$), where 1 cP=1 $mPa^{-s}$.

In some or any embodiments, absolute viscosity of the resuspended liquid formulation at the storage and/or administration temperature is 15 cP or less, or 14, 13, 12, 11, 10, 9, 8, 7, 6, 5, or 4 cP or less. In some or any embodiments, the formulation is injectable through a syringe that is a 20 Gauge needle or finer (e.g., a 25 Gauge needle, a 27 Gauge needle or finer) using a clinically acceptable amount of force.

In some or any embodiments, the formulation comprises excipients including, but not limited to sucrose, trehalose and sorbitol, or other sugars or polyols.

In some or any embodiments, the formulations have a pH ranging from about 2 to about 12, or about 6 to about 9, or about 6 to 8.5, or about 7 to about 7.5 and an osmolality ranging from about 180 to about 420 mOsm/kg, or about 200 to about 400 mOsm/kg, or about 250 to about 350 mOsm/kg. While isotonic (250-350 mOsm/kg) and physiologic pH (about 7-7.5) is preferred, formulations may be prepared outside of these ranges.

The formulation is optionally resuspended in a suspension vehicle prior to parenteral administration. Exemplary suspension vehicles include, but are not limited to glutamate, sorbitol, HEPES, dextrose and water. In some embodiments, the suspension vehicle is dextrose and the dextrose is provided in an amount ranging from about 1% to about 10% dextrose or from about 5% to about 10% dextrose or from about 1% to about 5% dextrose, or from about 2% to about 4% dextrose (e.g., about 1% dextrose, about 2% dextrose, about 3% dextrose, about 4% dextrose, about 5% dextrose, about 6% dextrose, about 7% dextrose, about 8% dextrose, about 9% dextrose or about 10% dextrose). In some embodiments, the suspension vehicle is sorbitol and the sorbitol is provided in an amount ranging from about 1% to about 10% sorbitol or from about 5% to about 10% sorbitol or from about 1% to about 5% sorbitol, or from about 2% to about 4% sorbitol (e.g., about 1% sorbitol, about 2% sorbitol, about 3% sorbitol, about 4% sorbitol, about 5% sorbitol, about 6% sorbitol, about 7% sorbitol, about 8% sorbitol, about 9% sorbitol or about 10% sorbitol). In some embodiments, the suspension vehicle is glutamate and the glutamate is provide in an amount ranging from 1 mM to about 20 mM glutamate or from about 10 mM to about 15 mM or from about 5 to about 10 mM or from about 8 mM to about 12 mM (or about 1 mM glutamate, about 2 mM glutamate, about 3 mM glutamate, about 4 mM glutamate, about 5 mM glutamate, about 6 mM glutamate, about 7 mM glutamate, about 8 mM glutamate, about 9 mM glutamate, about 10 mM glutamate, about 11 mM glutamate, about 12 mM glutamate, about 13 mM glutamate, about 14 mM glutamate, about 15 mM glutamate, about 16 mM glutamate, about 17 mM glutamate, about 18 mM glutamate, about 19 mM glutamate or about 20 mM glutamate). In some embodiments, the suspension vehicle comprises a combination of sorbitol and glutamate (e.g., about 1 mM to about 20 mM glutamate (including the intermediate ranges identified above) and about 1% to about 10% sorbitol (including the intermediate ranges identified above)). In some embodiments, the suspension vehicle comprises about 10 mM glutamate and about 5% sorbitol.

In other embodiments, the suspension vehicle is selected from the group consisting of (1) HEPES and PEG-3350 (e.g., 0.5 M HEPES and 20% PEG-3350, pH 7.5); (2) Tris and PEG-3350 (e.g., 0.5 M Tris and 50% PEG-3350, pH8) and (3) Tris and PEG-3350 (e.g., 0.5M Tris and 50% PEG-3350, pH 8.5).

Optionally, the formulation suitable for parenteral administration (e.g., subcutaneous or intramuscular) is presented in a container, such as a single dose vial, multidose vial, syringe, pre-filled syringe or injection device. In some or any embodiments, the container comprises a single dose of an anti-sclerostin antibody (e.g., about 70 to about 450 mg of anti-sclerostin antibody). In some embodiments, the dose comprises at least about 5 mg, 15 mg, 25 mg, 50 mg, about 60 mg, about 70 mg, about 80 mg, about 90 mg, about 100 mg, about 120 mg, about 150 mg, about 200 mg, about 240 mg, about 250 mg, about 280 mg, about 300 mg, about 350 mg, about 400 mg, about 420 mg, about 450 mg, about 500 mg, about 550 mg, about 600 mg, about 650 mg, about 700 mg, about 750 mg, about 800 mg, about 850 mg, about 900 mg, about 950 mg or up to about 1,000 mg of anti-sclerostin antibody. Ranges between any and all of these endpoints are also contemplated, e.g. about 50 mg to about 80 mg, about 70 mg to about 140 mg, about 70 mg about to about 350 mg, about 70 mg to about 280, about 70 mg to about 210 mg, about 75 mg to about 100 mg, about 100 mg to about 150 mg, about 140 mg to about 210 mg, or about 150 mg to about 200 mg, or about 280 mg to about 410 mg of anti-sclerostin antibody. The dose is administered at any interval, such as multiple times a week (e.g., twice or three times per week), once a week, once every two weeks, once every three weeks, or once every four weeks. For example, in some or any embodiments, a dose of anti-sclerostin antibody ranging from about 120 mg to about 210 mg is administered twice a week. In some or any embodiments, a dose of about 140 mg of the anti-sclerostin antibody is administered twice a week. Any of the doses described herein may be administered as divided doses. For example, a dose of 140 mg of anti-sclerostin antibody may be administered as two injections of 70 mg of anti-sclerostin antibody. Similarly, a dose of 210 mg of anti-sclerostin antibody may be administered as two injections of 105 mg of anti-sclerostin antibody.

In some or any embodiments, a formulation comprising crystals of an anti-sclerostin antibody described herein retains at least 50% (or at least 60%, or at least 65%, or at least 70%, or at least 75%, or at least 80%, or at least 85%, or at least 90%, or at least 95%) or more of the in vivo activity of the same antibody that has not been crystallized. For example, in some embodiments, a formulation comprising crystals of Ab30 retains at least about 50% to about 100%, or at least about 70% to about 100%, or at least 80% to at least 100% or at least 90% to about 100% (e.g., about 50%, about 60%, about 70%, about 80%, about 90% or about 100%) of the level of activity, when given at the same (or similar) dose and administered in the same (or similar) manner, as an Ab30 antibody that has not been crystallized. The formulation can be administered in a single dose or in multiple doses as described elsewhere herein. In some embodiments, the in vivo activity is an increase in bone mineral density for the total body (e.g., head, trunk, arms, and legs) or at the hip (e.g., total hip and/or femoral neck), spine (e.g., lumbar spine), wrist, finger, shin bone and/or heel compared to baseline.

In some or any embodiments, a formulation comprising Ab-30, Ab-30R, Ab-30Rm or Ab-31 crystals as described herein when administered to a mammalian subject mediates an increase in bone mineral density (compared to baseline or control) that is at least about 70% (or at least about 80% or at least about 90% or at least about 100%) of the level of bone mineral density increase mediated by an Ab-30, Ab-30R, Ab-30Rm or Ab-31 antibody, that has not been crystallized (when administered at the same (or similar) dose and via the same (or similar) route of administration; e.g., at a dose described herein, such as of about 100 mg/ml, administered by subcutaneous injection). The formulation can be administered in a single dose or in multiple doses as described elsewhere herein.

In one exemplary embodiment, a container may contain about 70 mg or 75 mg of the formulation of anti-sclerostin antibody and would be suitable for administering a single dose of about 1 mg/kg. In other embodiments, a container may contain about 50 mg, or about 60 mg, or about 70 mg, or about 80 mg, or about 90 mg, or about 100 mg, or about 120 mg, or about 130 mg, or about 140 mg or about 150 mg, or about 160 mg, or about 170 mg, or about 180 mg, or about 190 mg, or about 200 mg, or about 210 mg or about 220 mg or about 230 mg; or about 240 mg, or at about 250 mg, or about 250 mg to about 450 mg; or about 280 mg or 290 mg or 300 mg; or about 350 mg or 360 mg; or about 420 mg or 430 mg or 440 mg or 450 mg of the formulation of anti-sclerostin antibody. In any of such embodiments, the container may be suitable for administering a single dose of about 2 to about 6 mg/kg, or about 1 mg/kg to about 4 mg/kg, or about 3 mg/kg to about 5 mg/kg, or about 1 mg/kg to about 3 mg/kg body weight (e.g., about 2 mg/kg, or about 3 mg/kg, or about 4 mg/kg, or about 5 mg/kg or about 6 mg/kg body weight). In any of these embodiments, the container may comprise the antibody at a high protein concentration such as those described herein. In any of these embodiments, the container may comprise a powdered or lyophilized formulation and be for suspension in a volume of about 0.5-2 mL.

Also disclosed are methods of resuspending any of the foregoing powdered formulations comprising adding a sterile diluent to achieve a high protein concentration such as those described herein.

Also disclosed herein is a kit comprising such a container and a label comprising instructions to use the appropriate volume or amount of the formulation necessary to achieve a dose of from about 0.5-20 mg/kg, or 0.5-10 mg/kg of patient body weight. In some embodiments, the dose of formulation comprises between about 0.1 to about 50 milligrams (e.g., between about 5 and about 50 milligrams), or about 1 to about 100 milligrams, of anti-sclerostin antibody per kilogram of body weight (mg/kg). For example, the dose of anti-sclerostin antibody may comprise at least about 0.1 mg/kg, 0.5 mg/kg, 1 mg/kg, about 2 mg/kg, about 3 mg/kg, about 4 mg/kg, about 5 mg/kg, about 6 mg/kg, about 7 mg/kg, about 8 mg/kg, about 9 mg/kg, about 10 mg/kg, about 20 mg/kg, about 25 mg/kg, about 26 mg/kg, about 27 mg/kg, about 28 mg/kg, about 29 mg/kg, about 30 mg/kg, about 31 mg/kg, about 32 mg/kg, about 33 mg/kg, about 34 mg/kg, about 35 mg/kg, about 36 mg/kg, about 37 mg/kg, about 38 mg/kg, about 39 mg/kg, about 40 mg/kg, about 41 mg/kg, about 42 mg/kg, about 43 mg/kg, about 44 mg/kg, about 45 mg/kg, about 46 mg/kg, about 47 mg/kg, about 48 mg/kg, or about 49 mg/kg, or about 50 mg/kg, about 55 mg/kg, about 60 mg/kg, about 65 mg/kg, about 70 mg/kg, about 75 mg/kg, about 80 mg/kg, about 85 mg/kg, about 90 mg/kg, about 95 mg/kg, or up to about 100 mg/kg. Ranges between any and all of these endpoints are also contemplated, e.g., about 1 mg/kg to about 3 mg/kg, about 1 mg/kg to about 5 mg/kg, about 1 mg/kg to about 10 mg/kg, about 1 mg/kg to about 20 mg/kg, about 1 mg/kg to about 40 mg/kg, about 5 mg/kg to about 30 mg/kg, about 5 mg/kg to about 20 mg/kg, about 2 mg/kg to about 6 mg/kg, about 1 mg/kg to about 4 mg/kg, or about 3 mg/kg to about 5 mg/kg.

Also disclosed herein are formulations (e.g., powder (i.e., lyophilized) and/or liquid formulations) that are stable at room temperature and/or 4° C. for at least 6 months, 7 months, 8 months, 9 months, 10 months, 11 months, 1 year, 18 months, 2 years, 3 years, 4 years, 5 years, 6 years, 7 years, 8 years, 9 years, 10 years or longer. In some embodiments, the formulation comprises Ab-30 crystals and the formulation is stable at room temperature and/or 4° C. for at least 6 months, 7 months, 8 months, 9 months, 10 months, 11 months, 1 year, 18 months, 2 years, 3 years, 4 years, 5 years, 6 years, 7 years, 8 years, 9 years, 10 years or more. In some embodiments, the Ab-30 formulation is stable at 4° C. and/or room temperature for at least 9 months.

Also described herein are methods of using the formulations described herein to treat any disorder associated with decreased bone density (bone-related disorders), including but not limited to, achondroplasia, cleidocranial dysostosis, enchondromatosis, fibrous dysplasia, Gaucher's Disease, hypophosphatemic rickets, Marfan's syndrome, multiple hereditary exotoses, neurofibromatosis, osteogenesis imperfecta, osteopetrosis, osteopoikilosis, sclerotic lesions, pseudoarthrosis, pyogenic osteomyelitis, periodontal disease, anti-epileptic drug induced bone loss, primary or secondary hyperparathyroidism, familial hyperparathyroidism syndromes, weightlessness induced bone loss, osteoporosis in men, postmenopausal bone loss, osteoarthritis, renal osteodystrophy, infiltrative disorders of bone, oral bone loss, osteonecrosis of the jaw, juvenile Paget's disease, melorheostosis, metabolic bone diseases, mastocytosis, sickle cell anemia/disease, organ transplant related bone loss, kidney transplant related bone loss, systemic lupus erythematosus, ankylosing spondylitis, epilepsy, juvenile arthritides, thalassemia, mucopolysaccharidoses, Fabry Disease, Turner Syndrome, Down Syndrome, Klinefelter Syndrome, leprosy, Perthe's Disease, adolescent idiopathic scoliosis, infantile onset multi-system inflammatory disease, Winchester Syndrome, Menkes Disease, Wilson's Disease, ischemic bone disease (such as Legg-Calve-Perthes disease or regional migratory osteoporosis), anemic states, conditions caused by steroids, glucocorticoid-induced bone loss, heparin-induced bone loss, bone marrow disorders, scurvy, malnutrition, calcium deficiency, osteoporosis, osteopenia, alcoholism, chronic liver disease, postmenopausal state, chronic inflammatory conditions, rheumatoid arthritis, inflammatory bowel disease, ulcerative colitis, inflammatory colitis, Crohn's disease, oligomenorrhea, amenorrhea, pregnancy, diabetes mellitus, hyperthyroidism, thyroid disorders, parathyroid disorders, Cushing's disease, acromegaly, hypogonadism, immobilization or disuse, reflex sympathetic dystrophy syndrome, regional osteoporosis, osteomalacia, bone loss associated with joint replacement, HIV associated bone loss, bone loss associated with loss of growth hormone, bone loss associated with cystic fibrosis, chemotherapy-associated bone loss, tumor-induced bone loss, cancer-related bone loss, hormone ablative bone loss, multiple myeloma, drug-induced bone loss, anorexia nervosa, disease-associated facial bone loss, disease-associated cranial bone loss, disease-associated bone loss of the jaw, disease-associated bone loss of the skull, bone loss associated with aging, facial bone loss associated with aging, cranial bone loss associated with aging, jaw bone loss associated with aging, skull bone loss associated with aging, or bone loss associated with space travel.

The formulations described herein are useful for improving outcomes in orthopedic procedures, dental procedures, implant surgery, joint replacement, bone grafting, bone cosmetic surgery and bone repair such as fracture healing, nonunion healing, delayed union healing and facial reconstruction. One or more formulations may be administered before, during and/or after the procedure, replacement, graft, surgery or repair.

Also contemplated are dental implants, matrices, gels and wound dressings comprising formulation described herein. In some embodiments, the dental implants, matrices, gels and wound dressings are coated with the formulation. In other embodiments, the formulation is applied to a target area (i.e., diseased gingival area or diseased periodontal pocket of the subject), optionally prior to (or after) application of a dental implant, matrices or wound dressing. In these embodiments, the formulation is applied by any means known in the art. In some embodiments, the formulation is administered to a target area by subcutaneous injection prior to the application of the dental implant, matrix or wound dressing. In other embodiments, the formulation is administered to the affected area by brushing or otherwise coating the affected area prior to the application of the dental implant, matrix or wound dressing.

In another aspect, described herein are methods of increasing bone mineral density in a mammalian subject comprising administering a formulation described herein to the mammalian subject in an amount effective to increase bone mineral density. In some embodiments, the method optionally increases the level of a marker of bone formation. In some embodiments the bone mineral density is increased for at least about 7 days, 2 weeks, 3 weeks, 4 weeks, 1 month, 5 weeks, 6 weeks, 7 weeks, 8 weeks, 2 months, 3 months or longer. In related aspects, described herein is a method of treating a bone-related disorder in a mammalian subject comprising administering a formulation described herein to the subject in an amount effective to treat the bone-related disorder.

In some embodiments, the formulation increases the level of a marker of bone formation by at least about 10% compared to bone marker levels absent treatment. The formulation can be administered via a single dose or in multiple doses. For example, the formulation described herein can be administered in a short-term therapy regimen to, e.g., increase bone formation, and/or can be administered long-term to prevent loss of bone mineral density in a maintenance therapeutic regimen.

In any of the preceding methods, the level of the marker of bone formation is increased by at least about 10%, about 20%, about 30%, about 40%, about 50%, about 60%, about 70%, about 80%, about 90%, about 100% or more for at least about 2 weeks, 3 weeks, 30 days, 1 month, 6 weeks, 2 months or longer, compared to pre-treatment levels or normal levels for that patient population. By way of non-limiting example, the level of the marker of bone formation by 3 weeks after treatment is increased by, e.g., at least about 20% compared to pre-treatment levels or normal levels for that patient population. In one exemplary embodiment, the marker of bone resorption is serum level of C-telopeptide of type I collagen (CTX). In other exemplary embodiments, the marker of bone formation is bone-specific alkaline phosphatase (BSAP), osteocalcin (OstCa), and/or N-terminal extension of procollagen type 1 (P1NP).

In another aspect, described herein is a method of treating a bone-related disorder, wherein the method comprises administering to a mammal a formulation described herein in an amount effective to increase bone mineral density for the total body (e.g., head, trunk, arms, and legs) or at the hip (e.g., total hip and/or femoral neck), spine (e.g., lumbar spine), wrist, finger, shin bone and/or heel by about 1%, about 2%, about 3%, about 4%, about 5%, about 6%, about 8%, about 10%, about 12%, about 15%, about 18%, about 20%, about 25%, or 30% or more. In some embodiments, the bone mineral density of the mammalian subject before treatment is characteristic of osteoporosis or osteopenia, and one or more doses of the formulation are administered in an amount and for a time effective to improve bone mineral density such that the bone mineral density is no longer characteristic of osteoporosis and/or osteopenia. For example, one or more doses may be administered for an initial time period to increase bone mineral density to within 2.5, or one, standard deviations of the density normal for a young adult (i.e., a T-score≥−2.5 or a T-score≥−1). In exemplary embodiments, the initial time period is about 3 months or less, 6 months or less, 9 months or less, 1 year or less, 18 months or less, or longer. The method may further comprise subsequently administering one or more amounts of a formulation described herein effective to maintain bone mineral density, optionally for a maintenance time period of at least about 6 months, 1 year, 2 years or longer (e.g., over the life-time of the subject).

In another aspect, described herein is a method of treating a bone-related disorder in a mammalian subject by administering a formulation described herein, wherein the formulation comprises an anti-sclerostin antibody described herein at a dose of 0.1 mg/kg, 0.5 mg/kg, 1 mg/kg, about 2 mg/kg, about 3 mg/kg, about 4 mg/kg, about 5 mg/kg, about 6 mg/kg, about 7 mg/kg, about 8 mg/kg, about 9 mg/kg, about 10 mg/kg, about 20 mg/kg, about 25 mg/kg, about 26 mg/kg, about 27 mg/kg, about 28 mg/kg, about 29 mg/kg, about 30 mg/kg, about 31 mg/kg, about 32 mg/kg, about 33 mg/kg, about 34 mg/kg, about 35 mg/kg, about 36 mg/kg, about 37 mg/kg, about 38 mg/kg, about 39 mg/kg, about 40 mg/kg, about 41 mg/kg, about 42 mg/kg, about 43 mg/kg, about 44 mg/kg, about 45 mg/kg, about 46 mg/kg, about 47 mg/kg, about 48 mg/kg, or about 49 mg/kg, or about 50 mg/kg, about 55 mg/kg, about 60 mg/kg, about 65 mg/kg, about 70 mg/kg, about 75 mg/kg, about 80 mg/kg, about 85 mg/kg, about 90 mg/kg, about 95 mg/kg, or up to about 100 mg/kg. Ranges between any and all of these endpoints are also contemplated, e.g., about 1 mg/kg to about 3 mg/kg, about 1 mg/kg to about 5 mg/kg, about 1 mg/kg to about 10 mg/kg, about 1 mg/kg to about 20 mg/kg, about 1 mg/kg to about 40 mg/kg, about 5 mg/kg to about 30 mg/kg, about 5 mg/kg to about 20 mg/kg, about 2 mg/kg to about 6 mg/kg, about 1 mg/kg to about 4 mg/kg, or about 3 mg/kg to about 5 mg/kg.

In some embodiments, a dose from about 50 milligrams to about 1,000 milligrams is administered a subject (e.g., a human subject). For example, in some embodiments, the formulation comprises an anti-sclerostin antibody described herein at a dose of about 5 mg, 15 mg, 25 mg, 50 mg, about 60 mg, about 70 mg, about 80 mg, about 90 mg, about 100 mg, about 120 mg, about 150 mg, about 200 mg, about 240 mg, about 250 mg, about 280 mg, about 300 mg, about 350 mg, about 400 mg, about 420 mg, about 450 mg, about 500 mg, about 550 mg, about 600 mg, about 650 mg, about 700 mg, about 750 mg, about 800 mg, about 850 mg, about 900 mg, about 950 mg or up to about 1,000 mg of anti-sclerostin antibody. Ranges between any and all of these endpoints are also contemplated, e.g. about 50 mg to about 80 mg, about 70 mg to about 140 mg, about 70 mg to about 350 mg, about 70 mg to about 280 mg, about 70 mg to about 210, about 75 mg to about 100 mg, about 100 mg to about 150 mg, about 140 mg to about 210 mg, or about 150 mg to about 200 mg, or about 280 to about 410 mg.

In any of the methods described herein, the dose is administered at any interval, such as multiple times a week (e.g., twice or three times per week), once a week, once every two weeks, once every three weeks, or once every four weeks. In some or any embodiments, a formulation comprising an anti-sclerostin antibody described herein at a dose ranging from about 120 mg to about 210 mg is administered twice a week. In some or any embodiments, a formulation comprising an anti-sclerostin antibody described herein at a dose of about 140 mg of the formulation is administered twice a week. Any of the doses described herein may be administered as divided doses. For example, a formulation comprising an anti-sclerostin antibody described herein as a dose of 140 mg of anti-sclerostin antibody may be administered as two injections of 70 mg of anti-sclerostin antibody. Similarly, a dose of 210 mg of anti-sclerostin antibody may be administered as two injections of 105 mg of anti-sclerostin antibody.

Additionally, described herein is method of treating a bone-related disorder in a mammalian subject suffering from or at risk of hypocalcemia or hypercalcemia, a mammalian subject in which treatment with a parathyroid hormone or analog thereof is contraindicated, or a mammalian subject in which treatment with a bisphosphonate is contraindicated. The method comprises administering to the mammalian subject a formulation described herein in amount effective to increase the level of a marker of bone formation, without resulting in hypocalcemia or hypercalcemia (e.g., clinically-significant hypocalcemia or hypercalcemia).

In yet another aspect, described herein is the use of anti-sclerostin antibody crystals described herein in the preparation of a medicament for treating a bone-related disorder in a first amount for a first period of time, wherein the amount is effective to increase bone mineral density at the hip, spine, wrist, finger, shin bone and/or heel by at least about 3%, followed by a second amount of for a second period of time effective to maintain bone mineral density.

Also provided is the use of anti-sclerostin antibody crystals described herein to treat a bone-related disorder first amount for a first period of time, wherein the amount is effective to increase bone mineral density at the hip, spine, wrist, finger, shin bone and/or heel by at least about 3%, followed by a second amount of for a second period of time effective to maintain bone mineral density. Exemplary doses range from, about 0.1 to about 20 mg/kg, or about 0.1 to about 12 mg/kg, or about 0.5 to about 12 mg/kg, or about 1 to about 10 mg/kg, or about 1 to about 8 mg/kg, or about 2 to about 8 mg/kg, or about 3 to about 8 mg/kg. In some embodiments, a dose from about 50 milligrams to about 1,000 milligrams is administered a subject (e.g., a human subject). For example, in some embodiments, the formulation comprising an anti-sclerostin antibody described herein at a dose of about 5 mg, 15 mg, 25 mg, 50 mg, about 60 mg, about 70 mg, about 80 mg, about 90 mg, about 100 mg, about 120 mg, about 150 mg, about 200 mg, about 240 mg, about 250 mg, about 280 mg, about 300 mg, about 350 mg, about 400 mg, about 420 mg, about 450 mg, about 500 mg, about 550 mg, about 600 mg, about 650 mg, about 700 mg, about 750 mg, about 800 mg, about 850 mg, about 900 mg, about 950 mg or up to about 1,000 mg of anti-sclerostin antibody. Ranges between any and all of these endpoints are also contemplated, e.g. about 50 mg to about 80 mg, about 70 mg to about 140 mg, about 70 mg to about 350 mg, about 70 mg to about 280 mg, about 70 mg to about 210, about 75 mg to about 100 mg, about 100 mg to about 150 mg, about 140 mg to about 210 mg, or about 150 mg to about 200 mg, or about 280 to about 410 mg.

In some or any embodiments, a method or use described herein further comprises administering a second bone-enhancing therapeutic for the treatment of bone-related disorder described herein. Many therapeutics of this type are known in the art. In some embodiments, the bone-enhancing therapeutic is selected from the group consisting of an anti-resorptive drug, a bone-forming agent, an estrogen receptor modulator (including, but not limited to, raloxifene, bazedoxifene and lasofoxifene) and a drug that has an inhibitory effect on osteoclasts. In some embodiments, the second bone-enhancing agent is selected from the group consisting of, a bisphosphonate (including, but not limited to, alendronate sodium (FOSAMAX®), risedronate, ibandronate sodium (BONIVA®) and zoledronic acid (RECLAST®)), an estrogen or estrogen analogue, a calcium source, Tibolone, calcitonin, a calcitriol and hormone replacement therapy. In some embodiments, the second bone-enhancing agent includes, but is not limited to parathyroid hormone (PTH) or a peptide fragment thereof, PTH-related protein (PTHrp), bone morphogenetic protein, osteogenin, NaF, a $PGE_2$ agonist, a statin, an anti-DKK1 antibody or inhibitor, an anti-RANK ligand (RANKL) antibody (e.g., PROLIA®) or RANKL inhibitor, strontium ranelate, vitamin D, or a vitamin D derivative or mimic thereof. In some embodiments, the second bone-enhancing agent is Forteo® (Teriparatide, or recombinant human parathyroid hormone analog (1-34)) or Preotact® (parathyroid hormone). In some or any embodiments, the bone-enhancing agent is Protelos®.

In some embodiments, the second bone-enhancing agent is administered concurrently with the formulation (e.g., for a length of time within the treatment period). In other embodiments, the second bone-enhancing agent is administered for a length of time once the treatment period with the anti-sclerostin antibody has ended (i.e., for a maintenance period). In such embodiments, the second bone-enhancing agent is administered for a maintenance period of about 1 week to about 5 years.

The method may further comprise subsequently administering one or more amounts of the formulation effective to maintain bone mineral density, optionally for a maintenance period of at least about 12 weeks, 6 months, 1 year, 2 years, 3 years, 4 years, 5 years or longer (e.g., over the lifetime of the subject) after the treatment period has ended.

Additional aspects of the invention are defined or summarized in the following numbered paragraphs:

1. A crystal of an anti-sclerostin IgG antibody comprising light and heavy chain variable regions of SEQ ID NOS: 3 and 5, preferably having the amino acid sequences of SEQ ID NOS: 13 and 15.

2. A sterile formulation comprising a crystal of an anti-sclerostin IgG antibody, wherein at least 70% of the antibody is in a crystalline form.

3. A sterile formulation comprising a crystal of an anti-sclerostin IgG antibody, wherein at least 90% of the antibody is in a crystalline form.

4. The formulation of paragraph 2 or paragraph 3, wherein the IgG antibody comprises light and heavy chain variable regions of SEQ ID NOS: 3 and 5, preferably having the amino acid sequences of SEQ ID NOS: 13 and 15.

5. The crystal or formulation of any of the preceding paragraphs, wherein the crystal has a length of up to 500 μm.

6. The crystal or formulation of any of the preceding paragraphs, wherein the crystal has a shape selected from the group consisting of ellipsoids, rods and needles.

7. The formulation of any of the preceding claims, comprising crystals having a length of up to about 500 μm and a shape selected from the group consisting of ellipsoids, rods and needles or mixtures thereof.

8. The crystal or formulation of any of the preceding paragraphs, wherein the crystal comprises a salt selected from the group consisting of sodium dihydrogen phosphate, di-potassium hydrogen phosphate, sodium chloride, ammonium sulfate, potassium sodium tartrate tetrahydrate, tacsimate, sodium citrate dihydrate, sodium acetate trihydrate, di-ammonium tartrate, sodium malonate, acetate, calcium acetate, cacodylate, CHES, lithium sulfate, magnesium chloride, zinc acetate, cesium chloride, ammonium phosphate, sodium phosphase, potassium phosphate, sodium fluoride, potassium iodide, sodium idodide, ammonium iodide, sodium thiocyanate, potassium thiocyanate, sodium formate, potassium formate and ammonium formate.

9. The formulation of any of the preceding paragraphs, that is a lyophilized formulation.

10. The formulation of any of the preceding paragraphs, that is a liquid formulation.

11. The formulation of paragraph 10, comprising a concentration of at least about 100 mg of said antibody per ml of formulation.

12. The formulation of paragraph 10, comprising at least about 140 mg of antibody dispersed in 1.5 ml or less of liquid.

13. The formulation of paragraph 11 or paragraph 12, that is injectable through a syringe having a 20 Gauge needle or finer using a clinically acceptable amount of force.

14. The formulation of any of the preceding paragraphs, that retains at least 50% the in vivo activity, when given at the same dose and in the same manner, of a liquid formulation of said antibody that has not been crystallized.

15. The formulation of paragraph 11 or paragraph 12, that, when administered to a mammalian subject, mediates an increase in bone mineral density that is at least about 70% or of the level of bone mineral density increase mediated by a liquid formation of the antibody that has not been crystallized, when the formulation and liquid formulation of the antibody that has not been crystallized is administered to the subject at the same dose and in the same manner.

16. The formulation of paragraph 14 or paragraph 15, that is administered as a single dose.

17. The formulation of paragraph 14 or paragraph 15, that is administered in multiple doses.

18. The formulation of any of the preceding paragraphs comprising at least 20% PEG-3350.

19. The formulation of any of the preceding paragraphs comprising at least 10% PEG-8000.

20. The formulation of any of the preceding paragraphs, wherein the osmolality of the formulation ranges from about 180 to about 420 mOsm/kg.

21. A container comprising at least 50 mg of the antibody crystal of paragraph 1 for suspension in a volume of 0.5-2 mL.

22. A container comprising the formulation of paragraph 2 or paragraph 3.

23. The container of paragraph 21 or 22, wherein the container is a vial, syringe or injection device.

24. The container of paragraph 23, wherein the syringe needle is 20 Gauge or finer.

25. A method of resuspending the formulation of paragraph 9, comprising contacting the formulation with about 0.5-2 mL of a sterile suspension vehicle.

26. The method of paragraph 25, wherein the suspension vehicle is selected from the group consisting of glutamate, sorbitol, HEPES, dextrose and water or combinations thereof.

27. A method of making a crystal of an anti-sclerostin IgG antibody comprising light and heavy chain variable regions of SEQ ID NOS: 3 and 5, preferably having the amino acid sequences of SEQ ID NOS: 13 and 15, the method comprising combining a solution of the antibody with a crystallization reagent comprising a salt selected from the group consisting of sodium dihydrogen phosphate, di-potassium hydrogen phosphate, sodium chloride, ammonium sulfate, ammonium acetate, potassium sodium tartrate tetrahydrate, tacsimate, sodium citrate dihydrate, sodium acetate trihydrate, di-ammonium tartrate, sodium malonate, acetate, calcium acetate, cacodylate, CHES, lithium sulfate, lithium acetate dihydrate, magnesium chloride, magnesium acetate tetrahydrate, magnesium formate, magnesium nitrate, magnesium sulfate, zinc acetate, zinc chloride, zinc sulfate, cesium chloride, ammonium phosphate, sodium phosphase, potassium phosphate, sodium fluoride, potassium iodide, sodium idodide, ammonium iodide, sodium thiocyanate, potassium thiocyanate, sodium formate, potassium formate and ammonium formate, optionally at pH of about 6 to about 8, such that a crystal is formed.

28. The method of paragraph 27, wherein the concentration of the salt is from about 0.1 M to about 10 M.

29. The method of paragraph 27, wherein the reagent further comprises 2-methyl-2,4-pentanediol (MPD) or polyethylene glycol (PEG).

30. The method of paragraph 27, wherein the MPD is present at a concentration of about 0.1% to about 50%.

31. The method of paragraph 27, wherein the PEG has a molecular weight of about 400 kDa to about 20,000 kDa.

32. The method of paragraph 31, wherein the PEG is present at a concentration of 0.1% to about 50%.

33. A method of making a crystal of an anti-sclerostin IgG antibody comprising light and heavy chain variable regions of SEQ ID NOS: 3 and 5, preferably having the amino acid sequences of SEQ ID NOS: 13 and 15, the method comprising combining a solution of the antibody with a crystallization reagent comprising a member selected from the group consisting of succinic acid, PEG-1000, PEG-8000 and isopropanol, such that a crystal is formed.

34. The method of paragraph 33, wherein the crystallization reagent comprises
(a) from about 0.1 M to about 5 M succinic acid, from about 0.1 M to about 5 M HEPES and from about 0.1% (w/v) to about 60% (w/v) polyethylene glycol monomethyl ether 2000;
(b) from about 1% (w/v) to about 50% (w/v) PEG-8000, from about 0.05 M to about 5 M imidazole and from about 0.1 to about 5 M calcium acetate;
(c) from about 1% (w/v) to about 50% (w/v) PEG-8000, from about 0.05 M to about 5 M TRIS and from about 0.05 M to about 5 M magnesium chloride
(d) from about 10% to about 80% (w/v) PEG-1000, from about 0.05 M to about 5 M sodium/potassium phosphate and from about 0.05 M to about 5 M sodium chloride;
(e) from about 1% (w/v) to about 20% (w/v) PEG-8000, from about 0.05 M to about 5 M cacodylate, from about 0.1 M to about 2 M calcium acetate, and from about 10% to about 30% (w/v) glycerol; or
(f) from about 10% to about 30% isopropanol and from about 0.1 M to about 2 M sodium/potassium phosphate.

35. The method of any one of paragraphs 27-34, further comprising removing at least a portion of the crystallization reagent after crystals have formed.

36. The method of paragraph 35, wherein the portion of crystallization reagent is removed by centrifugation.

37. The method of paragraph 35, wherein the crystals are placed in a solution containing an organic additive.

38. The method of paragraph 37, further comprising the addition of an excipient to the solution.

39. The method of paragraph 38, wherein the excipient is selected from the group consisting of sucrose, trehalose, and sorbitol.

40. The method of paragraph 37, wherein the organic additive is ethanol or isopropanol.

41. The method of paragraph 27 or paragraph 33, further comprising drying crystals that have formed.

42. The method of paragraph 41, wherein the crystals are dried by exposure to air, or by exposure to a vacuum, or by exposure to nitrogen gas.

43. The method of paragraph 27 or 33, wherein at least 80% of the antibody is crystallized.

44. The method of any of paragraphs 27-43, that is a batch crystallization method, 45. An antibody crystal produced by the method of paragraph 27 or paragraph 33.

46. A method of increasing bone mineral density, treating a disorder associated with decreased bone density, treating a bone-related disorder, or improving outcomes in a procedure, replacement, graft, surgery or repair in a mammalian subject comprising administering the formulation of any of the preceding paragraphs in an amount effective to increase bone mineral density in the subject.

47. A crystal of an anti-sclerostin IgG antibody comprising light and heavy chain variable regions of SEQ ID NOS: 23 and 25, preferably having the amino acid sequences of SEQ ID NOS: 33 and 35.

48. The crystal of paragraph 47, wherein the crystal has a length of about 100 µM to about 500 µM or about 5 µM to about 50 µM.

49. The crystal of paragraph 47 or 48, wherein the crystal has an ellipsoidal shape.

50. The crystal of any one of paragraphs 47-49, wherein the crystal comprises a salt selected from the group consisting of sodium chloride, potassium chloride, sodium acetate, potassium phosphate and histidine.

51. A sterile formulation comprising the antibody crystal of paragraph 47, wherein at least 70% of the antibody is in crystalline form.

52. The crystal or formulation of any one of paragraphs 47-51, wherein the crystal has a length of up to about 500 µm.

53. The crystal or formulation of any one of the paragraphs 47-51 wherein the crystal has a shape selected from the group consisting of ellipsoids, rods and needles.

54. The formulation of any one of the paragraphs 51-53, comprising crystals having a length of up to about 500 μm and a shape selected from the group consisting of ellipsoids, rods and needles or mixtures thereof.

55. A method of making a crystal of an anti-sclerostin IgG antibody comprising light and heavy chain variable regions of SEQ ID NOS: 23 and 25, preferably having the amino acid sequences of SEQ ID NOS: 33 and 35, the method comprising combining a solution of the antibody with a crystallization reagent comprising a salt selected from the group consisting of potassium phosphate and histidine, optionally at pH of about 6 to about 8, such that a crystal is formed.

56. The method of paragraph 55, wherein the concentration of the salt is from about 1-30 mM, optionally about 10 mM.

57. The method of paragraph 55 or 56, wherein the crystallization reagent further comprises polyethylene glycol (PEG).

58. The method of paragraph 55, further comprising removing at least a portion of the crystallization reagent after crystals have formed.

59. The method of paragraph 58, wherein the portion of crystallization reagent is removed by centrifugation.

60. The method of paragraph 55, wherein the crystals are placed in a solution containing an organic additive.

61. The method of paragraph 55, further comprising the addition of an excipient to the solution.

62. The method of paragraph 61, wherein the excipient is selected from the group consisting of sucrose, trehalose, or sorbitol.

63. The method of paragraph 60, wherein the organic additive is ethanol or isopropanol.

64. The method of paragraph 55, further comprising drying crystals that have formed.

65. The method of paragraph 64, wherein the crystals are dried by exposure to air, or by exposure to a vacuum, or by exposure to nitrogen gas.

66. An antibody crystal produced by the method of any of paragraphs 55-65.

67. The formulation of any one of paragraphs 51-54 that is a lyophilized formulation.

68. The formulation of any one of paragraphs 51-54 that is a liquid formulation.

69. The formulation of paragraph 68, comprising a concentration of at least about 100 mg of said antibody per ml of formulation.

70. The formulation of any one of paragraphs 51-54, wherein the crystal comprises a salt selected from the group consisting of sodium chloride, potassium chloride, sodium acetate, potassium phosphate and histidine.

71. The formulation of any one of paragraphs 51-54, comprising sucrolose, trehalose and/or sorbitol.

72. The formulation of paragraph 68, wherein the osmolality of the formulation ranges from about 180 to about 420 mOsm/kg.

73. The formulation of paragraph 68, comprising at least about 140 mg or antibody dispersed in 1.5 ml or less of liquid.

74. The formulation of paragraph 69 or 73, that is injectable through a syringe having 20 Gauge needle or finer using a clinically acceptable amount of force.

75. The formulation of any of paragraphs 51-54 and 66-75, that retains at least 50% of the in vivo activity, when given at the same dose and in the same manner, of a liquid formulation of said antibody that has not been crystallized.

76. A container comprising at least 50 mg or more of an antibody crystal of paragraph 66 for suspension in a volume of 0.5-2 mL.

77. A container comprising a formulation of paragraph 51.

78. The container of paragraph 77, wherein the container is a vial, syringe or injection device.

79. The container of paragraph 78, wherein the syringe has a needle having a 20 Gauge or finer.

80. A method of resuspending the formulation of paragraph 67, comprising contacting the crystal with about 0.5-2 mL of sterile suspension vehicle.

81. The formulation of any one of paragraphs 51-54 and 66-75 that retains at least 50% of the in vivo activity, when given at the same dose and in the same manner, of a liquid formulation of said antibody that has not been crystallized.

82. The formulation of any one of paragraphs 51-54 and 66-75, that, when administered to a mammalian subject, mediates an increase in bone mineral density that is at least about 70% of the level of bone mineral density increase mediated by a liquid formulation of said antibody that has not been crystallized, wherein the formulation and the liquid formulation of the antibody that has not been crystallized is administered to the subject at the same dose and in the same manner.

83. The formulation of claim 81 or 82, that is administered as a single dose.

84. The formulation of claim 81 or 82, that is administered in multiple doses.

85. A method of increasing bone mineral density, treating a disorder associated with decreased bone density, treating a bone-related disorder, or improving outcomes in a procedure, replacement, graft, surgery or repair in a mammalian subject comprising administering the formulation of any one of paragraphs 51-54 and 66-75 in an amount effective to increase bone mineral density in the subject.

It should be understood that while various embodiments in the specification are presented using "comprising" language, under various circumstances, a related embodiment may also be described using "consisting of" or "consisting essentially of" language. It is to be noted that the term "a" or "an", refers to one or more, for example, "an immunoglobulin molecule," is understood to represent one or more immunoglobulin molecules. As such, the terms "a" (or "an"), "one or more," and "at least one" can be used interchangeably herein.

It should also be understood that when describing a range of values, the characteristic being described could be an individual value found within the range. For example, "a pH from about pH 4 to about pH 6," could be, but is not limited to, pH 4, 4.2, 4.6, 5.1, 5.5 etc. and any value in between such values. Additionally, "a pH from about pH 4 to about pH 6," should not be construed to mean that the pH of a formulation in question varies 2 pH units in the range from pH 4 to pH 6 during storage, but rather a value may be picked in that range for the pH of the solution, and the pH remains buffered at about that pH. In some embodiments, when the term "about" is used, it means the recited number plus or minus 5%, 10%, 15% or more of that recited number. The actual variation intended is determinable from the context.

In any of the ranges described herein, the endpoints of the range are included in the range. However, the description also contemplates the same ranges in which the lower and/or the higher endpoint is excluded. Additional features and variations of the invention will be apparent to those skilled in the art from the entirety of this application, including the drawing and detailed description, and all such features are intended as aspects of the invention. Likewise, features of the invention described herein can be re-combined into additional embodiments that also are intended as aspects of the invention, irrespective of whether the combination of features is specifically mentioned above as an aspect or embodiment of the invention. Also, only such limitations which are described herein as critical to the invention should be viewed as such; variations of the invention lacking limitations which have not been described herein as critical are intended as aspects of the invention.

BRIEF DESCRIPTION OF THE FIGURES

FIG. 1A provides the osmolality data for the various Ab-30Rm crystallization screens.

FIG. 2 shows Ab-30Rm crystal morphology in #12 0.05 M Tris pH 8.0 and at different percentages of PEG-3350, as observed and recorded using a Carl Zeiss Axiocam MRc Microscope.

DETAILED DESCRIPTION

Figure 1B:
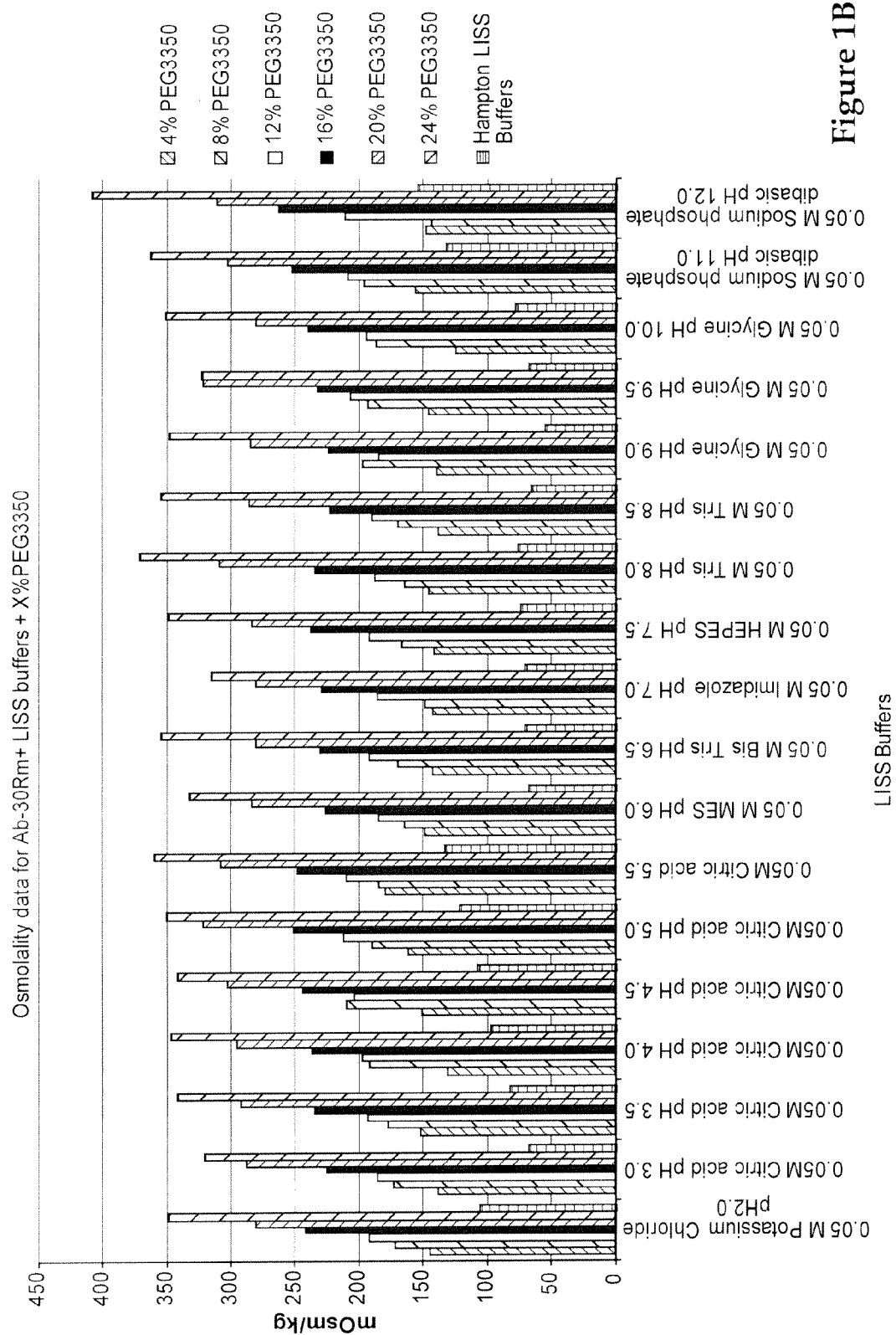
FIG. 1B is a graph showing the osmolality data of compositions Ab-30Rm, LISS Buffers and X % PEG-3350.

Described herein are crystals of anti-sclerostin immunoglobulin type G (IgG) antibodies, suitable for use in formulations for parenteral administration; methods of using such crystals of Ab-30 or Ab-31 to prepare formulations for use as medicaments; formulations comprising high concentrations of a crystalline anti-sclerostin antibody, methods of using these formulations for treatment, methods of administering these formulations, e.g., subcutaneously or intramuscularly, and containers or kits comprising these formulations.

I. Antibodies in the Formulation

In some embodiments, the anti-sclerostin antibody in the formulation is present at a concentration (a "high protein concentration") of at least about 100 mg/ml, about 101 mg/ml, about 102 mg/ml, about 103 mg/ml, about 104 mg/ml, about 105 mg/ml, about 106 mg/ml, about 107 mg/ml, about 108 mg/ml, about 109 mg/ml, about 110 mg/ml, about 111 mg/ml, about 112 mg/ml, about 113 mg/ml, about 114 mg/ml, about 115 mg/ml, about 116 mg/ml, about 117 mg/ml, about 118 mg/ml, about 119 mg/ml, about 120 mg/ml, about 121 mg/ml, about 122 mg/ml, about 123 mg/ml, about 124 mg/ml, about 125 mg/ml, about 126 mg/ml, about 127 mg/ml, about 128 mg/ml, about 129 mg/ml, about 130 mg/ml, about 131 mg/ml, about 132 mg/ml, about 132 mg/ml, about 133 mg/ml, about 134 mg/ml, about 135 mg/ml, about 136 mg/ml, about 137 mg/ml, about 138 mg/ml, about 139 mg/ml, about 140 mg/ml, about 141 mg/ml, about 142 mg/ml, about 143 mg/ml, about 144 mg/ml, about 145 mg/ml, about 146 mg/ml, about 147 mg/ml, about 148 mg/ml, about 149 mg/ml, about 150 mg/ml, about 151 mg/ml, about 152 mg/ml, about 153 mg/ml, about 154 mg/ml, about 155 mg/ml, about 156 mg/ml, about 157 mg/ml, about 158 mg/ml, about 159 mg/ml, about 160 mg/ml, about 161 mg/ml, about 162 mg/ml, about 163 mg/ml, about 164 mg/ml, about 165 mg/ml, about 166 mg/ml, about 167 mg/ml, about 168 mg/ml, about 169 mg/ml, about 170 mg/ml, about 171 mg/ml, about 172 mg/ml, about 173 mg/ml, about 174 mg/ml, about 175 mg/ml, about 176 mg/ml, about 177 mg/ml, about 178 mg/ml, about 179 mg/ml, about 180 mg/ml, about 181 mg/ml, about 182 mg/ml, about 183 mg/ml, about 184 mg/ml, about 185 mg/ml, about 186 mg/ml, about 187 mg/ml, about 188 mg/ml, about 189 mg/ml, about 190 mg/ml, about 191 mg/ml, about 192 mg/ml, about 193 mg/ml, about 194 mg/ml, about 195 mg/ml, about 196 mg/ml, about 197 mg/ml, about 198 mg/ml, about 199 mg/ml, about 200 mg/ml, and may range up to, e.g., about 400 mg/ml, about 390 mg/ml, about 380 mg/ml, about 370 mg/ml, about 360 mg/ml, about 350 mg/ml, about 340 mg/ml, about 330 mg/ml, about 320 mg/ml, about 310 mg/ml, about 300 mg/ml, about 290 mg/ml, about 280 mg/ml, about 270 mg/ml, about 260 mg/ml, about 250 mg/ml, or about 240 mg/ml. Any range featuring a combination of the foregoing endpoints is contemplated, including but not limited to: about 70 mg/ml to about 250 mg/ml, about 70 mg/ml to about 140 mg/ml, about 70 mg/ml to about 350 mg/ml, about 50 mg/ml to about 80 mg/ml, about 70 mg/ml to about 210 mg/ml, about 100 mg/ml to about 150 mg/ml, about 280 mg/ml to about 410 mg/ml, about 100 mg/ml to about 200 mg/ml, about 100 mg/ml to about 250 mg/ml, about 100 mg/ml to about 300 mg/ml, about 100 mg/ml to about 320 mg/ml or about 100 mg/ml to about 350 mg/ml.

The anti-sclerostin antibody is optionally formulated as a single dose (e.g., about 70 to about 450 mg of anti-sclerostin antibody). In some embodiments, the dose comprises at least about 5 mg, 15 mg, 25 mg, 50 mg, about 60 mg, about 70 mg, about 80 mg, about 90 mg, about 100 mg, about 120 mg, about 150 mg, about 200 mg, about 240 mg, about 250 mg, about 280 mg, about 300 mg, about 350 mg, about 400 mg, about 420 mg, about 450 mg, about 500 mg, about 550 mg, about 600 mg, about 650 mg, about 700 mg, about 750 mg, about 800 mg, about 850 mg, about 900 mg, about 950 mg or up to about 1,000 mg of anti-sclerostin antibody. Ranges between any and all of these endpoints are also contemplated, e.g. about 50 mg to about 80 mg, about 70 mg to about 140 mg, about 70 mg to about 350 mg, about 70 mg to about 280, about 70 mg to about 210 mg, about 75 mg to about 100 mg, about 100 mg to about 150 mg, about 140 mg to about 210 mg, or about 150 mg to about 200 mg, or about 280 mg to about 410 mg of anti-sclerostin antibody. The dose is administered at any interval, such as multiple times a week (e.g., twice or three times per week), once a week, once every two weeks, once every three weeks, or once every four weeks. For example, in some or any embodiments, a dose of anti-sclerostin antibody ranging from about 120 mg to about 210 mg is administered twice a week. In some or any embodiments, a dose of about 140 mg of the anti-sclerostin antibody is administered twice a week. Any of the doses described herein may be administered as divided doses. For example, a dose of 140 mg of anti-sclerostin antibody may be administered as two injections of 70 mg of anti-sclerostin antibody. Similarly, a dose of 210 mg of anti-sclerostin antibody may be administered as two injections of 105 mg of anti-sclerostin antibody and a dose of 140 mg of anti-sclerostin antibody may be administered as seven injections of 20 mg of anti-sclerostin antibody.

In some embodiments, the formulation comprises about 70 mg or 75 mg of anti-sclerostin antibody, which is suitable for administering a single dose of about 1 mg/kg. In other embodiments, the formulation comprises about 50 mg, or about 60 mg, or about 70 mg, or about 80 mg, or about 90 mg, or about 100 mg, or about 120 mg, or about 130 mg, or about 140 mg or about 150 mg, or about 160 mg, or about 170 mg, or about 180 mg, or about 190 mg, or about 200 mg, or about 210 mg or about 220 mg or about 230 mg; or about 240 mg, about 250 mg, or about 250 mg to about 450 mg; or about 280 mg or 290 mg or about 300 mg; or about 350 mg or 360 mg; or about 420 mg or 430 mg or 440 mg or 450 mg of the anti-sclerostin antibody. In any of such embodiments, the formulation comprises an amount of anti-sclerostin antibody suitable for administering a single dose of about 2 to about 6 mg/kg, or about 1 mg/kg to about 4 mg/kg, or about 3 mg/kg to about 5 mg/kg, or about 1 mg/kg to about 3 mg/kg body weight (e.g., about 2 mg/kg, or about 3 mg/kg, or about 4 mg/kg, or about 5 mg/kg or about 6 mg/kg body weight).

In some embodiments, the anti-sclerostin antibody is Ab-30. In some embodiments, the anti-sclerostin antibody is Ab-31. Antibodies Ab-30 and Ab-31 were previously described in U.S. Patent Application Publication No. 2007/0110747, the disclosure of which, including sequence listing, is incorporated herein by reference in its entirety. In other embodiments, the anti-sclerostin antibody is Ab-30R (SEQ ID NOs: 16-19) or Ab-30Rm (SEQ ID NOs: 17 and 19-21).

The anti-sclerostin antibody described herein binds to sclerostin of SEQ ID NO: 1 with a Kd of $10^{-6}$ M or less, or $10^{-7}$ M or less, or $10^{-8}$ M or less, or $10^{-9}$ M or less. Affinity can be determined by any means known in the art, including via Biacore technology and ELISA as described in, e.g., US Patent Application Publication Bo. 2007/0110747.

In some embodiments, the antibody comprises the heavy and/or light chain of antibody Ab-30, Ab-30R, Ab-30Rm, or Ab-31. The amino acid sequences of the mature full length light and heavy chains of antibodies Ab-30, Ab-30R, Ab-30Rm, or Ab-31, including the constant region, are set forth in SEQ ID NOs: 13 and 15; SEQ ID NOs: 16 and 19; SEQ ID NOs: 20 and 19; and SEQ ID NOs: 33 and 35, respectively. The corresponding cDNA sequence encoding the full length light and heavy chains of antibodies Ab-30 and Ab-31, including the constant region, are set forth in SEQ ID NOs: 12 and 14; SEQ ID NOs: 32 and 34 respectively.

The term "Ab-30 antibody" as used herein refers to an IgG immunoglobulin composed of two heavy chains and two light chains, wherein the heavy chain comprises SEQ ID NO: 5 (Ab-30 heavy chain variable region) fused to an IgG constant region, and the light chain comprises SEQ ID NO: 3 (Ab-30 light chain variable region) fused to a light chain constant region. Preferably Ab-30 comprises the mature heavy and light chain amino acid sequences set forth in SEQ ID NOs: 15 and 13, respectively. In some embodiments, the antibody comprises the heavy and/or light chain variable region of antibody Ab-30 SEQ ID NO: 5 (Ab-30 heavy chain variable region) fused to a human heavy chain constant region of isotype IgG1, 2, 3 or 4 (e.g., native, consensus or modified, and a number of modifications that are known not to affect binding are known in the art), and/or SEQ ID NO: 3 (Ab-30 light chain variable region) fused to a human light chain constant region (e.g., native, consensus or modified to have a number of modifications that are known not to affect binding SEQ ID NO: 17 (Ab-30R heavy chain variable region) fused to a human heavy chain constant region of isotype IgG1, 2, 3 or 4, and/or SEQ ID NO: 16 (Ab-30R light chain variable region) fused to a human light chain constant region; SEQ ID NO: 17 (Ab-30Rm heavy chain variable region) fused to a human heavy chain constant region of isotype IgG1, 2, 3 or 4, and/or SEQ ID NO: 20 (Ab-30Rm light chain variable region) fused to a human light chain constant region.

The term "Ab-31 antibody" as used herein refers to an IgG immunoglobulin composed of two heavy chains and two light chains, wherein the heavy chain comprises SEQ ID NO: 25 (Ab-31 heavy chain variable region) fused to an IgG constant region, and the light chain comprises SEQ ID NO: 23 (Ab-31 light chain variable region) fused to a light chain constant region. Preferably Ab-31 comprises the mature heavy and light chain amino acid sequences set forth in SEQ ID NOs: 35 and 33, respectively. Thus, in some embodiments, the antibody comprises the heavy and/or light chain variable region of antibody Ab-31 SEQ ID NO: 25 (Ab-30 heavy chain variable region) fused to a human heavy chain constant region of isotype IgG1, 2, 3 or 4 (e.g., (e.g., native, consensus or modified to have a number of modifications that are known not to affect binding) and/or SEQ ID NO: 23 (Ab-31 light chain variable region) fused to a human light chain constant region (e.g., (e.g., native, consensus or modified to have a number of modifications that are known not to affect binding).

In some embodiments, the antibody comprises amino acid sequences obtainable by expressing in mammalian host cells the cDNA encoding the heavy and/or light chain, or alternatively the heavy and/or light chain variable region, of antibody Ab-30, Ab-30R, Ab-30Rm, or Ab-31. The term "antibody" refers to an intact immunoglobulin, e.g. in the case of IgG, a tetrameric immunoglobulin composed of two heavy chains and two light chains (e.g., chimeric, humanized, or human versions preferably having full length heavy and/or light chains, optionally with mutations within the framework or constant regions that retain the anti-sclerostin binding properties).

An "isolated" antibody refers to an antibody, as that term is defined herein, that has been separated from a component of its natural environment. Contaminant components of its natural environment are materials that would interfere with diagnostic or therapeutic uses for the antibody, and may include enzymes, hormones, and other proteinaceous or nonproteinaceous solutes. In certain embodiments, the antibody will be purified (1) to greater than 95% by weight of antibody, and most preferably more than 99% by weight, (2) to a degree sufficient to obtain at least 15 residues of N-terminal or internal amino acid sequence, or (3) to homogeneity by SDS-PAGE under reducing or nonreducing conditions using Coomassie blue or, preferably, silver stain. Isolated naturally occurring antibody includes the antibody in situ within recombinant cells since at least one component of the antibody's natural environment will not be present. Ordinarily, however, isolated antibody will be prepared by at least one purification step.

A "monoclonal" antibody refers to an antibody obtained from a population of substantially homogeneous antibodies, i.e., the individual antibodies comprising the population are identical except for possible naturally occurring mutations that may be present in minor amounts, compared to a "polyclonal" antibody which refers to a mixed population of antibodies of diverse sequence that bind diverse epitopes. The phrase "humanized antibody" refers to an antibody derived from a sequence of a non-human antibody, typically a rodent monoclonal antibody, which comprises modifications that render the sequence more human-like. Alternatively, a humanized antibody may be derived from a chimeric antibody. The phrase "human" antibody refers to an antibody derived from human sequences, e.g., through screening libraries of human antibody genes through known techniques such as phage display, or produced using transgenic animals that have no endogenous immunoglobulin production and are engineered to contain human immunoglobulin loci.

An "immunoglobulin G" or "native IgG antibody" is a tetrameric glycoprotein. In a naturally-occurring immunoglobulin, each tetramer is composed of two identical pairs of polypeptide chains, each pair having one "light" (about 25 kDa) and one "heavy" chain (about 50-70 kDa). The amino-terminal portion of each chain includes a "variable" ("V") region of about 100 to 110 or more amino acids primarily responsible for antigen recognition. The carboxy-terminal portion of each chain defines a constant region primarily responsible for effector function. Immunoglobulins can be assigned to different classes depending on the amino acid sequence of the constant domain of their heavy chains. Heavy chains are classified as mu ($\mu$), delta ($\Delta$), gamma ($\gamma$), alpha ($\alpha$), and epsilon ($\epsilon$), and define the antibody's isotype as IgM, IgD, IgG, IgA, and IgE, respectively. Several of these may be further divided into subclasses or isotypes, e.g., IgG1, IgG2, IgG3, IgG4, IgA1 and IgA2. Different isotypes have different effector functions; for example, IgG1 and IgG3 isotypes have antibody-dependent cellular cytotoxicity (ADCC) activity. Human light chains are classified as kappa ($\kappa$) and lambda ($\lambda$) light chains. Within light and heavy chains, the variable and constant regions are joined by a "J" region of about 12 or more amino acids, with the heavy chain also including a "D" region of about 10 more amino acids. See generally, Fundamental Immunology, Ch. 7 (Paul, W., ed., 2nd ed. Raven Press, N.Y. (1989)).

The term "hypervariable" region refers to amino acid residues from a complementarity determining region or CDR (i.e., residues 24-34 (L1), 50-56 (L2) and 89-97 (L3) in the light chain variable domain and 31-35 (H1), 50-65 (H2) and 95-102 (H3) in the heavy chain variable domain as described by Kabat et al., Sequences of Proteins of Immunological Interest, 5th Ed. Public Health Service, National Institutes of Health, Bethesda, Md. (1991)). "Framework" or FR residues are those variable region residues other than the hypervariable region residues.

The term "variant" when used in connection with antibodies refers to a polypeptide sequence of an antibody that contains at least one amino acid substitution, deletion, or insertion in the variable region or the portion equivalent to the variable region, provided that the variant retains the desired binding affinity or biological activity. In addition, the antibodies as described herein may have amino acid modifications in the constant region to modify effector function of the antibody, including half-life or clearance, ADCC and/or CDC activity. Such modifications can enhance pharmacokinetics or enhance the therapeutic effectiveness of the antibody, for example. See Shields et al., J. Biol. Chem., 276(9):6591-6604 (2001), incorporated by reference herein in its entirety. In the case of IgG1, modifications to the constant region, particularly the hinge or CH2 region, may increase or decrease effector function, including ADCC and/or CDC activity. In other embodiments, an IgG2 constant region is modified to decrease antibody-antigen aggregate formation. In the case of IgG4, modifications to the constant region, particularly the hinge region, may reduce the formation of half-antibodies.

The term "modification" when used in connection with antibodies or polypeptides described herein, includes but is not limited to, one or more amino acid change(s) (including substitutions, insertions or deletions); chemical modifications that do not interfere with sclerostin-binding activity; covalent modification by conjugation to therapeutic or diagnostic agents; labeling (e.g., with radionuclides or various enzymes); covalent polymer attachment such as pegylation (derivatization with polyethylene glycol) and insertion or substitution by chemical synthesis of non-natural amino acids. In some embodiments, modified polypeptides (including antibodies) of the invention will retain the binding properties of unmodified molecules of the invention.

The term "derivative" when used in connection with antibodies or polypeptides of the invention refers to antibodies or polypeptides that are covalently modified by conjugation to therapeutic or diagnostic agents, labeling (e.g., with radionuclides or various enzymes), covalent polymer attachment such as pegylation (derivatization with polyethylene glycol) and insertion or substitution by chemical synthesis of non-natural amino acids. In some embodiments, derivatives of the invention will retain the binding properties of underivatized molecules of the invention.

Proteins and non-protein agents may be conjugated to the antibodies by methods that are known in the art. Conjugation methods include direct linkage, linkage via covalently attached linkers, and specific binding pair members (e.g., avidin-biotin). Such methods include, for example, that described by Greenfield et al., Cancer Research 50, 6600-6607 (1990) for the conjugation of doxorubicin and those described by Arnon et al., Adv. Exp. Med. Biol. 303, 79-90 (1991) and by Kiseleva et al., Mol. Biol. (USSR) 25, 508-514 (1991) for the conjugation of platinum compounds.

II. Production of Crystals, Crystal Formulations and Compositions

Polypeptide crystals are grown by controlled crystallization of polypeptides from aqueous solutions or from aqueous solutions containing organic solvents or additives. Solution conditions that may be controlled include, for example, the rate of evaporation of solvent, organic solvents or additives, the presence of appropriate co-solutes and buffers, pH, and temperature. A comprehensive review of the various factors affecting the crystallization of proteins has been published by McPherson (1985, Methods Enzymol 114: 112-120). In addition, McPherson and Gilliland (1988, J Crystal Growth, 90: 51-59) have compiled comprehensive lists of polypeptides that have been crystallized, as well as the conditions under which they were crystallized. A compendium of crystals and crystallization recipes, as well as a repository of coordinates of solved protein structures, is maintained by the Protein Data Bank at the Brookhaven National Laboratory (www.resb.org/pdb/; Bernstein et al., 1977, J Mol Biol 112: 535-542). It should be noted, however, that the conditions reported in most of the above-cited references have been optimized to yield, in most instances, a few large, diffraction quality crystals. Accordingly, it will be appreciated by those of skill in the art that these conditions vary from protein to protein, and do not provide a high yielding process for the large scale production of crystals of any given polypeptide.

In general, crystals are produced by combining the polypeptide (i.e., antibody) to be crystallized with an appropriate aqueous solvent or aqueous solvent containing appropriate crystallization agents, such as salts or organic solvents or additives (collectively the "crystallization reagent"). The solvent is combined with the polypeptide and may be subjected to agitation at a temperature determined experimentally to be appropriate for the induction of crystallization and acceptable for the maintenance of polypeptide activity and stability. Laboratory-scale methods for crystallization include hanging drop vapor diffusion, sitting drop vapor diffusion, microdialysis, microbatch, under oil, in gel and sandwich drop methods. The solvent can optionally include co-crystallization additives, such as precipitants, fatty acids, reducing agents, glycerol, sulfobetaine, surfactants, polyols, divalent cations, co-factors, or chaotropes, as well as buffer species to control pH.

"Co-crystallization additives" include compounds that facilitate crystallization of a polypeptide and/or compounds that stabilize the protein and protect against denaturation. Examples of co-solutes include ammonium acetate, ammonium chloride, ammonium fluoride, ammonium formate, ammonium nitrate, ammonium phosphate, ammonium sulfate, cadmium chloride, cadmium sulfate, calcium acetate, calcium chloride, cesium chloride, cobaltous chloride, $CH_3(CH_2)_{15}N(CH_3)_3^+Br.^-$ (CTAB), di-ammonium citrate, di-ammonium hydrogen phosphate, di-ammonium phosphate, di-ammonium tartrate, di-potassium phosphate, di-sodium phosphate, di-sodium tartrate, DL-malic acid, ferric chloride, L-proline, lithium acetate, lithium chloride, lithium nitrate, lithium sulfate, magnesium acetate, magnesium chloride, magnesium formate, magnesium nitrate, magnesium sulfate, nickel chloride, potassium acetate, potassium bromide, potassium chloride, potassium citrate, potassium fluoride, potassium formate, potassium nitrate, potassium phosphate, potassium sodium tartrate, potassium sulfate, potassium thiocyanate, sodium acetate, sodium bromide, sodium chloride, sodium citrate, sodium fluoride, sodium formate, sodium malonate, sodium nitrate, sodium phosphate, sodium sulfate, sodium thiocyanate, succinic acid, tacsimate, tri-ammonium citrate, tri-lithium citrate, trimethylamine N-oxide, tri-potassium citrate, tri-sodium citrate, zinc acetate, zinc sulfate, and other compounds that function to supply co-solutes. "Crystallization buffers" include compounds that maintain the pH of a solution in a desired range to facilitate crystallization of a polypeptide. Examples include ACES (N-(2-acetamido)-2-aminoethanesulfonic acid), BES (N,N-bis(2-hydroxyethyl)-2-aminoethanesulfonic acid), Bicine (N,N-Bis(2-hydroxyethyl)glycine), BIS-TRIS (2,2-bis-(hydroxymethyl)-2,2',2"-nitrilotriethanol), boric acid, CAPS (3-[cyclohexylamino]-1-propanesulfonic acid), EPPS (HEPPS, 4-(2-Hydroxyethyl)piperazine-1-propanesulfonic acid), Gly-Gly ($NH_2CH_2CONHCH_2COOH$, glycyl-glycine), HEPES (4-(2-hydroxyethyl)piperazine-1-ethanesulfonic acid), imidazole, MES (2-morpholinoethanesulfonic acid), MOPS (3-(N-morpholino)-propanesulfonic acid), PIPES (piperazine-1,4-bis(2-ethanesulfonic acid)), sodium acetate, sodium bicarbonate, sodium phosphate monobasic (sodium dihydrogen phosphate), TAPS (N-[tris-(hydroxymethyl)methyl]-3-aminopropanesulfonic acid), TAPSO (N-[tris(hydroxymethyl)methyl]-3-amino-2-hydroxypropanesulfonic acid), TES (N-[tris(hydroxymethyl)methyl]-2-aminoethanesulfonic acid), Tricine (N-[tris(hydroxymethyl)methyl]glycine), Tris-HCl, TRIZMA (2-amino-2-(hydroxymethyl)-1,3-propanediol), and other compounds that function to maintain a solution at or near a specified pH.

The selection of precipitants are one factor affecting crystallization. For example, PEG products, e.g., of molecular weight 600 to 20,000 kD, can be used. PEG-3350 is a long polymer precipitant or dehydrant which works by volume exclusion effect. Lyotropic salts, such as ammonium sulfate, promote precipitation processes, as do short-chain fatty acids, such as caprylic acid. Polyionic species also are useful precipitants.

Antibodies for use in formulations for subcutaneous injection, for example, preferably are precipitated at a physiologic pH range and in a crystallization reagent that provides isotonic osmolality.

The need for additives, co-solutes, buffers, etc. and their concentrations are determined experimentally to facilitate crystallization. Some examples of suitable crystallization conditions for a polypeptide are described in Example 1 below.

Ab-30, in particular, is easily crystallized under a variety of conditions. Various morphologies of Ab-30 crystals can be grown under scale-up conditions whereby the antibody in a liquid formulation is added to a volume of known crystallization reagent and stored in a sealed container. Ab-30 crystals can be grown under these conditions in less than 24 hours, at room temperature or refrigerated temperatures (4° C.) and have been shown to produce slow release and high yield.

In an industrial-scale process, the controlled precipitation leading to crystallization can best be carried out by the simple combination of polypeptide, precipitant, co-solutes and, optionally, buffers in a batch process. As another option, polypeptides may be crystallized by using polypeptide precipitates as the starting material ("seeding"). In this case, polypeptide precipitates are added to a crystallization solution and incubated until crystals form. Alternative laboratory crystallization methods, such as dialysis or vapor diffusion, can also be adopted. McPherson, supra and Gilliland, supra, include a comprehensive list of suitable conditions in their reviews of the crystallization literature. Occasionally, in cases in which the crystallized polypeptide is to be cross-linked, incompatibility between an intended crosslinking agent and the crystallization medium might require exchanging the crystals into a more suitable solvent system.

According to some embodiments, polypeptide crystals, crystal formulations and compositions are prepared by the following process: first, the polypeptide is crystallized. Next, excipients or ingredients as described herein are added directly to the mother liquor. Alternatively, the crystals are suspended in a solution of excipient or other formulary ingredients, after the mother liquor is removed, for a minimum of 1 hour to a maximum of 24 hours. The excipient concentration is typically between about 0.01% to 30% w/w, which corresponds to a polypeptide crystal concentration of 99.99% to 70% w/w, respectively. In one embodiment, the excipient concentration is between about 0.1% to 10%, which corresponds to a crystal concentration of 99.9 to 90% w/w, respectively. The mother liquor can be removed from the crystal slurry either by filtration, buffer exchange, or by centrifugation. Subsequently, the crystals are washed optionally with solutions of 50% to 100% one or more organic solvents or additives such as, for example, ethanol, methanol, isopropanol or ethyl acetate, either at room temperature or at temperatures between −20° C. to 25° C. The crystals are dried by passing a stream of nitrogen, air, or inert gas over the crystals. Alternatively, the crystals are dried by air drying or by lyophilization or by vacuum drying. The drying is carried out for a minimum 1 hour to a maximum of 72 hours after washing, until the moisture content of the final product is below 10% by weight, most preferably below 5%. Finally, micronizing of the crystals can be performed if necessary. The drying of polypeptide crystals is the removal of water, organic solvent or additive, or liquid polymer by means including drying with $N_2$, air, or inert gases; vacuum oven drying; lyophilization; washing with a volatile organic solvent or additive followed by evaporation of the solvent; or evaporation in a fume hood. Typically, drying is achieved when the crystals become a free-flowing powder. Drying may be carried out by passing a stream of gas over wet crystals. The gas may be selected from the group consisting of: nitrogen, argon, helium, carbon dioxide, air or combinations thereof. The polypeptide crystals of the invention can be further processed to achieve a desired particle size distribution by micronizing in a suitable mill, such as a jet mill, and the components of the particle or powder formulation may be mixed before or after micronizing. The diameter of the particles achieved can be in the range of 0.1 to 100 micrometers, or in the range of 0.2 to 10 micrometers, or in the range of 10 to 50 micrometers, or in the range of 0.5 to 2 micrometers. In one embodiment, the particles formed from the polypeptide crystals are in the range of 0.5 to 1 micrometers, which is a suitable range for e.g., inhalation.

According to some embodiments, when preparing protein crystals, protein crystal formulations or compositions, enhancers (such as surfactants) are not added during crystallization. Excipients or ingredients are added to the mother liquor after crystallization, at a concentration of between about 1%-10% w/w, alternatively at a concentration of between about 0.1%-25% w/w, alternatively at a concentration of between about 0.1%-50% w/w. These concentrations correspond to crystal concentrations of 99%-90% w/w, 99.9%-75% w/w and 99.9%-50% w/w, respectively. The excipient or ingredient is incubated with the crystals in the mother liquor for about 0.1-3 hrs, alternatively the incubation is carried out for 0.1-12 hrs, alternatively the incubation is carried out for 0.1-24 hrs.

In some or any embodiments, the ingredient or excipient is dissolved in a solution other than the mother liquor, and the protein crystals are removed from the mother liquor and suspended in the excipient or ingredient solution. The ingredient or excipient concentrations and the incubation times are the same as those described above.

Polypeptide Crystals

As used herein, "crystal" or "crystalline" refers to one form of the solid state of matter, which is distinct from a second form—the amorphous solid state. Crystals display characteristic features including a lattice structure, characteristic shapes, and optical properties such as refractive index and birefringence. A crystal consists of atoms arranged in a pattern that repeats periodically in three dimensions (C. S. Barrett, Structure of Metals, 2nd ed., McGraw-Hill, New York, 1952, p. 1). In contrast, amorphous material is a non-crystalline solid form of matter, sometimes referred to as an amorphous precipitate. Such precipitates have no molecular lattice structure characteristic of the crystalline solid state and do not display birefringence or other spectroscopic characteristics typical of the crystalline forms of matter.

Polypeptide crystals are polypeptide molecules arranged in a crystal lattice. Polypeptide crystals contain a pattern of specific polypeptide-polypeptide interactions that are repeated periodically in three dimensions. The polypeptide crystals of this invention are to be distinguished from amorphous solid forms or precipitates of polypeptides, such as those obtained by lyophilizing a polypeptide solution.

In polypeptide crystals, the polypeptide molecules form asymmetric units which are arranged together to form symmetric units. The geometric structure of the symmetric units of polypeptide crystals can be, for example, cubic, hexagonal, monoclinic, orthorhombic, tetragonal, triclinic, or trigonal. The overall structure of the crystals in their entirely can be, for example, in the form of bipyramids, cubes, needles, plates, prisms, rhomboids, rods, or spheres, or combinations thereof. Other observed forms include block-shaped, UFO shaped, football shaped, leaf shaped, wheat shaped, singlet shaped, feather-shaped, straw-shaped, chrysanthemum-shaped, spherical or mixtures thereof. In some embodiments, the crystals are observed in clusters. Crystals that are of the "cubic" structural class can more specifically have octadecahedral or dodecahedral crystal forms. The diameter of the crystals is defined as the Martin's diameter. It is measured as the length of the line, parallel to the ocular scale, that divides the randomly oriented crystals into two equal projected areas. Crystals in forms such as needles or rods will also have a maximal dimension that is referred to herein as the length of the crystal. The crystals are also characterized by x-ray diffraction.

Testing Properties of Crystalline Polypeptides

After polypeptide crystals are formed, they can be subjected to various analyses to confirm their polypeptide content and to further examine their physical structure. For example, if necessary, individual crystals can be removed from the crystallization solution and washed with aqueous or organic solvents or additives, then dried (for example, by air drying, by passing a stream of inert gas over the crystal, by lyophilization, or by vacuum). Crystals can be isolated, removed from the crystal growth drop, and then mounted for X-ray diffraction.

Crystals can also be characterized by a variety of means described in the art. See, e.g., Basu et al., Expert Opin. Biol. Thera. 4, 301-317 (2004), incorporated herein by reference in its entirety for its disclosure of protein crystal production and formulation procedures, and analytical tools for characterizing crystals and their component protein. While powder X-ray diffraction is commonly used to identify crystalline material, it requires very large and perfect protein crystals and is not commonly applied to the protein microcrystals typically used in crystalline formulations. Electron diffraction and solid state nuclear magnetic resonance (ss-NMR) can be applied to characterize crystals. Crystal size, shape and morphology (e.g., surface morphology) can be inspected, for example, by light microscopy, transmission electron microscopy, scanning electron microscopy, atomic force microscopy, and/or light scattering (e.g., photon correlation spectroscopy or DLS, low angle laser light scattering or LAALS). Total surface area and porosity of crystals can also be characterized. Mass spectrometry, micro-attenuated total reflectance Fourier transform infrared spectroscopy (FTIR) and/or differential scanning calorimetry (DSC) can provide information about protein primary and secondary structure.

As another example, polypeptide crystals can be removed from crystallization solution and washed or rinsed, or the majority of crystallization solution can be removed from the crystals and replaced with a different solution. In this way, the particular salt that was used in the crystallization procedure can be replaced in the crystal lattice with a different salt. In one embodiment of the invention, crystallized Ab-30, Ab-30R, Ab-30Rm, or Ab-31 antibodies are separated from the crystallization buffer and placed in a solution containing a salt of sodium, potassium, or magnesium (for example, sodium acetate, sodium chloride, sodium citrate, sodium phosphate, sodium sulfate, potassium chloride, potassium citrate, or magnesium sulfate). For X-ray diffraction, the replacement solution can contain heavy atoms useful in determining the atomic coordinates of the crystallized polypeptide. As a further embodiment, antibody Ab-30, Ab-30R, Ab-30Rm, or Ab-31 can be co-crystallized with sclerostin for determination of the detailed structure of the Ab-30, Ab-30R, Ab-30Rm, or Ab-31-sclerostin interaction.

In a further example, polypeptide crystals can be removed from crystallization solution and solubilized in an appropriate buffer for further testing, such as an SDS-containing buffer for analysis of the polypeptide that had been crystallized by gel electrophoresis. Methods for analysis of proteins by gel electrophoresis are well known and include staining a gel with silver or Coomassie blue dye, and comparing the electrophoretic migration of the polypeptide that had been crystallized with the migration of polypeptide markers of known molecular weight. In another method, the polypeptide is visualized in the gel by use of a labeled antibody that specifically binds to the polypeptide. Polypeptides that have been crystallized can also be solubilized in buffers appropriate for amino acid sequencing by Edman degradation, for mass spectrometry, for other spectrographic scattering, refraction, diffraction, or absorption studies, or for labeling of the polypeptide by attachment of a label molecule to the polypeptide.

III. Formulations for Therapeutic Administration

As used herein, the term "composition" as used herein means a mixture comprising at least two components. In particular, described herein are compositions comprising a crystalline anti-sclerostin antibody, and compositions prepared using a crystalline anti-sclerostin antibody. In some embodiments, the composition or formulation comprising or prepared using a crystalline anti-sclerostin antibody is suitable for injection and/or administration to a patient in need thereof. Compositions to be administered for pharmaceutical purposes to patients are substantially sterile and do not contain agents that are unduly toxic or infectious to the recipient.

In some embodiments, crystalline anti-sclerostin antibodies such as crystalline antibody Ab-30, Ab-30R, Ab-30Rm, or Ab-31 are administered in the form of a physiologically acceptable composition (also referred to herein as a pharmaceutical composition or as a pharmaceutical formulation) comprising a crystalline anti-sclerostin antibody that is formulated with one or more of the following: physiologically acceptable carriers, excipients, or diluents. Such carriers, excipients, or diluents are nontoxic to recipients at the dosages and concentrations employed. Ordinarily, the preparation of such compositions entails combining the crystalline anti-sclerostin antibody with one or more of the following: buffers, antioxidants such as ascorbic acid, low molecular weight polypeptides (such as those having fewer than 10 amino acids), proteins, amino acids, carbohydrates such as glucose, sucrose or dextrins, chelating agents such as EDTA, glutathione and other stabilizers and excipients. In liquid formulations, neutral buffered saline or saline mixed with nonspecific serum albumin are exemplary appropriate diluents. In accordance with appropriate industry standards, preservatives may also be added, such as benzyl alcohol. Further examples of components that may be employed in pharmaceutical formulations are presented in Remington's Pharmaceutical Sciences, 16$^{th}$ Ed., Mack Publishing Company, Easton, Pa., 1980, and in the Handbook of Pharmaceutical Excipients, published jointly by the American Pharmaceutical Association and the Pharmaceutical Society of Great Britain.

In one embodiment, it is contemplated that the formulation described herein is prepared in a bulk formulation and as such, the components of the pharmaceutical composition are adjusted so that they are higher than would be required for administration, and are diluted appropriately prior to administration.

The antibody crystals described herein can be formulated as a solid crystalline or powder formulation in forms suitable for storage and handling, and in forms suitable for inhalation or pulmonary administration, for example in the form of powders for the preparation of aerosol formulations. In an further embodiment, the antibody crystals can be formulated in a liquid solution of such crystals, or in a slurry of such crystals. In another embodiment, the antibody crystals are used to prepare a liquid formulation, such as an aqueous formulation, for therapeutic administration.

A. Solid Formulations of Antibody Crystals

Solid formulations of antibody crystals include crystals that have been substantially isolated from liquid solution or dried, and are present as free crystals or as particles in, for example, powder form. In the present context, the term "powder" refers to a collection of essentially dry particles, i.e. the moisture content being below about 10% by weight, or below 6% by weight, or below 4% by weight. Polypeptide crystals or powders can be optionally combined with carriers or surfactants. Suitable carrier agents include, but are not limited to, 1) carbohydrates, e.g., monosaccharides such as fructose, galactose, glucose and sorbose; 2) disaccharides, such as lactose and trehalose; 3) polysaccharides, such as raffinose, maltodextrins and dextrans; 4) alditols, such as mannitol and xylitol; 5) inorganic salts, such as sodium chloride; and 6) organic salts, such as sodium citrate and sodium ascorbate. In certain embodiments, the carrier is selected from the group consisting of trehalose, raffinose, mannitol, sorbitol, xylitol, inositol, sucrose, sodium chloride, and sodium citrate. Surfactants can be selected from the group consisting of salts of fatty acids, bile salts or phospholipids. Fatty acids salts include salts of $C_{10-14}$ fatty acids, such as sodium caprate, sodium laurate, and sodium myristate. Bile salts include salts of ursodeoxycholate, taurocholate, glycocholate, and taurodihydrofusidate. In one embodiment, the surfactant is a salt of taurocholate such as sodium taurocholate. Phospholipids that can be used as surfactants include lysophosphatidylcholine. The molar ratio of crystalline polypeptide to surfactant in a powder formulation of the present invention is for example 9:1 to 1:9, or between 5:1 to 1:5, or between 3:1 to 1:3.

B. Crystals in Solution or Slurries

Also described herein is a method for rendering polypeptide crystals suitable for storage in suspensions comprising replacing the crystallization buffer (the mother liquor) with a non-aqueous solvent. In yet another embodiment, the crystalline slurry can be rendered solid by spinning out the first solvent and washing the remaining crystalline solid using a second organic solvent or additive to remove water, followed by evaporation of the non-aqueous solvent. Non-aqueous slurries of crystalline therapeutic proteins are especially useful for subcutaneous delivery.

In one such embodiment, the polypeptide crystals described herein are combined with liquid organic additives with the object of stabilizing the polypeptide crystals. Such a mixture can be characterized as an aqueous-organic mixture that comprises n % organic additive, where n is between 1 and 99, and m % aqueous solution, where m is 100–n. Examples of organic additives include phenolic compounds, such as m-cresol or phenol or a mixture thereof, and acetone, methyl alcohol, methyl isobutyl ketone, chloroform, 1-propanol, isopropanol, 2-propanol, acetonitrile, 1-butanol, 2-butanol, ethyl alcohol, cyclohexane, dioxane, ethyl acetate, dimethylformamide, dichloroethane, hexane, isooctane, methylene chloride, tert-butyl alcohol, toluene, carbon tetrachloride, or combinations thereof.

C. Liquid Formulations

Another embodiment provided herein is an aqueous formulation that allows for stable long-term storage of a pharmaceutical composition wherein a crystalline anti-sclerostin antibody is the active ingredient used in the preparation of the pharmaceutical composition. This formulation is useful, in part, because it is more convenient to use for the patient, as this formulation does not require any extra steps such as rehydrating. As used herein, a "solution" or "liquid formulation" is a liquid preparation that contains one or more chemical substances dissolved in a suitable solvent or mixture of mutually miscible solvents.

Reconstitution is the dissolution of polypeptide crystals or crystal formulations or compositions in an appropriate buffer or pharmaceutical formulation.

Resuspension refers to the suspension of polypeptide crystals in an appropriate buffer or pharmaceutical formulation. In some em D. Components of Pharmaceutical Formulations The present pharmaceutical composition is prepared by combining, in addition to a crystalline anti-sclerostin antibody as described above, one or more of the following types of ingredients or excipients listed in the paragraphs below, many or all of which are available from commercial suppliers. It will be understood by one of ordinary skill in the art that the combining of the various components to be included in the composition can be done in any appropriate order, namely, the buffer can be added first, middle or last and the tonicity modifier can also be added first, middle or last. It is also to be understood by one of ordinary skill in the art that some of these chemicals can be incompatible in certain combinations, and accordingly, are easily substituted with different chemicals that have similar properties but are compatible in the relevant mixture. There is knowledge in the art regarding the suitability of various combinations of excipients and other ingredients or materials present in, for example, the containers used for storage of the pharmaceutical composition and/or the devices used for therapeutic administration (see, for example, Akers, 2002, J Pharm Sci 91: 2283-2300).

Non-limiting examples of additional agents that can be included in the formulations described herein include acidifying agents (including, but not limited to, acetic acid, glacial acetic acid, citric acid, fumaric acid, hydrochloric acid, diluted hydrochloric acid, malic acid, nitric acid, phosphoric acid, diluted phosphoric acid, sulfuric acid, tartaric acid, and other suitable acids); active ingredients (including, but not limited to, additional active ingredients to reduce injection site discomfort, and non-steroidal anti-inflammatory drugs such as, for example, tromethamine, in an appropriate dosage); aerosol propellants (including, but not limited to, butane, dichlorodifluoromethane, dichlorotetrafluoroethane, isobutane, propane and trichloromonofluoromethane); alcohol denaturants (including, but not limited to, denatonium benzoate, methyl isobutyl ketone, sucrose octacetate); alkalizing agents (including, but not limited to, strong ammonia solution, ammonium carbonate, diethanolamine, diisopropanolamine, potassium hydroxide, sodium bicarbonate, sodium borate, sodium carbonate, sodium hydroxide, trolamine); anticaking agents (including, but not limited to, calcium silicate, magnesium silicate, colloidal silicon dioxide and talc); antifoaming agents (including, but not limited to, dimethicone and simethicone); chelating agents (also called sequestering agents) (including, but not limited to, edetate disodium, ethylenediaminetetraacetic acid and salts and edetic acid); coating agents (including, but not limited to, sodium carboxymethylcellulose, cellulose acetate, cellulose acetate phthalate, ethylcellulose, gelatin, pharmaceutical glaze, hydroxypropyl cellulose, hydroxypropyl methylcellulose, hydroxypropyl methylcellulose phthalate, methacrylic acid copolymer, methylcellulose, polyethylene glycol, polyvinyl acetate phthalate, shellac, sucrose, titanium dioxide, carnauba wax, microcystalline wax and zein); colors (including, but not limited to, caramel, erythrosine (FD&C Red No. 3); FD&C Red No. 40; FD&C Yellow No. 5; FD&C Yellow No. 6; FD&C Blue No. 1; red, yellow, black, blue or blends and ferric oxide); complexing agents (including, but not limited to, ethylenediaminetetraacetic acid (EDTA) and salts thereof, edetic acid, gentisic acid ethanolmaide and oxyquinoline sulfate); desiccants (including, but not limited to, calcium chloride, calcium sulfate and silicon dioxide); filtering aids (including, but not limited to, powdered cellulose and purified siliceous earth); flavors and perfumes (including, but not limited to, anethole, anise oil, benzaldehyde, cinnamon oil, cocoa, ethyl vanillin, menthol, methyl salicylate, monosodium glutamate, orange flower oil, orange oil, peppermint, peppermint oil, peppermint spirit, rose oil, stronger rose water, thymol, tolu balsam tincture, vanilla, vanilla tincture and vanillin); humectants (including, but not limited to, glycerin, hexylene glycol, propylene glycol and sorbitol); ointment bases (including, but not limited to, lanolin, anhydrous lanolin, hydrophilic ointment, white ointment, yellow ointment, polyethylene glycol ointment, petrolatum, hydrophilic petrolatum, white petrolatum, rose water ointment and squalane); plasticizers (including, but not limited to, castor oil, diacetylated monoglycerides, diethyl phthalate, glycerin, mono- and diacetylated monoglycerides, polyethylene glycol, propylene glycol, triacetin and triethyl citrate); polymer membranes (including, but not limited to, cellulose acetate); solvents (including, but not limited to, acetone, alcohol, diluted alcohol, amylene hydrate, benzyl benzoate, butyl alcohol, carbon tetrachloride, chloroform, corn oil, cottonseed oil, ethyl acetate, glycerin, hexylene glycol, isopropyl alcohol, methyl alcohol, methylene chloride, methyl isobutyl ketone, mineral oil, peanut oil, polyethylene glycol, propylene carbonate, propylene glycol, sesame oil, water for injection, sterile water for injection, sterile water for irrigation and purified water); sorbents (including, but not limited to powdered cellulose, charcoal, purified siliceous earth; and carbon dioxide sorbents: barium hydroxide lime and soda lime); stiffening agents (including, but not limited to, hydrogenated castor oil, cetostearyl alcohol, cetyl alcohol, cetyl esters wax, hard fat, paraffin, polyethylene excipient, stearyl alcohol, emulsifying wax, white wax and yellow wax); suppository bases (including, but not limited to, cocoa butter, hard fat and polyethylene glycol); Suspending and/or viscosity-increasing agents (including, but not limited to, acacia, agar, alginic acid, aluminum monostearate, bentonite, purified bentonite, magma bentonite, carbomer 934p, carboxymethylcellulose calcium, carboxymethylcellulose sodium, carboxymethycellulose sodium 12, carrageenan, microcrystalline and carboxymethylcellulose sodium cellulose, dextrin, gelatin, guar gum, hydroxyethyl cellulose, hydroxypropyl cellulose, hydroxypropyl methylcellulose, magnesium aluminum silicate, methylcellulose, pectin, polyethylene oxide, polyvinyl alcohol, povidone, propylene glycol alginate, silicon dioxide, colloidal silicon dioxide, sodium alginate, tragacanth and xanthan gum); sweetening agents (including, but not limited to, aspartame, dextrates, dextrose, excipient dextrose, fructose, mannitol, saccharin, calcium saccharin, sodium saccharin, sorbitol, solution sorbitol, sucrose, compressible sugar, confectioner's sugar and syrup); tablet binders (including, but not limited to, acacia, alginic acid, sodium carboxymethylcellulose, microcrystalline cellulose, dextrin, ethylcellulose, gelatin, liquid glucose, guar gum, hydroxypropyl methylcellulose, methycellulose, polyethylene oxide, povidone, pregelatinized starch and syrup); tablet and/or capsule diluents (including, but not limited to, calcium carbonate, dibasic calcium phosphate, tribasic calcium phosphate, calcium sulfate, microcrystalline cellulose, powdered cellulose, dextrates, dextrin, dextrose excipient, fructose, kaolin, lactose, mannitol, sorbitol, starch, pregelatinized starch, sucrose, compressible sugar and confectioner's sugar); tablet disintegrants (including, but not limited to, alginic acid, microcrystalline cellulose, croscarmellose sodium, corspovidone, polacrilin potassium, sodium starch glycolate, starch and pregelatinized starch); tablet and/or capsule lubricants (including, but not limited to, calcium stearate, glyceryl behenate, magnesium stearate, light mineral oil, polyethylene glycol, sodium stearyl fumarate, stearic acid, purified stearic acid, talc, hydrogenated vegetable oil and zinc stearate); ehicles (include, but are not limited toflavored and/or sweetened (aromatic elixir, compound benzaldehyde elixir, iso-alcoholic elixir, peppermint water, sorbitol solution, syrup, tolu balsam syrup); oleaginous (almond oil, corn oil, cottonseed oil, ethyl oleate, isopropyl myristate, isopropyl palmitate, mineral oil, light mineral oil, myristyl alcohol, octyldodecanol, olive oil, peanut oil, persic oil, sesame oil, soybean oil, squalane); solid carriers such as sugar spheres; and sterile vehicles (bacteriostatic water for injection, bacteriostatic sodium chloride injection); and water-repelling agents (including, but not limited to, cyclomethicone, dimethicone and simethicone).

Aggregation inhibitors, which reduce a polypeptide's tendency to associate in inappropriate or unwanted ternary or quaternary complexes, can also be included in the formulations described herein. Suitable aggregation inhibitors include the amino acids L-arginine and/or, L-cysteine, which can act to reduce aggregation of polypeptides containing an Fc domain over long periods, e.g., two years or more. The concentration of the aggregation inhibitor in the formulation can be between about 1 mM to 1 M, or about 10 mM to about 200 mM, or about 10 mM to about 100 mM, or about 15 mM to about 75 mM, or about 5 mM to about 10 mM, or about 5 mM to about 15 mM, or about 10 mM to about 20 mM, or about 150 mM to about 250 mM, or about 25 mM.

Antioxidants may also be included in the formulations described herein. Antioxidants contemplated for use in the preparation of the formulations include amino acids such as glycine and lysine, chelating agents such as EDTA and DTPA, and free-radical scavengers such as sorbitol and mannitol. Additional antioxidants include ascorbic acid, ascorbyl palmitate, butylated hydroxyanisole, butylated hydroxytoluene, hypophosphorous acid, monothioglycerol, propyl gallate, sodium bisulfite, sodium formaldehyde sulfoxylate, sodium metabisulfite, sodium thiosulfate, sulfur dioxide, tocopherol, and tocopherols excipient. Also contemplated for use in inhibiting oxidation is nitrogen or carbon dioxide overlay. Nitrogen or carbon dioxide overlay can be introduced to the headspace of a vial or prefilled syringe during the filling process.

Buffering agents, which maintain the pH of the pharmaceutical formulation in a desired range, can also be included in the formulations described herein. When the pH of the pharmaceutical composition is set at or near physiological levels, comfort of the patient upon administration is maximized. In particular, in certain embodiments the pH of a pharmaceutical composition is within a pH range of about 4.0 to 8.4, or a pH range of about 5.0 to 8.0, or a pH range of about 5.8 to 7.4, or about 6.2 to 7.0. It is to be understood that the pH can be adjusted as necessary to maximize stability and solubility of the polypeptide in a particular formulation and as such, a pH outside of physiological ranges, yet tolerable to the patient, is within the scope of the invention. Various buffers suitable for use in the pharmaceutical composition of the invention include histidine, alkali salts (sodium or potassium phosphate or their hydrogen or dihydrogen salts), sodium citrate/citric acid, sodium acetate/acetic acid, potassium citrate, maleic acid, ammonium acetate, tris-(hydroxymethyl)-aminomethane (tris), various forms of acetate and diethanolamine, ammonium carbonate, ammonium phosphate, boric acid, lactic acid, phosphoric acid, potassium metaphosphate, potassium phosphate monobasic, sodium lactate solution, and any other pharmaceutically acceptable pH buffering agent known in the art. pH-adjusting agents such as hydrochloric acid, sodium hydroxide, or a salt thereof, may also be included in order to obtain the desired pH. One suitable buffer is sodium phosphate for maintaining pharmaceutical compositions at or near pH 6.2. In another example, acetate is a more efficient buffer at pH 5 than pH 6 so less acetate may be used in a solution at pH 5 than at pH 6. The concentration of the buffer in the formulation can be between about 1 mM to about 1 M, or about 0.1 mM to about 1 mM or about 0.1 mM to about 0.5 mM or about 10 mM to about 300 mM.

Polymeric carriers can also be included in the formulations described herein. Polymeric carriers are polymers used for encapsulation of polypeptide crystals for delivery of polypeptide, including biological delivery. Such polymers include biocompatible and biodegradable polymers. The polymeric carrier may be a single polymer type or it may be composed of a mixture of polymer types. Polymers useful as the polymeric carrier, include for example, poly(acrylic acid), poly(cyanoacrylates), poly(amino acids), poly(anhydrides), poly(depsipeptide), poly(esters) such as poly(lactic acid) or PLA, poly(lactic-co-glycolic acid) or PLGA, poly (B-hydroxybutryate), poly(caprolactone) and poly(dioxanone); poly(ethylene glycol), poly((hydroxypropyl)methacrylamide, poly [(organo)phosphazene], poly(ortho esters), poly(vinyl alcohol), poly(vinylpyrrolidone), maleic anhydride-alkyl vinyl ether copolymers, pluronic polyols, albumin, natural and synthetic polypeptides, alginate, cellulose and cellulose derivatives, collagen, fibrin, gelatin, hyaluronic acid, oligosaccharides, glycaminoglycans, sulfated polysaccharides, or any conventional material that will encapsulate polypeptide crystals.

Preservatives, such as antimicrobial preservatives, are also contemplated for use in the formulations described herein. Suitable preservatives include, but are not limited to, benzalkonium chloride, benzalkonium chloride solution, benzelthonium chloride, benzoic acid, benzyl alcohol, butylparaben, cetylpyridinium chloride, chlorobutanol, chlorocresol, cresol, dehydroacetic acid, ethylparaben, methylparaben, methylparaben sodium, phenol, phenylethyl alcohol, phenylmercuric acetate, phenylmercuric nitrate, potassium benzoate, potassium sorbate, propylparaben, propylparaben sodium, sodium benzoate, sodium dehydroacetate, sodium propionate, sorbic acid, thimerosal, and thymol. The amount of preservative included will be in the range of 0% to 2% (w/v) or about 1% (w/v).

Solubilizing agents and stabilizers (also referred to as emulsifying agents, co-solutes, or co-solvents) that increase the solubility of the polypeptide and/or stabilize the polypeptide while in solution (or in dried or frozen forms) can also be added to a pharmaceutical composition. Examples of solubilizing and stabilizing agents include but are not limited to sugars/polyols such as: sucrose, lactose, glycerol, xylitol, sorbitol, mannitol, maltose, inositol, trehalose, glucose; polymers such as: serum albumin (bovine serum albumin (BSA), human SA (HSA), or recombinant HA), dextran, PVA, hydroxypropyl methylcellulose (HPMC), polyethyleneimine, gelatin, polyvinylpyrrolidone (PVP), hydroxyethylcellulose (HEC); non-aqueous solvents such as: polyhydric alcohols (e.g., PEG, ethylene glycol and glycerol), dimethylsulfoxide (DMSO), and dimethylformamide (DMF); amino acids such as: proline, L-methionine, L-serine, sodium glutamic acid, alanine, glycine, lysine hydrochloride, sarcosine, and gamma-aminobutyric acid; surfactants such as: Tween-80, Tween-20, SDS, polysorbate, polyoxyethylene copolymer; and miscellaneous stabilizing excipients such as: potassium phosphate, sodium acetate, ammonium sulfate, magnesium sulfate, sodium sulfate, trimethylamine N-oxide, betaine, metal ions (e.g., zinc, copper, calcium, manganese, and magnesium), CHAPS, monolaurate, 2-O-beta-mannoglycerate; or any of the following: acacia, cholesterol, diethanolamine (adjunct), glyceryl monostearate, lanolin alcohols, lecithin, mono- and di-glycerides, monoethanolamine (adjunct), oleic acid (adjunct), oleyl alcohol (stabilizer), poloxamer, polyoxyethylene 50 stearate, polyoxyl 35 caster oil, polyoxyl 40 hydrogenated castor oil, polyoxyl 10 oleyl ether, polyoxyl 20 cetostearyl ether, polyoxyl 40 stearate, polysorbate 20, polysorbate 40, polysorbate 60, polysorbate 80, propylene glycol diacetate, propylene glycol monostearate, sodium lauryl sulfate, sodium stearate, sorbitan monolaurate, sorbitan monooleate, sorbitan monopalmitate, sorbitan monostearate, stearic acid, trolamine, emulsifying wax; wetting and/or solubilizing agents such as benzalkonium chloride, benzethonium chloride, cetylpyridinium chloride, docusate sodium, nonoxynol 9, nonoxynol 10, octoxynol 9, polyoxyl 50 stearate, tyloxapol; or any combination of the above. The concentration of solubilizers/stabilizers in the formulation can be between about 0.001% to 5% weight, or about 0.1% to 2% weight. In one embodiment, the stabilizer is selected from sorbitan mono-9-octadecenoate poly(oxy-1,2-ethanediyl) derivatives, including but not limited to, polysorbate 80 or polysorbate 20. The amount of polysorbate 20 or 80 to be used in this embodiment is in the range of 0.001% to 1.0% (w/v), such as 0.005% (w/v), in single use or in multi-dose formulations. In another embodiment, free L-methionine in the range of 0.05 mM to 50 mM is included in the formulation: the amount of free L-methionine is 0.05 mM to 5 mM for single use formulations, and 1 mM to 10 mM for multi-dose formulations.

Tonicity modifiers can also be included in the formulations described herein. Tonicity modifiers are understood to be molecules that contribute to the osmolality of a solution. The osmolality of a pharmaceutical composition is preferably regulated in order to maximize the active ingredient's stability and also to minimize discomfort to the patient upon administration. Serum is approximately 300+/−50 milliosmolals per kilogram. It is generally preferred that a pharmaceutical composition be isotonic with serum, i.e., having the same or similar osmolality, which is achieved by addition of a tonicity modifier, thus it is contemplated that the osmolality will be from about 180 to about 420 milliosmolals, however, it is to be understood that the osmolality can be either higher or lower as specific conditions require. Examples of tonicity modifiers suitable for modifying osmolality include, but are not limited to amino acids (e.g., arginine, cysteine, histidine and glycine), salts (e.g., sodium chloride, potassium chloride and sodium citrate) and/or saccharides (e.g., sucrose, glucose, dextrose, glycerin, and mannitol). The concentration of the tonicity modifier in the formulation can be between about 1 mM to 1 M, or about 10 mM to about 200 mM. In one embodiment, the tonicity modifier is sodium chloride within a concentration range of 0 mM to 200 mM. In another embodiment, the tonicity modifier is sorbitol or trehalose and no sodium chloride is present.

In certain embodiments, the formulation comprises a compound selected from the following, or any combination thereof: salts of 1) amino acids such as glycine, arginine, aspartic acid, glutamic acid, lysine, asparagine, glutamine, proline; 2) carbohydrates, e.g. monosaccharides such as glucose, fructose, galactose, mannose, arabinose, xylose, ribose; 3) disaccharides, such as lactose, trehalose, maltose, sucrose; 4) polysaccharides, such as maltodextrins, dextrans, starch, glycogen; 5) alditols, such as mannitol, xylitol, lactitol, sorbitol; 6) glucuronic acid, galacturonic acid; 7) cyclodextrins, such as methyl cyclodextrin, hydroxypropyl-β-cyclodextrin; 8) inorganic salts, such as sodium chloride, potassium chloride, magnesium chloride, phosphates of sodium and potassium, boric acid ammonium carbonate and ammonium phosphate; 9) organic salts, such as acetates, citrate, ascorbate, lactate; 10) emulsifying or solubilizing agents such as acacia, diethanolamine, glyceryl monostearate, lecithin, monoethanolamine, oleic acid, oleyl alcohol, poloxamer, polysorbates, sodium lauryl sulfate, stearic acid, sorbitan monolaurate, sorbitan monostearate, and other sorbitan derivatives, polyoxyl derivatives, wax, polyoxyethylene derivatives, sorbitan derivatives; 11) viscosity increasing reagents such as agar, alginic acid and its salts, guar gum, pectin, polyvinyl alcohol, polyethylene oxide, cellulose and its derivatives propylene carbonate, polyethylene glycol, hexylene glycol, tyloxapol; and 12) particular ingredients such as sucrose, trehalose, lactose, sorbitol, lactitol, inositol, salts of sodium and potassium such as acetate, phosphates, citrates, borate, glycine, arginine, polyethylene oxide, polyvinyl alcohol, polyethylene glycol, hexylene glycol, methoxy polyethylene glycol, gelatin, and hydroxypropyl-β-cyclodextrin.

E. Sustained-Release Forms

In some embodiments, sustained-release forms (also called "controlled-release" forms) of crystalline anti-sclerostin antibodies are used, including sustained-release forms of crystalline antibody Ab-30, Ab-30R, Ab-30Rm, or Ab-31; sustained- or controlled-release forms comprising crystalline antibody Ab-30, Ab-30R, Ab-30Rm, or Ab-31 and a substance for extending the physical release or biological availability of the crystalline antibody Ab-30, Ab-30R, Ab-30Rm, or Ab-31 over a desired period of time.

Sustained-release forms suitable for use in the disclosed methods include, but are not limited to, crystalline antibody Ab-30, Ab-30R, Ab-30Rm, or Ab-31 that is encapsulated in a sustained-release material such as a slowly-dissolving biocompatible polymer (for example, the polymeric carriers described herein, the alginate microparticles described in U.S. Pat. No. 6,036,978, or the polyethylene-vinyl acetate and poly(lactic-glucolic acid) compositions described in U.S. Pat. No. 6,083,534), admixed with such a polymer (including topically applied hydrogels), and/or encased in a biocompatible semi-permeable implant. Further embodiments of the invention include additional sustained-release forms such as polymeric microparticles, wherein a mixture of the active ingredient and sustained-release means such as polymers (for example, PLGA) are dispersed within a continuous phase, and the resulting dispersion is directly lyophilized to remove water and organic solvents or additives and form said microparticles (U.S. Pat. No. 6,020,004, incorporated herein by reference in its entirety); injectable gel compositions comprising a biodegradable anionic polysaccharide such as an alginate ester, a polypeptide, and at least one bound polyvalent metal ion (U.S. Pat. No. 6,432,449, incorporated herein by reference in its entirety); injectable biodegradable polymeric matrices having reverse thermal gelation properties and optionally pH-responsive gelation/de-gelation properties (U.S. Pat. Nos. 6,541,033 and 6,451,346, incorporated herein by reference in their entireties); biocompatible polyol:oil suspensions, such as those wherein the suspension comprises polyol in the range of from about 15% to about 30% by weight (U.S. Pat. No. 6,245,740, incorporated by reference in its entirety). Such sustained release forms are suitable for continuous delivery of polypeptides through administration in the form of a depot, wherein the depot can be an implant, or can be in the form of injectable microspheres, nanospheres, or gels. The above listed U.S. patents (U.S. Pat. Nos. 6,036,978; 6,083,534; 6,020,004; 6,432,449; 6,541,033; 6,451,346, and 6,245,740) are incorporated in their entirety by reference herein. In addition, sustained- or controlled-release forms of crystalline polypeptides of the invention comprise types of sustained release materials such as those described in Kim, C., 2000, "Controlled Release Dosage Form Design", Techonomic Publishing Co., Lancaster Pa., which include the following: natural polymers (gelatin, sodium alginic acid, xanthan gum, arabic gum, or chitosan), semi-synthetic polymers or cellulose derivatives (e.g., methylcellulose, ethylcellulose, hydroxyethylcellulose, hydroxypropylcellulose, hydroxyethylmethylcellulose, hydroxypropylmethylcellulose, sodium carboxymethylcellulose, cellulose acetate, cellulose acetate butyrate, cellulose acetate proprionate, cellulose acetatephthalate, or hydroxypropylmethylcellulose phthalate), and synthetic polymers (e.g., ion exchange resins (methacrylic acid, sulfonated polystyrene/divinylbenzene), polyacrylic acid (Carbopol), poly(MMA/MAA), poly(MMA/DEAMA), poly(MMA/EA), poly(vinylacetate phthalate), poly(vinyl alcohol), poly(vinyl pyrrolidone), poly(lactic acid), poly(glycolic acid), poly(lactic/glycolic acid), polyethylene glycol, polyethylene oxide, poly(dimethyl silicone), poly(hydroxyethyl methacrylate), poly(ethylene/vinyl acetate), poly(ethylene/vinyl alcohol), polybutadiene, poly(anhydride), poly(orthoester), and poly(glutamic acid)).

Further embodiments disclosed herein include Ab-30, Ab-30R, Ab-30Rm, or Ab-31 crystals encapsulated in at least one polymeric carrier to form microspheres by virtue of encapsulation within the matrix of the polymeric carrier to preserve their native and biologically active tertiary structure, as described in U.S. Pat. No. 6,541,606, which is incorporated in its entirety by reference herein. Ab-30, Ab-30R, Ab-30Rm, or Ab-31 crystals or formulations thereof are suspended in a polymeric carrier, such as PLGA, which is dissolved in an organic solvent or additive. Such encapsulated Ab-30, Ab-30R, Ab-30Rm, or Ab-31 crystals maintain the biological activity of antibody Ab-30, Ab-30R, Ab -30Rm, or Ab-31 for a longer period of time than antibody Ab-30, Ab-30R, Ab-30Rm, or Ab -31 in solution when stored under comparable conditions.

IV. Kits

As an additional aspect, described herein are kits which comprise one or more formulations described herein packaged in a manner which facilitates their use for administration to subjects. In one embodiment, such a kit includes a formulation described herein (e.g., a composition comprising any of the antibodies described therein), packaged in a container such as a sealed bottle, vessel, single-use or multi-use vial, prefilled syringe, or prefilled injection device, optionally with a label affixed to the container or included in the package that describes use of the compound or composition in practicing the method. In one aspect, the compound or composition is packaged in a unit dosage form. The kit may further include a device suitable for administering the composition according to a specific route of administration. Preferably, the kit contains a label that describes use of an antibody described herein or formulation described herein.

V. Dosages

The dosage regimen involved in a method for treating a condition described herein will be determined by the attending physician, considering various factors which modify the action of drugs, e.g., the age, condition, body weight, sex and diet of the patient, the severity of any infection, time of administration and other clinical factors. In various aspects, the daily regimen is in the range of 0.1-50 mg of a preparation of antibody per kilogram of body weight (calculating the mass of the protein alone, without chemical modification). In some embodiments, the dosage is about 0.5 mg/kg to 20 mg/kg, or about 0.5-10 mg/kg, or about 1 mg/kg to about 3 mg/kg, or about 1 mg/kg to about 4 mg/kg, or about 1 mg/kg to about 5 mg/kg, or about 2 mg/kg to about 4 mg/kg, or about 2 mg/kg to about 5 mg/kg, about 1 mg/kg to about 3 mg/kg, about 1 mg/kg to about 5 mg/kg, about 2 mg/kg to about 6 mg/kg, or about 3 mg/kg to about 5 mg/kg, about 1 mg/kg to about 10 mg/kg, about 1 mg/kg to about 20 mg/kg, about 1 mg/kg to about 40 mg/kg, about 5 mg/kg to about 30 mg/kg or about 5 mg/kg to about 20 mg/kg.

The formulations are generally administered parenterally, e.g., intravenously, subcutaneously, intramuscularly, via aerosol (intrapulmonary or inhalational administration), or via depot for long-term release. In some embodiments, the formulation is administered intravenously by an initial bolus followed by a continuous infusion to maintain therapeutic circulating levels of drug product. In other embodiments, the formulation is administered as a one-time dose. Those of ordinary skill in the art will readily optimize effective dosages and administration regimens as determined by good medical practice and the clinical condition of the individual patient. The frequency of dosing will depend on the pharmacokinetic parameters of the agents and the route of administration. The optimal pharmaceutical formulation will be determined by one skilled in the art depending upon the route of administration and desired dosage. See for example, Remington's Pharmaceutical Sciences, 18th Ed. (1990, Mack Publishing Co., Easton, Pa. 18042) pages 1435-1712, the disclosure of which is hereby incorporated by reference. Such formulations may influence the physical state, stability, rate of in vivo release, and rate of in vivo clearance of the administered agents. Depending on the route of administration, a suitable dose may be calculated according to body weight, body surface area or organ size. Further refinement of the calculations necessary to determine the appropriate dosage for treatment involving each of the above mentioned formulations is routinely made by those of ordinary skill in the art without undue experimentation, especially in light of the dosage information and assays disclosed herein, as well as the pharmacokinetic data observed in the human clinical trials discussed above. Appropriate dosages may be ascertained through use of established assays for determining blood level dosages in conjunction with appropriate dose-response data.

As studies are conducted, further information will emerge regarding the appropriate dosage levels and duration of treatment for various diseases and conditions.

VI. Therapeutic Uses of the Formulation

The formulations described herein are useful for treating or preventing bone-related disorders, such as bone-related disorders associated with abnormal osteoblast or osteoclast activity. In some embodiments, the formulation is administered to a subject suffering from a bone related disorder selected from the group consisting of achondroplasia, cleidocranial dysostosis, enchondromatosis, fibrous dysplasia, Gaucher's Disease, hypophosphatemic rickets, Marfan's syndrome, multiple hereditary exotoses, neurofibromatosis, osteogenesis imperfecta, osteopetrosis, osteopoikilosis, sclerotic lesions, pseudoarthrosis, pyogenic osteomyelitis, periodontal disease, anti-epileptic drug induced bone loss, primary and secondary hyperparathyroidism, familial hyperparathyroidism syndromes, weightlessness induced bone loss, osteoporosis in men, postmenopausal bone loss, osteoarthritis, renal osteodystrophy, infiltrative disorders of bone, oral bone loss, osteonecrosis of the jaw, juvenile Paget's disease, melorheostosis, metabolic bone diseases, mastocytosis, sickle cell anemia/disease, organ transplant related bone loss, kidney transplant related bone loss, systemic lupus erythematosus, ankylosing spondylitis, epilepsy, juvenile arthritides, thalassemia, mucopolysaccharidoses, Fabry Disease, Turner Syndrome, Down Syndrome, Klinefelter Syndrome, leprosy, Perthe's Disease, adolescent idiopathic scoliosis, infantile onset multi-system inflammatory disease, Winchester Syndrome, Menkes Disease, Wilson's Disease, ischemic bone disease (such as Legg-Calve-Perthes disease and regional migratory osteoporosis), anemic states, conditions caused by steroids, glucocorticoid-induced bone loss, heparin-induced bone loss, bone marrow disorders, scurvy, malnutrition, calcium deficiency, osteoporosis, osteopenia, alcoholism, chronic liver disease, postmenopausal state, chronic inflammatory conditions, rheumatoid arthritis, inflammatory bowel disease, ulcerative colitis, inflammatory colitis, Crohn's disease, oligomenorrhea, amenorrhea, pregnancy, diabetes mellitus, hyperthyroidism, thyroid disorders, parathyroid disorders, Cushing's disease, acromegaly, hypogonadism, immobilization or disuse, reflex sympathetic dystrophy syndrome, regional osteoporosis, osteomalacia, bone loss associated with joint replacement, HIV associated bone loss, bone loss associated with loss of growth hormone, bone loss associated with cystic fibrosis, chemotherapy-associated bone loss, tumor-induced bone loss, cancer-related bone loss, hormone ablative bone loss, multiple myeloma, drug-induced bone loss, anorexia nervosa, disease-associated facial bone loss, disease-associated cranial bone loss, disease-associated bone loss of the jaw, disease-associated bone loss of the skull, bone loss associated with aging, facial bone loss associated with aging, cranial bone loss associated with aging, jaw bone loss associated with aging, skull bone loss associated with aging, and bone loss associated with space travel.

In some embodiments, the formulations described herein are useful for improving outcomes in orthopedic procedures, dental procedures, implant surgery, joint replacement, bone grafting, bone cosmetic surgery and bone repair such as fracture healing, nonunion healing, delayed union healing and facial reconstruction. One or more compositions may be administered before, during and/or after the procedure, replacement, graft, surgery or repair.

The formulation need not cure the subject of the disorder or completely protect against the onset of a bone-related disorder to achieve a beneficial biological response. The formulation may be used prophylactically, meaning to protect, in whole or in part, against a bone-related disorder or symptom thereof. The formulation also may be used therapeutically to ameliorate, in whole or in part, a bone-related disorder or symptom thereof, or to protect, in whole or in part, against further progression of a bone-related disorder or symptom thereof. Indeed, the materials and methods of the invention are particularly useful for increasing bone mineral density and maintaining the increased bone mineral density over a period of time.

One or more administrations of a formulation described herein may be carried out over a therapeutic period of, for example, about 1 week to about 18 months (e.g., about 1 month to about 12 months, about 1 month to about 9 months or about 1 month to about 6 months or about 1 month to about 3 months). In some embodiments, a subject is administered one or more doses of a formulation described herein over a therapeutic period of, for example about 1 month to about 12 months (e.g., about 2 months, about 3 months, about 4 months, about 5 months, about 6 months, about 7 months, about 8 months, about 9 months, about 10 months, or about 11 months). In some embodiments, a subject is administered one or more doses of the formulation to maintain bone mineral density. The term "maintain bone mineral density" as used herein means that the increased bone mineral density resulting from the initial dose of the formulation does not fall more than about 1% to about 5% over the course of about 6 months, about 9 months about 1 year, about 18 months, about 2 years, or over the course of the patient's life). It will be appreciated that a patient can require alternate treatment phases for increasing bone density and maintaining bone density.

In addition, it may be advantageous to administer multiple doses of the formulation or space out the administration of doses, depending on the therapeutic regimen selected for a particular subject. The formulation can be administered periodically over a time period of one year or less (e.g., 9 months or less, 6 months or less, or 3 months or less). In this regard, the formulation can be administered to the human once every about 3 days, or about 7 days, or 2 weeks, or 3 weeks, or 4 weeks, or 5 weeks, or 6 weeks, or 7 weeks, or 8 weeks, or 9 weeks, or 10 weeks, or 11 weeks, or 12 weeks, or 13 weeks, or 14 weeks, or 15 weeks, or 16 weeks, or 17 weeks, or 18 weeks, or 19 weeks, or 20 weeks, or 21 weeks, or 22 weeks, or 23 weeks, or 6 months, or 12 months.

VII. Monitoring Therapy

Anti-sclerostin antibody-mediated increases in bone mineral content or bone density may be measured using single- and dual-energy X-ray absorptiometry, ultrasound, computed tomography, radiography, and magnetic resonance imaging. The amount of bone mass may also be calculated from body weights or by using other methods (see Guinness-Hey, Metab. Bone Dis. Relat. Res., 5:177-181 (1984)). Animal models are used in the art for testing the effect of the pharmaceutical compositions and methods on, for example, parameters of bone loss, bone resorption, bone formation, bone strength, or bone mineralization that mimic conditions of human disease such as osteoporosis and osteopenia. Examples of such models include the ovariectomized rat model (Kalu, Bone and Mineral, 15:175-192 (1991); Frost and Jee, Bone and Mineral, 18:227-236 (1992); and Jee and Yao, J. Musculoskel. Neuron. Interact., 1:193-207 (2001)). The methods for measuring anti-sclerostin antibody activity described herein also may be used to determine the efficacy of other sclerostin inhibitors.

In humans, bone mineral density can be determined clinically using dual x-ray absorptiometry (DXA) of, for example, the hip and spine. Other techniques include quantitative computed tomography (QCT), ultrasonography, single-energy x-ray absorptiometry (SXA), and radiographic absorptiometry. Common central skeletal sites for measurement include the spine and hip; peripheral sites include the forearm, finger, wrist and heel. Except for ultrasonography, the American Medical Association notes that BMD techniques typically involve the use of x-rays and are based on the principle that attenuation of the radiation depends on thickness and composition of the tissues in the radiation path. All techniques involve the comparison of results to a normative database.

Alternatively, a physiological response to one or more sclerostin binding agents can be gauged by monitoring bone marker levels. Bone markers are products created during the bone remodeling process and are released by bone, osteoblasts, and/or osteoclasts. Fluctuations in bone resorption and/or bone formation "marker" levels imply changes in bone remodeling/modeling. The International Osteoporosis Foundation (IOF) recommends using bone markers to monitor bone density therapies (see, e.g., Delmas et al., Osteoporos Int., Suppl. 6:S2-17 (2000), incorporated herein by reference). Markers indicative of bone resorption (or osteoclast activity) include, for example, C-telopeptide (e.g., C-terminal telopeptide of type 1 collagen (CTX) or serum cross-linked C-telopeptide), N-telopeptide (N-terminal telopeptide of type 1 collagen (NTX)), deoxypyridinoline (DPD), pyridinoline, urinary hydroxyproline, galactosyl hydroxylysine, and tartrate-resistant acid phosphatase (e.g., serum tartrate-resistant acid phosphatase isoform 5b). Bone formation/mineralization markers include, but are not limited to, bone-specific alkaline phosphatase (BSAP), peptides released from N- and C-terminal extension of type I procollagen (P1NP, PICP), and osteocalcin (OstCa). Several kits are commercially-available to detect and quantify markers in clinical samples, such as urine and blood.

VIII. Combination Therapy

Treatment of a pathology by combining two or more agents that target the same pathogen or biochemical pathway sometimes results in greater efficacy and diminished side effects relative to the use of the therapeutically relevant dose of each agent alone. In some cases, the efficacy of the drug combination is additive (the efficacy of the combination is approximately equal to the sum of the effects of each drug alone), but in other cases the effect can be synergistic (the efficacy of the combination is greater than the sum of the effects of each drug given alone). As used herein, the term "combination therapy" means the two compounds can be delivered in a simultaneous manner, e.g., concurrently, or wherein one of the compounds is administered first, followed by the second agent, e.g., sequentially. The desired result can be either a subjective relief of one or more symptoms or an objectively identifiable improvement in the recipient of the dosage.

In some embodiments, the formulation is administered along with a standard of care therapeutic for the treatment of decreased bone mineral density. As used herein, the term "standard of care" refers to a treatment that is generally accepted by clinicians for a certain type of patient diagnosed with a type of illness. In some embodiments, the standard of care therapeutic is selected from the group consisting of an anti-resorptive drug, a bone-forming agent, an estrogen receptor antagonist (including, but not limited to, raloxifene, bazedoxifene and lasofoxifene) and a drug that has a stimulatory effect on osteoclasts. In some embodiments, the anti-resorptive drug includes, but is not limited to, a bisphosphonate (including, but not limited to, alendronate, risedronate, ibandronate and zoledronate), an estrogen or estrogen analogue, a selective estrogen receptor modulator (SERM) and a calcium source, Tibolone, calcitonin, a calcitriol and hormone replacement therapy. In some embodiments, the bone-forming agent includes, but is not limited to parathyroid hormone (PTH) or a peptide fragment thereof, PTH-related protein (PTHrp), bone morphogenetic protein, osteogenin, NaF, a $PGE_2$ agonist, a statin, an anti-DKK antibody, and a RANK ligand (RANKL). In some embodiments, the drug having a stimulatory effect on osteoclasts includes, but it not limited to, vitamin D, or a vitamin D derivative or mimic thereof.

In some embodiments, the formulation is administered to a subject when treatment of a standard of care therapeutic described herein is contraindicated.

EXAMPLES

Example 1

Crystallization of Ab-30

Antibody Ab-30, consisting of two mature heavy chains (SEQ ID NO: 15) and two mature light chains (SEQ ID NO: 13) recombinantly produced by DNA encoding each of these chains, was crystallized under a variety of conditions.

Crystallization of Ab-30 was achieved using a crystallization screen (Index Screen; Hampton Research, Aliso Viejo, Calif.), which employs a method for crystallization of macromolecules known as "hanging drop" vapor diffusion. A drop composed of a mixture of the polypeptide sample and the crystallization reagent (the "crystallization buffer" or the "mother liquor") is deposited on the underside of a sialanized coverslip, and then the drop on the coverslip is sealed with grease and placed over typically a 24 well VDX tray causing a vapor equilibrium with a liquid reservoir of reagent. To achieve equilibrium, water vapor exchanges between the drop and a 1 ml reservoir solution in the well of the tray. As water leaves the drop, the polypeptide sample undergoes an increase in relative concentration which may eventually lead to supersaturation. It is the increased concentration of the polypeptide sample that is required for crystallization to take place. Typically the drop contains a lower concentration of reagent than the reservoir, and typically, the drop contained half the concentration of reagent in the reservoir, because equal volumes of sample and reagent were mixed to form the drop.

In these experiments, the initial polypeptide concentration in the drop was usually 0.1-300 mg/mL or between 3-100 mg/mL.

The crystallization screen was set up in 24-well VDX polypropylene tissue culture trays. Each position in the VDX tray contained 1 mL of reagent reservoir, with the reagent reservoir in each well differing in composition from that in the other wells, to establish an array of differing crystallization buffer conditions. 1-10 µL of polypeptide solution at each polypeptide concentration was added to 1-10 µl of reservoir solution to form the drops. Trays were incubated either at 4° C. or at ambient room temperature.

Crystallization Conditions:

Ab-30 crystallization was observed at both 4° C. and room temperature using a plurality of reagents (see Tables 1-8 below).

TABLE 1

Crystallization conditions producing Ab-30 crystals after one day at room temperature.

| Crystallization screen | Crystallization conditions | Crystal Morphology |
|---|---|---|
| INDX #18 | 0.49M Sodium dihydrogen Phosphate, 0.91M di-Potassium hydrogen Phosphate, pH 6.9 | rods |
| INDX #22 | 0.8M Succinic Acid pH 7 | rod clusters |
| INDX #30 | 0.1M Sodium Chloride, 0.1M Bis-Tris pH 6.5, 1.5M Ammonium Sulfate | rods |
| INDX #31 | 0.8M Potassium Sodium Tartrate tetrahydrate, 0.1M Tris pH 8.5; 0.50% w/v Polyethylene Glycol Monomethyl ether 5000 | rod clusters |
| INDX #34 | 1M Succinic Acid pH 7.0, 0.1M HEPES pH 7.0, 1% w/v Polyethylene | rod clusters |
| INDX #35 | 1M Ammonium Sulfate, 0.1M HEPES pH 7.0, 0.50% w/v Polyethylene Glycol 8000 | rod clusters |
| INDX #36 | 15% v/v Tacsimate pH 7.0, 0.1M HEPES pH 7.0, 2% w/v Polyethylene Glycol 3350 | rods, rod clusters |

TABLE 2

Crystallization conditions producing Ab-30 crystals after one day at 4° C.

| Crystallization screen | Crystallization conditions | Crystal Morphology |
|---|---|---|
| INDX #12 | 0.1M Tris pH 8.5, 3M Sodium Chloride | not recorded |
| INDX #18 | 0.49M Sodium dihydrogen Phosphate, 0.91M di-Potassium hydrogen Phosphate, pH 6.9 | rods |
| INDX #22 | 0.8M Succinic Acid pH 7 | rod clusters |
| INDX #31 | 0.8M Potassium Sodium Tartrate tetrahydrate, 0.1M Tris pH 8.5; 0.50% w/v Polyethylene Glycol Monomethyl ether 5000 | rod clusters |
| INDX #35 | 1M Ammonium Sulfate, 0.1M HEPES pH 7.0, 0.50% w/v Polyethylene Glycol 8000 | rod clusters |
| INDX #36 | 15% v/v Tacsimate pH 7.0, 0.1M HEPES pH 7.0, 2% w/v Polyethylene Glycol 3350 | rods, rod clusters |

TABLE 3

Crystallization conditions producing Ab-30 crystals after two days at room temperature.

| Crystallization Screen | Crystallization conditions | Crystal morphology |
|---|---|---|
| SALT-RX#1 | 1.8M Sodium Acetate pH 7.0, 0.1M Bis-Tris Propane, pH 7 | Seeds or small rods |
| SALT-RX#19 | 0.7M tri-Sodium Citrate dehydrate, 0.1M Bis-Tris Propane pH 7 | rod clusters |
| SALT-RX#20 | 0.7M tri-Sodium Citrate dihydrate, 0.1M Tris pH 8.5 | rods |
| INDX#17 | 1.26M Sodium dihydrogen Phosphate, 0.14M di-Potassium hydrogen Phosphate | rods |

TABLE 4

Crystallization conditions producing Ab-30 crystals after two days at 4°c.

| Crystallization Screen | Crystallization conditions | Crystal morphology |
|---|---|---|
| SALT-RX#1 | 1.8M Sodium Acetate pH 7.0, 0.1M Bis-Tris Propane, pH 7 | rods |
| SALT-RX#19 | 0.7M tri-Sodium Citrate dehydrate, 0.1M Bis-Tris Propane pH 7 | seeds |
| SALT-RX#20 | 0.7M tri-Sodium Citrate dihydrate, 0.1M Tris pH 8.5 | rod clusters |

TABLE 5

Additional commercially available screen conditions producing Ab-30 crystals at room temperature.

| Crystallization Screen | Crystallization conditions | Crystal morphology |
|---|---|---|
| SALT-RX#2 | 2.8M Sodium Acetate pH 7.0, 0.1M Bis-Tris Propane pH 7.0 | not recorded |
| INDX #24 | 2.8M Sodium Acetate trihydrate pH 7.0 | needles |
| INDX #26 | 1.1M di-Ammonium Tartrate pH 7.0 | rod clusters |
| INDX #28 | 35% v/v Tacsimate pH 7.0 | chrysanthemums |
| INDX #33 | 1.1M Sodium Malonate pH 7.0, 0.1M HEPES pH 7.0, 0.50% v/v Jeffamine ED-2001 Reagent pH 7.0 | not recorded |
| WIZ I #9 | 0.1M Acetate, pH 4.5, 1M $(NH_4)_2HPO_4$ | Rods |
| WIZ I #12 | 0.2M Ca(OAc)$_2$, 0.1M Imidazole pH 8, 20% w/v PEG-1000 | not recorded |
| WIZ I #13 | 0.1M Cacodylate, pH 6.5, 1.26M $(NH_4)_2SO_4$ | not recorded |
| WIZ I #22 | 0.1M Tris pH 8.5, 10% v/v 2-propanol | Rods |
| WIZ I #26 | 0.1M CHES pH 9.5, 10% w/v PEG-3000 | Rods |
| WIZ I #29 | 0.2M NaCl, 0.1M CHES pH 9.5, 10% w/v PEG-8000 | not recorded |
| WIZ I #30 | 0.2M NaCl, 0.1M Acetate pH 4.5, 1.26M $(NH_4)_2SO_4$ | small crystals |
| WIZ I #35 | 0.1M Acetate pH 4.5, 20% v/v 1,4-butanediol | not recorded |
| WIZ I #37 | 0.1M Imidazole pH 8, 2.5M NaCl | not recorded |
| WIZ I #39 | 0.2M Li$_2$SO$_4$, 0.1M Phosphate-citrate pH 4.2, 20% w/v PEG-1000 | not recorded |
| WIZ I #42 | 0.1M Tris pH 7.0, 15% v/v Ethanol | needles |
| WIZ I #46 | 0.2M Ca(OAc)$_2$, 0.1M Imidazole pH 7.0, 10% w/v PEG-8000 | small crystals |
| WIZ II #10 | 0.1M Tris pH 8.5, 1M $(NH_4)_2HPO_4$ | Rods |
| WIZ II #12 | 0.2M Li$_2$SO$_4$, 0.1M Cacodylate, pH 6.5, 30% v/v PEG-400 | small crystals |
| WIZ II #15 | 0.1M HEPES pH 7.5, 1.26M $(NH_4)_2HPO_4$ | Rods |
| WIZ II #21 | 0.1M Acetate pH 4.5, 35% v/v 2-methyl-2,4-pentanediol | small crystals |
| WIZ II #22 | 0.1M Imidazole pH 8.0, 10% v/v 2-propanol | Rods |
| WIZ II #25 | 0.2M NaCl, 0.1M HEPES pH 7.5, 35% v/v 2-methyl-2,4-pentanediol | small crystals |
| WIZ II #26 | 0.1M CHES pH 9.5, 30% v/v PEG-400 | small crystals |
| WIZ II #27 | 0.2M MgCl$_2$, 0.1M Cacodylate pH 6.5, 10% w/v PEG-3000 | Rods |
| WIZ II #30 | 0.2M Zn(OAc)$_2$, 0.1M Imidazole pH 8.0, 20% v/v 1,4-butanediol | small crystals |
| WIZ II #32 | 0.1M Tris pH 8.5, 20% w/v PEG-1000 | small crystals |
| WIZ II #38 | 0.2M Li$_2$SO$_4$, 0.1M Acetate pH 4.5, 2.5M NaCl | small crystals |
| WIZ II #42 | 0.2M NaCl, 0.1M HEPES pH 7.5, 30% v/v PEG-400 | rods |
| WIZ III #22 | 0.1M Tris pH 8.5, 20% v/v Ethanol | needles |
| WIZ III #25 | 10% w/v PEG 8000, 10% w/v PEG 1000 | small crystals |
| WIZ III #28 | 0.1M HEPES, pH 7.5, 70% v/v MPD | small crystals |
| WIZ III #29 | 0.1M Tris pH 8.0, 40% v/v MPD | small crystals |
| WIZ III #35 | 0.16M Calcium Acetate, 0.08M Cacodylate pH 6.5, 4.4% w/v PEG 8000, 20% v/v Glycerol | Rods |
| WIZ III #38 | 2% v/v Dioxane, 0.1M Citrate pH 5.5, 15% w/v PEG 10,000 | small crystals |
| WIZ III #39 | 0.1M HEPES pH 7.5, 20% v/v Jeffamine M-600 | Rods |
| WIZ III #40 | 0.1M Bicine, pH 9.0, 10% v/v MPD | Rods |
| WIZ III #41 | 0.2M Calcium Chloride, 0.1M HEPES pH 7.5, 28% v/v PEG 400 | small crystals |
| WIZ III #42 | 0.2M Lithium Sulfate, 0.1M Tris pH 8.5, 30% w/v PEG 4000 | small crystals |
| WIZ III #46 | 0.2M Ammonium Phosphate (monobasic), 0.1M Tris pH 8.5, 50% v/v MPD | small crystals |

TABLE 5-continued

Additional commercially available screen conditions producing Ab-30 crystals at room temperature.

| Crystallization Screen | Crystallization conditions | Crystal morphology |
|---|---|---|
| WIZ III #58 | 0.1M HEPES pH 7.5, 20% w/v PEG 10,000 | small crystals |
| WIZ IV #13 | 0.8M Succinic Acid pH 7.0 | Rods |
| WIZ IV #14 | 40% (v/v) PEG 400, 0.1M Tris base/Hydrochloric acid pH 8.5, 0.2M Lithium sulfate | Rods |
| WIZ IV #26 | 10% (w/v) PEG2000MME, 0.1M Sodium acetate/Acetic acid pH 5.5, 0.2M Ammonium Sulfate | Rods |
| WIZ IV #31 | 20% (w/v) Polyacrylic acid 5100, 0.1M HEPES/Sodium hydroxide pH 7.0, 0.02M Magnesium Chloride | Rods |
| WIZ IV #33 | 0.8M Potassium phosphate (dibasic), 0.1M HEPES/Sodium hydroxide pH 7.5, 0.8M Sodium phosphate | Rods |
| CS-CRYO # 36 | 0.065 Tris Hydrochloride pH 8.5, 5.2% w/v Polyethylene Glycol 8,000, 35% Glycerol | Rods |
| CS-CRYO #46 | 0.16M Calcium Acetate Hydrate, 0.08M Sodium Cacodylate Trihydrate pH 6.5, 14.4% w/v Polyethylene Glycol 8,000, 20% Glycerol | needles |
| PPT 33% #3 | 0.66M Ammonium Sulfate, 0.33% v/v MPD, 0.1M HEPES pH 7.5 | Rods |
| PPT 33% #4 | 0.66M Ammonium Sulfate, 1.65% v/v PEG 400, 0.05M Magnesium Sulfate, 0.1M Tris base pH 8.5 | needles |
| PPT 33% #10 | 6.6% v/v Glycerol, 0.825M Potassium Phosphate Monobasic/Sodium Phosphate Dibasic pH 7.5 | Rods |
| PPT 33% #13 | 1.65% v/v Isopropanol, 0.66M Ammonium Citrate/Citric Acid pH 6.5 | Rods |
| PPT 33% #14 | 1.65% v/v PEG 400, 0.66M Ammonium Citrate/Citric Acid pH 7.5 | Rods |
| PPT 33% #17 | 0.561 Lithium Sulfate, 2.24% v/v MPD, 0.085M Imidazole pH 6.5 | needles |
| PPT 33% #18 | 0.66M Lithium Sulfate, 0.66% v/v PEG 400, 0.1M Tris base pH 8.5 | small needles |
| PPT 33% #24 | 6.6% v/v PEG 400, 0.165 Potassium Phosphate Monobasic/Sodium Phosphate Dibasic pH 7.5 | Rods |
| PPT 33% #34 | 13.2% v/v Isopropanol, 4.65% w/v PEG 8000, 0.1M Imidazole pH 6.5 | needles |
| PPT 33% #35 | 6.6% v/v Isopropanol, 4.95% w/v PEG 3350, 0.2M Ammonium Citrate/Citric Acid pH 7.5 | rods |
| PPT 33% #39 | 6.6% v/v PEG 400, 4.95% w/v PEG 1000, 0.15M Potassium Phosphate Monobasic/Sodium Phosphate Dibasic pH 6.5 | Rods |
| PPT 33% #41 | 8.25% v/v PEG 400, 6/6% w/v PEG 3350, 0.1M Magnesium Chloride, 0.1M Tris base pH 8.5 | Rods |
| PPT 33% #43 | 9.9% w/v PEG 1500, 3.3% v/v Isopropanol, 0.1M Calcium Chloride, 0.1M Imidazole pH 6.5 | Rods |
| PPT 33% #45 | 9.9% w/v PEG 1500, 2.64% v/v MPD, 0.1M Tris base pH 8.5 | Small |
| PPT 33% #46 | 8.25% w/v PEG 3350, 4.95% v/v Isopropanol, 0.2M Ammonium Citrate/Citric Acid pH 4.5 | Rods |
| PPT 33% #48 | 8.25% w/v PEG 3350, 4.95% v/v MPD, 0.2M Lithium Sulfate, 0.1M Imidazole pH 6.5 | Rods |
| PPT 67% #4 | 1.34M Ammonium Sulfate, 3.35% v/v PEG 400, 0.05M Magnesium Sulfate, 0.1M Tris base pH 8.5 | Rods |
| PPT 67% #5 | 2.613M Sodium Chloride, 1.34% v/v PEG 400, 0.1M Magnesium Chloride, 0.1M Acetate pH 5.5 | Rods |
| PPT 67% #9 | 1.34% v/v PEG 400, 1.34M Potassium Phosphate Monobasic/Sodium Phosphate Dibasic pH 6.5 | Rods |
| PPT 67% #31 | 20.1% v/v MPD, 5.36% w/v PEG 8000, 0.5M Sodium Chloride, 0.1M Tris base pH 8.5 | Rods |
| PPT 67% #35 | 13.4% v/v Isopropanol, 10.05% w/v PEG 3350, 0.2M Ammonium Citrate/Citric Acid pH 7.5 | Rods |
| PPT 67% #39 | 13.4% v/v PEG 400, 10.05% w/v PEG 1000, 0.15M Potassium Phosphate Monobasic/Sodium Phosphate Dibasic pH 6.5 | Rods |

TABLE 6

Additional commercially available screen conditions producing Ab-30 crystals at 4° C.

| Crystallization Screen | Crystallization conditions | Crystal morphology |
| --- | --- | --- |
| INDX #17 | pH 5.6, 1.26M Sodium dihydrogen Phosphate, 0.14M di-Potassium hydrogen Phosphate | not recorded |
| INDX #26 | 1.1M di-Ammonium Tartrate pH 7.0 | small crystals |
| INDX #28 | 35% v/v Tacsimate pH 7.0 | small crystals |
| INDX #33 | 1.1M Sodium Malonate pH 7.0, 0.1M HEPES pH 7.0, 0.50% v/v Jeffamine ED-2001 Reagent pH 7.0 | small crystals |
| WIZ I #2 | 0.2M NaCl, 0.1M HEPES, 10% v/v 2-propanol | small crystals |
| WIZ I #9 | 0.1M Acetate pH 4.5, 1M $(NH_4)_2HPO_4$ | Rods |
| WIZ I #13 | 0.1M Cacodylate pH 6.5, 1.26M $(NH_4)_2SO_4$ | not recorded |
| WIZ I #18 | 0.2M NaCl, 0.1M Imidazole pH 8, 1M K/Na Tartrate | small crystals |
| WIZ I #22 | 0.1M Tris pH 8.5, 10% v/v 2-propanol | Rods |
| WIZ I #25 | 0.2M $MgCl_2$, 0.1M Tris pH 8.5, 30% v/v PEG-400 | small crystals |
| WIZ I #34 | 0.1M Imidazole pH 8, 1M $(NH_4)_2HPO_4$ | small crystals |
| WIZ I #35 | 0.1M Acetate pH 4.5, 20% v/v 1,4-butanediol | not recorded |
| WIZ I #37 | 0.1M Imidazole pH 8, 2.5M NaCl | not recorded |
| WIZ I #40 | 0.2M $Ca(OAc)_2$, 0.1M MES pH 6.0, 10% v/v 2-propanol | small crystals |
| WIZ I #42 | 0.1M Tris pH 7.0, 15% v/v Ethanol | needles |
| WIZ I #43 | 0.1M Na/K phosphate pH 6.2, 35% v/v 2-methyl-2,4-pentanediol | not recorded |
| WIZ I #44 | 0.2M $Ca(OAc)_2$, 0.1M Acetate pH 4.5, 30% v/v PEG 400 | not recorded |
| WIZ I #46 | 0.2M $Ca(OAc)_2$, 0.1M Imidazole pH 7.0, 10% w/v PEG-8000 | small crystals |
| WIZ II #5 | 0.2M NaCl, 0.1M HEPES pH 7.5, 20% v/v 1,4-butanediol | not recorded |
| WIZ II #6 | 0.2M $Li_2SO_4$, 0.1M Phosphate-citrate pH 4.2, 10% v/v 2-propanol | not recorded |
| WIZ II #10 | 0.1M Tris pH 8.5, 1M $(NH_4)_2HPO_4$ | small crystals |
| WIZ II #13 | 0.2M $Li_2SO_4$, 0.1M Citrate pH 5.5, 15% v/v Ethanol | small crystals |
| WIZ II #14 | 0.2M NaCl, 0.1M Na/K phosphate pH 6.2, 20% w/v PEG-1000 | Rods |
| WIZ II #17 | 0.2M $MgCl_2$, 0.1M Tris pH 7.0, 2.5M NaCl | small crystals |
| WIZ II #20 | 0.2M $Zn(OAc)_2$, 0.1M MES pH 6.0, 15% v/v Ethanol | small crystals |
| WIZ II #21 | 0.1M Acetate pH 4.5, 35% v/v 2-methyl-2, 4-pentanediol | small crystals |
| WIZ II #22 | 0.1M Imidazole pH 8.0, 10% v/v 2-propanol | needles |
| WIZ II #23 | 0.2M $MgCl_2$, 0.1M HEPES pH 7.5, 15% v/v Ethanol | small crystals |
| WIZ II #27 | 0.2M $MgCl_2$, 0.1M Cacodylate pH 6.5, 10% w/v PEG-3000 | Rods |
| WIZ II #29 | 0.2M NaCl, 0.1M CHES pH 9.5, 1.26M $(NH_4)_2SO_4$ | small crystals |
| WIZ II #33 | 0.2M NaCl, 0.1M Citrate pH 5.5, 1M $(NH_4)_2SO_4$ | small crystals |
| WIZ II #36 | 0.2M NaCl, 0.1M Phosphate-citrate pH 4.2, 10% w/v PEG-3000 | small crystals |
| WIZ II #45 | 0.1M MES pH 6.0, 1.26M $(NH_4)_2SO_4$ | Rods |
| WIZ II #46 | 0.2M NaCl, 0.1M Imidazole pH 8.0, 1M $(NH_4)_2HPO_4$ | small crystals |
| WIZ II #48 | 0.1M MES pH 6.0, 1M K/Na Tartrate | small crystals |
| WIZ III #8 | 0.2M Potassium nitrate, 20% w/v PEG 3350 | Rods |
| WIZ III #22 | 0.1M Tris pH 8.5, 20% v/v Ethanol | needles |
| WIZ III #23 | 2% v/v Dioxane, 0.1M Bicine pH 9.0, 10% w/v PEG 20,000 | small crystals |
| WIZ III #24 | 0.1M Sodium Acetate pH 4.6, 2M Ammonium Sulfate | small crystals |
| WIZ III #27 | 0.2M Magnesium Chloride, 0.1M HEPES pH 7.5, 30% v/v PEG 400 | small crystals |
| WIZ III #32 | 0.04M Potassium Phosphate (monobasic), 16% w/v PEG 8000, 20% v/v Glycerol | small crystals |
| WIZ III #33 | 0.1M MES pH 6.5, 1.6M Magnesium Sulfate | small crystals |
| WIZ III #40 | 0.1M Bicine pH 9.0, 10% v/v MPD | Rods |
| Peg-Ion #1 | 0.2M Sodium Fluoride 20% w/v PEG 3,350 pH 7.3 | small crystals |
| Peg-Ion #2 | 0.2M Potassium Fluoride 20% w/v PEG 3,350 pH 7.3 | small crystals |
| Peg-Ion #10 | 0.2M Sodium Iodide 20% w/v PEG 3,350 pH 7.0 | small crystals |
| Peg-Ion #11 | 0.2M Potassium Iodide 20% w/v PEG 3,350 pH 7.0 | small crystals |
| Peg-Ion #12 | 0.2M Ammonium Iodide 20% w/v PEG 3,350 pH 6.2 | small crystals |
| Peg-Ion #13 | 0.2M Sodium Thiocyanate 20% w/v PEG 3,350 pH 6.9 | small crystals |
| Peg-Ion #14 | 0.2M Potassium Thiocyanate 20% w/v PEG 3,350 pH 7.0 | small crystals |
| Peg-Ion #21 | 0.2M Sodium Formate 20% w/v PEG 3,350 pH 7.2 | small crystals |
| Peg-Ion #22 | 0.2M Potassium Formate 20% w/v PEG 3,350 pH 7.3 | small crystals |
| Peg-Ion #23 | 0.2M Ammonium Formate 20% w/v PEG 3,350 pH 6.6 | small crystals |
| CS-CRYO #36 | 0.065 Tris Hydrochloride pH 8.5, 5.2% w/v Polyethylene Glycol 8,000, 35% Glycerol | Rods |

TABLE 7

Additional crystallization conditions producing Ab-30 crystals at room temperature.

| Crystallization Screen | Crystallization conditions | Crystal morphology |
|---|---|---|
| GRAS #1 | 19.90% Isopropanol, 0.02M Na—K phosphate pH 7.5 | Small |
| GRAS #2 | 45.39% Isopropanol | Small |
| GRAS #50 | 0.40M Na citrate, 0.06M Tris-HCl pH 7.5, 2.36% Glycerol | needles, rods, blocks |
| GRAS #53 | 46.10% Ethanol, 0.03M Na Acetate pH 4.5, 4.94% Glycerol | Small |
| GRAS #54 | 43.29% Ethanol, 0.01% Tween-80 | Small |
| GRAS #58 | 49.65% Isopropanol, 0.06M Tris-HCl pH 6.5 | Small |
| GRAS #65 | 33.74% Isopropanol, 0.06M Glutamic acid pH 6.5 | Small |
| GRAS #67 | 39.35% Isopropanol, 0.03M Na Acetate pH 4.5, 0.01M EDTA | Small |
| GRAS #68 | 38.05% Isopropanol, 0.02M Na—K phosphate pH 7.5 | Small |
| GRAS #70 | 1.60M Na acetate, 3.41% Ethanol | needles |
| GRAS #74 | 0.29M Na citrate, 0.08M Na—K phosphate pH 7.5 | needles, blocks |
| GRAS #78 | 1.82M Na acetate | needles |
| GRAS #81 | 13.29% Ethanol, 0.01% Tween-80 | Small |
| GRAS #82 | 0.71M Na citrate, 0.01M Histidine pH 5.5, 6.29% Glycerol | Small |
| GRAS #83 | 2.04M Na acetate, 0.07M Tris-HCl pH 8.5 | small needles |
| GRAS #85 | 20.18% Isopropanol, 0.01M Histidine pH 5.5, 0.09M Na—K phosphate | small needles |
| GRAS #88 | 12.78% Ethanol, 0.05M Na—K phosphate pH 5.5, 0.01% Tween-80 | small needles |
| GRAS #96 | 0.38M Na citrate, 0.03M Na acetate pH 6.5, 0.01% Tween-20 | needles, blocks |

TABLE 8

Additional crystallization conditions producing Ab-30 crystals at 4° C.

| Crystallization Screen | Crystallization conditions |
|---|---|
| GRAS #4 | 0.79M Na citrate, 0.01M Histidine pH 6.5 |
| GRAS #5 | 39.39% Isopropanol, 0.8M Tris-HCl pH 7.5 |
| GRAS #10 | 1.9M Na acetate, 0.05M Na—K phosphate pH7.5, 7.07% Isopropanol |
| GRAS #11 | 0.96M Na—K phosphate, 0.01M EDTA, 1.86% Glycerol |
| GRAS #12 | 0.96M Na—K phosphate, 0.01M EDTA, 1.86% Glycerol |
| GRAS #15 | 18.90% Ethanol, 0.02M EDTA |
| GRAS #16 | 0.41M Na acetate, 0.10M Na—K phosphate pH 7.5, 4.12% Glycerol |
| GRAS #17 | 1.77M Na acetate, 6.00% Sucrose, 0.01% Tween-80 |
| GRAS #18 | 1.97M Na acetate |
| GRAS #22 | 2.31M Na acetate, 0.05M Na—K phosphate pH 7.5 |
| GRAS #24 | 1.43M Na—K phosphate, 0.03M Na citrate pH 4.5, 4.63% Glycerol |
| GRAS #50 | 0.40M Na citrate, 0.06M Tris-HCl pH 7.5, 2.36% Glycerol |
| GRAS #54 | 43.29% Ethanol, 0.01% Tween-80 |
| GRAS #57 | 0.76M Na citrate, 0.01M Na citrate pH 4.5, 0.02M EDTA |
| GRAS #60 | 1.77M Na—K phosphate |
| GRAS #64 | 0.51M NaCl, 0.06M Na citrate pH 7.5 |
| GRAS #66 | 12.13% Isopropanol, 9.21% Ethanol, 9.24% Glycerol |
| GRAS #70 | 1.60M Na acetate, 3.41% Ethanol |

TABLE 8

Additional crystallization conditions producing Ab-30 crystals under Index #36 and additives (salts) at room temperature.

| Crystallization Screen | Crystallization conditions | Crystal morphology |
|---|---|---|
| INDX #36 | 15% v/v Tacsimate pH 7.0, 0.1M HEPES pH 7.0, 2% w/v Polyethylene Glycol 3350, 10 mM Ammonium Acetate | rods |
| INDX #36 | 15% v/v Tacsimate pH 7.0, 0.1M HEPES pH 7.0, 2% w/v Polyethylene Glycol 3350, 10 mM Lithium Acetate Dihydrate | rods |
| INDX #36 | 15% v/v Tacsimate pH 7.0, 0.1M HEPES pH 7.0, 2% w/v Polyethylene Glycol 3350, 10 mM Magnesium Acetate Tetrahydrate | rods |
| INDX #36 | 15% v/v Tacsimate pH 7.0, 0.1M HEPES pH 7.0, 2% w/v Polyethylene Glycol 3350, 10 mM Zinc Acetate | rods |
| INDX #36 | 15% v/v Tacsimate pH 7.0, 0.1M HEPES pH 7.0, 2% w/v Polyethylene Glycol 3350, 10 mM Magnesium Chloride | rods |
| INDX #36 | 15% v/v Tacsimate pH 7.0, 0.1M HEPES pH 7.0, 2% w/v Polyethylene Glycol 3350, 10 mM Zinc Chloride | rods |

TABLE 8-continued

Additional crystallization conditions producing Ab-30 crystals under Index #36 and additives (salts) at room temperature.

| Crystallization Screen | Crystallization conditions | Crystal morphology |
|---|---|---|
| INDX #36 | 15% v/v Tacsimate pH 7.0, 0.1M HEPES pH 7.0, 2% w/v Polyethylene Glycol 3350, 10 mM magnesium formate | rods |
| INDX #36 | 15% v/v Tacsimate pH 7.0, 0.1M HEPES pH 7.0, 2% w/v Polyethylene Glycol 3350, 10 mM Magnesium nitrate | rods |
| INDX #36 | 15% v/v Tacsimate pH 7.0, 0.1M HEPES pH 7.0, 2% w/v Polyethylene Glycol 3350, 10 mM Magnesium sulfate | Rods |
| INDX #36 | 15% v/v Tacsimate pH 7.0, 0.1M HEPES pH 7.0, 2% w/v Polyethylene Glycol 3350, 10 mM Zinc sulfate | rods |
| INDX #36 | 15% v/v Tacsimate pH 7.0, 0.1M HEPES pH 7.0, 2% w/v Polyethylene Glycol 3350, 10 mM Calcium acetate, 10 mM Zinc acetate | rods |

TABLE 9

Additional crystallization conditions producing Ab-30 crystals using Index #36 and additives (amino acids) at room temperature.

| Crystallization Screen | Crystallization conditions | Crystal morphology |
|---|---|---|
| INDX #36 | 15% v/v Tacsimate pH 7.0, 0.1M HEPES pH 7.0, 2% w/v Polyethylene Glycol 3350, 10 mM Arginine | Rods |
| INDX #36 | 15% v/v Tacsimate pH 7.0, 0.1M HEPES pH 7.0, 2% w/v Polyethylene Glycol 3350, 20 mM Arginine | Rods |
| INDX #36 | 15% v/v Tacsimate pH 7.0, 0.1M HEPES pH 7.0, 2% w/v Polyethylene Glycol 3350, 40 mM Arginine | Rods |
| INDX #36 | 15% v/v Tacsimate pH 7.0, 0.1M HEPES pH 7.0, 2% w/v Polyethylene Glycol 3350, 80 mM Arginine | Rods |
| INDX #36 | 15% v/v Tacsimate pH 7.0, 0.1M HEPES pH 7.0, 2% w/v Polyethylene Glycol 3350, 100 mM Arginine | Rods |
| INDX #36 | 15% v/v Tacsimate pH 7.0, 0.1M HEPES pH 7.0, 2% w/v Polyethylene Glycol 3350, 10 mM Cysteine | Rods |
| INDX #36 | 15% v/v Tacsimate pH 7.0, 0.1M HEPES pH 7.0, 2% w/v Polyethylene Glycol 3350, 20 mM Cysteine | Rods |
| INDX #36 | 15% v/v Tacsimate pH 7.0, 0.1M HEPES pH 7.0, 2% w/v Polyethylene Glycol 3350, 40 mM Cysteine | Rods |
| INDX #36 | 15% v/v Tacsimate pH 7.0, 0.1M HEPES pH 7.0, 2% w/v Polyethylene Glycol 3350, 80 mM Cysteine | Rods |
| INDX #36 | 15% v/v Tacsimate pH 7.0, 0.1M HEPES pH 7.0, 2% w/v Polyethylene Glycol 3350, 100 mM Cysteine | Rods |
| INDX #36 | 15% v/v Tacsimate pH 7.0, 0.1M HEPES pH 7.0, 2% w/v Polyethylene Glycol 3350, 10 mM Methionine | Rods |
| INDX #36 | 15% v/v Tacsimate pH 7.0, 0.1M HEPES pH 7.0, 2% w/v Polyethylene Glycol 3350, 20 mM Methionine | Rods |
| INDX #36 | 15% v/v Tacsimate pH 7.0, 0.1M HEPES pH 7.0, 2% w/v Polyethylene Glycol 3350, 40 mM Methionine | Rods |
| INDX #36 | 15% v/v Tacsimate pH 7.0, 0.1M HEPES pH 7.0, 2% w/v Polyethylene Glycol 3350, 80 mM Methionine | Rods |
| INDX #36 | 15% v/v Tacsimate pH 7.0, 0.1M HEPES pH 7.0, 2% w/v Polyethylene Glycol 3350, 100 mM Methionine | Rods |
| INDX #36 | 15% v/v Tacsimate pH 7.0, 0.1M HEPES pH 7.0, 2% w/v Polyethylene Glycol 3350, 10 mM Proline | Rods |
| INDX #36 | 15% v/v Tacsimate pH 7.0, 0.1M HEPES pH 7.0, 2% w/v Polyethylene Glycol 3350, 20 mM Proline | Rods |
| INDX #36 | 15% v/v Tacsimate pH 7.0, 0.1M HEPES pH 7.0, 2% w/v Polyethylene Glycol 3350, 40 mM Proline | Rods |
| INDX #36 | 15% v/v Tacsimate pH 7.0, 0.1M HEPES pH 7.0, 2% w/v Polyethylene Glycol 3350, 80 mM Proline | Rods |
| INDX #36 | 15% v/v Tacsimate pH 7.0, 0.1M HEPES pH 7.0, 2% w/v Polyethylene Glycol 3350, 100 mM Proline | Rods |

TABLE 10

Additional crystallization conditions producing AB-30 crystals using Index #36 and additives (cryoprotectants) at room temperature.

| Crystallization Screen | Crystallization conditions | Crystal morphology |
|---|---|---|
| INDX #36 | 15% v/v Tacsimate pH 7.0, 0.1M HEPES pH 7.0, 2% w/v Polyethylene Glycol 3350, 1% Ethylene Glycol | Rods |
| INDX #36 | 15% v/v Tacsimate pH 7.0, 0.1M HEPES pH 7.0, 2% w/v Polyethylene Glycol 3350, 2% Ethylene Glycol | Rods |
| INDX #36 | 15% v/v Tacsimate pH 7.0, 0.1M HEPES pH 7.0, 2% w/v Polyethylene Glycol 3350, 3% Ethylene Glycol | Rods |
| INDX #36 | 15% v/v Tacsimate pH 7.0, 0.1M HEPES pH 7.0, 2% w/v Polyethylene Glycol 3350, 4% Ethylene Glycol | Rods |
| INDX #36 | 15% v/v Tacsimate pH 7.0, 0.1M HEPES pH 7.0, 2% w/v Polyethylene Glycol 3350, 5% Ethylene Glycol | Rods |
| INDX #36 | 15% v/v Tacsimate pH 7.0, 0.1M HEPES pH 7.0, 2% w/v Polyethylene Glycol 3350, 6% Ethylene Glycol | Rods |
| INDX #36 | 15% v/v Tacsimate pH 7.0, 0.1M HEPES pH 7.0, 2% w/v Polyethylene Glycol 3350, 7% Ethylene Glycol | Rods |
| INDX #36 | 15% v/v Tacsimate pH 7.0, 0.1M HEPES pH 7.0, 2% w/v Polyethylene Glycol 3350, 8% Ethylene Glycol | Rods |
| INDX #36 | 15% v/v Tacsimate pH 7.0, 0.1M HEPES pH 7.0, 2% w/v Polyethylene Glycol 3350, 9% Ethylene Glycol | Rods |
| INDX #36 | 15% v/v Tacsimate pH 7.0, 0.1M HEPES pH 7.0, 2% w/v Polyethylene Glycol 3350, 10% Ethylene Glycol | Rods |
| INDX #36 | 15% v/v Tacsimate pH 7.0, 0.1M HEPES pH 7.0, 2% w/v Polyethylene Glycol 3350, 15% Ethylene Glycol | Rods |
| INDX #36 | 15% v/v Tacsimate pH 7.0, 0.1M HEPES pH 7.0, 2% w/v Polyethylene Glycol 3350, 20% Ethylene Glycol | Rods |
| INDX #36 | 15% v/v Tacsimate pH 7.0, 0.1M HEPES pH 7.0, 2% w/v Polyethylene Glycol 3350, 25% Ethylene Glycol | Rods |
| INDX #36 | 15% v/v Tacsimate pH 7.0, 0.1M HEPES pH 7.0, 2% w/v Polyethylene Glycol 3350, 30% Ethylene Glycol | Rods |
| INDX #36 | 15% v/v Tacsimate pH 7.0, 0.1M HEPES pH 7.0, 2% w/v Polyethylene Glycol 3350, 40% Ethylene Glycol | Rods |
| INDX #36 | 15% v/v Tacsimate pH 7.0, 0.1M HEPES pH 7.0, 2% w/v Polyethylene Glycol 3350, 1% Glycerol | Rods |
| INDX #36 | 15% v/v Tacsimate pH 7.0, 0.1M HEPES pH 7.0, 2% w/v Polyethylene Glycol 3350, 2% Glycerol | Rods |
| INDX #36 | 15% v/v Tacsimate pH 7.0, 0.1M HEPES pH 7.0, 2% w/v Polyethylene Glycol 3350, 3% Glycerol | Rods |
| INDX #36 | 15% v/v Tacsimate pH 7.0, 0.1M HEPES pH 7.0, 2% w/v Polyethylene Glycol 3350, 4% Glycerol | Rods |
| INDX #36 | 15% v/v Tacsimate pH 7.0, 0.1M HEPES pH 7.0, 2% w/v Polyethylene Glycol 3350, 5% Glycerol | Rods |
| INDX #36 | 15% v/v Tacsimate pH 7.0, 0.1M HEPES pH 7.0, 2% w/v Polyethylene Glycol 3350, 6% Glycerol | Rods |
| INDX #36 | 15% v/v Tacsimate pH 7.0, 0.1M HEPES pH 7.0, 2% w/v Polyethylene Glycol 3350, 7% Glycerol | Rods |
| INDX #36 | 15% v/v Tacsimate pH 7.0, 0.1M HEPES pH 7.0, 2% w/v Polyethylene Glycol 3350, 8% Glycerol | Rods |
| INDX #36 | 15% v/v Tacsimate pH 7.0, 0.1M HEPES pH 7.0, 2% w/v Polyethylene Glycol 3350, 9% Glycerol | Rods |
| INDX #36 | 15% v/v Tacsimate pH 7.0, 0.1M HEPES pH 7.0, 2% w/v Polyethylene Glycol 3350, 10% Glycerol | Rods |
| INDX #36 | 15% v/v Tacsimate pH 7.0, 0.1M HEPES pH 7.0, 2% w/v Polyethylene Glycol 3350, 1% Sucrose | Rods |
| INDX #36 | 15% v/v Tacsimate pH 7.0, 0.1M HEPES pH 7.0, 2% w/v Polyethylene Glycol 3350, 2% Sucrose | Rods |
| INDX #36 | 15% v/v Tacsimate pH 7.0, 0.1M HEPES pH 7.0, 2% w/v Polyethylene Glycol 3350, 3% Sucrose | Rods |
| INDX #36 | 15% v/v Tacsimate pH 7.0, 0.1M HEPES pH 7.0, 2% w/v Polyethylene Glycol 3350, 4% Sucrose | Rods |
| INDX #36 | 15% v/v Tacsimate pH 7.0, 0.1M HEPES pH 7.0, 2% w/v Polyethylene Glycol 3350, 5% Sucrose | Rods |
| INDX #36 | 15% v/v Tacsimate pH 7.0, 0.1M HEPES pH 7.0, 2% w/v Polyethylene Glycol 3350, 6% Sucrose | Rods |
| INDX #36 | 15% v/v Tacsimate pH 7.0, 0.1M HEPES pH 7.0, 2% w/v Polyethylene Glycol 3350, 7% Sucrose | Rods |
| INDX #36 | 15% v/v Tacsimate pH 7.0, 0.1M HEPES pH 7.0, 2% w/v Polyethylene Glycol 3350, 8% Sucrose | Rods |
| INDX #36 | 15% v/v Tacsimate pH 7.0, 0.1M HEPES pH 7.0, 2% w/v Polyethylene Glycol 3350, 9% Sucrose | Rods |
| INDX #36 | 15% v/v Tacsimate pH 7.0, 0.1M HEPES pH 7.0, 2% w/v Polyethylene Glycol 3350, 10% Sucrose | Rods |
| INDX #36 | 15% v/v Tacsimate pH 7.0, 0.1M HEPES pH 7.0, 2% w/v Polyethylene Glycol 3350, 1% Trehalose | Rods |
| INDX #36 | 15% v/v Tacsimate pH 7.0, 0.1M HEPES pH 7.0, 2% w/v Polyethylene Glycol 3350, 2% Trehalose | Rods |

TABLE 10-continued

Additional crystallization conditions producing AB-30 crystals using Index #36 and additives (cryoprotectants) at room temperature.

| Crystallization Screen | Crystallization conditions | Crystal morphology |
|---|---|---|
| INDX #36 | 15% v/v Tacsimate pH 7.0, 0.1M HEPES pH 7.0, 2% w/v Polyethylene Glycol 3350, 3% Trehalose | Rods |
| INDX #36 | 15% v/v Tacsimate pH 7.0, 0.1M HEPES pH 7.0, 2% w/v Polyethylene Glycol 3350, 4% Trehalose | Rods |
| INDX #36 | 15% v/v Tacsimate pH 7.0, 0.1M HEPES pH 7.0, 2% w/v Polyethylene Glycol 3350, 5% Trehalose | Rods |
| INDX #36 | 15% v/v Tacsimate pH 7.0, 0.1M HEPES pH 7.0, 2% w/v Polyethylene Glycol 3350, 6% Trehalose | Rods |
| INDX #36 | 15% v/v Tacsimate pH 7.0, 0.1M HEPES pH 7.0, 2% w/v Polyethylene Glycol 3350, 7% Trehalose | Rods |
| INDX #36 | 15% v/v Tacsimate pH 7.0, 0.1M HEPES pH 7.0, 2% w/v Polyethylene Glycol 3350, 8% Trehalose | Rods |
| INDX #36 | 15% v/v Tacsimate pH 7.0, 0.1M HEPES pH 7.0, 2% w/v Polyethylene Glycol 3350, 9% Trehalose | Rods |
| INDX #36 | 15% v/v Tacsimate pH 7.0, 0.1M HEPES pH 7.0, 2% w/v Polyethylene Glycol 3350, 10% Trehalose | Rods |
| INDX #36 | 15% v/v Tacsimate pH 7.0, 0.1M HEPES pH 7.0, 2% w/v Polyethylene Glycol 3350, 15% Trehalose | Rods |
| INDX #36 | 15% v/v Tacsimate pH 7.0, 0.1M HEPES pH 7.0, 2% w/v Polyethylene Glycol 3350, 20% Trehalose | Rods |
| INDX #36 | 15% v/v Tacsimate pH 7.0, 0.1M HEPES pH 7.0, 2% w/v Polyethylene Glycol 3350, 1% Xylitol | Rods |
| INDX #36 | 15% v/v Tacsimate pH 7.0, 0.1M HEPES pH 7.0, 2% w/v Polyethylene Glycol 3350, 2% Xylitol | Rods |
| INDX #36 | 15% v/v Tacsimate pH 7.0, 0.1M HEPES pH 7.0, 2% w/v Polyethylene Glycol 3350, 3% Xylitol | Rods |
| INDX #36 | 15% v/v Tacsimate pH 7.0, 0.1M HEPES pH 7.0, 2% w/v Polyethylene Glycol 3350, 4% Xylitol | Rods |
| INDX #36 | 15% v/v Tacsimate pH 7.0, 0.1M HEPES pH 7.0, 2% w/v Polyethylene Glycol 3350, 5% Xylitol | Rods |
| INDX #36 | 15% v/v Tacsimate pH 7.0, 0.1M HEPES pH 7.0, 2% w/v Polyethylene Glycol 3350, 6% Xylitol | Rods |
| INDX #36 | 15% v/v Tacsimate pH 7.0, 0.1M HEPES pH 7.0, 2% w/v Polyethylene Glycol 3350, 7% Xylitol | Rods |
| INDX #36 | 15% v/v Tacsimate pH 7.0, 0.1M HEPES pH 7.0, 2% w/v Polyethylene Glycol 3350, 8% Xylitol | Rods |
| INDX #36 | 15% v/v Tacsimate pH 7.0, 0.1M HEPES pH 7.0, 2% w/v Polyethylene Glycol 3350, 9% Xylitol | Rods |
| INDX #36 | 15% v/v Tacsimate pH 7.0, 0.1M HEPES pH 7.0, 2% w/v Polyethylene Glycol 3350, 10% Xylitol | Rods |
| INDX #36 | 15% v/v Tacsimate pH 7.0, 0.1M HEPES pH 7.0, 2% w/v Polyethylene Glycol 3350, 15% Xylitol | Rods |
| INDX #36 | 15% v/v Tacsimate pH 7.0, 0.1M HEPES pH 7.0, 2% w/v Polyethylene Glycol 3350, 20% Xylitol | Rods |

TABLE 11

Additional crystallization conditiond producing Ab-30 crystals using Index #36 and additives (varying percentages of Polysorbate 20) at room temperature.

| Crystallization screen | Crystallization conditions | Crystal morphology |
|---|---|---|
| INDX #36 | 15% v/v Tacsimate pH 7.0, 0.1M HEPES pH 7.0, 2% w/v Polyethylene Glycol 3350, 0.05% Polysorbate 20 | Rods |
| INDX #36 | 15% v/v Tacsimate pH 7.0, 0.1M HEPES pH 7.0, 2% w/v Polyethylene Glycol 3350, 0.10% Polysorbate 20 | Rods |
| INDX #36 | 15% v/v Tacsimate pH 7.0, 0.1M HEPES pH 7.0, 2% w/v Polyethylene Glycol 3350, 0.15% Polysorbate 20 | Rods |
| INDX #36 | 15% v/v Tacsimate pH 7.0, 0.1M HEPES pH 7.0, 2% w/v Polyethylene Glycol 3350, 0.20% Polysorbate 20 | Rods |
| INDX #36 | 15% v/v Tacsimate pH 7.0, 0.1M HEPES pH 7.0, 2% w/v Polyethylene Glycol 3350, 0.25% Polysorbate 20 | Rods |
| INDX #36 | 15% v/v Tacsimate pH 7.0, 0.1M HEPES pH 7.0, 2% w/v Polyethylene Glycol 3350, 0.30% Polysorbate 20 | Rods |
| INDX #36 | 15% v/v Tacsimate pH 7.0, 0.1M HEPES pH 7.0, 2% w/v Polyethylene Glycol 3350, 0.35% Polysorbate 20 | Rods |
| INDX #36 | 15% v/v Tacsimate pH 7.0, 0.1M HEPES pH 7.0, 2% w/v Polyethylene Glycol 3350, 0.40% Polysorbate 20 | Rods |

TABLE 11-continued

Additional crystallization conditiond producing Ab-30 crystals using Index #36 and additives (varying percentages of Polysorbate 20) at room temperature.

| Crystallization screen | Crystallization conditions | Crystal morphology |
| --- | --- | --- |
| INDX #36 | 15% v/v Tacsimate pH 7.0, 0.1M HEPES pH 7.0, 2% w/v Polyethylene Glycol 3350, 0.45% Polysorbate 20 | Rods |
| INDX #36 | 15% v/v Tacsimate pH 7.0, 0.1M HEPES pH 7.0, 2% w/v Polyethylene Glycol 3350, 0.50% Polysorbate 20 | Rods |

Various morphologies of Ab-30 crystals can be grown under scale-up conditions whereby the antibody in a liquid formulation is added to a volume of known crystallization reagent and stored in a sealed container. Ab-30 crystals can be grown under these conditions in less than 24 hours, at room temperature or refrigerated temperatures (4° C.) and have been shown to produce slow release and high yield.

Ab-30 crystals produced under some of the conditions provided in Tables 1-11 have been shown to withstand storage at 4° C. for a period of greater than 6 months and at room temperature (RT) for a period of 21 months (Index#36 and different concentration of cryoprotectants), 22 months (Index#36 and amino acids), 32 months (Index#36 and salts), and 25 months (Index#36 with different percentages of Polysorbate 20). Exemplary crystallization conditions producing such Ab-30 crystals and the length of storage time at 4° C. and room temperature are provided below in Tables 12 and 13, respectively.

TABLE 12

| Crystallization screen | Crystallization conditions | Length of storage time at 4° C. |
| --- | --- | --- |
| WIZ I #22 | 0.1M Tris pH 8.5, 10% v/v 2-propanol | 9 months |
| WIZ I #9 | 0.1M Acetate pH 4.5, 1M $(NH_4)_2HPO_4$ | 9 months |
| WIZ I #42 | 0.1M Tris pH 7.0, 15% v/v Ethanol | 10 months |
| WIZ III #40 | 0.1M Bicine pH 9.0, 10% v/v MPD | 10 months |

TABLE 13

| Crystallization Screen | Crystallization conditions at room temperature | Length of storage time at room temperature |
| --- | --- | --- |
| INDX #36 | 15% v/v Tacsimate pH 7.0, 0.1M HEPES pH 7.0, 2% w/v Polyethylene Glycol 3350 | 21 months |
| INDX #36 | 15% v/v Tacsimate pH 7.0, 0.1M HEPES pH 7.0, 2% w/v Polyethylene Glycol 3350, 3% Ethylene Glycol | 21 months |
| INDX #36 | 15% v/v Tacsimate pH 7.0, 0.1M HEPES pH 7.0, 2% w/v Polyethylene Glycol 3350, 4% Ethylene Glycol | 21 months |
| INDX #36 | 15% v/v Tacsimate pH 7.0, 0.1M HEPES pH 7.0, 2% w/v Polyethylene Glycol 3350, 5% Ethylene Glycol | 21 months |
| INDX #36 | 15% v/v Tacsimate pH 7.0, 0.1M HEPES pH 7.0, 2% w/v Polyethylene Glycol 3350, 9% Ethylene Glycol | 21 months |
| INDX #36 | 15% v/v Tacsimate pH 7.0, 0.1M HEPES pH 7.0, 2% w/v Polyethylene Glycol 3350, 15% Ethylene Glycol | 21 months |
| INDX #36 | 15% v/v Tacsimate pH 7.0, 0.1M HEPES pH 7.0, 2% w/v Polyethylene Glycol 3350, 25% Ethylene Glycol | 21 months |
| INDX #36 | 15% v/v Tacsimate pH 7.0, 0.1M HEPES pH 7.0, 2% w/v Polyethylene Glycol 3350, 30% Ethylene Glycol | 21 months |
| INDX #36 | 15% v/v Tacsimate pH 7.0, 0.1M HEPES pH 7.0, 2% w/v Polyethylene Glycol 3350, 35% Ethylene Glycol | 21 months |
| INDX #36 | 15% v/v Tacsimate pH 7.0, 0.1M HEPES pH 7.0, 2% w/v Polyethylene Glycol 3350, 40% Ethylene Glycol | 21 months |
| INDX #36 | 15% v/v Tacsimate pH 7.0, 0.1M HEPES pH 7.0, 2% w/v Polyethylene Glycol 3350, 1% Glycerol | 21 months |
| INDX #36 | 15% v/v Tacsimate pH 7.0, 0.1M HEPES pH 7.0, 2% w/v Polyethylene Glycol 3350, 2% Glycerol | 21 months |
| INDX #36 | 15% v/v Tacsimate pH 7.0, 0.1M HEPES pH 7.0, 2% w/v Polyethylene Glycol 3350, 3% Glycerol | 21 months |
| INDX #36 | 15% v/v Tacsimate pH 7.0, 0.1M HEPES pH 7.0, 2% w/v Polyethylene Glycol 3350, 4% Glycerol | 21 months |
| INDX #36 | 15% v/v Tacsimate pH 7.0, 0.1M HEPES pH 7.0, 2% w/v Polyethylene Glycol 3350, 5% Glycerol | 21 months |
| INDX #36 | 15% v/v Tacsimate pH 7.0, 0.1M HEPES pH 7.0, 2% w/v Polyethylene Glycol 3350, 6% Glycerol | 21 months |
| INDX #36 | 15% v/v Tacsimate pH 7.0, 0.1M HEPES pH 7.0, 2% w/v Polyethylene Glycol 3350, 8% Glycerol | 21 months |
| INDX #36 | 15% v/v Tacsimate pH 7.0, 0.1M HEPES pH 7.0, 2% w/v Polyethylene Glycol 3350, 9% Glycerol | 21 months |
| INDX #36 | 15% v/v Tacsimate pH 7.0, 0.1M HEPES pH 7.0, 2% w/v Polyethylene Glycol 3350, 10% Glycerol | 21 months |
| INDX #36 | 15% v/v Tacsimate pH 7.0, 0.1M HEPES pH 7.0, 2% w/v Polyethylene Glycol 3350, 1% Sucrose | 21 months |

TABLE 13-continued

| Crystallization Screen | Crystallization conditions at room temperature | Length of storage time at room temperature |
|---|---|---|
| INDX #36 | 15% v/v Tacsimate pH 7.0, 0.1M HEPES pH 7.0, 2% w/v Polyethylene Glycol 3350, 2% Sucrose | 21 months |
| INDX #36 | 15% v/v Tacsimate pH 7.0, 0.1M HEPES pH 7.0, 2% w/v Polyethylene Glycol 3350, 3% Sucrose | 21 months |
| INDX #36 | 15% v/v Tacsimate pH 7.0, 0.1M HEPES pH 7.0, 2% w/v Polyethylene Glycol 3350, 4% Sucrose | 21 months |
| INDX #36 | 15% v/v Tacsimate pH 7.0, 0.1M HEPES pH 7.0, 2% w/v Polyethylene Glycol 3350, 5% Sucrose | 21 months |
| INDX #36 | 15% v/v Tacsimate pH 7.0, 0.1M HEPES pH 7.0, 2% w/v Polyethylene Glycol 3350, 6% Sucrose | 21 months |
| INDX #36 | 15% v/v Tacsimate pH 7.0, 0.1M HEPES pH 7.0, 2% w/v Polyethylene Glycol 3350, 7% Sucrose | 21 months |
| INDX #36 | 15% v/v Tacsimate pH 7.0, 0.1M HEPES pH 7.0, 2% w/v Polyethylene Glycol 3350, 8% Sucrose | 21 months |
| INDX #36 | 15% v/v Tacsimate pH 7.0, 0.1M HEPES pH 7.0, 2% w/v Polyethylene Glycol 3350, 10% Sucrose | 21 months |
| INDX #36 | 15% v/v Tacsimate pH 7.0, 0.1M HEPES pH 7.0, 2% w/v Polyethylene Glycol 3350, 1% Trehalose | 21 months |
| INDX #36 | 15% v/v Tacsimate pH 7.0, 0.1M HEPES pH 7.0, 2% w/v Polyethylene Glycol 3350, 2% Trehalose | 21 months |
| INDX #36 | 15% v/v Tacsimate pH 7.0, 0.1M HEPES pH 7.0, 2% w/v Polyethylene Glycol 3350, 3% Trehalose | 21 months |
| INDX #36 | 15% v/v Tacsimate pH 7.0, 0.1M HEPES pH 7.0, 2% w/v Polyethylene Glycol 3350, 4% Trehalose | 21 months |
| INDX #36 | 15% v/v Tacsimate pH 7.0, 0.1M HEPES pH 7.0, 2% w/v Polyethylene Glycol 3350, 5% Trehalose | 21 months |
| INDX #36 | 15% v/v Tacsimate pH 7.0, 0.1M HEPES pH 7.0, 2% w/v Polyethylene Glycol 3350, 6% Trehalose | 21 months |
| INDX #36 | 15% v/v Tacsimate pH 7.0, 0.1M HEPES pH 7.0, 2% w/v Polyethylene Glycol 3350, 7% Trehalose | 21 months |
| INDX #36 | 15% v/v Tacsimate pH 7.0, 0.1M HEPES pH 7.0, 2% w/v Polyethylene Glycol 3350, 8% Trehalose | 21 months |
| INDX #36 | 15% v/v Tacsimate pH 7.0, 0.1M HEPES pH 7.0, 2% w/v Polyethylene Glycol 3350, 10% Trehalose | 21 months |
| INDX #36 | 15% v/v Tacsimate pH 7.0, 0.1M HEPES pH 7.0, 2% w/v Polyethylene Glycol 3350, 15% Trehalose | 21 months |
| INDX #36 | 15% v/v Tacsimate pH 7.0, 0.1M HEPES pH 7.0, 2% w/v Polyethylene Glycol 3350, 20% Trehalose | 21 months |
| INDX #36 | 15% v/v Tacsimate pH 7.0, 0.1M HEPES pH 7.0, 2% w/v Polyethylene Glycol 3350, 1% Xylitol | 21 months |
| INDX #36 | 15% v/v Tacsimate pH 7.0, 0.1M HEPES pH 7.0, 2% w/v Polyethylene Glycol 3350, 2% Xylitol | 21 months |
| INDX #36 | 15% v/v Tacsimate pH 7.0, 0.1M HEPES pH 7.0, 2% w/v Polyethylene Glycol 3350, 3% Xylitol | 21 months |
| INDX #36 | 15% v/v Tacsimate pH 7.0, 0.1M HEPES pH 7.0, 2% w/v Polyethylene Glycol 3350, 4% Xylitol | 21 months |
| INDX #36 | 15% v/v Tacsimate pH 7.0, 0.1M HEPES pH 7.0, 2% w/v Polyethylene Glycol 3350, 5% Xylitol | 21 months |
| INDX #36 | 15% v/v Tacsimate pH 7.0, 0.1M HEPES pH 7.0, 2% w/v Polyethylene Glycol 3350, 7% Xylitol | 21 months |
| INDX #36 | 15% v/v Tacsimate pH 7.0, 0.1M HEPES pH 7.0, 2% w/v Polyethylene Glycol 3350, 9% Xylitol | 21 months |
| INDX #36 | 15% v/v Tacsimate pH 7.0, 0.1M HEPES pH 7.0, 2% w/v Polyethylene Glycol 3350, 15% Xylitol | 21 months |
| INDX #36 | 15% v/v Tacsimate pH 7.0, 0.1M HEPES pH 7.0, 2% w/v Polyethylene Glycol 3350, 20 mM Arginine | 22 months |
| INDX #36 | 15% v/v Tacsimate pH 7.0, 0.1M HEPES pH 7.0, 2% w/v Polyethylene Glycol 3350, 80 mM Arginine | 22 months |
| INDX #36 | 15% v/v Tacsimate pH 7.0, 0.1M HEPES pH 7.0, 2% w/v Polyethylene Glycol 3350, 80 mM Cysteine | 22 months |
| INDX #36 | 15% v/v Tacsimate pH 7.0, 0.1M HEPES pH 7.0, 2% w/v Polyethylene Glycol 3350, 100 mM Cysteine | 22 months |
| INDX #36 | 15% v/v Tacsimate pH 7.0, 0.1M HEPES pH 7.0, 2% w/v Polyethylene Glycol 3350, 10 mM Methionine | 22 months |
| INDX #36 | 15% v/v Tacsimate pH 7.0, 0.1M HEPES pH 7.0, 2% w/v Polyethylene Glycol 3350, 40 mM Methionine | 22 months |

TABLE 13-continued

| Crystallization Screen | Crystallization conditions at room temperature | Length of storage time at room temperature |
|---|---|---|
| INDX #36 | 15% v/v Tacsimate pH 7.0, 0.1M HEPES pH 7.0, 2% w/v Polyethylene Glycol 3350, 80 mM Methionine | 22 months |
| INDX #36 | 15% v/v Tacsimate pH 7.0, 0.1M HEPES pH 7.0, 2% w/v Polyethylene Glycol 3350, 100 mM Methionine | 22 months |
| INDX #36 | 15% v/v Tacsimate pH 7.0, 0.1M HEPES pH 7.0, 2% w/v Polyethylene Glycol 3350, 10 mM Proline | 22 months |
| INDX #36 | 15% v/v Tacsimate pH 7.0, 0.1M HEPES pH 7.0, 2% w/v Polyethylene Glycol 3350, 20 mM Proline | 22 months |
| INDX #36 | 15% v/v Tacsimate pH 7.0, 0.1M HEPES pH 7.0, 2% w/v Polyethylene Glycol 3350, 40 mM Proline | 22 months |
| INDX #36 | 15% v/v Tacsimate pH 7.0, 0.1M HEPES pH 7.0, 2% w/v Polyethylene Glycol 3350, 80 mM Proline | 22 months |
| INDX #36 | 15% v/v Tacsimate pH 7.0, 0.1M HEPES pH 7.0, 2% w/v Polyethylene Glycol 3350, 0.05% Polysorbate 20 | 25 months |
| INDX #36 | 15% v/v Tacsimate pH 7.0, 0.1M HEPES pH 7.0, 2% w/v Polyethylene Glycol 3350, 0.10% Polysorbate 20 | 25 months |
| INDX #36 | 15% v/v Tacsimate pH 7.0, 0.1M HEPES pH 7.0, 2% w/v Polyethylene Glycol 3350, 0.15% Polysorbate 20 | 25 months |
| INDX #36 | 15% v/v Tacsimate pH 7.0, 0.1M HEPES pH 7.0, 2% w/v Polyethylene Glycol 3350, 0.20% Polysorbate 20 | 25 months |
| INDX #36 | 15% v/v Tacsimate pH 7.0, 0.1M HEPES pH 7.0, 2% w/v Polyethylene Glycol 3350, 0.25% Polysorbate 20 | 25 months |
| INDX #36 | 15% v/v Tacsimate pH 7.0, 0.1M HEPES pH 7.0, 2% w/v Polyethylene Glycol 3350, 0.30% Polysorbate 20 | 25 months |
| INDX #36 | 15% v/v Tacsimate pH 7.0, 0.1M HEPES pH 7.0, 2% w/v Polyethylene Glycol 3350, 0.35% Polysorbate 20 | 25 months |
| INDX #36 | 15% v/v Tacsimate pH 7.0, 0.1M HEPES pH 7.0, 2% w/v Polyethylene Glycol 3350, 0.40% Polysorbate 20 | 25 months |
| INDX #36 | 15% v/v Tacsimate pH 7.0, 0.1M HEPES pH 7.0, 2% w/v Polyethylene Glycol 3350, 0.45% Polysorbate 20 | 25 months |
| INDX #36 | 15% v/v Tacsimate pH 7.0, 0.1M HEPES pH 7.0, 2% w/v Polyethylene Glycol 3350, 0.50% Polysorbate 20 | 25 months |
| INDX #36 | 15% v/v Tacsimate pH 7.0, 0.1M HEPES pH 7.0, 2% w/v Polyethylene Glycol 3350 | 26 months |
| INDX #36 | 15% v/v Tacsimate pH 7.0, 0.1M HEPES pH 7.0, 2% w/v Polyethylene Glycol 3350, 10 mM Zinc acetate | 31 months |
| INDX #36 | 15% v/v Tacsimate pH 7.0, 0.1M HEPES pH 7.0, 2% w/v Polyethylene Glycol 3350, 10 mM Magnesium Acetate Tetrahydrate | 32 months |
| INDX #36 | 15% v/v Tacsimate pH 7.0, 0.1M HEPES pH 7.0, 2% w/v Polyethylene Glycol 3350, 10 mM Magnesium nitrate | 32 months |
| INDX #36 | 15% v/v Tacsimate pH 7.0, 0.1M HEPES pH 7.0, 2% w/v Polyethylene Glycol 3350, 10 mM Magnesium sulfate | 32 months |
| INDX #36 | 15% v/v Tacsimate pH 7.0, 0.1M HEPES pH 7.0, 2% w/v Polyethylene Glycol 3350, 10 mM Zinc sulfate | 32 months |
| PEG Screen Index #36 | 15% v/v Tacsimate pH 7.0, 0.1M HEPES pH 7.0, 2% w/v Polyethylene Glycol 3350 | 4 years and 3 months - The tray was set up at 4° C. originally and was stored at RT the last 6 months |

The foregoing Example demonstrates that Ab-30 was crystallizable under a variety of crystallization conditions, but crystals did not form under every condition tested. Approximately 2000 crystallization conditions were tested in a number of different commercially-available (i.e., Hampton Research, Emerald Bioscience) and proprietary screens, but only approximately 775 conditions produced Ab-30 crystals.

Example 2

Batch Crystallization of Ab-30

50 μL of Ab-30 at 75.7 mg/mL was mixed with 50 μL of crystallization conditions (GRAS Screen, Index Screen, Wizard I Screen, Wizard II Screen and Wizard III Screen) to make a total of 100 μL batch volume in a 1.5 mL microcentrifuge tube. 40 μL of Ab-30 (75.7 mg/mL) was mixed with 20 μL of Low Iconic Strength Screen buffers and with 50 μL of 4% PEG-3350 to make a total 110 μL batch volume. The crystallization conditions used were as described below in Table 14.

TABLE 14

| Crystallization screen | Crystallization conditions | % Efficiency | Morphology |
|---|---|---|---|
| GRAS 1 | Isopropanol, 19.9%, Na—K-Phosphate, 0.02M, pH 7.5 | 85.783 | Ellipsoids |
| GRAS 2 | Isopropanol, 45.39% | N/A | N/A |
| GRAS 50 | Na-Citrate, 0.40M, TRIS-HCL, 0.06M, pH 7.5, Glycerol, 2.36% | 70.012 | Ellipsoids |
| GRAS 53 | Ethanol, 46.10%, Glutamic acid, 0.03M, pH 4.5, Glycerol 4.94% | N/A | N/A |
| GRAS 54 | Ethanol, 43.29%, Tween-80, 0.01% | N/A | N/A |
| GRAS 58 | Isopropanol, 49.65%, TRIS-HCL, 0.06M, pH 6.5 | N/A | N/A |
| GRAS 65 | Isopropanol, 33.74%, Glutamic acid, 0.06M, pH 6.5 | N/A | N/A |
| GRAS 67 | Isopropanol, 39.35%, Glutamic acid, 0.03M, pH 4.5, EDTA, 0.01M | N/A | N/A |
| GRAS 68 | Isopropanol, 38.05%, Na—K-Phosphoate, 0.02M, pH 7.5 | 77.647 | Ellipsoids |
| GRAS 70 | Na-Acetate, 1.60M, Ethanol, 3.41% | 69.462 | Ellipsoids |
| GRAS 74 | Na-Citrate, 0.29M, Na—K-Phosphate, 0.08M, pH 7.5 | 73.229 | Ellipsoids |
| GRAS 78 | Na-Acetate, 1.82M | 73.561 | Ellipsoids |
| GRAS 81 | Ethanol, 13.29%, Tween-80, 0.01% | N/A | N/A |
| GRAS 82 | Na-Citrate, 0.71M, Histidine, 0.01M, pH 5.5, Glycerol, 6.29% | 82.633 | Ellipsoids |
| GRAS 83 | Na-Acetate, 2.04M, TRIS-HCL, 0.07M, pH 8.5 | 67.999 | Ellipsoids |
| GRAS 85 | Isopropanol, 20.18%, Histidine, 0.01M, pH 5.5, Ka-K-Phosphate, 0.09M | N/A | N/A |
| GRAS 88 | Ethanol, 12.78%, Na—K-Phosphate, 0.05M, Tween-80, 0.01% | 72.536 | Ellipsoids |
| GRAS 96 | Na-Ctrate, 0.38M, Na-Acetate, 0.03M, pH 6.5, Tween-20, 0.01% | 75.029 | Ellipsoids |
| INDX #17 | 1.4 Sodium phosphate monobasic monohydrate/potassium phosphate dibasic, pH 5.6 | 53.209 | Rods |
| INDX#18 | 1.4 Sodium phosphate monobasic monohydrate/potassium phosphate dibasic, pH 6.9 | 79.667 | Rods |
| INDX#22 | 0.8M Succinic Acid, pH 7.0 | 82.371 | Rods |
| INDX#24 | 2.8 Sodium acetate trihydrate, pH 7.0 | 76.762 | Rods |
| INDX#26 | 1.1M Ammonium tartrate dibasic, pH 7.0 | N/A | N/A |
| INDX#28 | 35% v/v Tacsimate, pH 7.0 | 83.178 | Rods |
| INDX#30 | 0.1M Sodium chloride, 0.1M BIS-TRIS, pH 6.5, 1.5M Ammonium sulfate | 70.106 | Rods |
| INDX#31 | 0.8M Potassium sodium tartrate tetrahydrate, 0.1M Tris, pH 8.5, 0.5% w/v polyethylene glycol monomethyl ether 5,000 | 79.394 | Rods |
| INDX#33 | 1.1M Sodium malonare, pH 7.0, 0.1M HEPES, pH 7.0, 0.5% v/v Jeffamine ED-2001, pH 7.0 | 85.613 | Rods |
| INDX#34 | 1.0 Succinic acid, pH 7.0, 0.1M HEPES, pH 7.0, 1% w/v polyethylene glycol monomethyl ether 2,000 | 87.384 | Rods |
| INDX#35 | 1.0M Ammonium sulfate, 0.1M HEPES, pH 7.0, 0.5% w/v/ PEG-8000 | 51.844 | Rods |
| INDX#36 | 15% v/v Tacsimate pH 7.0, 0.1M HEPES, pH 7.0, 2% w/v PEG-3350 | 76.235 | Rods |
| INDX#36-1 | 15% v/v Tacsimate pH 7.0, 0.1M HEPES, pH 7.0, 2% w/v PEG-3350 | 52.485 | Ellipsoids |
| INDX#36-2 | 15% v/v Tacsimate pH 7.0, 0.1M HEPES, pH 7.0, 2% w/v PEG-3350, 10 mM ammonium acetate | 70.246 | Tiny crystals |
| INDX#36-3 | 15% v/v Tacsimate pH 7.0, 0.1M HEPES, pH 7.0, 2% w/v PEG-3350, 10 mM lithium acetate dehydrate | 66.129 | Ellipsoids (small) |
| INDX#36-4 | 15% v/v Tacsimate pH 7.0, 0.1M HEPES, pH 7.0, 2% w/v PEG-3350, 10 mM magnesium acetate tetrahydrate | 57.306 | Ellipsoids |
| INDX#36-5 | 15% v/v Tacsimate pH 7.0, 0.1M HEPES, pH 7.0, 2% w/v PEG-3350, 10 mM zince acetate | 50.297 | Ellipsoids |
| INDX#36-6 | 15% v/v Tacsimate pH 7.0, 0.1M HEPES, pH 7.0, 2% w/v PEG-3350, 10 mM magnesium chloride | 51.951 | Ellipsoids |
| INDX#36-7 | 15% v/v Tacsimate pH 7.0, 0.1M HEPES, pH 7.0, 2% w/v PEG-3350, 10 mM zinc chloride | 48.838 | Ellipsoids |
| INDX#36-8 | 15% v/v Tacsimate pH 7.0, 0.1M HEPES, pH 7.0, 2% w/v PEG-3350, 10 mM magnesium formate | 62.074 | Ellipsoids (small) |

TABLE 14-continued

| Crystallization screen | Crystallization conditions | % Efficiency | Morphology |
|---|---|---|---|
| INDX#36-9 | 15% v/v Tacsimate pH 7.0, 0.1M HEPES, pH 7.0, 2% w/v PEG-3350, 10 mM magnesium nitrate | 49.246 | Ellipsoids |
| INDX#36-10 | 15% v/v Tacsimate pH 7.0, 0.1M HEPES, pH 7.0, 2% w/v PEG-3350, 10 mM magnesium sulfate | 70.490 | Tiny crystals |
| INDX#36-11 | 15% v/v Tacsimate pH 7.0, 0.1M HEPES, pH 7.0, 2% w/v PEG-3350, 10 mM zinc sulfate | 54.408 | Ellipsoids |
| INDX#36-12 | 15% v/v Tacsimate pH 7.0, 0.1M HEPES, pH 7.0, 2% w/v PEG-3350, 10 mM calcium acetate and zinc acetate | 64.613 | Ellisoid |
| WIZ I #2 | 10% v/v 2-propanol, 0.1M HEPES, pH 7.5, 0.2M NaCl | N/A | N/A |
| WIZ I #9 | 1.0M ammonium phosphate dibasic, 0.1M acetate, pH 4.5 | 48.48 | Ellipsoids |
| WIZ I #12 | 20% w/v PEG-1000, 0.1M imidazole, pH 8.0, 0.2M calcium acetate | 47.87 | Ellipsoids |
| WIZ I #13 | 1.26M ammonium sulfate, 0.1M cacodylate, pH 6.5 | N/A | N/A |
| WIZ I #18 | 1.0M K—Na tartrate, 0.1M imidazole, pH 8.0, 0.2M NaCl | 62.14 | Ellipsoids |
| WIZ I #22 | 10% v/v 2-propanol, 0.1M Tris, pH 8.5 | N/A | Rods |
| WIZ I #26 | 10% w/v PEG-3000, 0.1M CHES, pH 9.5 | 48.04 | Rods |
| WIZ I #29 | 10% w/v PEG-8000, 0.1M CHES, pH 9.5, 0.2M NaCl | 87.73 | Ellipsoids |
| WIZ I #30 | 1.26M Ammonium sulfate, 0.1M acetate, pH 4.5, 0.2M NaCl | N/A | N/A |
| WIZ I #35 | 20% v/v 1,4-butanediol, 0.1M acetate, pH 4.5 | N/A | N/A |
| WIZ I #37 | 2.5M NaCl, 0.1M imidazole, pH 8.0 | N/A | N/A |
| WIZ I #39 | 20% w/v PEG-1000, 0.1M phosphate-citrate, pH 4.2, 0.2M lithium sulfate | N/A | N/A |
| WIZ I #42 | 15% v/v ethanol, 0.1M Tris, pH 7.0 | N/A | N/A |
| WIZ I #46 | 10% w/v PEG-8000, 0.1M imidazole, pH 8.0, 0.2M calcium acetate | 91.46 | Ellipsoids |
| WIZ II #10 | 1.0M ammonium phosphate dibasic, 0.1M Tris, pH 8.5 | 49.026 | Ellipsoids |
| WIZ II #12 | 30% v/v PEG-400, cacodylate, pH 6.5, 0.2M lithium sulfate | 59.491 | Ellipsoids |
| WIZ II #13 | 15% v/v ethanol, 0.1M citrate, pH 5.5, 0.2M lithium sulfate | N/A | N/A |
| WIZ II #14 | 20% w/v PEG-1000, 0.1M Na/K phosphate, pH 6.2, 0.2M NaCl | 90.258 | Ellipsoids |
| WIZ II #15 | 1.26M ammosium sulfate, 0.1M HEPES, pH 7.5 | 64.775 | Ellipsoids |
| WIZ II #21 | 35% v/v 2-methyl-2,4-pentanediol, 0.1M acetate, pH 4.5 | N/A | N/A |
| WIZ II #22 | 10% v/v 2-proponol, 0.1M imidazole, pH 8.0 | 80.572 | Ellipsoids |
| WIZ II #25 | 35% v/v 2-methyl-2,4-pentanediol, 0.1M HEPES, pH 7.5, 0.2M NaCl | N/A | N/A |
| WIZ II #26 | 30% v/v PEG-400, 0.1M CHES, pH 9.5 | N/A | N/A |
| WIZ II #27 | 10% w/v PEG-3000, 0.1M cacodylate, pH 6.5, 0.2M magnesium chloride | 54.811 | Ellipsoids |
| WIZ II #30 | 20% v/v 1,4-butanediol, 0.1M imidazole, pH 8.0, 0.2M zinc acetate | N/A | N/A |
| WIZ II #32 | 20% w/v PEG-1000, 0.1M Tris, pH 8.5 | N/A | N/A |
| WIZ II #37 | 1.0M K/Na tartrate, 0.1M Tris, pH 7.0, 0.2M lithium sulfate | 74.353 | Ellipsoids |
| WIZ II #38 | 2.5M NaCl, 0.1M acetate, pH 4.5, 0.2M lithium sulfate | N/A | N/A |
| WIZ II #42 | 30% v/v PEG-400, 0.1M HEPES, pH 7.5, 0.2M NaCl | 82.982 | Ellipsoids |
| WIZ II #43 | 10% w/v PEG-8000, 0.1M Tris. pH 7.0, 0.2M magnesium chloride | 91.443 | Ellipsoids |
| WIZ III #13 | 8% w/v PEG-4000, 0.1M sodium acetate, pH 4.65 | N/A | N/A |
| WIZ III #22 | 20% v/v ethanol, 0.1M Tris, pH 8.5 | 51.597 | Rods |
| WIZ III #25 | 10% w/v PEG-100, 10% w/v PEG-8000 | N/A | N/A |
| WIZ III #28 | 70% v/v MPD, 0.1M HEPES, pH 7.5 | N/A | N/A |
| WIZ III #29 | 40% v/v MPD, 0.1M Tris, pH 8.0 | N/A | N/A |
| WIZ III #35 | 14.4% w/v PEG-8000, 0.8M cacodylate, pH 6.5, 0.16M calcium acetate, 20% v/v glycerol | 92.195 | Ellipsoids |
| WIZ III #36 | 30% v/v Jeffamine M-600*, pH 7.0, 0.1M MES, pH 6.5, 0.05 cesium chloride | N/A | N/A |
| WIZ III #38 | 15% w/v PEG-10,000, 0.1M citrate, pH 5.5, 2% v/v dioxane | N/A | N/A |
| WIZ III #39 | 20% v/v Jeffamine M600* pH 7.0, 0.1M HEPES, pH 7.5 | N/A | N/A |

TABLE 14-continued

| Crystallization screen | Crystallization conditions | % Efficiency | Morphology |
|---|---|---|---|
| WIZ III #40 | 10% v/v MPD, 0.1M Bicine, pH 9.0 | N/A | N/A |
| WIZ III #41 | 28% w/v PEG-400, 0.1M HEPES, pH 7.5, 0.2M Calcium chloride | N/A | N/A |
| WIZ III #42 | 30% w/v PEG-4000, 0.1M Tris, pH 8.5, 0.2M lithium sulfate | N/A | N/A |
| WIZ III #46 | 50% v/v MPD, 0.1M Tris, pH 8.5, 0.2M ammonium chloride | N/A | N/A |
| WIZ III #48 | 20% w/v PEG-10,000, 0.1M HEPES, pH 7.5 | N/A | N/A |
| LISS #1 | 0.5M Potassium Chloride, 4% PEG-3350, pH 2 | N/A | N/A |
| LISS #2 | 0.05M citric acid, 4% PEG-3350, pH 3 | N/A | N/A |
| LISS #3 | 0.05M citric acid, 4% PEG-3350, pH 3.5 | N/A | N/A |
| LISS #4 | 0.05M citric acid, 4% PEG-3350, pH 4 | N/A | N/A |
| LISS #5 | 0.05M citric acid, 4% PEG-3350, pH 4.5 | N/A | N/A |
| LISS #6 | 0.05M citric acid, 4% PEG-3350, pH 5 | 87.632 | Ellipsoids |
| LISS #7 | 0.05M citric acid, 4% PEG-3350, pH 5.5 | 88.526 | Rods |
| LISS #8 | 0.05M MES, 4% PEG-3350, pH 6 | N/A | N/A |
| LISS #9 | 0.05M Bis Tris, 4% PEG-3350, pH 6.5 | N/A | N/A |
| LISS #10 | 0.05M Imidazole, 4% PEG-3350, pH 7 | 78.786 | Ellipsoids |
| LISS #11 | 0.05M HEPES, 4% PEG-3350, pH 7.5 | N/A | Heavy precipitation |
| LISS #12 | 0.05M Tris, 4% PEG-3350, pH 8 | N/A | Heavy precipitation |
| LISS #13 | 0.05M Tris, 4% PEG-3350, pH 8.5 | N/A | Heavy precipitation |
| LISS #14 | 0.05M Glycine, 4% PEG-3350, pH 9 | N/A | N/A |
| LISS #15 | 0.05M Glycine, 4% PEG-3350, pH 9.5 | N/A | Medium precipitation |
| LISS #16 | 0.05M Glycine, 4% PEG-3350, pH 10 | N/A | Heavy precipitation |
| LISS #17 | 0.05M sodium phosphate dibasic, 4% PEG-3350, pH 11 | N/A | Heavy precipitation |
| LISS #18 | 0.05M sodium phosphate dibasic, 4% PEG-3350, pH 11 | N/A | Rods |

Ab-30 was batch crystallized in a total of 104 conditions representing a percentage yield range of 40%-92% at room temperature (see Table 14). All of these conditions had crystal hits at room temperature by hanging drop vapor diffusion but not all of them crystallized in the batch form. Out of the 104 batch crystallized conditions there were only 8 conditions with percentage yield greater than 85% on day one at room temperature (i.e., INDX #34, WIZ I #46, WIZ II #43, WIZ II #14, WIZ III #35 and GRAS 1). The highest yield achieved for Ab-30 crystals was 92.195% for WIZ #35 on day one. Crystal yield changed based on crystal growth conditions. Ab-30 crystallized both at room temperature and at 4° C. but only the room temperature crystal hits were considered based on efficiency of crystallization at room temperature.

Example 3

Batch Crystallization of Ab-30, Suspension and Dissolution Studies

200 μl of Ab-30 (75.7 mg/ml) was mixed with 200 μl of crystallization condition (as described below in Table 15) in a 1.5 ml microcentrifuge tube at room temperature. The tube was vortexed after addition of the crystallization condition and was visually checked for clarity, opalescence or precipitate formation. A picture was taken of each microcentrifuge tube for each crystallization condition tested at day 0 and day 1 with Zeiss microscope equipped with Axiocam software. The morphology of the crystals produced under each crystallization condition was recorded. Crystals were harvested at day 3 for all three dissolution rate studies irrespective of time it took to reach highest percent yield for individual condition except for study 4 (crystal dissolution based on crystal packing where the crystals were harvested on day 8).

Crystals were spun down at 10,000 rpm for 15 minutes and supernatant was removed and the crystals were resuspended in different vehicles (as described below in Table 15). The microcentrifuge tubes were stored at room temperature during the course of the experiment. Percentage yield was measured using UV spec as A280 nm. The microcentrifuge tubes were spun down on a bench top centrifuge at 10,000 rpm for 15 minutes. A 1:100 dilution was performed in water and the A280 was read on a UV spec.

TABLE 15

| Study No. | Crystallization conditions | Suspension Vehicle | Morphology |
|---|---|---|---|
| 1 | INDX #36 | Water | Ellipsoids |
|  | INDX #36 | 10 mM Acetate, 9% sucrose and 0.004% PS20, pH 5.2 | Ellipsoids |
|  | INDX #36 | Saline | Ellipsoids |
|  | INDX #36 | Dextrose | Ellipsoids |
|  | INDX #36 | PBS | Ellipsoids |
| 2 | INDX #36 | 0.05M HEPES, pH 7.5, 20% PEG-350 | Ellipsoids |
|  | INDX #36 | 0.05M HEPES, pH 8.0, 20% PEG-350 | Ellipsoids |
|  | INDX #36 | 0.05M HEPES, pH 8.5, 20% PEG-350 | Ellipsoids |
|  | INDX #36 | 10 mM Glutamate, 5% sorbitol, pH 4.8 | Ellipsoids |
|  | INDX #36 | 10 mM Glutamate, 5% sorbitol, pH 5.0 | Ellipsoids |

TABLE 15-continued

| Study No. | Crystallization conditions | Suspension Vehicle | Morphology |
|---|---|---|---|
| 3 | WIZ III #35 | PBS | Ellipsoids |
|   | GRAS #88 | PBS | Rods |
|   | WIZ I #26 | PBS | Rods |
|   | Peg Ion #1 | PBS | Precipitation |
|   | GRAS #1 | PBS | Ellipsoids (tiny) |
|   | GRAS #82 | PBS | Ellipsoids (tiny) |
|   | GRAS #83 | PBS | Ellipsoids (tiny) |
| 4 | INDX #36-1 | PBS | Ellipsoids |
|   | INDX #36-2 | PBS | Ellipsoids |
|   | INDX #36 + 10 mM calcium acetate | PBS | Ellipsoids |
|   | INDX #36-3 | PBS | Ellipsoids |
|   | INDX #36-4 | PBS | Ellipsoids |
|   | INDX #36-5 | PBS | Ellipsoids |
|   | INDX #36-12 | PBS | Ellipsoids |
|   | INDX #36-6 | PBS | Ellipsoids |
|   | INDX #36-7 | PBS | Ellipsoids |
|   | INDX #36-8 | PBS | Ellipsoids |
|   | INDX #36-9 | PBS | Ellipsoids |
|   | INDX #36-10 | PBS | Ellipsoids |
|   | INDX #36-11 | PBS | Ellipsoids |
| 5 | WIZ III #35* | Dextrose | Ellipsoids |
|   | GRAS #88* | Dextrose | Rods |
|   | WIZ I #26* | Dextrose | Rods |
|   | GRAS #1* | Dextrose | Ellipsoids (tiny) |
|   | GRAS #82* | Dextrose | Ellipsoids (tiny) |
|   | GRAS #83* | Dextrose | Ellipsoids (tiny) |
|   | WIZ III #35** | Dextrose | Ellipsoids |
|   | GRAS #88** | Dextrose | Rods |
|   | WIZ I #26** | Dextrose | Rods |
|   | GRAS #1** | Dextrose | Ellipsoids (tiny) |
|   | GRAS #82** | Dextrose | Ellipsoids (tiny) |
|   | GRAS #83** | Dextrose | Ellipsoids (tiny) |

Crystal Dissolution and Suspension Vehicles:

Dissolution rate experiments for Studies 1-4 were performed at room temperature. Dissolution rate experiments for Study 5 samples marked with an asterisk (*) were stored at 4° C. and Study 5 samples marked with a double asterisk (**) were stored at 37° C. In study #1 and #2 the crystal growth condition was kept constant, which was Hampton Research Index Screen #36, and the crystals were resuspended in different vehicles to monitor crystal dissolution rates. Index #36 was chosen as a growth condition since it forms crystals very readily. In study #3 the crystal growth conditions and morphology were variable but the crystal suspension vehicle, PBS, was consistent for all conditions.

Figure 3A:
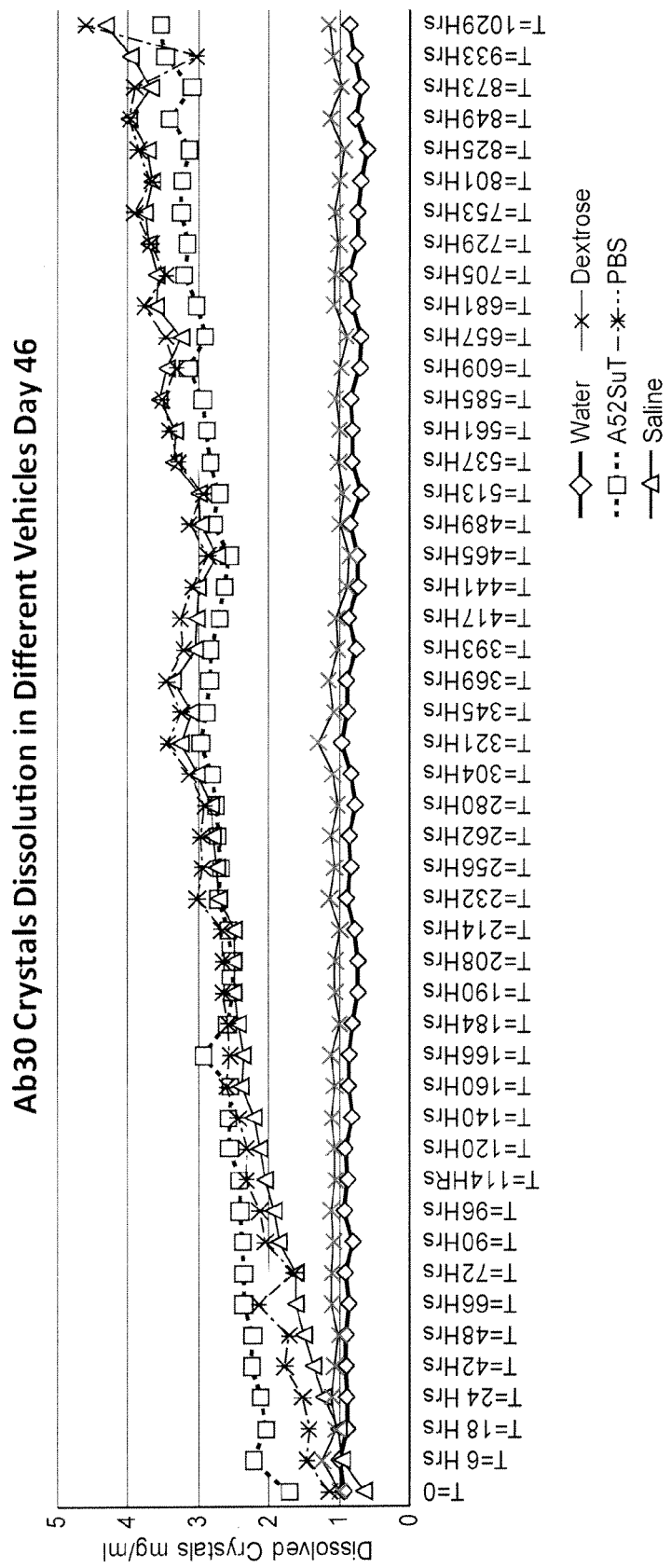
FIGS. 3A and 3B are graphs showing the dissolution rate of Ab-30 crystals in various suspension vehicles.
Figure 3B:
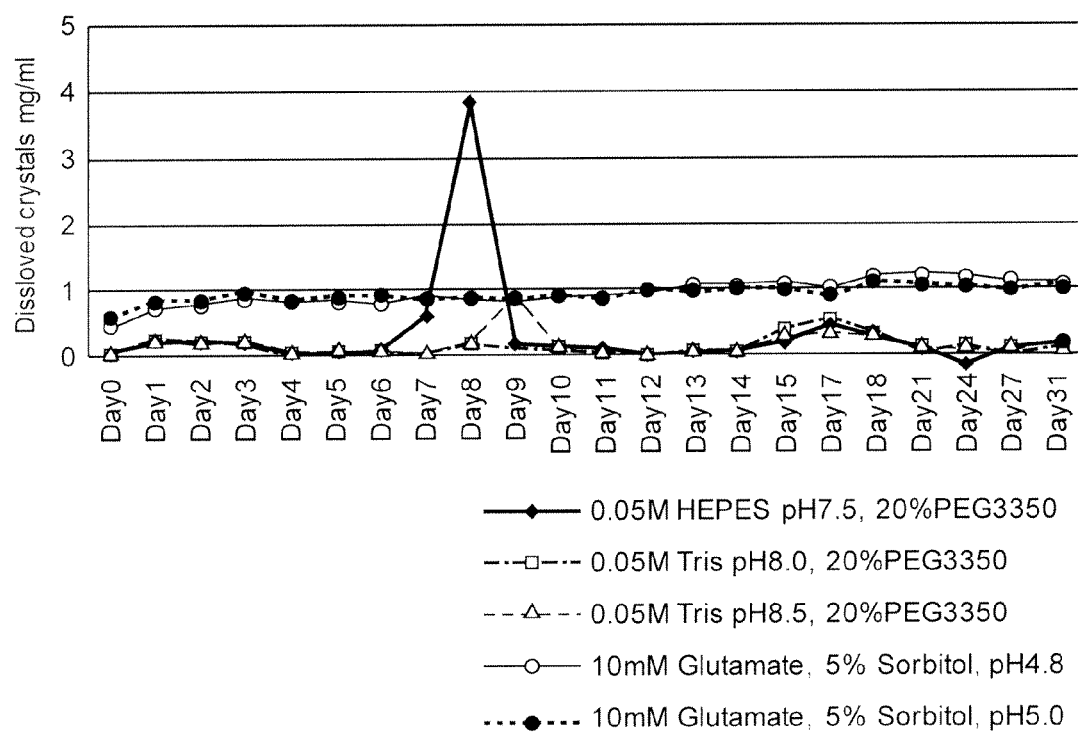
Figure 4:
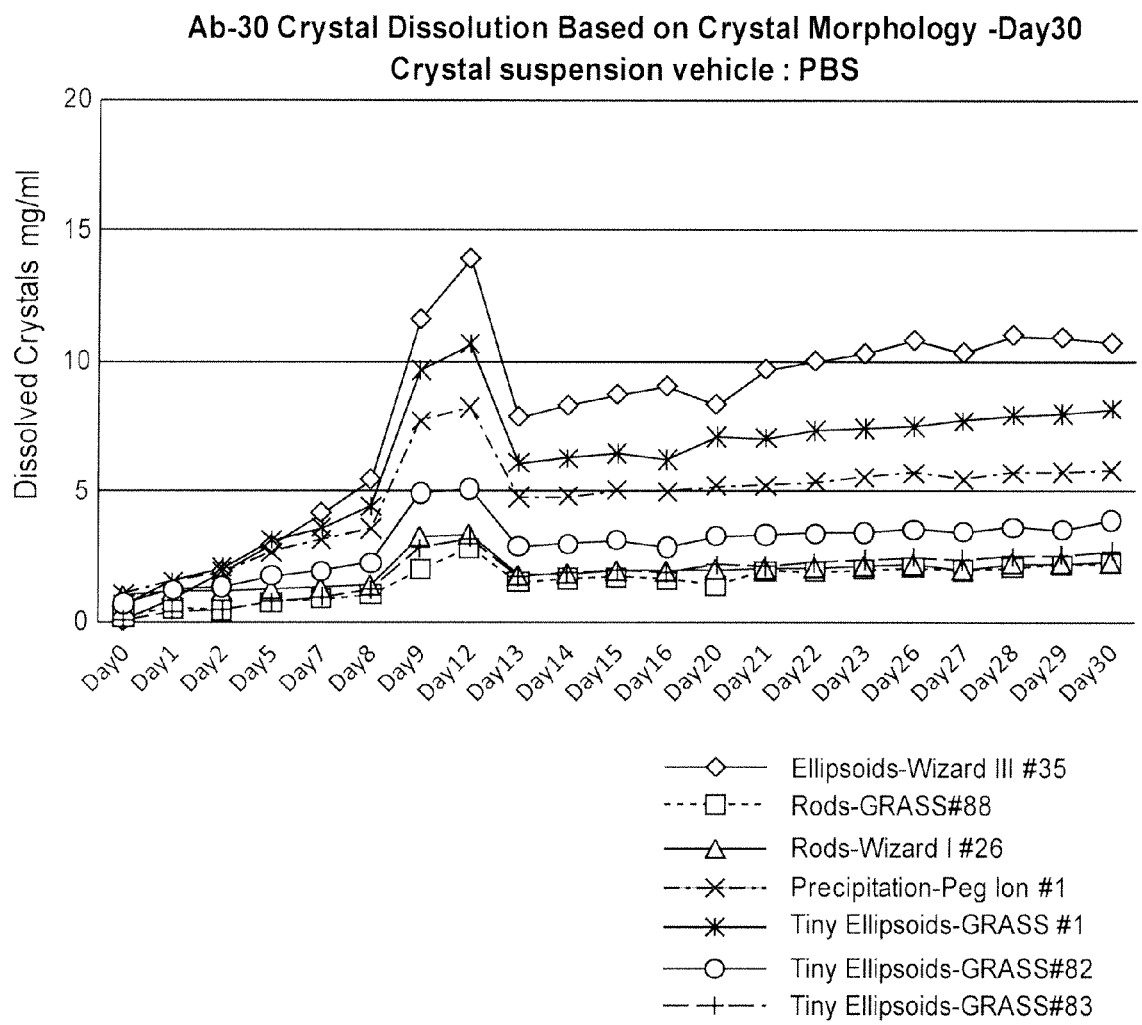
FIG. 4 is a graph showing the dissolution rate of Ab-30 crystals based on crystal morphology.
Figure 5A:
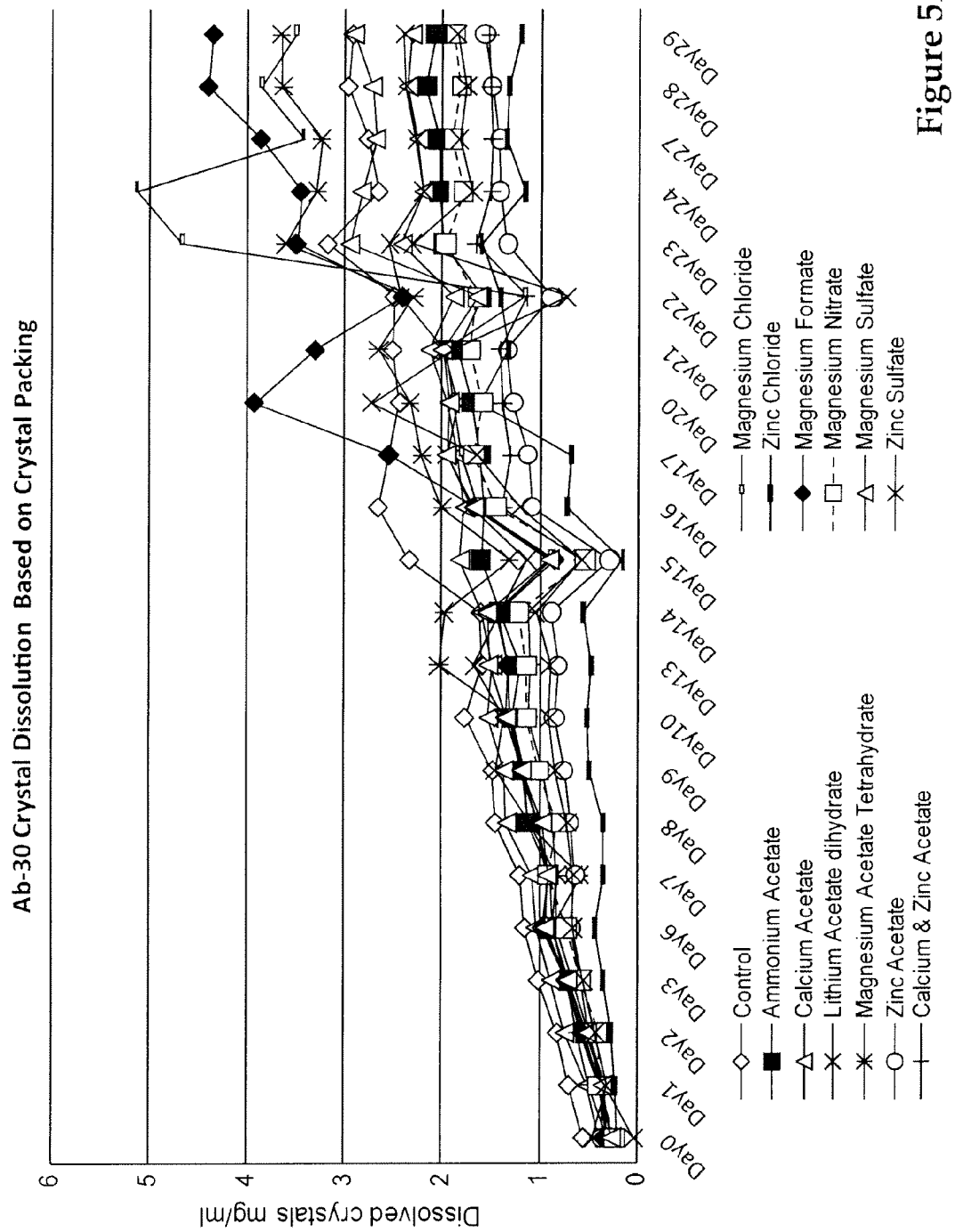
FIGS. 5A-5F are graphs showing the dissolution rate of Ab-30 crystals based on crystal packing.
Figure 5B:
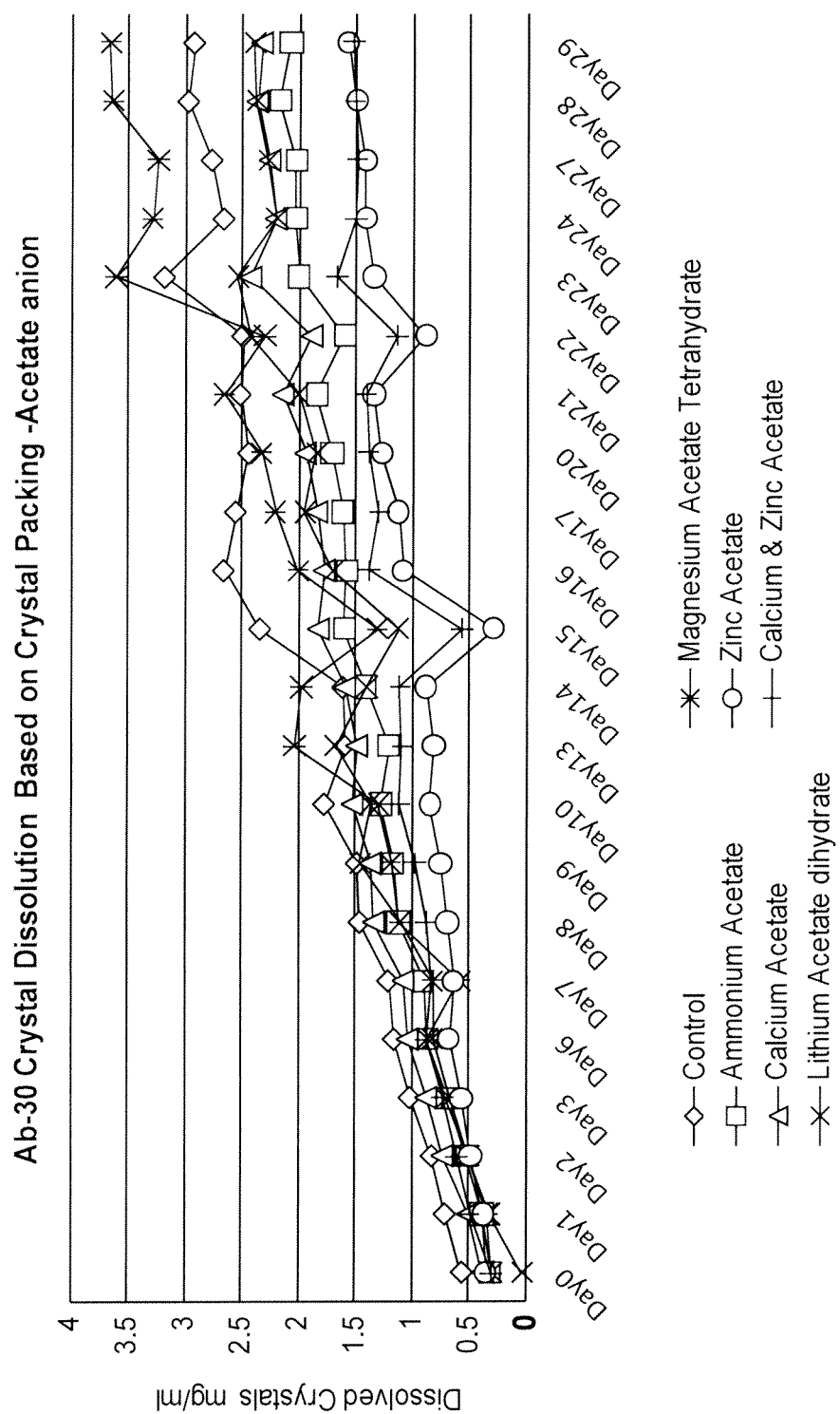
Figure 5C:
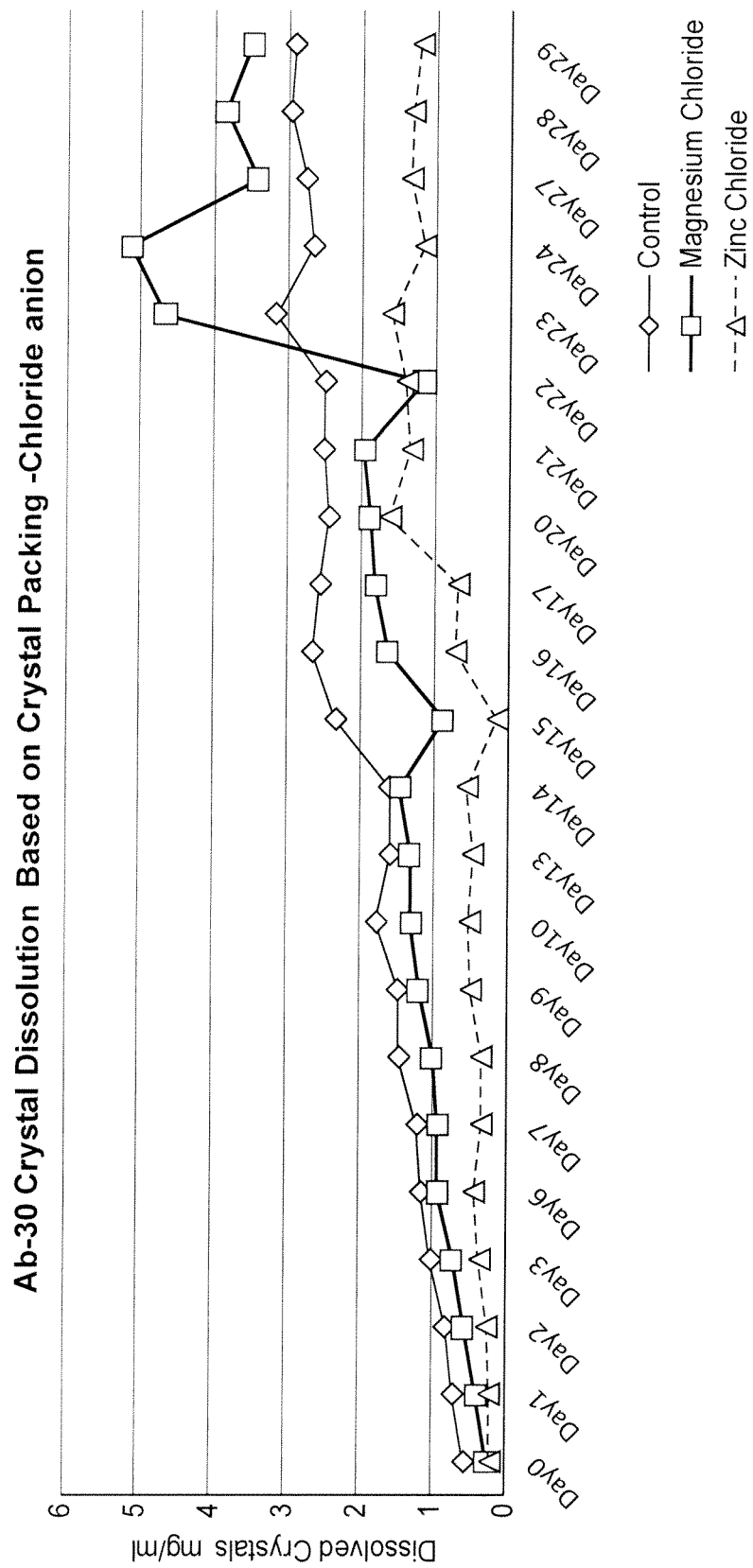
Figure 5D:
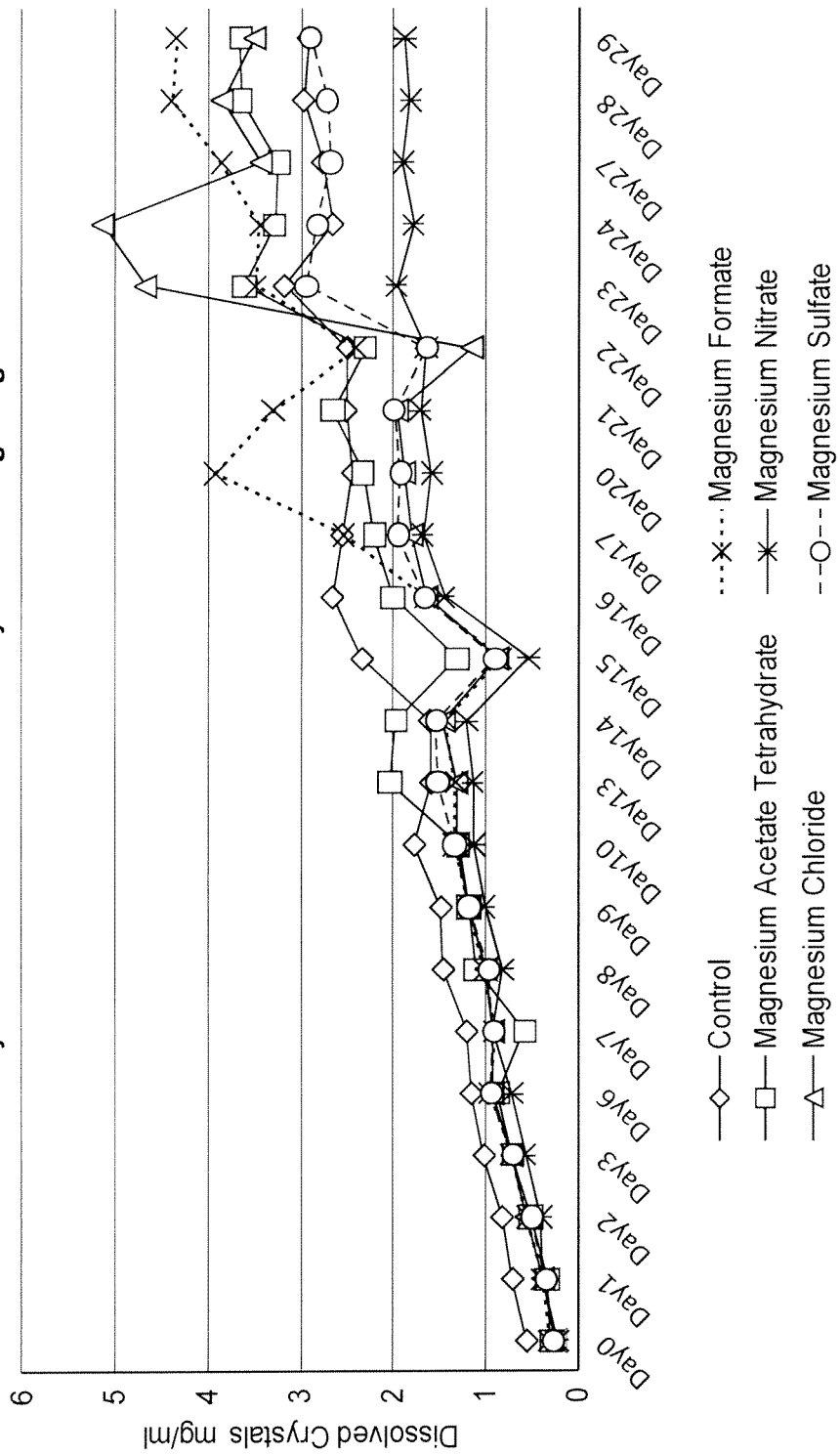
Figure 5E:
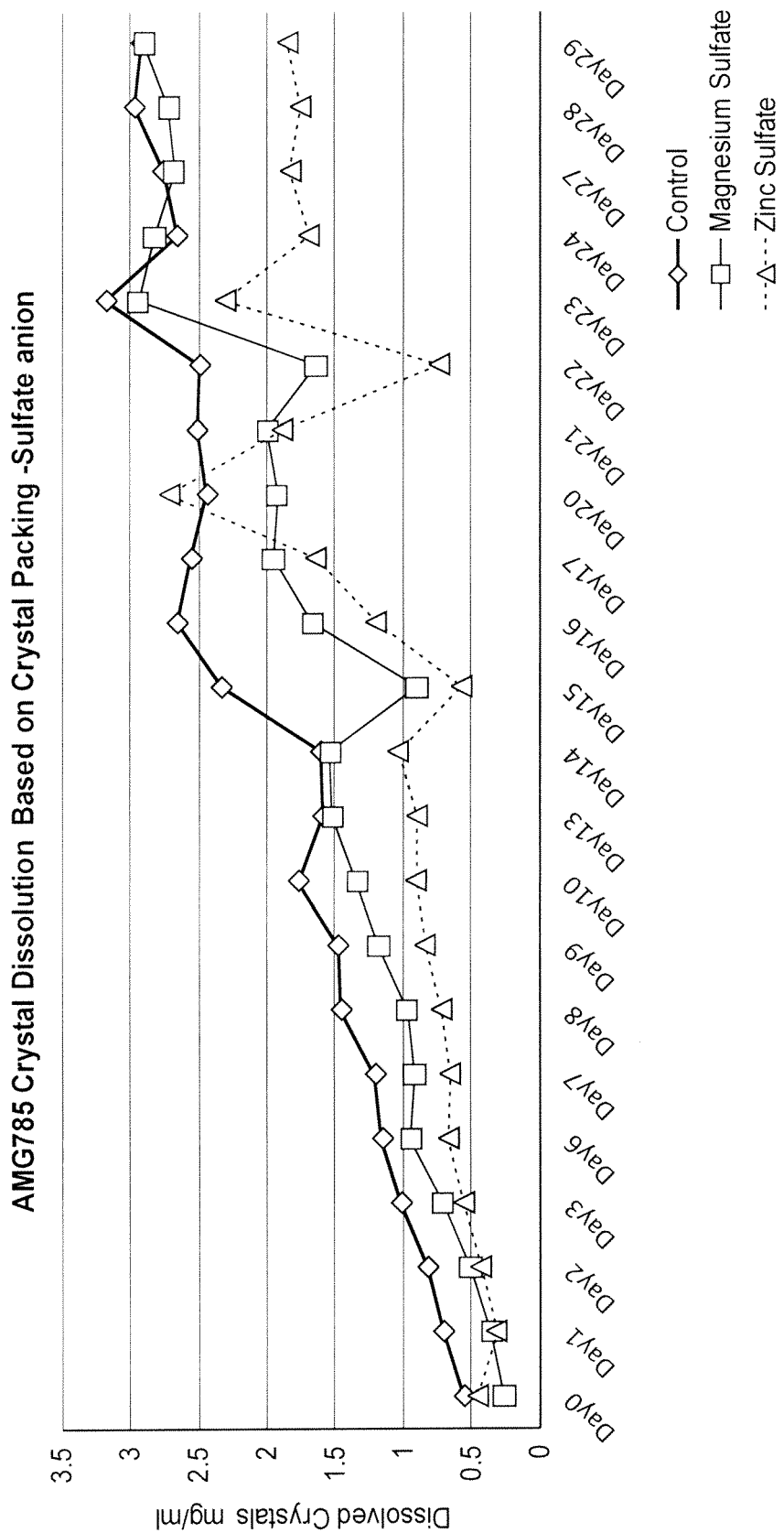
Figure 5F:
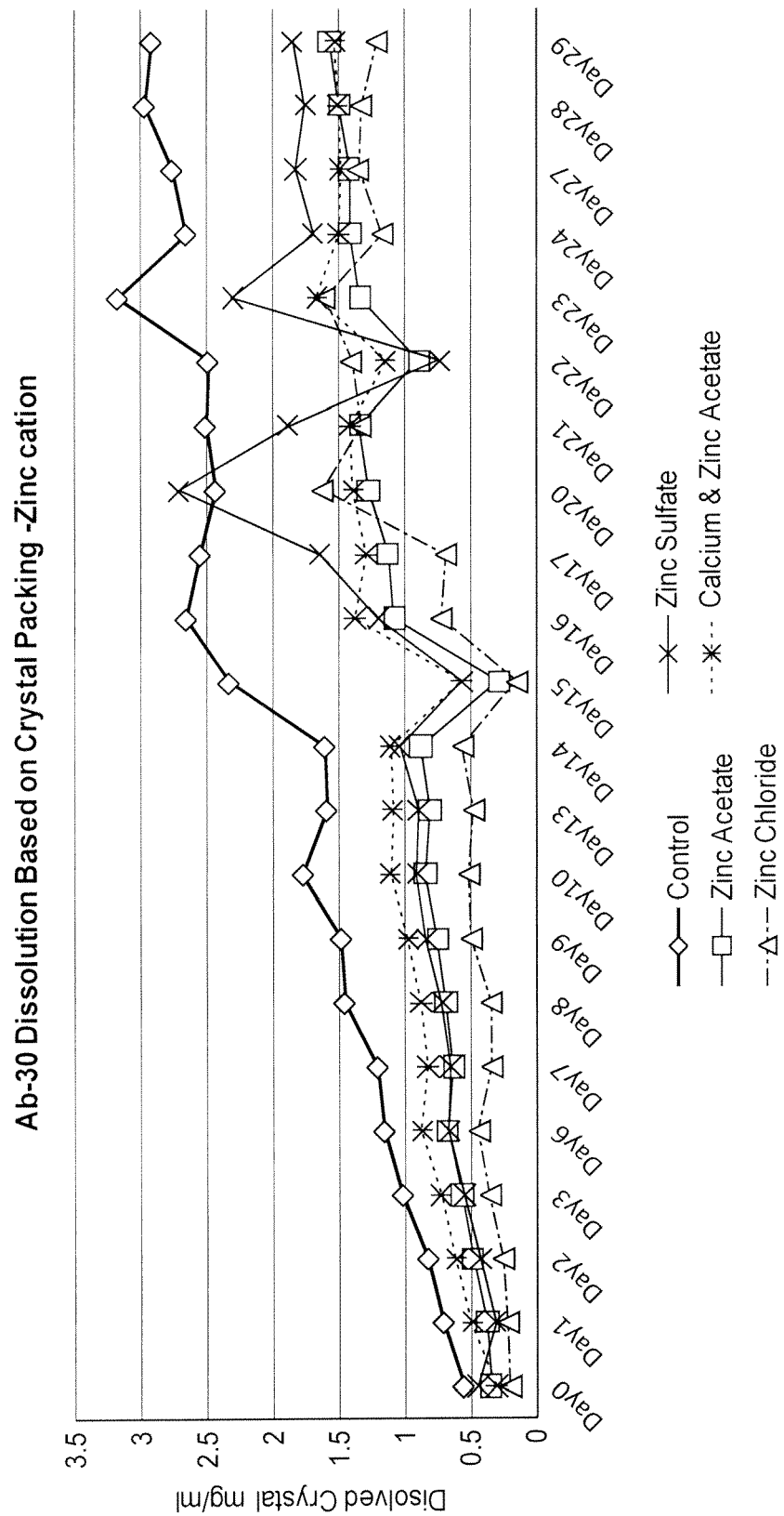

A52SuT (10 mM Acetate, 9% Sucrose, 0.004% Polysorbate20, pH5.2), saline and PBS showed the most difference in dissolution rates. Water and Dextrose did not show much dissolution activity after 42 days when compared to T=0. Hence, water and dextrose are ideal vehicles to wash the Ab-30 crystals without losing much of the crystals during the wash step. The Low Ionic Strength Screen buffers 0.05 M HEPES pH7.5 20% PEG-3350, 0.05M Tris pH8.0 20% PEG-3350, 0.05 M Tris pH8.5 20% PEG-3350 showed extremely slow dissolution rates practically close to baseline over the course of a month. One possibility for the slow dissolution of the crystals in these buffers might be due to crystal coating by 20% PEG-3350. 10 mM Glutamate, 5% Sorbitol at pH4.8 and 10 mM Glutamate, 5% Sorbitol at pH 5.0 showed dissolution rates at about 1 mg/ml similar to water and dextrose dissolution rates in study #1. A52SuT, saline, dextrose, PBS and 10 mM Glutamate buffers are isotonic and injectable (See FIGS. 3 and 4).

Crystal Dissolution and Crystal Morphology:

In study #3 the crystal growth conditions and the morphology were different while the suspension vehicle PBS was same for all conditions. A total of four different morphologies were considered: ellipsoids, rods, precipitation and tiny ellipsoids. The mg/ml crystal dissolution was different based on the crystal morphology but overall all the morphologies followed a similar dissolution pattern with peak dissolution at Day 12. Based on the dissolution profiles obtained it can be concluded the crystal dissolution depends on the crystal morphology, crystal size, crystal growth condition and even crystal packing.

Crystal Dissolution and Crystal Packing:

In study #4 the crystal growth conditions were different while the crystal morphology and suspension vehicle (PBS) were consistent in all the conditions. Ab-30 was grown in Index36 along with different additives (10 mM salts). The data for this study suggests that the different cations and anions in the additives have an impact on the crystal packing (FIGS. 5A-5F). Out of all the additives, Zinc salts showed the least dissolution suggesting that Zinc can be added for a sustained release effect. Zinc chloride showed the least dissolution compared to other Zinc salts while Magnesium nitrate showed the least dissolution among Magnesium salts.

Figure 6A:
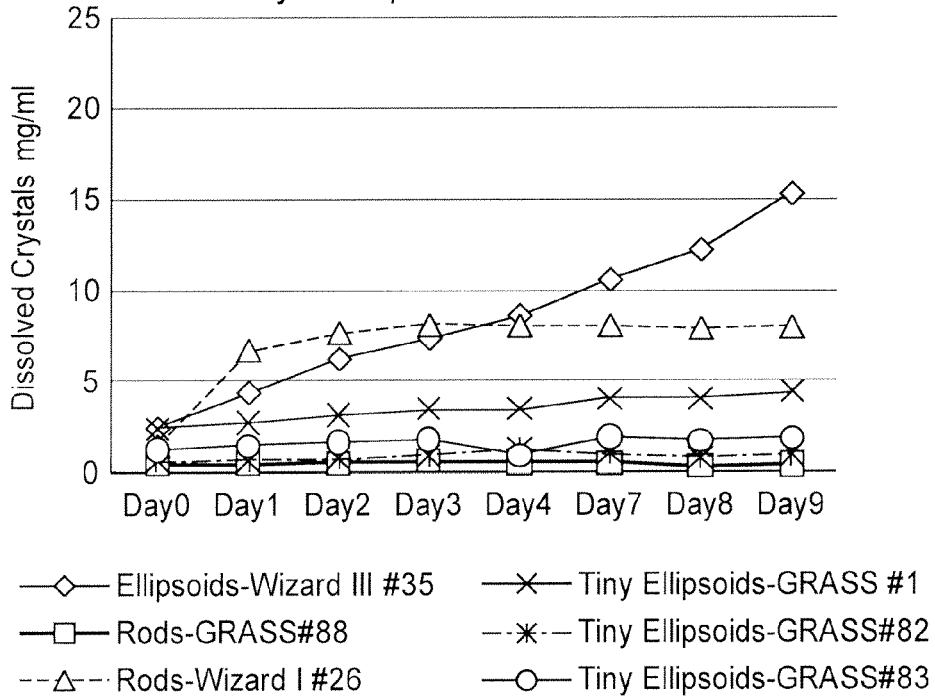
FIGS. 6A and 6B are graphs showing the dissolution rate of Ab-30 crystals based on temperature and crystal morphology.
Figure 6B:
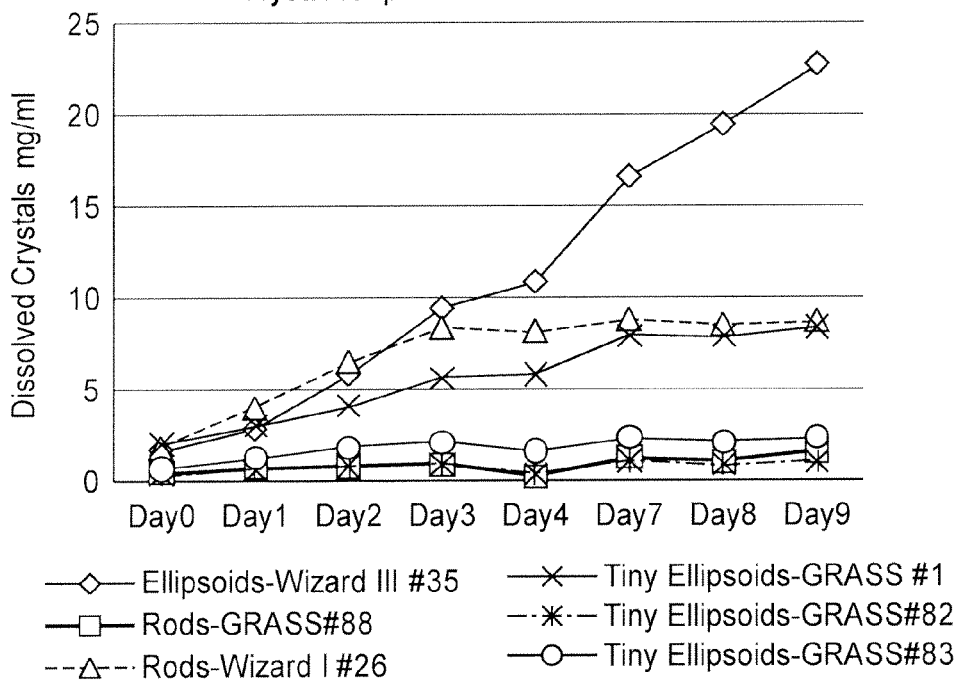

Crystal Dissolution Based on Temperature and Crystal Morphology:

In study #5 the crystal growth conditions, crystal morphology, crystal storage temperature were different but the suspension vehicle dextrose was kept the same for all the conditions. The crystals were resuspended in dextrose, stored at 4° C. and 37° C. and dissolution rates were monitored for 9 days. The crystal dissolution rates were mostly not dependent on temperature (except WIZ III #35) wherein the dissolution rate was higher at 37° C. vs. 4° C.) or morphology as expected. Instead the dissolution rates were related to crystal growth conditions. The trend for dissolution rates was similar irrespective of the temperature for a particular crystal growth condition (FIGS. 6A and 6B). This may not be the case for all the Ab-30 crystals grown in different conditions and resuspended in the same or different suspension vehicles at different temperatures.

In summary, crystal dissolution depends upon more than one factor namely the crystal growth solution and its components, crystal shape, size, length, crystal morphology, crystal suspension vehicle, temperature and/or crystal packing. One or more of the above mentioned factors can be changed in various combinations for formulating different kinds (liquid, solid or slurries) of formulation.

Example 4

Assaying Protein Content of Ab-30 Crystals

Salts are often present in the sample or countersolvent, and these salts may form crystals during crystallization attempts. One popular method of distinguishing the growth of salt crystals from the target crystals of interest is through exposure to a staining dye such as IZIT™, manufactured by Hampton Research of Laguna Niguel, Calif. The IZIT™ dye stains protein crystals blue, but does not stain salt crystals.

Ab-30 crystals produced under crystallization conditions of 15% v/v Tacsimate pH 7.0, 0.1 M HEPES pH 7.0, 2% w/v Polyethylene Glycol 8000 were confirmed to be protein crystals by staining (IZIT™ dye; Hampton Research) and were recorded as crystallization hits.

Example 5

Crystalline Anti-Sclerostin Antibody Formulation

This Example illustrates a formulation of anti-sclerostin antibody crystals comprising a high concentration of protein with a potential for slow release, using an anti-sclerostin antibody comprising the Ab-30Rm heavy and light chains set forth in SEQ ID NOS: 19 and 21, respectively.

Briefly, a total of 108 crystallization conditions were screened for Ab-30Rm using the Low Ionic Strength Screen (Harris et al, (1995) Crystallization of intact monoclonal antibodies, Proteins: Structure, Function and Genetics 23, 285-289; Hampton Research, Aliso Viejo, Calif.). Two conditions were narrowed down for a formulation based on pH, osmolality, injectable ingredients and percent crystallization efficiency. A formulation for Ab-30Rm crystals suitable for subcutaneous injection in animal study was successfully produced.

Materials and Methods

Hanging Drop Vapor Diffusion and Visual Examination of Protein Crystal Hits:

Ab-30Rm crystals were grown using the hanging drop vapor diffusion method using VDX 24 well plates with sealant (Hampton Research, Aliso Viejo, Calif. (HR3-170)). 1 ml of dehydrant 24% PEG-3350 was pipetted in the well solution. 4 µl of 4 mg/ml Ab-30Rm in A5SuT (10 mM Sodium Acetate (from acetic acid), 9% Sucrose, 0.004% Polysorbate 20 pH5.0)+20 of Low Ionic Strength Buffer+5 ul of x % PEG-3350 was added on to a cover slip (HR3-233, 22 mm diameter by 0.22 mm thick siliconized glass cover slips: Hampton Research, Aliso Viejo, Calif.) for a final volume of 11 µl. The cover slip was inverted without mixing the drop and placed on an already gapped sealant to form an air tight seal. In the hanging drop vapor diffusion experiment, crystals are formed the when equilibrium is reached between the drop and the well solution.

A total of 108 conditions were set up using the Low Ionic Strength Screen (LISS) (HR2-120, Hampton Research). LISS is a three part crystallization screen with 18 buffers in a pH range of 2-12, 6 different percentages of precipitant PEG-3350 and 24% PEG-3350 as the dehydrant. See Table 16 below.

TABLE 16

| LISS Screen | 4% | 8% | 12% | 16% | 20% | 24% |
|---|---|---|---|---|---|---|
| 0.05M. Potassium chloride, pH 2 | | | C | | | |
| 0.05M citric acid, pH 3 | | | | | | |
| 0.05M citric acid, pH 3.5 | | | | | | |
| 0.05M citric acid, pH 4 | | | | | | |
| 0.05M citric acid, pH 4.5 | | | | | | |
| 0.05M citric acid, pH 5 | | | | | | |
| 0.05M citric acid, pH 5.5 | | | | | | |
| 0.05M MES, pH 6 | | | | | | |
| 0.05M Bis Tris, pH 6.5 | | C | | | | |
| 0.05M Imidazole, pH 7 | | C | C | C | | |
| 0.05M HEPES, pH 7.5 | | C | C | | C | |
| 0.05M Tris, pH 8 | | C | C | C | C | C |
| 0.05M Tris, pH 8.5 | | C | C | C | C | |
| 0.05M Glycine, pH 9 | | C | C | C | | |
| 0.05M Glycine, pH 9.5 | | | | | | |
| 0.05M Glycine, pH 10 | | | | | | |
| 0.05M Sodium phosphate dibasic, pH 11 | | | | | | |
| 0.05M Sodium phosphate dibasic, pH 12 | | | | | | |

C = crystals obtained

Crystal trays were scanned everyday for a week and then once a week using Carl Zeiss Stemi SV11 Microscope equipped with software Axiovison 4.0. Crystal hits were recorded and characterized using an in house crystal scoring system and morphology description.

The following two sets of conditions are exemplary conditions for an antibody crystal formulation: (a) A5SuT+ 0.05 M Tris pH 8.0+22% PEG-3350 (final pH about 7.2, osmolality was 340 mOsm/kg and % efficiency 95%); (b) A5SuT+0.05 M Tris pH 8.0+24% PEG-3350 (final pH about 7.2, osmolality was 412 mOsm/kg and % efficiency 99%).

pH Measurement: pH was measured using an Mettler Toledo MP230 pH meter and was calibrated against pH 4.0 and pH 7.0 buffers standards. For pH measurement sample was prepared by adding 40 µl of protein, 20 µl of the LISS buffer and 50 µl of the respective percentage of PEG-3350 in an eppendorf tube and vortexed.

Osmolality:

Osmolality was measured using Advanced Instruments 2020 Multi sample Osmometer, Norwood, Mass. The instrument measures Osmolality by using the Freezing Point Depression method. For Osmolality measurements of Ab-30Rm in the Low Ionic Screen 8 µl of protein, 2 µl of LISS buffer and 5 µl of x % PEG-3350 was mixed. Exactly 20 µl of this mixture was placed in the disposable microsample tubes (Advanced Instruments, Norwood, Mass. Catalog #202825) and were placed into the instrument carousel.

Efficiency:

% Efficiency was calculated by spinning down the 1.5 ml eppedorf tubes at 10,000 rpm for 15 minutes, making a 1:100 dilution of the supernatant with mili-Q water and reading it on a UV-VIS spec at A280.

Batch Crystallization and Details for Animal Study Experiment:

Ab-30Rm at a concentration of 24.39 mg/ml in A5SuT was used for initial Ab-30Rm crystal screening and batch crystallization. For final batch crystallization studies for animal study Ab-30Rm at a concentration of 31.148 mg/ml in A5SuT was used. The liquid formulation for Ab-30Rm for animal studies was 100 mg/ml in A5SuT while the crystal slurry for the formulation was in 0.05 M Tris pH 8.0 and 22% PEG-3350 at 100 mg/ml, pH 7.2.

The formulation for Ab-30Rm was prepared by adding 400 µl of Ab-30Rm in A5SuT+200 µl of 0.05 M Tris pH8.0 buffer+500 µl of 22% PEG-3350 precipitant to a final volume of 1.1 ml in a 1.5 ml eppendorf tube which turned cloudy on mixing. The solution eventually turned clear on day two with the formation of distinguishable crystals. The crystals were harvested after six days and spun down at 3000 rpm for 15 minutes and the supernatant was removed so that there was no soluble protein left in the tube. The supernatant was replaced with mother liquor. The mother liquor was prepared as follows: 200 µl 0.05 M Tris pH8.0 buffer+500 µl 22% PEG-3350 precipitant in an eppendorf tube. Note that there was no A5SuT added to this. There was 12.46 mg of protein in 1.1 ml batch and hence 124.9 µl of mother liquor was added to reach a 100 mg/ml final concentration. 100 mg/ml slurries from two additional eppendorf tubes were mixed in one 3 cc vial to prepare a separate vial for each rat. The formulation buffer was prepared as follows: 400 µl of A5SuT buffer+200 µl 0.05 M Tris pH8.0 buffer+500 µl of 22% PEG-3350 precipitant to make a final volume of 1.1 ml. At 100 mg/ml the final injection volume was in between 200 µl-250 µl depending on the weight of an individual rat and a 27 G½ needle was used for the subcutaneous injection.

A single dose study lasting 8 weeks was performed with 28 6-month old female SD rats weighing between 400-500 grams. The final dose was 50 mg/kg (20-25 mg protein was required for each rat) 10 individual rats were used for each liquid and powder formulation while 8 rats were used for the placebo (A52SuT+0.05 M Tris pH8.0+22% PEG-3350).

Results and Discussion:

Ab-30Rm was screened using Hampton Low Ionic Screen Strength Screen (LISS) and a total of 20 crystal hits were obtained at pH 2 and in between pH 6.5-9.0. 8% and 12% PEG-3350 had the most crystal hits of all the different percentages of PEG-3350 screened. 0.05 M Tris at pH 8.0 was the only condition that had crystals from 8%-24% PEG-3350 except at 4% PEG-3350. Most crystal hits obtained for Ab-30Rm fall within the pH range of pH 7.0-7.5 which is important in animal studies to avoid tissue necrosis after a subcutaneous injection.

Based on the Osmolality data, some of 16% and 24% PEG-3350 and all of 20% PEG-3350 conditions fell within the Osmolality range. Acceptable Osmolality range for subcutaneous injection is about 250-350 mOsm/Kg (see FIG. 1A). When the Osmolality and the crystals hits were overlaid, there were only three conditions that fell within the Osmolality range that also had crystal hits (FIG. 1B).

PEG-3350 falls under the chemical factors effecting crystallization and can be characterized as a long chain polymer precipitant which works by volume exclusion effect. The morphology of Ab-30Rm crystals degraded with the increase in PEG-3350 concentrations as seen in the screening with LISS (FIG. 2). Higher percentage PEG-3350 crystal hits had biphasic separation and/or precipitation. Ab-30Rm crystals took about a week to grow which is slow if the same conditions were to be used for batch crystallization.

The rate of crystallization is not necessarily the same in the hanging drop vapor diffusion and batch crystallization. To increase the rate of crystallization the pH range was manipulated, another of the chemical factors effecting crystallization and concentration of Ab-30Rm focusing on HEPES and Tris conditions with 12% PEG-3350 only. Ab-30Rm was put through HEPES Grid Screen pH 6.8-8.2 and Tris Grid Screen pH 7.0-9.0. No change in rate of crystallization was observed in either of the grid screen but there was an increased abundance in crystals at pH higher than 7.5 seen in both the grid screens. Hence, to change the rate of crystallization another attempt was made by exploring the concentration of the precipitant PEG-3350.

LISS conditions #10-14 with a pH range of 7-9.0 were used and PEG-3350 from 4% to 24% in increments of 2% was explored. 0.05MTris pH8.0 at 22% and 24% PEG-3350 gave the first crystal hits at day 2. These conditions were batch crystallized at 55 µl, 110 µl and 1 ml total volume all giving crystal hits at day 2. The rate of crystallization for 22% and 24% PEG-3350 is the same in an 11 µl hanging drop vapor diffusion and batch crystallization. Final pH measured for both the conditions lies within the pH range of 7-7.5 with pH=7.203 for 22% PEG-3350 and pH=7.354 for 24% PEG-3350. Osmolality for 0.05M Tris 22% PEG-3350 is 340 mOsm/kg while that for 0.05 M Tris pH8.0 is 412 mOsm/kg which is over the Osmolality range. % Efficiency was measured by spinning the crystals at 10,000 rpm for 15 minutes, A280 nm measured for the supernatant. Dissolution rates for Ab-30Rm crystals in water is 11 minutes, in saline is 6 minutes and in PBS is 15 minutes.

Isotonic and injectable conditions were achieved for an Ab-30Rm formulation for animal study with a final pH of 7.203, osmolality of 340 mOsmo/kg and 95% crystallization efficiency. Liquid vs resuspending antibody crystal formulations were tested in the animal study.

The foregoing Example demonstrates that Ab-30Rm was crystallizable under a variety of crystallization conditions, but crystals did not form under every condition tested. Approximately 240 crystallization conditions were tested in a number of different commercially-available (i.e., Hampton Research) screens, but only approximately 50 conditions produced Ab-30Rm crystals. Interestingly, Ab-30R (which has one amino acid difference compared to Ab-30Rm) only produced crystals in 5 of the approximately 1120 conditions tested in a number of different commercially-available (i.e., Hampton Research, Emerald Bioscience) and proprietary screens.

The foregoing Example also demonstrates that formulations comprising Ab-30Rm crystals of sufficient pH and osmolality for administration to a mammal were obtained.

Example 6

In Vivo Testing of Anti-Sclerostin Antibody "Liquid" and "Crystal/Crystallized" Formulations in Rats Female Sprague Dawley (SD) rats were obtained from Charles River Laboratories and housed in clean caging, two animals per cage. Room temperature was maintained between 68 and 72° F., and relative humidity was maintained between 34 and 73%. The laboratory housing the cages had a 12-hour light/dark cycle and met all AAALAC specifications.

Subcutaneous injection of test article (liquid Ab-30Rm and crystal/crystallized Ab-30Rm) and buffer (vehicle control) was done when the rats were about 6.5 months old. At the start of the study (day 0) 9 rats were injected with buffer made with the following ratios of ingredients: take 400 microliters of A5SuT (10 mM Sodium Acetate pH 5, 9% sucrose, 0.004% polysorbate 20 [Tween]), then add 200 microliters of 0.05 M Tris pH 8 and then add 500 microliters of 22% PEG-3350. This is the buffer/vehicle group. At the start of the study (day 0) 10 rats were injected at 50 mg/kg with a 100 mg/ml solution of "crystal/crystallized" Ab-30Rm in a suspension made of the following ratios of ingredients: 200 microliters of 0.05 M Tris pH 8 and 500 microliters of 22% PEG-3350. This is the "crystal/crystallized" group. At the start of the study (day 0) 10 rats were injected at 50 mg/kg with a 100 mg/ml solution of "liquid" Ab-30Rm (non-crystallized) in A5SuT. This is the "liquid" group.

Areal bone mineral density (BMD) was determined from anesthetized rats (isoflurane) by dual-energy X-ray absorptiometry (DXA, Hologic QDR 4500a, Hologic Inc., Bedford, Mass.). Baseline BMD was determined 4 days before treatment was initiated. BMD was also determined at weeks 2, 3, 4, 6 and 8 after treatment (day 0). The region of interest (ROI) included the lumbar vertebrae (LV1-5) and the "leg" (femur-tibia [entire femur in addition to the part of tibia above tibia/fibular junction]).

Statistical analysis was performed using GraphPad Prism. A one-way analysis of variance (ANOVA) followed by Dunnett's test was used to determine statistical differences. Group means for each data set were considered significantly different when the P value was less than 0.05 (P<0.05). Data were analyzed as absolute BMD (g/cm$^2$) and also separately as percent change in BMD from baseline (calculated for each individual animal).

Figure 7A:
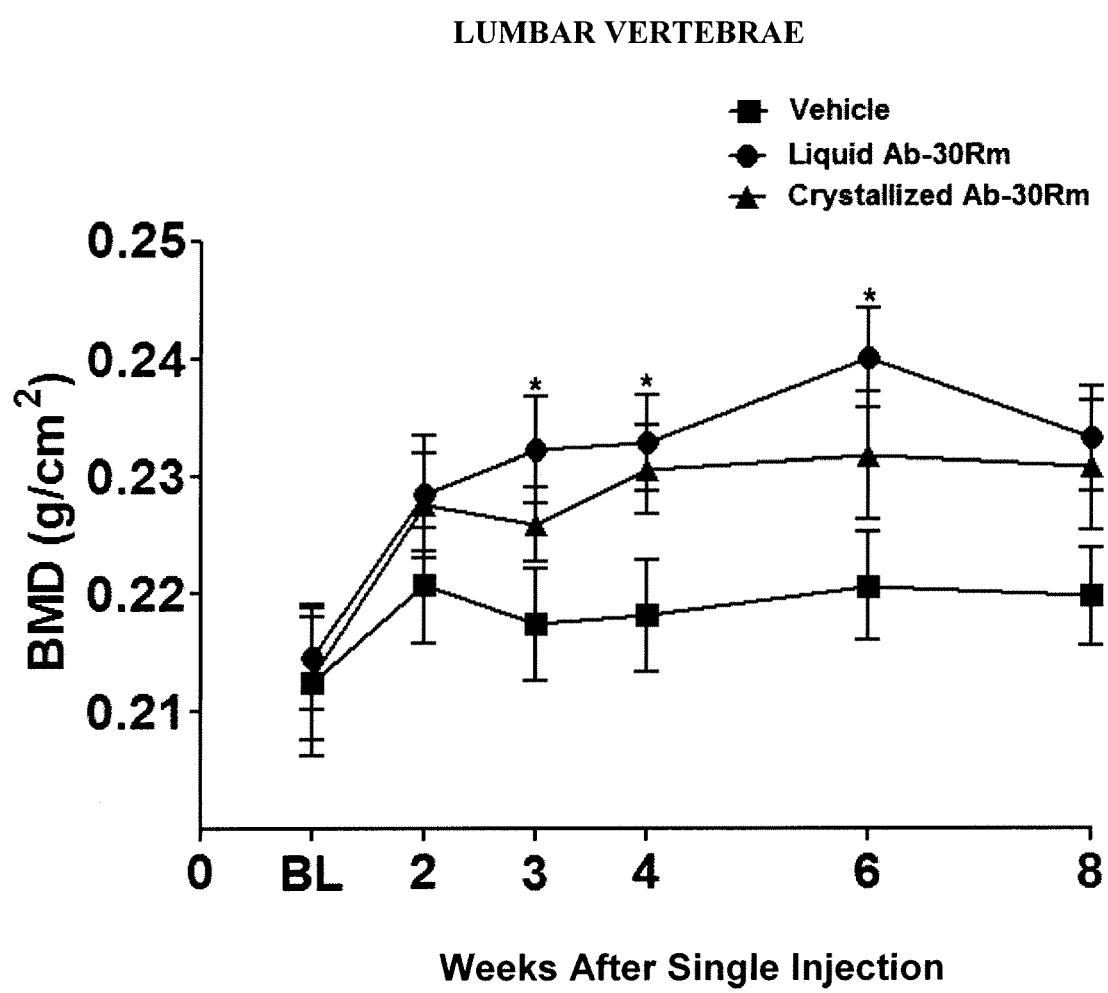
FIG. 7A shows bone mineral density (BMD) in rats as absolute BMD and FIG. 7B shows BMD as percent change from baseline measured at lumbar vertebrae over time after administration of a single injection of buffer/vehicle or a single injection of "liquid" Ab-30Rm (50 mg/kg of a 100 mg/ml solution) or a single injection of "crystal/crystalline" Ab-30Rm (50 mg/kg of a 100 mg/ml solution). BL=baseline. Data are shown as mean+/−standard error of the mean (SEM). Statistically significant differences versus buffer/vehicle control group are indicated by asterisks. *$p<0.05$ vs. Vehicle by ANOVA Dunnett's Test. N=9 for buffer/vehicle group. N=10 for the "liquid" Ab-30Rm group. N=10 for the "crystal/crystalline" Ab-30Rm group.
Figure 7B:
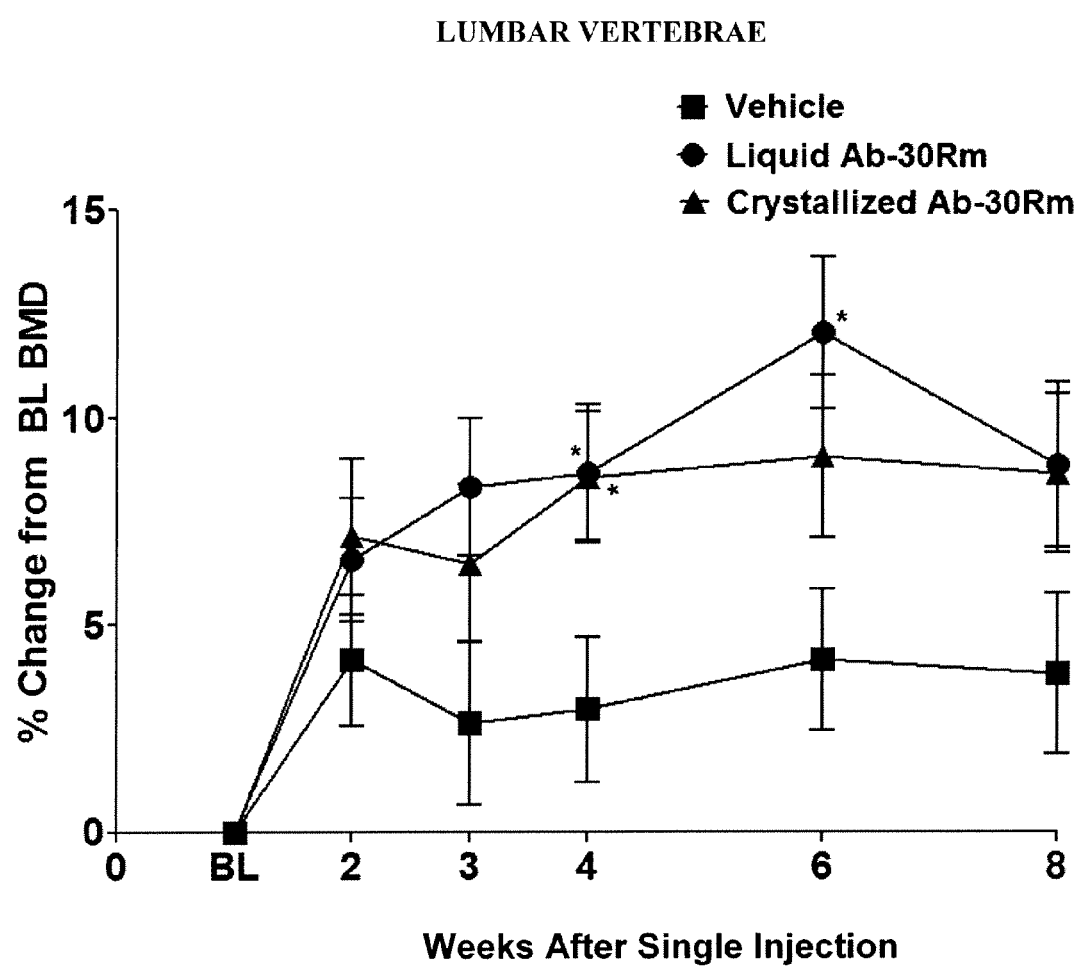
Figure 8A:
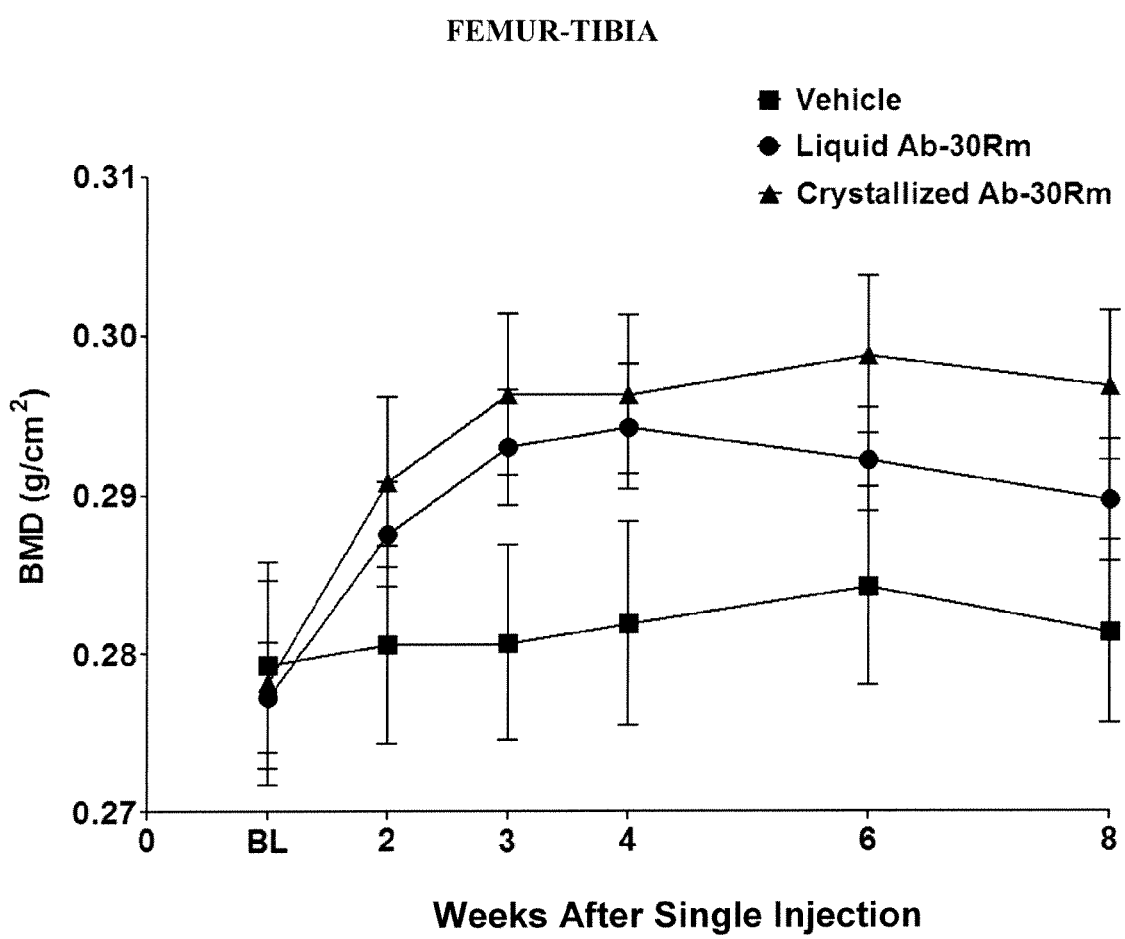
FIG. 8A shows bone mineral density (BMD) in rats as absolute BMD and FIG. 8B shows BMD as percent change from baseline measured at leg (femur-tibia) over time after administration of a single injection of buffer/vehicle or a single injection of "liquid" Ab-30Rm (50 mg/kg of a 100 mg/ml solution) or a single injection of "crystal/crystalline" Ab-30Rm (50 mg/kg of a 100 mg/ml solution). BL=baseline. Data are shown as mean+/−standard error of the mean (SEM). Statistically significant differences versus buffer/vehicle control group are indicated by asterisks. For FIG. 8B *$p<0.05$, $p<0.01$, *$p<0.001$ vs. Vehicle by ANOVA Dunnett's Test. N=8 for each group N=9 for buffer/vehicle group. N=10 for the "liquid" Ab-30Rm group. N=10 for the "crystal/crystalline" Ab-30Rm group.
Figure 8B:
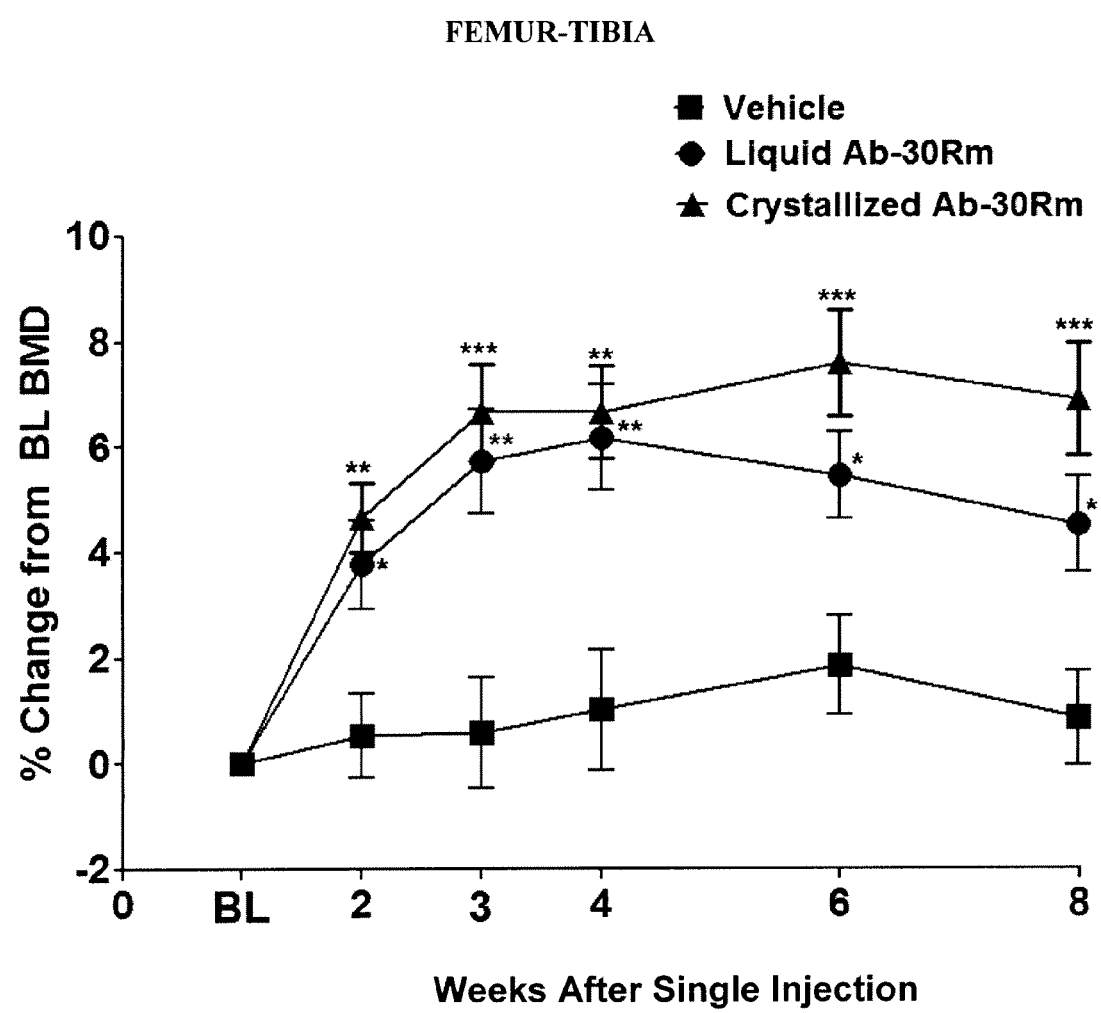

The BMD data (absolute BMD and percent change in BMD from base line) for the 3 animal groups indicated that a single administration of the "liquid" formulation of Ab-30Rm and a single administration of the "crystal/crystallized" formulation of Ab-30Rm resulted in similar increases in BMD in this rat study. Statistically significant increases versus the buffer/vehicle group were found for both the "liquid" Ab-30Rm group (FIGS. 7A and 7B) and the "crystal/crystallized" Ab-30Rm group (FIG. 7B) at the lumbar vertebrae skeletal site and the "leg" (femur-tibia) skeletal site (FIG. 8B). These data demonstrate positive bone effects for both the "liquid" and the "crystal/crystallized" Ab-30Rm formulations.

Example 7

Crystalline Ab-30 Formulations

This Example illustrates formulations of anti-sclerostin antibody crystals comprising a high concentration of protein with a potential for slow release, comprising anti-sclerostin antibody Ab-30 consisting of two mature heavy chains (SEQ ID NO: 15) and two mature light chains (SEQ ID NO: 13) recombinantly produced by DNA encoding each of these chains.

Briefly, a total of 104 crystallization conditions were screened for Ab-30 using the GRAS Screen, Index Screen Wizard I Screen, Wizard II Screen and Wizard III Screen. Four conditions were narrowed down for a formulation based on percent crystallization efficiency (i.e., WIZ III #35, GRAS #1, INDX #34, INDX #36 and WIZ I #46). Formulations for Ab-30 resuspended in 5% dextrose suitable for subcutaneous injection in animal study were successfully produced.

Example 8

In Vivo Testing of Anti-Sclerostin Antibody Ab-30 "Liquid" and "Crystal/Crystallized" Formulations in Rats Female Sprague Dawley (SD) rats were obtained from Charles River Laboratories and housed in clean caging, two animals per cage. Room temperature was maintained between 68 and 72° F., and relative humidity was maintained between 34 and 73%. The laboratory housing the cages had a 12-hour light/dark cycle and met all AAALAC specifications.

Subcutaneous injection of test article (liquid Ab-30 and various crystal/crystallized forms of Ab-30) and buffer (vehicle control) was administered when the rats were about 6.5 months old. At the start of the study (day 0) 8 rats were injected with 5% Dextrose (source: Baxter IV bag). This is the buffer/vehicle group. At the start of the study (day 0) 8 rats were injected at 100 mg/kg with a 100 mg/ml solution of one of the following "crystal/crystallized" Ab-30 formulation WIZ III #35, said crystals having been resuspended in 5% Dextrose (source: Baxter IV bag) ("Group W35");

"crystal/crystallized" Ab-30 formulation INDX #34, said crystals having been resuspended in 5% Dextrose (source: Baxter IV bag) ("Group I34");

"crystal/crystallized" Ab-30 formulation INDX #36, said crystals having been resuspended in 5% Dextrose (source: Baxter IV bag) ("Group I36");

"crystal/crystallized" Ab-30 formulation WIZ I #46, said crystals having been resuspended in 5% Dextrose (source: Baxter IV bag) ("Group W46"); or "liquid" Ab-30 (non-crystallized) in A5Su (10 mM Sodium Acetate pH 5, 9% sucrose) ("liquid group").

Areal bone mineral density (BMD) was determined from anesthetized rats (isoflurane) by dual-energy X-ray absorptiometry (DXA, Hologic QDR 4500a, Hologic Inc., Bedford, Mass.). Baseline BMD was determined 7 days before treatment was initiated. BMD was also determined at weeks 2 and 4 after treatment (day 0). The region of interest (ROI) included the lumbar vertebrae (LV1-5) and the "leg" (femur-tibia [entire femur in addition to the part of tibia above tibia/fibular junction]).

Statistical analysis was performed using GraphPad Prism. A one-way analysis of variance (ANOVA) followed by Dunnett's test was used to determine statistical differences. Group means for each data set were considered significantly different when the P value was less than 0.05 (P<0.05). Data were analyzed as absolute BMD (g/cm$^2$) and also separately as percent change in BMD from baseline (calculated for each individual animal).

Figure 9A:
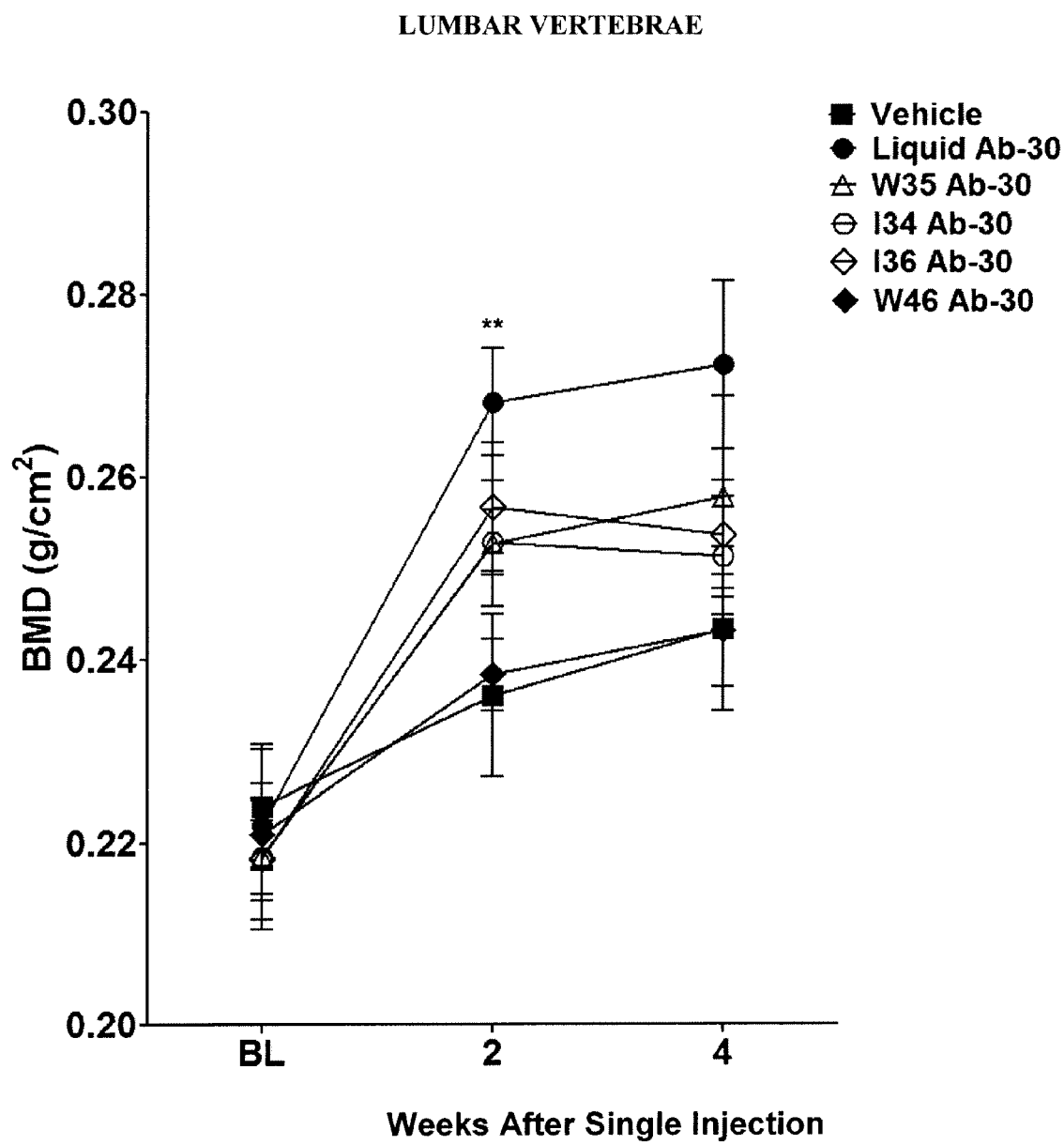
FIG. 9A shows bone mineral density (BMD) in rats as absolute BMD and FIG. 9B shows BMD as percent change from baseline measured at lumbar vertebrae over time after administration of a single injection of buffer/vehicle or a single injection of "liquid" Ab-30 (100 mg/kg of a 100 mg/ml solution) or a single injection of "crystal/crystalline" Ab-30 (100 mg/kg of a 100 mg/ml solution) of crystal formulation W35, I34, I36 or W46. BL=baseline. Data are shown as mean+/−standard error of the mean (SEM). Statistically significant differences versus buffer/vehicle control group are indicated by asterisks. For FIG. 9A **$p<0.01$ vs. Vehicle by ANOVA Dunnett's Test. For FIG. 9B *$p<0.05$, $p<0.01$, *$p<0.001$ vs. Vehicle by ANOVA Dunnett's Test.
Figure 9B:
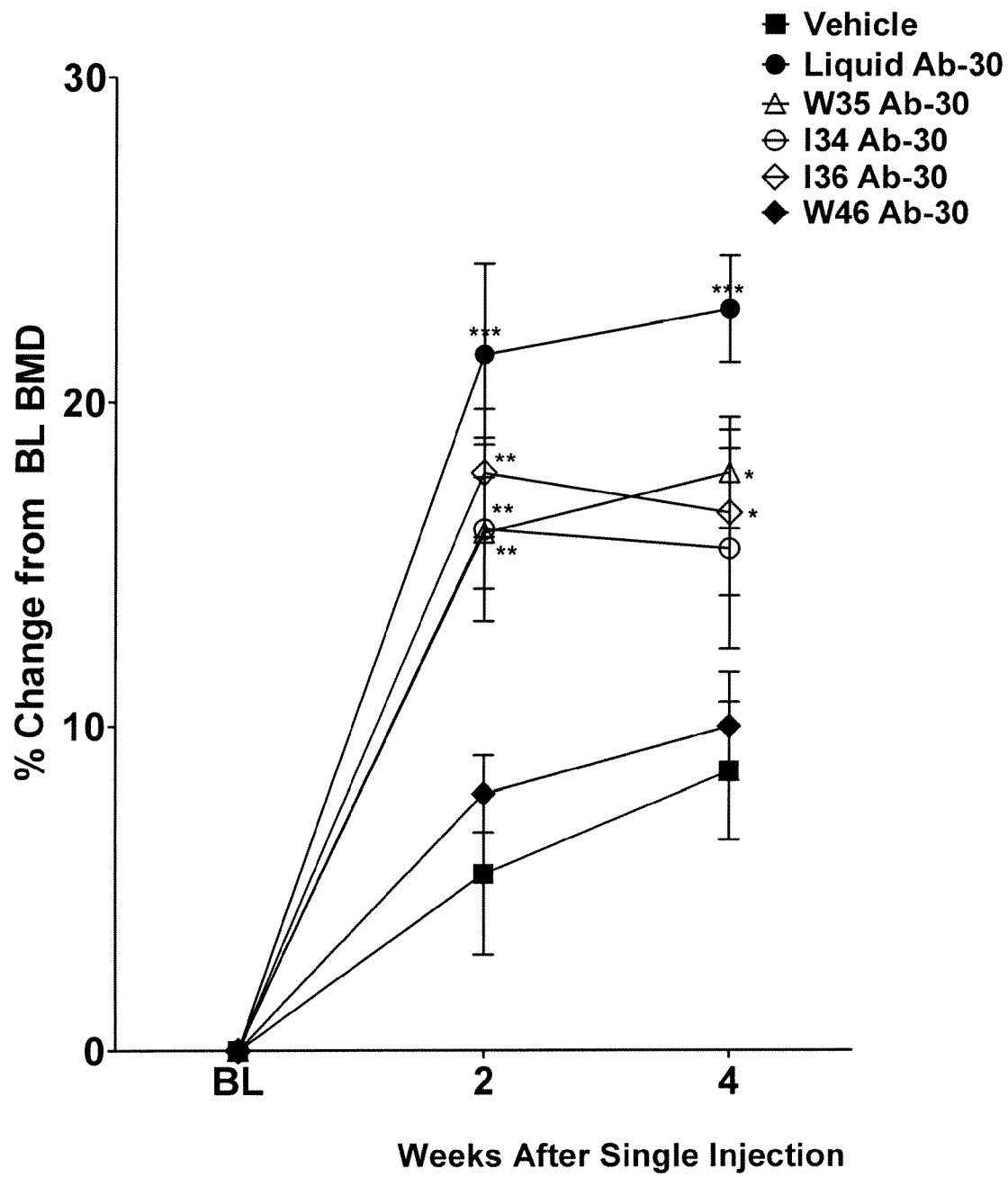
Figure 10A:
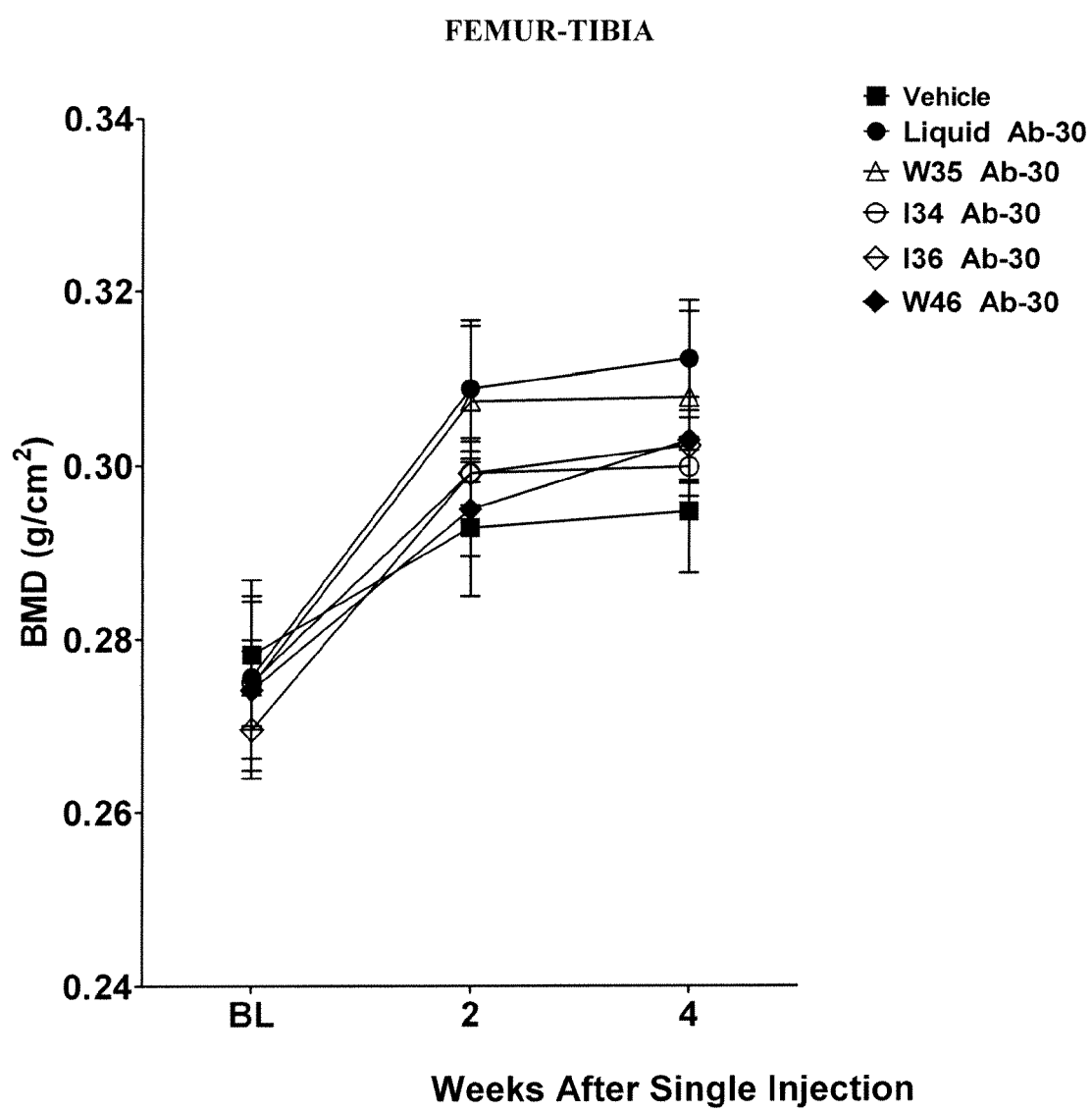
FIG. 10A shows bone mineral density (BMD) in rats as absolute BMD (A) and FIG. 10B shows BMD as percent change from baseline (B) measured at leg (femur-tibia) over time after administration of a single injection of buffer/vehicle or a single injection of "liquid" Ab-30 (100 mg/kg of a 100 mg/ml solution) or a single injection of "crystal/crystalline" Ab-30 (100 mg/kg of a 100 mg/ml solution) of crystal formulation W35, I34, I36 or W46. BL=baseline. Data are shown as mean+/−standard error of the mean (SEM). Statistically significant differences versus buffer/vehicle control group are indicated by asterisks. For FIG. 10B *$p<0.05$, $p<0.01$, *$p<0.001$ vs. Vehicle by ANOVA Dunnett's Test. N=8 for each group.
Figure 10B:
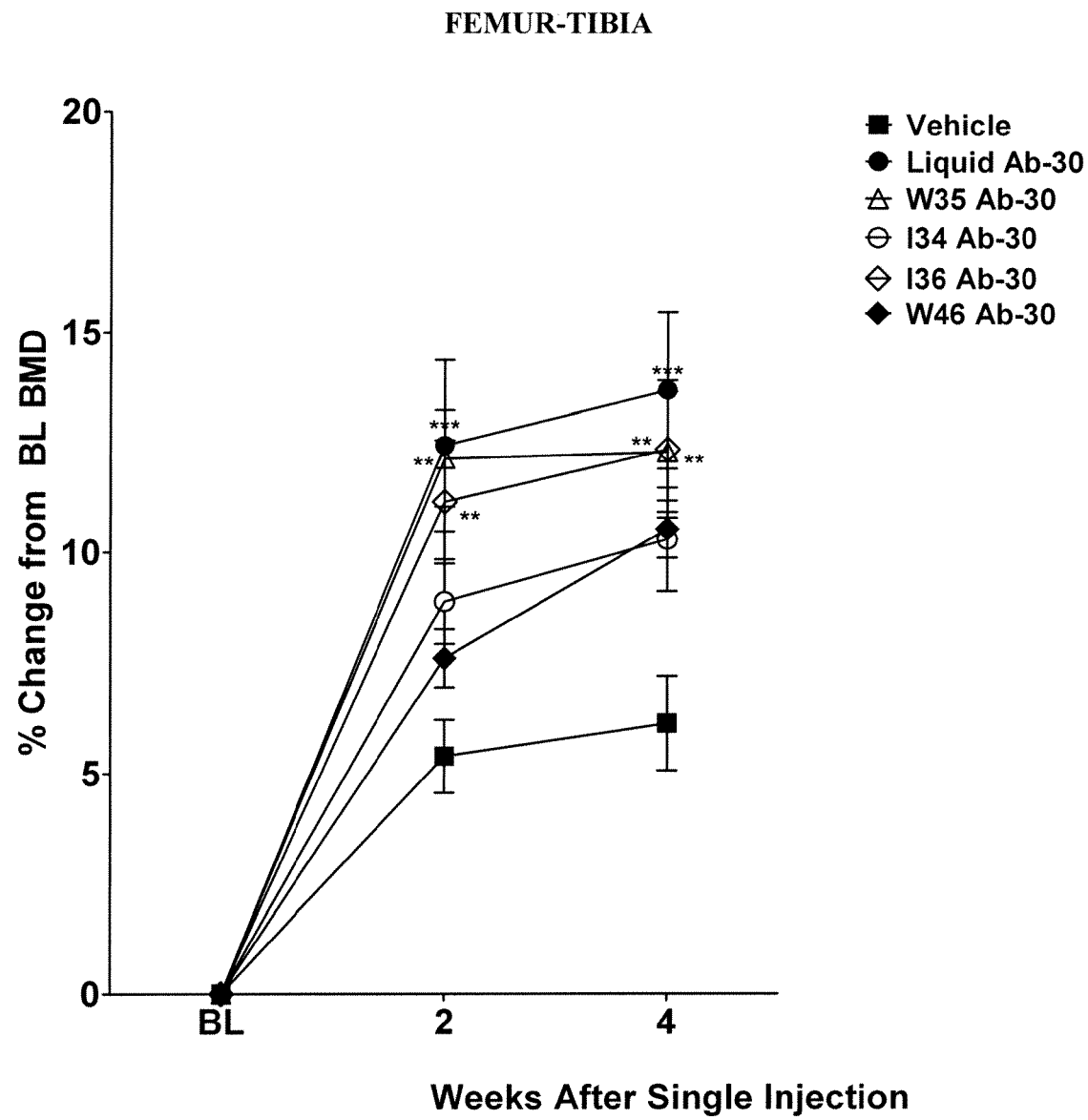

Statistically significant increases in BMD versus the buffer/vehicle group were found at lumbar vertebrae for both the "liquid" Ab-30 group (FIGS. 9A and 9B) and some (e.g., W35, I36) of the "crystal/crystallized" Ab-30 formulation groups (FIG. 9B). Statistically significant increases in BMD versus the buffer/vehicle group were also found at the "leg" (femur-tibia) skeletal site for both the "liquid" Ab-30 group (FIG. 10B) and some (e.g., W35, I36) of the "crystal/crystallized" Ab-30 formulation groups (FIG. 10B). These data demonstrate positive bone effects for both "liquid" and "crystal/crystallized" Ab-30 formulations.

Example 9

Crystallization of Anti-Sclerostin Antibody Ab-31

Antibody Ab-31, consisting of two mature heavy chains (SEQ ID NO: 35) and two mature light chains (SEQ ID NO: 33) was recombinantly produced by DNA encoding each of these chains, was crystallized under a variety of conditions.

Crystallization of Ab-31 was achieved using a crystallization screen (PEG/LiCl Grid Screen; Hampton Research, Aliso Viejo, Calif.), which employs a method for crystallization of macromolecules known as 'hanging drop' vapor diffusion. A drop composed of a mixture of the polypeptide sample and the crystallization reagent (the "crystallization buffer" or the "mother liquor") is deposited on the underside of a sialanized coverslip, and then the drop on the coverslip is sealed with grease and placed over typically a 24 well VDX tray causing a vapor equilibrium with a liquid reservoir of reagent. To achieve equilibrium, water vapor exchanges between the drop and a 1 ml reservoir solution in the well of the tray. As water leaves the drop, the polypeptide sample undergoes an increase in relative concentration which may eventually lead to supersaturation. It is the increased concentration of the polypeptide sample that is required for crystallization to take place. Typically the drop contains a lower concentration of reagent than the reservoir, and typically, the drop contained half the concentration of reagent in the reservoir, because equal volumes of sample and reagent were mixed to form the drop.

In these experiments, the initial protein concentration of Ab-31 in the drop was 30 mg/ml. The crystallization screen was set up in 24-well VDX polypropylene tissue culture trays. Each position in the VDX tray contained 1 mL of reagent reservoir, with the reagent reservoir in each well differing in composition from that in the other wells, to establish an array of differing crystallization buffer conditions. 1 mL of polypeptide solution at each polypeptide concentration was added to 1 µl of reservoir solution to form the drops. Trays were incubated either at 4° C. or at ambient room temperature.

Ab-31 crystallization was observed at both 4° C. and room temperature under the following crystallization conditions: 10 mM Histidine, pH 7.15 to pH 7.47 as well as 10 mM Potassium Phosphate, pH 7.2. The resulting crystals varied in length from about 100 µm to about 1000 µm and demonstrated an ellipsoidal shape as determined by Zeiss Stemi SV11 stereomicroscope with polarization, which was interfaced with a Zeiss AxioCam MRc digital camera which operated with AxioVision 4.0 software.

The foregoing Example demonstrates that Ab-31 was crystallizable under a variety of crystallization conditions, but crystals did not form under every condition tested. Approximately 250 different crystallization conditions were tested, but only approximately 36 conditions produced Ab-31 crystals.

Numerous modifications and variations in the practice of the invention are expected to occur to those of skill in the art upon consideration of the presently preferred embodiments thereof. Consequently, the only limitations which should be placed upon the scope of the invention are those which appear in the appended claims.

All of the U.S. patents, U.S. patent application publications, U.S. patent applications, foreign patents, foreign patent applications and non-patent publications referred to in this specification and/or listed in the Application Data Sheet, are incorporated herein by reference, in their entireties.

From the foregoing it will be appreciated that, although specific embodiments of the invention have been described herein for purposes of illustration, various modifications may be made without deviating from the spirit and scope of the invention.

What is claimed is:

1. A crystal of an anti-sclerostin IgG antibody comprising two light chains each comprised of SEQ ID NO: 3 and two heavy chains each comprised of SEQ ID NO: 5, wherein said crystals have a length of up to 500μM and a shape selected from the group consisting of ellipsoids, rods and needles or mixtures thereof.

2. A sterile formulation comprising the crystal of claim 1.

3. The formulation of claim 2, wherein the crystal comprises a salt selected from the group consisting of sodium dihydrogen phosphate, di-potassium hydrogen phosphate, sodium chloride, ammonium sulfate, potassium sodium tartrate tetrahydrate, tacsimate, sodium citrate dihydrate, sodium acetate trihydrate, di-ammonium tartrate, sodium malonate, acetate, calcium acetate, cacodylate, CHES, lithium sulfate, magnesium chloride, zinc acetate, cesium chloride, ammonium phosphate, sodium phosphase, potassium phosphate, sodium fluoride, potassium iodide, sodium idodide, ammonium iodide, sodium thiocyanate, potassium thiocyanate, sodium formate, potassium formate and ammonium formate.

4. The formulation of claim 2, that is a lyophilized formulation.

5. The formulation of claim 2, that is a liquid formulation.

6. The formulation of claim 5, comprising a concentration of at least about 100 mg of said antibody per ml of formulation.

7. The formulation of claim 5, comprising at least about 140 mg of antibody dispersed in 1.5 ml or less of liquid.

8. The formulation of claim 7 that is injectable through a syringe having a 20 Gauge needle or finer using a clinically acceptable amount of force.

9. A container comprising at least 50 mg of the antibody crystal of claim 1 for suspension in a volume of 0.5-2 mL.

10. A container comprising the formulation of claim 2.

11. A method of making acrystal of an anti-sclerostin IgG antibody comprising two light chains each comprised of SEQ ID NO: 3 and two heavy chains each comprised of SEQ ID NO: 5 , wherein said crystals have a length of up to 500 μm and a shape selected from the group consisting of ellipsoids, rods and needles or mixtures thereof, the method comprising combining a solution of the antibody with a crystallization reagent comprising a salt selected from the group consisting of sodium dihydrogen phosphate, di-potassium hydrogen phosphate, sodium chloride, ammonium sulfate, ammonium acetate, potassium sodium tartrate tetrahydrate, tacsimate, sodium citrate dihydrate, sodium acetate trihydrate, di-ammonium tartrate, sodium malonate, acetate, calcium acetate, cacodylate, CHES, lithium sulfate, lithium acetate dihydrate, magnesium chloride, magnesium acetate tetrahydrate, magnesium formate, magnesium nitrate, magnesium sulfate, zinc acetate, zinc chloride, zinc sulfate, cesium chloride, ammonium phosphate, sodium phosphase, potassium phosphate, sodium fluoride, potassium iodide, sodium idodide, ammonium iodide, sodium thiocyanate, potassium thiocyanate, sodium formate, potassium formate and ammonium formate, optionally at pH of about 6 to about 8, such that a crystal is formed.

12. The method of claim 11, wherein the concentration of the salt is from about 0.1 M to about 10 M.

13. A method of increasing bone mineral density, treating a disorder associated with decreased bone density, treating a bone-related disorder, or improving outcomes in a procedure, replacement, graft, surgery or repair in a mammalian subject comprising administering the formulation of claim 2 in an amount effective to increase bone mineral density in the subject.

* * * * *